United States Patent
Hancock et al.

(10) Patent No.: US 6,534,277 B1
(45) Date of Patent: Mar. 18, 2003

(54) METHOD FOR IDENTIFYING A COMPOUND TO BE TESTED FOR AN ABILITY TO REDUCE IMMUNE REJECTION BY DETERMINING STAT4 AND STAT6 PROTEINS

(75) Inventors: Wayne William Hancock, Medfield, MA (US); Engin Ozkaynak, Milford, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 24 days.

(21) Appl. No.: 09/972,800

(22) Filed: Oct. 5, 2001

Related U.S. Application Data

(63) Continuation of application No. 09/549,654, filed on Apr. 14, 2000, now abandoned.

(51) Int. Cl.[7] .................... G01N 33/53; C12Q 1/68
(52) U.S. Cl. ................... 435/7.1; 436/501; 435/6
(58) Field of Search .................. 435/7.1, 6; 436/501

(56) References Cited

U.S. PATENT DOCUMENTS

| | | |
|---|---|---|
| 5,474,771 A | 12/1995 | Lederman et al. |
| 5,563,036 A | 10/1996 | Peterson et al. |
| 5,565,321 A | 10/1996 | Spriggs et al. |
| 5,580,979 A | 12/1996 | Bachovchin |
| 5,674,492 A | 10/1997 | Armitage et al. |
| 5,683,693 A | 11/1997 | Noelle et al. |
| 5,710,129 A | 1/1998 | Lynch et al. |
| 5,712,094 A | 1/1998 | Seidel et al. |
| 5,747,037 A | 5/1998 | Noelle et al. |
| 5,776,902 A | 7/1998 | Bachovchin |
| 5,833,987 A | 11/1998 | Noelle et al. |
| 5,869,049 A | 2/1999 | Noelle et al. |
| 5,876,718 A | 3/1999 | Noelle et al. |
| 5,876,950 A | 3/1999 | Siadak et al. |
| 5,902,585 A | 5/1999 | Noelle et al. |
| 5,932,425 A | 8/1999 | Alkalay et al. |
| 5,942,229 A | 8/1999 | Noelle et al. |
| 5,945,513 A | 8/1999 | Aruffo et al. |
| 5,961,974 A | 10/1999 | Armitage et al. |
| 5,962,406 A | 10/1999 | Armitage et al. |
| 5,981,724 A | 11/1999 | Armitage et al. |
| 5,993,816 A | 11/1999 | Lederman et al. |
| 6,001,358 A | 12/1999 | Black et al. |

FOREIGN PATENT DOCUMENTS

| | | |
|---|---|---|
| EP | 0 555 880 | 8/1993 |
| EP | 0 585 943 | 3/1994 |
| EP | 0 897 983 | 2/1999 |
| WO | WO 93/08207 | 4/1993 |
| WO | WO 93/09812 | 5/1993 |
| WO | WO 94/17196 | 8/1994 |
| WO | WO 95/06480 | 3/1995 |
| WO | WO 95/06666 | 3/1995 |
| WO | WO 95/17202 | 6/1995 |
| WO | WO 96/40918 | 12/1996 |
| WO | WO 97/17446 | 5/1997 |
| WO | WO 97/20063 | 6/1997 |
| WO | WO 98/30241 | 7/1998 |
| WO | WO 98/39026 | 9/1998 |
| WO | WO 98/52606 | 11/1998 |
| WO | WO 98/58669 | 12/1998 |
| WO | WO 98/58672 | 12/1998 |
| WO | WO 99/00143 | 1/1999 |
| WO | WO 99/12566 | 3/1999 |
| WO | WO 99/45958 | 9/1999 |

OTHER PUBLICATIONS

GenBank Accession No. AA591015 (Barstead mouse proximal colon MPLRB6 cDNA), Sep. 16, 1997.
GenBank Accession No. AF058925 (Human Jak2 kinase mRNA, complete cds), Jun. 23, 1998.
GenBank Accession No. AF159854 (Human SOCS–3 mRNA, complete cds), Nov. 28, 2000.
GenBank Accession No. L78440 (Human STAT4 mRNA, complete cds), Aug. 3, 1996.
GenBank Accession No. NM–003150 (Human STAT3 mRNA), Jun. 27, 2002.
GenBank Accession No. NM–003153 (Human STAT6 mRNA), Jun. 21, 2002.
GenBank Accession No. NM–003331 (Human TYK2 mRNA), Oct. 31, 2002.
GenBank Accession No. NM–005419 (human STAT2 mRNA), Aug. 27, 2002.
GenBank Accession No. NM–007315 (Human STAT1 mRNA), Aug. 27, 2002.
Akira et al., 1994, "Molecular cloning of APRF, a novel IFN–stimulated gene factor 3 p91–related transcription factor involved in the gp130–mediated signaling pathway", Cell 77:63–71.
Armitage et al., 1993, "CD40L: a multi–functional ligand", Semin. Immunol. 5:401–412.

(List continued on next page.)

*Primary Examiner*—Elizabeth Kemmerer
*Assistant Examiner*—Ruixiang Li
(74) *Attorney, Agent, or Firm*—Pennie & Edmonds LLP

(57) ABSTRACT

The present invention relates to methods for identifying compounds that can reduce immune rejection, for example, transplant- or autoimmune disorder-related immune rejection. The present invention is based, in part, on the discovery, demonstrated herein, that immune rejection can be monitored by determining the amount of particular members of the Jak/Stat signal transduction pathway present within an affected tissue. The present invention is further based, in part, on the discovery, demonstrated herein, that immune rejection can be reduced and tolerance can be induced by modulating the amount of these particular members of the Jak/Stat signal transduction pathway present, expressed or active within an affected tissue. In particular, the results demonstrate that immune rejection can be monitored by determining the amount of mRNA or protein of Stat1, Stat3, Stat4, Stat6, SOCS1, or SOCS3 present, e.g., in an affected tissue.

9 Claims, 64 Drawing Sheets

OTHER PUBLICATIONS

Figure 10:
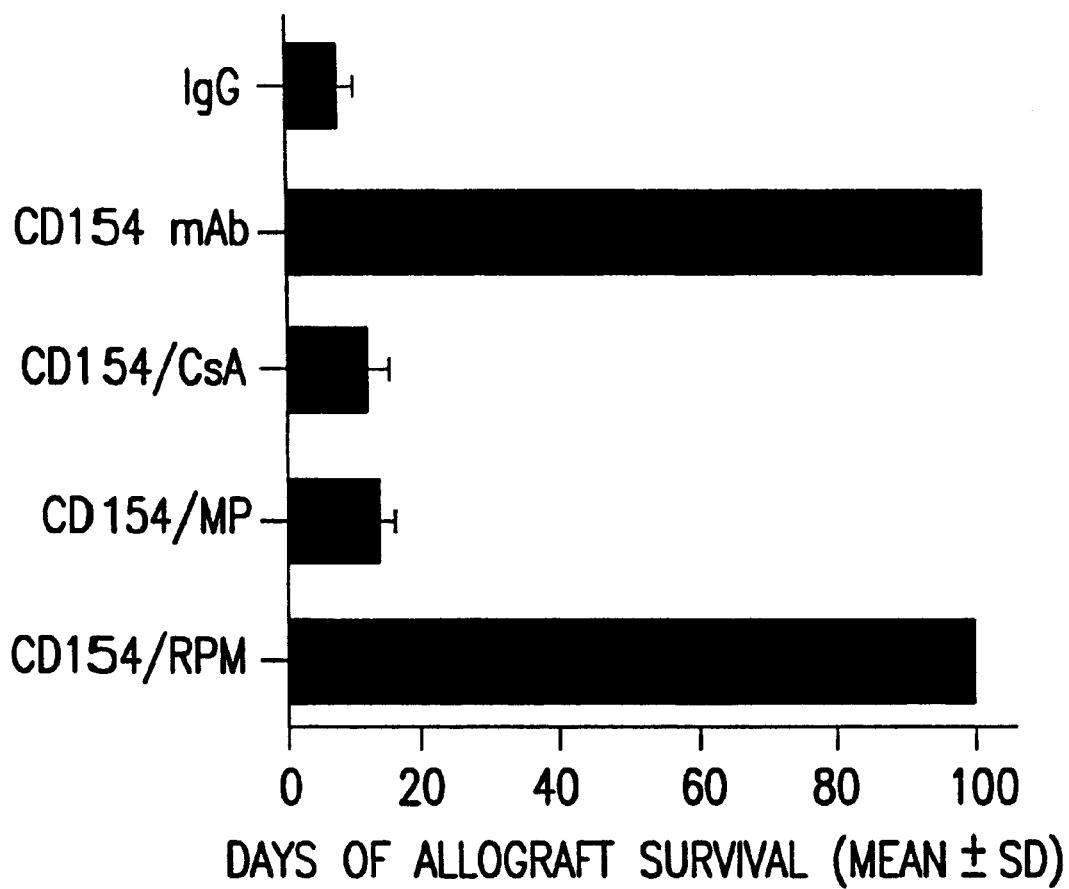

Baeuerle and Henkel, 1994, "Function and activation of NF–κ B in the immune system", Annu. Rev. Immunol. 12:141–179.

Banchereau et al., 1994, "The CD40 antigen and its ligand", Annu. Rev. Immunol. 12:881–922.

Billingham, 1990, "Dilemma of variety of histopathologic grading systems for acute cardiac allograft rejection by endomyocardial biopsy", J. Heart Transplant. 9(3 part 2):272–276.

Bischof and Melms, 1998, "Glucocorticoids inhibit CD40 ligand expression of peripheral $CD4^+$ lymphocytes", Cell. Immunol. 187:38–44.

Blair et al., 2000, "CD40 ligand (CD154) triggers a short-term $CD4^+$ T cell activation response that results in secretion of immunomodulatory cytokines and apoptosis", J. Exp. Med. 191:651–660.

Bluyssen and Levy, 1997, "Stat2 is a transcriptional activator that requires sequence–specific contacts provided by stat1 and p48 for stable interaction with DNA", J. Biol. Chem. 272:4600–4605.

Borel, 1989, "Pharmacology of cyclosporine (sandimmune) IV. Pharmacological properties in vivo", Pharm. Rev. 42:260–372.

Boulougouris et al., 1999, "IL–2–independent activation and proliferation in human T cells induced by CD28", J. Immunol. 163:1809–1816.

Bright et al., 1999, "Tyrphostin B42 inhibits IL–12–induced tyrosine phosphorylation and activation of Janus kinase–2 and prevents experimental allergic encephalomyelitis", J. Immunol. 162:6255–6262.

Caldenhoven et al., 1994, "Stimulation of the human intercellular adhesion molecule–1 promoter by interleukin–6 and interferon–γ involves binding of distinct factors to a palindromic response element", J. Biol. Chem. 269:21146–21154.

Cathcart et al., 1986, "Experimental arthritis in a nonhuman primate. I. Induction by bovine type II collagen", Lab. Invest. 54:26–31.

Caux et al., 1994, "Activation of human dendritic cells through CD40 cross–linking", J. Exp. Med. 180:1263–1272.

Cavicchi and Whittle, 1999, "Regulation of induction of nitric oxide synthase and the inhibitory actions of dexamethasone in the human intestinal epithelial cell line, Caco–2: influence of cell differentiation", Br. J. Pharmacol. 128:705–715.

Cella et al., 1996, "Ligation of CD40 on dendritic cells triggers production of high levels of interleukin–12 and enhances T cell stimulatory capacity: T–T help via APC activation", J. Exp. Med. 184:747–752.

Chin et al., 1996, "Cell growth arrest and induction of cyclin–dependent kinase inhibitor $p21^{WAF1/CIP1}$ mediated by STAT1", Science 272:719–722.

Chung et al., 1997, "Specific inhibition of Stat3 signal transduction by PIAS3", Science 278:1803–1805.

Coffer et al., 1995, "Transcriptional regulation of the junB promoter: analysis of STAT–mediated signal transduction", Oncogene 10:985–994.

Constantin et al., 1999, "Inhibition of experimental autoimmune encephalomyelitis by a tyrosine kinase inhibitor", J. Immunol. 162:1144–1149.

Constantin et al., 1998, "Tyrphostin AG490, a tyrosine kinase inhibitor, blocks actively induced experimental autoimmune encephalomyelitis", Eur. J. Immunol. 28:3523–3529.

Courtenay et al., 1980, "Immunisation against heterologous type II collagen induces arthritis in mice", Nature 283:666–668.

Csizmadia et al., 2000, "Quantitative analysis of NFκB and IκB proteins within mouse cardiac allografts", Transplant 2000 Joint Meeting, May 13–20, 2000, Chicago, IL.

Curiel et al., 1997, "Identification of a Stat–6–responsive element in the promoter of the human interleukin–4 gene", Eur. J. Immunol. 27:1982–1987.

Dalton and Jove, 1999, "Drug resistance in multiple myeloma: approaches to circumvention", Semin. Oncol. 26(suppl. 13):23–27.

Darnell, 1997, "STATs and gene regulation", Science 277:1630–1635.

Darnell et al., 1994, "Jak–STAT pathways and transcriptional activation in response to IFNs and other extracellular signaling proteins", Science 264:1415–1421.

Decker and Kovarik, 1999, "Transcription factor activity of STAT proteins: structural requirements and regulation by phosphorylation and interacting proteins", Cell. Mol. Life Sci. 55:1535–1546.

Endo et al., 1997, "A new protein containing an SH2 domain that inhibits JAK kinases", Nature 387:921–924.

Epinat and Gilmore, 1999, "Diverse agents act at multiple levels to inhibit the Rel/NF–κB signal transduction pathway", Oncogene 18:6896–6909.

Fellstrom and Larsson, 1993, "Pathogenesis and treatment perspectives of chronic graft rejection (CVR)", Immunol. Rev. 134:83–98.

Fend et al., 1999, "Immuno–LCM: laser capture microdissection of immunostained frozen sections for mRNA analysis", Am. J. Pathol. 154:61–66.

Flanders et al., 1999, "Prevention of type 1 diabetes from laboratory to public health", Autoimmun. 29:235–246.

Foster, 1999, "Relevance of systemic lupus erythematosus nephritis animal models to human disease", Semin. Nephrol. 19:12–24.

Fujitani et al., 1994, "Transcriptional activation of IL–6 response element in the junB promoter is mediated by multiple Stat family proteins", Biochem. Biophys. Res. Commun. 202:1181–1187.

Fuleihan et al., 1994, "Cyclosporin A inhibits CD40 ligand expression in T lymphocytes", J. Clin. Invest. 93:1315–1320.

Gao et al., 1997, "An interferon–γ–activated site (GAS) is necessary for full expression of the mouse iNOS gene in response to interferon–γ and lipopolysaccharide", J. Biol. Chem. 272:1226–1230.

Gazit et al., 1989, "Tyrphostins I: synthesis and biological activity of protein kinase inhibitors", J. Medicinal Chem. 32:2344–2352.

Ghislain and Fish, 1996, "Application of genomic DNA affinity chromatography identifies multiple interferon–α–regulated Stat2 complexes", J. Biol. Chem. 271:12408–12413.

Gianello, 1997, [Is there a place for gene therapy in organ transplantation?], Ann. Chir. 51:593–604 (in French w/English abstract).

Grigorieva et al., 2000, "Regulation of c–myc transcription by interleukin–2 (IL–2). Identification of a novel IL–2 response element interacting with STAT–4", J. Biol. Chem. 275:7343–7350.

Grisham et al., 1999, "Inhibition of NF–κB activation in vitro and in vivo: role of 26S proteasome", Meth. Enzymol. 300:345–363.

Guillen et al., 1986, "Acute cutaneous graft–versus–host disease to minor histocompatibility antigens in a murine model. Evidence that large granular lymphocytes are effector cells in the immune response", Lab Invest. 55:35–42.

Gummert et al., 1999, "Newer immunosuppressive drugs: a review", J. Am. Soc. Nephrol. 10:1366–1380.

Halloran and Lui, 1998, "Approved Immunosuppressants", Ch. 13 in: *Primer on Transplantation,* Norman and Suki, eds., pp. 93–102, 104–107.

Hancock et al., 1998, "Antibody–induced transplant arteriosclerosis is prevented by graft expression of anti–oxidant and anti–apoptotic genes", Nature Med. 4:1392–1396.

Hancock et al., 1996, "Costimulatory function and expression of CD40 ligand, CD80, and CD86 in vascularized murine cardiac allograft rejection", Proc. Natl. Acad. Sci USA 93:13967–13972.

Haque et al., 1998, "Protein–tyrosine phosphatase Shp–1 is a negative regulator of IL–4– and IL–13–dependent signal transduction", J. Biol. Chem. 273:33893–33896.

Harada et al., 1994, "Structure and expression of the human interferon regulatory factor 1 (IRF–1) and IRF–2 genes: implications for a gene network in the interferon system", Mol. Cell. Biol. 14:1500–1509.

Hariharan et al., 2000, "Improved graft survival after renal transplantation in the United States, 1988 to 1996", N. Eng. J. Med. 342:605–612.

Heim, 1999, "The Jak–STAT pathway: cytokine signalling from the receptor to the nucleus", J. Recept. Sig. Transduct. Res. 19:75–120.

Hilton, 1999, "Negative regulators of cytokine signal transduction", Cell. Mol. Life Sci.55:1568–1577.

Hilton et al, 1999, "Twenty proteins containing a C–terminal SOCS box form five structural classes", Proc. Natl. Acad. Sci. USA 95:114–119.

Holgate, 1997, "The cellular and mediator basis of asthma in relation to natural history", Lancet 350(suppl. II):5–9.

Holmdahl, 1999, "Autoimmunity: another pathway towards arthritis", Curr. Biol. 9:R528–R530.

Hou et al., 1994, "An interleukin–4–induced transcription factor: IL–4 Stat", Science 265:1701–1706.

Huang et al., 1999, "Role of the Janus kinase (JAK)/signal transducters and activators of transcription (STAT) cascade in advanced glycation end–product–induced cellular mitogenesis in NRK–49F cells", Biochem. J. 342:231–238.

Ishioka et al., 1999, "Utilization of MHC class I transgenic mice for development of minigene DNA vaccines encoding multiple HLA–restricted CTL epitopes", J. Immunol. 162:3915–3925.

Iwakoshi et al., 2000, "Treatment of allograft recipients with donor–specific transfusion and anti–CD154 antibody leads to detention of alloreactive $CD8^+$ T cells and prolonged graft survival in CTLA4–dependent manner", J. Immunol. 164:512–521.

Judge et al., 1999, "The role of CD80, CD86, and CTLA4 in alloimmune responses and the induction of long–term allograft survival", J. Immunol. 162:1947–1951.

Kaplan et al., 1996, "Stat6 is required for mediating responses to IL–4 and for development of Th2 cells", immunity 4:313–319.

Kaplan et al., 1996, "Impaired IL–12 responses and enhanced development of Th2 cells in Stat4–deficient mice", Nature 382:174–177.

Karras et al., 1997, "Induction of STAT protein signaling through the CD40 receptor in B lymphocytes", J. Immunol. 159:4350–4355.

Kawai et al., 2000, "Thromboembolic complications after treatment with monoclonal antibody against CD40 ligand", Nature Med. 6:114.

Kirk et al., 2000, Nature Med. 6:114 (reply to Kawai et al., 2000 Nature Med. 6:114).

Kirk, 1999, "Treatment with humanized monoclonal antibody against CD154 prevents acute renal allograft rejection in nonhuman primates", Nature Med. 5:686–693.

Kirk et al., 1997, "CTLA4–Ig and anti–CD40 ligand prevent renal allograft rejection in primates", Proc. Natl. Acad. Sci. USA 94:8789–8794.

Kita et al., 1999, "Prolonged cardiac allograft survival in rats systemically injected with adenoviral vectors containing CTLA4Ig–gene", Transplantation 68:758–766.

Klaus et al., 1994, "Costimulation through CD28 enhances T cell–dependent B cell activation via CD40–CD40L interaction", J. Immunol. 152:5643–5652.

Knechtle et al., 1999, "Inducing unresponsiveness by the use of the anti–CD3 immunotoxin. CTLA4–Ig, and anti–CD40 ligand", Transplant. Proc. 31(suppl. B):27S–28S.

Koglin et al., 2000, "Attenuated cardiac allograft vasculopathy in mice with targeted deletion of the transcription factor STAT4", Circulation 101:1034–1039.

Kotanides and Reich, 1996, "Interleukin–4–induced STAT6 recognizes and activates a target site in the promoter of the interleukin–4 receptor gene", J. Biol. Chem. 271:25555–25561.

Krogh et al., 1999, "Models to study the pathogenesis of thyroid autoimmunity", Biochimie 81:511–515.

Larsen et al., 1996, "Long–term acceptance of skin and cardiac allografts after blocking CD40 and CD28 pathways", Nature 381:434–438.

L'Azou et al., 1999, "In vitro models to study mechanisms involved in cyclosporine A–mediated glomerular contraction", Arch. Toxicol. 73:337–345.

Lenschow et al., 1996, "CD28/B7 system of T cell costimulation", Annu. Rev. Immunol. 14:233–258.

Leonard and O'Shea, 1998, "JAKS and STATS: biological implications", Annu. Rev. Immunol. 16:293–322.

Levitzki, 1992, "Tyrphostins: tyrosine kinase blockers as novel antiproliferative agents and dissectors of signal transduction", FASEB J. 6:3275–3282.

Levy, 1999, "Physiological significance of STAT proteins: investigations through gene disruption in vivo", Cell. Mol. Life Sci. 55:1559–1567.

Lew et al., 1991, "Overlapping elements in the guanylate–binding protein gene promoter mediate transcriptional induction by alpha and gamma interferons", Mol. Cell. Biol. 11:182–191.

Li et al., 1999, "Induction of allograft tolerance in the absence of Fas–mediated apoptosis", J. Immunol. 163:2500–2507.

Li et al., 1996, "Formation of STAT1–STAT2 heterodimers and their role in the activation of IRF–1 gene transcription by interferon–α", J. Biol. Chem. 271:5790–5794.

Lin et al., 1995, "Activation of NF–κB requires proteolysis of the inhibitor I κB–α: signal–induced phosphorylation of I κB–α alone does not release active NF–κB", Proc. Natl. Acad. Sci USA 92:552–556.

Linehan et al., 1998, "STAT6 is required for IL–4–induced germline Ig gene transcription and switch recombination", J. Immunol. 161:302–310.

Liu et al., 1998, "Inhibition of Stat1–mediated gene activation by PIAS1", Proc. Natl. Acad. Sci. USA 95:10626–10631.

Macchi et al., 1995, "Mutations of Jak–3 gene in patients with autosomal severe immune deficiency (SCID)", Nature 377:65–68.

Mandelbrot et al., 1999, "Expression of B7 molecules in recipient, not donor, mice determines the survival of cardiac allografts", J. Immunol. 163:3753–3757.

Marten et al., 1999, "Selection of CD8+ T cells with highly focused specificity during viral persistence in the central nervous system", J. Immunol. 162:3905–3914.

Masuhara et al., 1997, "Cloning and characterization of novel CIS family genes", Biochem. Biophys. Res. Comm. 239:439–446.

McWhinney et al., 1998, "Angiotensin II activates Stat5 through Jak2 kinase in cardiac myocytes", J. Mol. Cell. Cardiol. 30:751–761.

McWhinney et al., 1997, "The type I angiotensin II receptor couples to Stat1 and Stat3 activation through Jak2 kinase in neonatal rat cardiac myocytes", J. Mol. Cell. Cardiol. 29:2513–2524.

Meydan et al., 1996, "Inhibition of acute lymphoblastic leukaemia by a Jak–2 inhibitor", Nature 379:645–648.

Minamoto et al., 1997, "Cloning and functional analysis of new members of STAT induced STAT inhibitor (SSI) family: SSI–2 and SSI–3", Biochem. Biophys. Res. Comm. 237:79–83.

Morris, 1991, "Cyclosporine, FK–506 and other drugs in organ transplantation", Curr. Opin. Immunol. 3:748–751.

Naeger et al., 1999, "Identification of a STAT4 binding site in the interleukin–12 receptor required for signaling"J. Biol. Chem. 274:1875–1878.

Naka et al., 1997, "Structure and function of a new STAT–induced STAT inhibitor", Nature 387:924–929.

Nielsen et al., 1999, "Inhibition of constitutively activated Stat3 correlates with altered Bcl–2/Bax expression and induction of apoptosis in mycosis fungoides tumor cells", Leukemia 13:735–738.

Nielsen et al., 1997, "Constitutive activation of a slowly migrating isoform of Stat3 in mycosis fungoides: tyrphostin AG490 inhibits Stat3 activation and growth of mycosis fungoides tumor cell lines", Proc. Natl. Acad. Sci. USA 94:6764–6769.

Ochiai et al., 1999, "Role of JAK2 signal transduction pathway in activation and survival of human peripheral eosinophils by interferon–γ (IFN–γ)", Clin. Exp. Immunol. 118:340–343.

Oettgen and Geha, 1999, "IgE in asthma and atopy: cellular and molecular connections", J. Clin. Invest. 104:829–835.

Olsson et al., 1999, "CTLA–4 ligation suppressed CD28–induced NF–kappaB and AP–1 activity in mouse T cell blasts", J. Biol. Chem. 274:14400–14405.

O'Shea et al., 1997,"Advances in the understanding of cytokine signal transduction: the role of Jaks and STATs in immunoregulation and the pathogenesis of immunodeficiency", J. Clin. Immunol. 17:431–447.

O'Shea, 1997,"Jaks, STATs, cytokine signal transduction, and immunoregulation: are we there yet?", Immunity 7:1–11.

Ozkaynak et al., 2000, "Intragraft expression of signal transducers and activators of transcription (STATS) and suppressors of cytokine synthesis (SOCS) molecules in rejection vs. tolerance", Transplant 2000 Joint Meeting, May 13–17, 2000, Chicago, IL.

Paul, 1999, "Chronic allograft nephropathy: an update", Kidney Intl. 56:783–793.

Paulson et al., 1999, "Stat protein transactivation domains recruit p300/CBP through widely divergent sequences", J. Biol. Chem. 274:25343–25349.

Perico et al., 1995, "Immunosuppressive therapy abrogates unresponsiveness to renal allograft induced by thymic recognition of donor antigens", J. Amer. Soc. Nephrol. 5:1618–1623.

Pine et al., 1994, "Tyrosine phosphorylated p91 binds to a single element in the ISGF2/IRF–1 promoter to mediate induction by IFNα and IFNγ, and is likely to autoregulate the p91 gene", EMBO J. 13:158–167.

Piskurich et al., 1999, "Two distinct gamma interferon–inducible promoters of the major histocompatiblilty complex class II transactivator gene are differentially regulated by STAT1, interferon regulatory factor 1, and transforming growth factor β", Mol. Cell. Biol. 19:431–440.

Quelle et al., 1995, "Cloning of murine Stat6 and human Stat6, Stat proteins that are tyrosine phosphorylated in responses to IL–4 and IL–3 but are not required for mitogenesis", Mol. Cell. Biol. 15:3336–3343.

Racusen et al., 1999, "The Banff 97 working classification of renal allograft pathology", Kidney Int. 55:713–723.

Rasmussen et al., 1999, "Models to study the pathogenesis of thyroid autoimmunity", Biochimie 81:511–515.

Ray and Cohn, 1999, "Th2 cells and GATA–3 in asthma: new insights into the regulation of airway inflammation", J. Clin. Invest. 104:985–993.

Ripperger, 1995, "Transcription factors Stat3 and Stat5b are present in rat liver nuclei late in an acute phase response and bind interleukin–6 response elements", J. Biol. Chem. 270:29998–30006.

Rogge et al., 1999, "Antibodies to the IL–12 receptor β chain mark human Th1 but not Th2 cells in vitro and in vivo", J. Immunol. 162:3926–3932.

Romagnani, 1997, "The Th1/Th2 paradigm", Immunol. Today 18:263–266.

Russell et al., 1995, "Mutation of Jak3 in a patient with SCID: essential role of Jak3 in lymphoid development", Science 270:797–800.

Russell et al., 1994, "Interaction of IL–2Rβ and $\gamma_c$ chains with Jak1 and Jak3: implications of XSCID and XCID", Science 266:1042–1045.

Schindler and Brutsaert, 1999, "Interferons as a paradigm for cytokine signal transduction", Cell. Mol. Life Sci. 55:1509–1522.

Schindler et al., 1992, "Proteins of transcription factor ISGF–3: one gene encodes the 91–and 84–kDa ISGF–3 proteins that are activated by interferon α", Proc. Natl. Acad. Sci. USA 89:7836–7839.

Schubert et al., 1995, "The human gp39 promoter. Two distinct nuclear factors of activated T cell protein–binding elements contribute independently to transcriptional activation", J. Biol. Chem. 270:29624–29627.

Schutze et al., 1998, "Identification of expressed genes by laser–mediated manipulation of single cells", Nat. Biotechnol. 16:737–742.

Sha et al., 1995, "Targeted disruption of the p50 subunit of NF–κB leads to multifocal defects in immune responses", Cell 80:321–330.

Sharfe et al., 1995, "JAK3 protein tyrosine kinase mediates interleukin–7–induced activation of phosphatidylinositol–3' kinase", Blood 86:2077–2085.

Shimoda et al., 1996, "Lack of IL–4–induced Th2 response and IgE class switching in mice with disrupted Stat6 gene", Nature 380:630–633.

Sigal and Dumont, 1992, "Cyclosporin A, FK–506, and rapamycin: pharmacologic probes of lymphocyte signal transduction", Annu. Rev. Immunol. 19:519–560.

Simon et al., 1997, "Anti–apoptotic signals of granuylocyte–macrophage colony–stimulating factor are transduced via Jak2 tyrosine kinase in eosinophils", Eur. J. Immunol. 27:3536–3539.

Simone et al., 1998, "Laser–capture microdissection: opening the microscopic frontier to molecular analysis", Trends Genet. 14:272–276.

Sims et al., 1993, "A novel interferon–inducible domain: structural and functional analysis of the human interferon regulatory factor 1 gene promoter", Mol. Cell. Biol. 13:690–702.

Smiley et al., 2000, "Differential effects of cyclosporine A, methylprednisolone, mycophenolate, and rapamycin on CD154 induction and requirement for NFκB: implications for tolerance induction", Transplantation 70:415–419.

Smiley et al., 2000, "Activation–induced expression of CD40 ligand (CD40L) is required for CD40L antibody–mediated tolerance induction: differential effects of CSA, RPM, steroids and MMF, and requirement for NFκB", Transplant 2000 Joint Meeting, May 13–20, 2000, Chicago, IL.

Starr et al. 1997, "A family of cytokine–inducible inhibitors of signaling", Nature 387:917–921.

Storz et al., 1999, "Insulin selectively activates STAT5b but not STAT5a, via a JAK2–independent signaling pathway in Kym–1 rhabdomyosarcoma cells", FEBS Lett. 464:159–163.

Takeda et al., 1996, "Essential role of Stat6 in IL–4 signalling", Nature 380:627–630.

Taniguchi, 1995, "Cytokine signaling through nonreceptor protein tyrosine kinases", Science 268:251–255.

Thanos and Maniatis, 1995, "NF–κB: a lesson in family values", Cell 80:529–532.

Thierfelder et al., 1996, "Requirement for Sta4 in interleukin–12–mediated responses of natural killer and T cells", Nature 382:171–174.

Tinnell et al., 1998, "STAT6, NF–κB and C/EBP in CD23 expression and IgE production", Intl. Immunol. 10:1529–1538.

Traenecker et al., 1995, "Phosphorylation of human IκB–α on serines 32 and 36 controls IκB–α proteolysis and NF–κB activation in response to diverse stimuli", EMBO J. 14:2876–2883.

Trentham et al., 1977, "Autoimmunity to type II collagen an experimental model of arthritis", J. Exp. Med. 146:857–868.

Ullman et al., 1990, "Transmission of signals from the T lymphocyte antigen receptor to the genes responsible for cell proliferation and immune function: the missing link", Annu. Rev. Immunol. 8:421–452.

Vincent, 1999, Biogen News press release of Nov. 2, 1999.

Waldmann and Cobbold, 1998, "How do monoclonal antibodies induce tolerance? A role for infectious tolerance?", Annu. Rev. Immunol. 16:619–644.

Wang et al., 1999, "JAK3, STAT, and MAPK signaling pathways as novel molecular targets for the tyrphostin AG–490 regulation of IL–2–mediated T cell response", J. Immunol. 162:3897–3904.

Wegenka et al., 1993, "Acute–phase response factor, a nuclear factor binding to acute–phase response elements, is rapidly activated by interleukin–6 at the posttranslational level", Mol. Cell. Biol. 13:276–288.

Wells et al., 1999, "Requirement for T–cell apoptosis in the induction of peripheral transplantation tolerance", Nature Med. 5:1303–1307.

Yamamoto et al., 1997, "cDNA cloning, expression and chromosome mapping of the human STAT4 gene: both STAT4 and STAT1 genes are mapped to 2q32.2—>q32.3", Cytogenet. Cell. Genet. 77:207–210.

Yamamoto et al., 1994, "Stat4, a novel gamma interferon activation site–binding protein expressed in early myeloid differentiation", Mol. Cell. Biol. 14:4342–4349.

Yan et al., 1995, "The genomic structure of the STAT genes: multiple exons in coincident sites in Stat1 and Stat2", Nucl. Acids Res. 23:459–463.

Yeh and Pellegrini, 1999, "The Janus kinase family of protein tyrosine kinases and their role in signaling", Cell. Mol. Life Sci. 55:1523–1534.

Yoshimura et al., 1995, "A novel cytokine–inducible gene CIS encodes an SH2–containing protein that binds to tyrosine–phosphorylated interleukin 3 and erythropoietin receptors", EMBO J. 14:2816–2826.

You et al.. 1999, "Shp–2 tyrosine phosphatase functions as a negative regulator of the interferon–stimulated Jak/STAT pathway", Mol. Cell. Biol. 19:2416–2424.

Zamvil and Steinman, 1990, "The T lymphocyte in experimental allergic encephalomyelitis", Annu. Rev. Immunol. 8:579–621.

Zheng et al., 1999, "CTLA4 signals are required to optimally induce allograft tolerance with combined donor–specific transfusion and anti–CD154 monoclonal antibody treatment", J. Immunol. 162:4983–4990.

Zhong et al., 1994, "Stat3 and Stat4: members of the family of signal transducers and activators of transcription", Proc. Natl. Acad. Sci. USA 91:4806–4810.

Zhong et al., 1994, "Stat3: a STAT family member activated by tyrosine phosphorylation in response to epidermal growth factor and interleukin–6", Science 264:95–98.

Kuo and Leiden, 1999, Annu. Rev. Immunol. 17:149–87.

Khan, 1992, Curr. Opin. Immunol. 4:553–560.

```
attaaacctc tcgccgagcc cctccgcaga ctctgcgccg gaaagtttca tttgctgtat    60
gccatcctcg agagctgtct aggttaacgt tcgcactctg tgtatataac ctcgacagtc   120
ttggcaccta acgtgctgtg cgtagctgct cctttggttg aatccccagg cccttgttgg   180
ggcacaaggt ggcagg atg tct cag tgg tac gaa ctt cag cag ctt gac tca   232
               Met Ser Gln Trp Tyr Glu Leu Gln Gln Leu Asp Ser
                1               5                       10
```

```
aaa ttc ctg gag cag gtt cac cag ctt tat gat gac agt ttt ccc atg    280
Lys Phe Leu Glu Gln Val His Gln Leu Tyr Asp Asp Ser Phe Pro Met
            15                  20                  25
```

```
gaa atc aga cag tac ctg gca cag tgg tta gaa aag caa gac tgg gag    329
Glu Ile Arg Gln Tyr Leu Ala Gln Trp Leu Glu Lys Gln Asp Trp Glu
            30                  35                  40
```

```
cac gct gcc aat gat gtt tca ttt gcc acc atc cgt ttt cat gac ctc    376
His Ala Ala Asn Asp Val Ser Phe Ala Thr Ile Arg Phe His Asp Leu
45                  50                  55                  60
```

```
ctg tca cag ctg gat gat caa tat agt cgc ttt tct ttg gag aat aac    424
Leu Ser Gln Leu Asp Asp Gln Tyr Ser Arg Phe Ser Leu Glu Asn Asn
                    65                  70                  75
```

```
ttc ttg cta cag cat aac ata agg aaa agc aag cgt aat ctt cag gat    472
Phe Leu Leu Gln His Asn Ile Arg Lys Ser Lys Arg Asn Leu Gln Asp
                80                  85                  90
```

```
aat ttt cag gaa gac cca atc cag atg tct atg atc att tac agc tgt    520
Asn Phe Gln Glu Asp Pro Ile Gln Met Ser Met Ile Ile Tyr Ser Cys
                    95                  100                 105
```

```
ctg aag gaa gaa agg aaa att ctg gaa aac gcc cag aga ttt aat cag    568
Leu Lys Glu Glu Arg Lys Ile Leu Glu Asn Ala Gln Arg Phe Asn Gln
            110                 115                 120
```

```
gct cag tcg ggg aat att cag agc aca gtg atg tta gac aaa cag aaa    616
Ala Gln Ser Gly Asn Ile Gln Ser Thr Val Met Leu Asp Lys Gln Lys
125                 130                 135                 140
```

```
gag ctt gac agt aaa gtc aga aat gtg aag gac aag gtt atg tgt ata    664
Glu Leu Asp Ser Lys Val Arg Asn Val Lys Asp Lys Val Met Cys Ile
                145                 150                 155
```

FIG.1A

```
gag cat gaa atc aag agc ctg gaa gat tta caa gat gaa tat gac ttc    712
Glu His Glu Ile Lys Ser Leu Glu Asp Leu Gln Asp Glu Tyr Asp Phe
            160                 165                 170 aaa tgc aaa acc ttg cag aac aga gaa cac gag acc aat ggt gtg gca    760
Lys Cys Lys Thr Leu Gln Asn Arg Glu His Glu Thr Asn Gly Val Ala
            175                 180                 185 aag agt gat cag aaa caa gaa cag ctg tta ctc aag aag atg tat tta    808
Lys Ser Asp Gln Lys Gln Glu Gln Leu Leu Leu Lys Lys Met Tyr Leu
            190                 195                 200 atg ctt gac aat aag aga aag gaa gta gtt cac aaa ata ata gag ttg    856
Met Leu Asp Asn Lys Arg Lys Glu Val Val His Lys Ile Ile Glu Leu
205                 210                 215                 220 ctg aat gtc act gaa ctt acc cag aat gcc ctg att aat gat gaa cta    904
Leu Asn Val Thr Glu Leu Thr Gln Asn Ala Leu Ile Asn Asp Glu Leu
                225                 230                 235 gtg gag tgg aag cgg aga cag cag agc gcc tgt att ggg ggg ccg ccc    952
Val Glu Trp Lys Arg Arg Gln Gln Ser Ala Cys Ile Gly Gly Pro Pro
                240                 245                 250 aat gct tgc ttg gat cag ctg cag aac tgg ttc act ata gtt gcg gag   1000
Asn Ala Cys Leu Asp Gln Leu Gln Asn Trp Phe Thr Ile Val Ala Glu
                255                 260                 265 agt ctg cag caa gtt cgg cag cag ctt aaa aag ttg gag gaa ttg gaa   1048
Ser Leu Gln Gln Val Arg Gln Gln Leu Lys Lys Leu Glu Glu Leu Glu
                270                 275                 280 cag aaa tac acc tac gaa cat gac cct atc aca aaa aac aaa caa gtg   1096
Gln Lys Tyr Thr Tyr Glu His Asp Pro Ile Thr Lys Asn Lys Gln Val
285                 290                 295                 300 tta tgg gac cgc acc ttc agt ctt ttc cag cag ctc att cag agc tcg   1144
Leu Trp Asp Arg Thr Phe Ser Leu Phe Gln Gln Leu Ile Gln Ser Ser
                305                 310                 315 ttt gtg gtg gaa aga cag ccc tgc atg cca acg cac cct cag agg ccg   1192
Phe Val Val Glu Arg Gln Pro Cys Met Pro Thr His Pro Gln Arg Pro
                320                 325                 330
```

FIG.1B

```
ctg gtc ttg aag aca ggg gtc cag ttc act gtg aag ttg aga ctg ttg    1240
Leu Val Leu Lys Thr Gly Val Gln Phe Thr Val Lys Leu Arg Leu Leu
        335             340             345 gtg aaa ttg caa gag ctg aat tat aat ttg aaa gtc aaa gtc tta ttt    1288
Val Lys Leu Gln Glu Leu Asn Tyr Asn Leu Lys Val Lys Val Leu Phe
    350             355             360 gat aaa gat gtg aat gag aga aat aca gta aaa gga ttt agg aag ttc    1336
Asp Lys Asp Val Asn Glu Arg Asn Thr Val Lys Gly Phe Arg Lys Phe
365             370             375             380 aac att ttg ggc acg cac aca aaa gtg atg aac atg gag gag tcc acc    1384
Asn Ile Leu Gly Thr His Thr Lys Val Met Asn Met Glu Glu Ser Thr
                385             390             395 aat ggc agt ctg gcg gct gaa ttt cgg cac ctg caa ttg aaa gaa cag    1432
Asn Gly Ser Leu Ala Ala Glu Phe Arg His Leu Gln Leu Lys Glu Gln
            400             405             410 aaa aat gct ggc acc aga acg aat gag ggt cct ctc atc gtt act gaa    1480
Lys Asn Ala Gly Thr Arg Thr Asn Glu Gly Pro Leu Ile Val Thr Glu
        415             420             425 gag ctt cac tcc ctt agt ttt gaa acc caa ttg tgc cag cct ggt ttg    1528
Glu Leu His Ser Leu Ser Phe Glu Thr Gln Leu Cys Gln Pro Gly Leu
    430             435             440 gta att gac ctc gag acg acc tct ctg ccc gtt gtg gtg atc tcc aac    1576
Val Ile Asp Leu Glu Thr Thr Ser Leu Pro Val Val Val Ile Ser Asn
445             450             455             460 gtc agc cag ctc ccg agc ggt tgg gcc tcc atc ctt tgg tac aac atg    1624
Val Ser Gln Leu Pro Ser Gly Trp Ala Ser Ile Leu Trp Tyr Asn Met
                465             470             475 ctg gtg gcg gaa ccc agg aat ctg tcc ttc ttc ctg act cca cca tgt    1672
Leu Val Ala Glu Pro Arg Asn Leu Ser Phe Phe Leu Thr Pro Pro Cys
            480             485             490 gca cga tgg gct cag ctt tca gaa gtg ctg agt tgg cag ttt tct tct    1720
Ala Arg Trp Ala Gln Leu Ser Glu Val Leu Ser Trp Gln Phe Ser Ser
        495             500             505
```

FIG.1C

```
gtc acc aaa aga ggt ctc aat gtg gac cag ctg aac atg ttg gga gag       1768
Val Thr Lys Arg Gly Leu Asn Val Asp Gln Leu Asn Met Leu Gly Glu
    510             515                 520 aag ctt ctt ggt cct aac gcc agc ccc gat ggt ctc att ccg tgg acg       1816
Lys Leu Leu Gly Pro Asn Ala Ser Pro Asp Gly Leu Ile Pro Trp Thr
525             530                 535                 540 agg ttt tgt aag gaa aat ata aat gat aaa aat ttt ccc ttc tgg ctt       1864
Arg Phe Cys Lys Glu Asn Ile Asn Asp Lys Asn Phe Pro Phe Trp Leu
                545                 550                 555 tgg att gaa agc atc cta gaa ctc att aaa aaa cac ctg ctc cct ctc       1912
Trp Ile Glu Ser Ile Leu Glu Leu Ile Lys Lys His Leu Leu Pro Leu
                560                 565                 570 tgg aat gat ggg tgc atc atg ggc ttc atc agc aag gag cga gag cgt       1960
Trp Asn Asp Gly Cys Ile Met Gly Phe Ile Ser Lys Glu Arg Glu Arg
            575                 580                 585 gcc ctg ttg aag gac cag cag ccg ggg acc ttc ctg ctg cgg ttc agt       2008
Ala Leu Leu Lys Asp Gln Gln Pro Gly Thr Phe Leu Leu Arg Phe Ser
590                 595                 600 gag agc tcc cgg gaa ggg gcc atc aca ttc aca tgg gtg gag cgg tcc       2056
Glu Ser Ser Arg Glu Gly Ala Ile Thr Phe Thr Trp Val Glu Arg Ser
605             610                 615                 620 cag aac gga ggc gaa cct gac ttc cat gcg gtt gaa ccc tac acg aag       2104
Gln Asn Gly Gly Glu Pro Asp Phe His Ala Val Glu Pro Tyr Thr Lys
                625                 630                 635 aaa gaa ctt tct gct gtt act ttc cct gac atc att cgc aat tac aaa       2152
Lys Glu Leu Ser Ala Val Thr Phe Pro Asp Ile Ile Arg Asn Tyr Lys
                640                 645                 650 gtc atg gct gct gag aat att cct gag aat ccc ctg aag tat ctg tat       2200
Val Met Ala Ala Glu Asn Ile Pro Glu Asn Pro Leu Lys Tyr Leu Tyr
            655                 660                 665 cca aat att gac aaa gac cat gcc ttt gga aag tat tac tcc agg cca       2248
Pro Asn Ile Asp Lys Asp His Ala Phe Gly Lys Tyr Tyr Ser Arg Pro
        670                 675                 680
```

FIG. 1D

```
aag gaa gca cca gag cca atg gaa ctt gat ggc cct aaa gga act gga    2296
Lys Glu Ala Pro Glu Pro Met Glu Leu Asp Gly Pro Lys Gly Thr Gly
685             690             695             700 tat atc aag act gag ttg att tct gtg tct gaa gtt cac cct tct aga    2344
Tyr Ile Lys Thr Glu Leu Ile Ser Val Ser Glu Val His Pro Ser Arg
                705             710             715 ctt cag acc aca gac aac ctg ctc ccc atg tct cct gag gag ttt gac    2392
Leu Gln Thr Thr Asp Asn Leu Leu Pro Met Ser Pro Glu Glu Phe Asp
            720             725             730 gag gtg tct cgg ata gtg ggc tct gta gaa ttc gac agt atg atg aac    2440
Glu Val Ser Arg Ile Val Gly Ser Val Glu Phe Asp Ser Met Met Asn
        735             740             745 aca gta tag agcatgaatt tttttcatct tctctggcga cagttttcct            2489
Thr Val *
    750 tctcatctgt gattccctcc tgctactctg ttccttcaca tcctgtgttt ctagggaaat  2549
gaaagaaagg ccagcaaatt cgctgcaacc tgttgatagc aagtgaattt ttctctaact  2609
cagaaacatc agttactctg aagggcatca tgcatcttac tgaaggtaaa attgaaaggc  2669
attctctgaa gagtgggttt cacaagtgaa aaacatccag atacacccaa agtatcagga  2729
cgagaatgag ggtcctttgg gaaggagaa gttaagcaac atctagcaaa tgttatgcat   2789
aaagtcagtg cccaactgtt ataggttgtt ggataaatca gtggttattt agggaactgc  2849
ttgacgtagg aacggtaaat ttctgtggga gaattcttac atgttttctt tgctttaagt  2909
gtaactggca gttttccatt ggtttacctg tgaaatagtt caaagccaag tttatataca  2969
attatatcag tcctctttca aaggtagcca tcatggatct ggtaggggga aaatgtgtat  3029
tttattacat ctttcacatt ggctatttaa agacaaagac aaattctgtt tcttgagaag  3089
agaatattag ctttactgtt tgttatggct taatgacact agctaatatc aatagaagga  3149
tgtacatttc caaattcaca agttgtgttt gatatccaaa gctgaataca ttctgctttc  3209
atcttggtca catacaatta tttttacagt tctcccaagg gagttaggct attcacaacc  3269
actcattcaa aagttgaaat taaccataga tgtagataaa ctcagaaatt taattcatgt  3329
ttcttaaatg ggctactttg tccttttgt tattagggtg gtatttagtc tattagccac    3389
aaaattggga aaggagtaga aaaagcagta actgacaact tgaataatac accagagata  3449
atatgagaat cagatcattt caaaactcat ttcctatgta actgcattga gaactgcata  3509
tgtttcgctg atatatgtgt ttttcacatt tgcgaatggt tccattctct ctcctgtact  3569
ttttccagac acttttttga gtggatgatg tttcgtgaag tatactgtat ttttaccttt  3629
ttccttcctt atcactgaca caaaaagtag attaagagat gggtttgaca aggttcttcc  3689
cttttacata ctgctgtcta tgtggctgta tcttgttttt ccactactgc taccacaact  3749
atattatcat gcaaatgctg tattcttctt tggtggagat aaagatttct tgagttttgt  3809
tttaaaatta aagctaaagt atctgtattg cattaaatat aatatcgaca cagtgctttc  3869
```

FIG. 1E

```
cgtggcactg catacaatct gaggcctcct ctctcagttt ttatatagat ggcgagaacc  3929
taagtttcag ttgattttac aattgaaatg actaaaaaac aaagaagaca acattaaaaa  3989
caatattgtt tcta                                                    4003
```

FIG.1F

```
aagtcgcgac cagagccatt ggagggcgcg gggactgcaa ccctaatcag agcccaa atg    60
                                                                Met
                                                                  1 gcg cag tgg gaa atg ctg cag aat ctt gac agc ccc ttt cag gat cag      108
Ala Gln Trp Glu Met Leu Gln Asn Leu Asp Ser Pro Phe Gln Asp Gln
          5                  10                  15 ctg cac cag ctt tac tcg cac agc ctc ctg cct gtg gac att cga cag      156
Leu His Gln Leu Tyr Ser His Ser Leu Leu Pro Val Asp Ile Arg Gln
         20                  25                  30 tac ttg gct gtc tgg att gaa gac cag aac tgg cag gaa gct gca ctt      204
Tyr Leu Ala Val Trp Ile Glu Asp Gln Asn Trp Gln Glu Ala Ala Leu
         35                  40                  45 ggg agt gat gat tcc aag gct acc atg cta ttc ttc cac ttc ttg gat      252
Gly Ser Asp Asp Ser Lys Ala Thr Met Leu Phe Phe His Phe Leu Asp
50                  55                  60                  65 cag ctg aac tat gag tgt ggc cgt tgc agc cag gac cca gag tcc ttg      300
Gln Leu Asn Tyr Glu Cys Gly Arg Cys Ser Gln Asp Pro Glu Ser Leu
                 70                  75                  80 ttg ctg cag cac aat ttg cgg aaa ttc tgc cgg gac att cag ccc ttt      348
Leu Leu Gln His Asn Leu Arg Lys Phe Cys Arg Asp Ile Gln Pro Phe
             85                  90                  95 tcc cag gat cct acc cag ttg gct gag atg atc ttt aac ctc ctt ctg      396
Ser Gln Asp Pro Thr Gln Leu Ala Glu Met Ile Phe Asn Leu Leu Leu
            100                 105                 110 gaa gaa aaa aga att ttg atc cag gct cag agg gcc caa ttg gaa caa      444
Glu Glu Lys Arg Ile Leu Ile Gln Ala Gln Arg Ala Gln Leu Glu Gln
        115                 120                 125 gga gag cca gtt ctc gaa aca cct gtg gag agc cag caa cat gag att      492
Gly Glu Pro Val Leu Glu Thr Pro Val Glu Ser Gln Gln His Glu Ile
130                 135                 140                 145 gaa tcc cgg atc ctg gat tta agg gct atg atg gag aag ctg gta aaa      540
Glu Ser Arg Ile Leu Asp Leu Arg Ala Met Met Glu Lys Leu Val Lys
                150                 155                 160
```

FIG.2A

```
tcc atc agc caa ctg aaa gac cag cag gat gtc ttc tgc ttc cga tat    588
Ser Ile Ser Gln Leu Lys Asp Gln Gln Asp Val Phe Cys Phe Arg Tyr
            165             170             175 aag atc cag gcc aaa ggg aag aca ccc tct ctg gac ccc cat cag acc    636
Lys Ile Gln Ala Lys Gly Lys Thr Pro Ser Leu Asp Pro His Gln Thr
            180             185             190 aaa gag cag aag att ctg cag gaa act ctc aat gaa ctg gac aaa agg    684
Lys Glu Gln Lys Ile Leu Gln Glu Thr Leu Asn Glu Leu Asp Lys Arg
    195             200             205 aga aag gag gtg ctg gat gcc tcc aaa gca ctg cta ggc cga tta act    732
Arg Lys Glu Val Leu Asp Ala Ser Lys Ala Leu Leu Gly Arg Leu Thr
210             215             220             225 acc cta atc gag cta ctg ctg cca aag ttg gag gag tgg aag gcc cag    780
Thr Leu Ile Glu Leu Leu Leu Pro Lys Leu Glu Glu Trp Lys Ala Gln
            230             235             240 cag caa aaa gcc tgc atc aga gct ccc att gac cac ggg ttg gaa cag    828
Gln Gln Lys Ala Cys Ile Arg Ala Pro Ile Asp His Gly Leu Glu Gln
            245             250             255 ctg gag aca tgg ttc aca gct gga gca aag ctg ttt cac ctg agg        876
Leu Glu Thr Trp Phe Thr Ala Gly Ala Lys Leu Leu Phe His Leu Arg
            260             265             270 cag ctg ctg aag gag ctg aag gga ctg agt tgc ctg gtt agc tat cag    924
Gln Leu Leu Lys Glu Leu Lys Gly Leu Ser Cys Leu Val Ser Tyr Gln
    275             280             285 gat gac cct ctg acc aaa ggg gtg gac cta cgc aac gcc cag gtc aca    972
Asp Asp Pro Leu Thr Lys Gly Val Asp Leu Arg Asn Ala Gln Val Thr
290             295             300             305 gag ttg cta cag cgt ctg ctc cac aga gcc ttt gtg gta gaa acc cag   1020
Glu Leu Leu Gln Arg Leu Leu His Arg Ala Phe Val Val Glu Thr Gln
            310             315             320 ccc tgc atg ccc caa act ccc cat cga ccc ctc atc ctc aag act ggc   1068
Pro Cys Met Pro Gln Thr Pro His Arg Pro Leu Ile Leu Lys Thr Gly
            325             330             335
```

FIG.2B

```
agc aag ttc acc gtc cga aca agg ctg ctg gtg aga ctc cag gaa ggc    1116
Ser Lys Phe Thr Val Arg Thr Arg Leu Leu Val Arg Leu Gln Glu Gly
        340             345                 350 aat gag tca ctg act gtg gaa gtc tcc att gac agg aat cct cct caa    1164
Asn Glu Ser Leu Thr Val Glu Val Ser Ile Asp Arg Asn Pro Pro Gln
    355                 360                 365 tta caa ggc ttc cgg aag ttc aac att ctg act tca aac cag aaa act    1212
Leu Gln Gly Phe Arg Lys Phe Asn Ile Leu Thr Ser Asn Gln Lys Thr
370             375                 380                 385 ttg acc ccc gag aag ggg cag agt cag ggt ttg att tgg gac ttt ggt    1260
Leu Thr Pro Glu Lys Gly Gln Ser Gln Gly Leu Ile Trp Asp Phe Gly
                390                 395                 400 tac ctg act ctg gtg gag caa cgt tca ggt ggt tca gga aag ggc agc    1308
Tyr Leu Thr Leu Val Glu Gln Arg Ser Gly Gly Ser Gly Lys Gly Ser
            405                 410                 415 aat aag ggg cca cta ggt gtg aca gag gaa ctg cac atc atc agc ttc    1356
Asn Lys Gly Pro Leu Gly Val Thr Glu Glu Leu His Ile Ile Ser Phe
        420                 425                 430 acg gtc aaa tat acc tac cag ggt ctg aag cag gag ctg aaa acg gac    1404
Thr Val Lys Tyr Thr Tyr Gln Gly Leu Lys Gln Glu Leu Lys Thr Asp
    435                 440                 445 acc ctc cct gtg gtg att att tcc aac atg aac cag ctc tca att gcc    1452
Thr Leu Pro Val Val Ile Ile Ser Asn Met Asn Gln Leu Ser Ile Ala
450                 455                 460                 465 tgg gct tca gtt ctc tgg ttc aat ttg ctc agc cca aac ctt cag aac    1500
Trp Ala Ser Val Leu Trp Phe Asn Leu Leu Ser Pro Asn Leu Gln Asn
            470                 475                 480 cag cag ttc ttc tcc aac ccc ccc aag gcc ccc tgg agc ttg ctg ggc    1548
Gln Gln Phe Phe Ser Asn Pro Pro Lys Ala Pro Trp Ser Leu Leu Gly
        485                 490                 495 cct gct ctc agt tgg cag ttc tcc tcc tat gtt ggc cga ggc ctc aac    1596
Pro Ala Leu Ser Trp Gln Phe Ser Ser Tyr Val Gly Arg Gly Leu Asn
500                 505                 510
```

FIG.2C

```
tca gac cag ctg agc atg ctg aga aac aag ctg ttc ggg cag aac tgt    1644
Ser Asp Gln Leu Ser Met Leu Arg Asn Lys Leu Phe Gly Gln Asn Cys
    515             520             525 agg act gag gat cca tta ttg tcc tgg gct gac ttc act aag cga gag    1692
Arg Thr Glu Asp Pro Leu Leu Ser Trp Ala Asp Phe Thr Lys Arg Glu
530             535             540             545 agc cct cct ggc aag tta cca ttc tgg aca tgg ctg gac aaa att ctg    1740
Ser Pro Pro Gly Lys Leu Pro Phe Trp Thr Trp Leu Asp Lys Ile Leu
                550             555             560 gag ttg gta cat gac cac ctg aag gat ctc tgg aat gat gga cgc atc    1788
Glu Leu Val His Asp His Leu Lys Asp Leu Trp Asn Asp Gly Arg Ile
            565             570             575 atg ggc ttt gtg agt cgg agc cag gag cgc cgg ctg ctg aag aag acc    1836
Met Gly Phe Val Ser Arg Ser Gln Glu Arg Arg Leu Leu Lys Lys Thr
        580             585             590 atg tct ggc acc ttt cta ctg cgc ttc agt gaa tcg tca gaa ggg ggc    1884
Met Ser Gly Thr Phe Leu Leu Arg Phe Ser Glu Ser Ser Glu Gly Gly
    595             600             605 att acc tgc tcc tgg gtg gag cac cag gat gat gac aag gtg ctc atc    1932
Ile Thr Cys Ser Trp Val Glu His Gln Asp Asp Asp Lys Val Leu Ile
610             615             620             625 tac tct gtg caa ccg tac acg aag gag gtg ctg cag tca ctc ccg ctg    1980
Tyr Ser Val Gln Pro Tyr Thr Lys Glu Val Leu Gln Ser Leu Pro Leu
                630             635             640 act gaa atc atc cgc cat tac cag ttg ctc act gag gag aat ata cct    2028
Thr Glu Ile Ile Arg His Tyr Gln Leu Leu Thr Glu Glu Asn Ile Pro
            645             650             655 gaa aac cca ctg cgc ttc ctc tat ccc cga atc ccc cgg gat gaa gct    2076
Glu Asn Pro Leu Arg Phe Leu Tyr Pro Arg Ile Pro Arg Asp Glu Ala
        660             665             670 ttt ggg tgc tac tac cag gag aaa gtt aat ctc cag gaa cgg agg aaa    2124
Phe Gly Cys Tyr Tyr Gln Glu Lys Val Asn Leu Gln Glu Arg Arg Lys
    675             680             685
```

FIG.2D

```
tac ctg aaa cac agg ctc att gtg gtc tct aat aga cag gtg gat gaa    2172
Tyr Leu Lys His Arg Leu Ile Val Val Ser Asn Arg Gln Val Asp Glu
690             695             700             705 ctg caa caa ccg ctg gag ctt aag cca gag cca gag ctg gag tca tta    2220
Leu Gln Gln Pro Leu Glu Leu Lys Pro Glu Pro Glu Leu Glu Ser Leu
            710             715             720 gag ctg gaa cta ggg ctg gtg cca gag cca gag ctc agc ctg gac tta    2268
Glu Leu Glu Leu Gly Leu Val Pro Glu Pro Glu Leu Ser Leu Asp Leu
            725             730             735 gag cca ctg ctg aag gca ggg ctg gat ctg ggg cca gag cta gag tct    2316
Glu Pro Leu Leu Lys Ala Gly Leu Asp Leu Gly Pro Glu Leu Glu Ser
            740             745             750 gtg ctg gag tcc act ctg gag cct gtg ata gag ccc aca cta tgc atg    2364
Val Leu Glu Ser Thr Leu Glu Pro Val Ile Glu Pro Thr Leu Cys Met
            755             760             765 gta tca caa aca gtg cca gag cca gac caa gga cct gta tca cag cca    2412
Val Ser Gln Thr Val Pro Glu Pro Asp Gln Gly Pro Val Ser Gln Pro
770             775             780             785 gtg cca gag cca gat ttg ccc tgt gat ctg aga cat ttg aac act gag    2460
Val Pro Glu Pro Asp Leu Pro Cys Asp Leu Arg His Leu Asn Thr Glu
            790             795             800 cca atg gaa atc ttc aga aac tgt gta aag att gaa gaa atc atg ccg    2508
Pro Met Glu Ile Phe Arg Asn Cys Val Lys Ile Glu Glu Ile Met Pro
            805             810             815 aat ggt gac cca ctg ttg gct ggc cag aac acc gtg gat gag gtt tac    2556
Asn Gly Asp Pro Leu Leu Ala Gly Gln Asn Thr Val Asp Glu Val Tyr
            820             825             830 gtc tcc cgc ccc agc cac ttc tac act gat gga ccc ttg atg cct tct    2604
Val Ser Arg Pro Ser His Phe Tyr Thr Asp Gly Pro Leu Met Pro Ser
            835             840             845 gac ttc tag gaaccacatt tcctctgttc ttttcatatc tctttgccct           2653
Asp Phe *
850
```

FIG.2E

```
tcctactcct catagcatga tattgttctc caaggatggg aatcaggcat gtgtcccttc  2713
caagctgtgt taactgttca aactcaggcc tgtgtgactc cattggggtg agaggtgaaa  2773
gcataacatg ggtacagagg ggacaacaat gaatcagaac agatgctgag ccataggtct  2833
aaataggatc ctggaggctg cctgctgtgc tgggaggtat aggggtcctg ggggcaggcc  2893
agggcagttg acaggtactt ggagggctca gggcagtggc ttctttccag tatggaagga  2953
tttcaacatt ttaatagttg gttaggctaa actggtgcat actggcattg gccttggtgg  3013
ggagcacaga cacaggatag gactccattt ctttcttcca ttccttcatg tctaggataa  3073
cttgctttct tctttccttt actcctggct caagccctga atttcttctt ttcctgcagg  3133
ggttgagagc tttctgcctt agcctaccat gtgaaactct accctgaaga aagggatgga  3193
taggaagtag acctcttttt cttaccagtc tcctccccta ctctgccccc taagctggct  3253
gtacctgttc ctcccccata aaatgatcct gccaatct                          3291
```

FIG.2F

```
cagctggaat tcggggcggc ggcgcagact ggggaggggga gccgggggtt ccgacgtcgc    60
agccgaggga acaagcccca accggatcct ggacaggcac cccggcttgg cgctgtctct   120
cccctcggc  tcggagaggc ccttcggcct gagggagcct cgccgcccgt ccccggcaca   180
cgcgcagccc cggcctctcg gcctctgccg gagaaacagg atg gcc caa tgg aat     235
                                             Met Ala Gln Trp Asn
                                              1               5 cag cta cag cag ctt gac aca cgg tac ctg gag cag ctc cat cag ctc    283
Gln Leu Gln Gln Leu Asp Thr Arg Tyr Leu Glu Gln Leu His Gln Leu
            10                  15                  20 tac agt gac agc ttc cca atg gag ctg cgg cag ttt ctg gcc cct tgg    331
Tyr Ser Asp Ser Phe Pro Met Glu Leu Arg Gln Phe Leu Ala Pro Trp
            25                  30                  35 att gag agt caa gat tgg gca tat gcg gcc agc aaa gaa tca cat gcc    379
Ile Glu Ser Gln Asp Trp Ala Tyr Ala Ala Ser Lys Glu Ser His Ala
            40                  45                  50 act ttg gtg ttt cat aat ctc ctg gga gag att gac cag cag tat agc    427
Thr Leu Val Phe His Asn Leu Leu Gly Glu Ile Asp Gln Gln Tyr Ser
            55                  60                  65 cgc ttc ctg caa gag tcg aat gtt ctc tat cag cac aat cta cga aga    475
Arg Phe Leu Gln Glu Ser Asn Val Leu Tyr Gln His Asn Leu Arg Arg
 70                  75                  80                  85 atc aag cag ttt ctt cag agc agg tat ctt gag aag cca atg gag att    523
Ile Lys Gln Phe Leu Gln Ser Arg Tyr Leu Glu Lys Pro Met Glu Ile
            90                  95                  100 gcc cgg att gtg gcc cgg tgc ctg tgg gaa gaa tca cgc ctt cta cag    571
Ala Arg Ile Val Ala Arg Cys Leu Trp Glu Glu Ser Arg Leu Leu Gln
            105                 110                 115 act gca gcc act gcg gcc cag caa ggg ggc cag gcc aac cac ccc aca    619
Thr Ala Ala Thr Ala Ala Gln Gln Gly Gly Gln Ala Asn His Pro Thr
            120                 125                 130 gca gcc gtg gtg acg gag aag cag cag atg ctg gag cag cac ctt cag    667
Ala Ala Val Val Thr Glu Lys Gln Gln Met Leu Glu Gln His Leu Gln
            135                 140                 145
```

FIG.3A

| | | | | | | | | | | | | | | | |
|---|---|---|---|---|---|---|---|---|---|---|---|---|---|---|---|
| gat | gtc | cgg | aag | aga | gtg | cag | gat | cta | gaa | cag | aaa | atg | aaa | gtg | gta | 715 |
| Asp | Val | Arg | Lys | Arg | Val | Gln | Asp | Leu | Glu | Gln | Lys | Met | Lys | Val | Val | |
| 150 | | | | 155 | | | | | 160 | | | | | 165 | | |

| gag | aat | ctc | cag | gat | gac | ttt | gat | ttc | aac | tat | aaa | acc | ctc | aag | agt | 763 |
| Glu | Asn | Leu | Gln | Asp | Asp | Phe | Asp | Phe | Asn | Tyr | Lys | Thr | Leu | Lys | Ser | |
| | | | | 170 | | | | | 175 | | | | | 180 | | |

| caa | gga | gac | atg | caa | gat | ctg | aat | gga | aac | aac | cag | tca | gtg | acc | agg | 811 |
| Gln | Gly | Asp | Met | Gln | Asp | Leu | Asn | Gly | Asn | Asn | Gln | Ser | Val | Thr | Arg | |
| | | | 185 | | | | | 190 | | | | | 195 | | | |

| cag | aag | atg | cag | cag | ctg | gaa | cag | atg | ctc | act | gcg | ctg | gac | cag | atg | 859 |
| Gln | Lys | Met | Gln | Gln | Leu | Glu | Gln | Met | Leu | Thr | Ala | Leu | Asp | Gln | Met | |
| | | | 200 | | | | | 205 | | | | | 210 | | | |

| cgg | aga | agc | atc | gtg | agt | gag | ctg | gcg | ggg | ctt | ttg | tca | gcg | atg | gag | 907 |
| Arg | Arg | Ser | Ile | Val | Ser | Glu | Leu | Ala | Gly | Leu | Leu | Ser | Ala | Met | Glu | |
| | | 215 | | | | | 220 | | | | | 225 | | | | |

| tac | gtg | cag | aaa | act | ctc | acg | gac | gag | gag | ctg | gct | gac | tgg | aag | agg | 955 |
| Tyr | Val | Gln | Lys | Thr | Leu | Thr | Asp | Glu | Glu | Leu | Ala | Asp | Trp | Lys | Arg | |
| 230 | | | | | 235 | | | | | 240 | | | | | 245 | |

| cgg | caa | cag | att | gcc | tgc | att | gga | ggc | ccg | ccc | aac | atc | tgc | cta | gat | 1003 |
| Arg | Gln | Gln | Ile | Ala | Cys | Ile | Gly | Gly | Pro | Pro | Asn | Ile | Cys | Leu | Asp | |
| | | | | 250 | | | | | 255 | | | | | 260 | | |

| cgg | cta | gaa | aac | tgg | ata | acg | tca | tta | gca | gaa | tct | caa | ctt | cag | acc | 1051 |
| Arg | Leu | Glu | Asn | Trp | Ile | Thr | Ser | Leu | Ala | Glu | Ser | Gln | Leu | Gln | Thr | |
| | | | | 265 | | | | | 270 | | | | | 275 | | |

| cgt | caa | caa | att | aag | aaa | ctg | gag | gag | ttg | cac | caa | aaa | gtt | tcc | tac | 1099 |
| Arg | Gln | Gln | Ile | Lys | Lys | Leu | Glu | Glu | Leu | His | Gln | Lys | Val | Ser | Tyr | |
| | | | 280 | | | | | 285 | | | | | 290 | | | |

| aaa | ggg | gac | ccc | att | gta | cag | cac | cgg | ccg | atg | ctg | gag | gag | agg | atc | 1147 |
| Lys | Gly | Asp | Pro | Ile | Val | Gln | His | Arg | Pro | Met | Leu | Glu | Glu | Arg | Ile | |
| | | | 295 | | | | | 300 | | | | | 305 | | | |

| gtg | gag | ctg | ttc | aga | aac | tta | atg | aaa | agt | gcc | ttt | gtg | gtg | gag | cgg | 1195 |
| Val | Glu | Leu | Phe | Arg | Asn | Leu | Met | Lys | Ser | Ala | Phe | Val | Val | Glu | Arg | |
| 310 | | | | | 315 | | | | | 320 | | | | | 325 | |

FIG.3B

```
cag ccc tgc atg ccc atg cat cct gac cgg ccc ctc gtc atc aag acc    1243
Gln Pro Cys Met Pro Met His Pro Asp Arg Pro Leu Val Ile Lys Thr
                330                 335                 340 ggc gtc cag ttc act act aaa gtc agg ttg ctg gtc aag ttc cct gag    1291
Gly Val Gln Phe Thr Thr Lys Val Arg Leu Leu Val Lys Phe Pro Glu
                345                 350                 355 ttg aat tat cag ctt aaa att aaa gtg tgc att gac aaa gac tct ggg    1339
Leu Asn Tyr Gln Leu Lys Ile Lys Val Cys Ile Asp Lys Asp Ser Gly
                360                 365                 370 gac gtt gca gct ctc aga gga tcc cgg aaa ttt aac att ctg ggc aca    1387
Asp Val Ala Ala Leu Arg Gly Ser Arg Lys Phe Asn Ile Leu Gly Thr
    375                 380                 385 aac aca aaa gtg atg aac atg gaa gaa tcc aac aac ggc agc ctc tct    1435
Asn Thr Lys Val Met Asn Met Glu Glu Ser Asn Asn Gly Ser Leu Ser
390                 395                 400                 405 gca gaa ttc aaa cac ttg acc ctg agg gag cag aga tgt ggg aat ggg    1483
Ala Glu Phe Lys His Leu Thr Leu Arg Glu Gln Arg Cys Gly Asn Gly
                410                 415                 420 ggc cga gcc aat tgt gat gct tcc ctg att gtg act gag gag ctg cac    1531
Gly Arg Ala Asn Cys Asp Ala Ser Leu Ile Val Thr Glu Glu Leu His
                425                 430                 435 ctg atc acc ttt gag acc gag gtg tat cac caa ggt ctc aag att gac    1579
Leu Ile Thr Phe Glu Thr Glu Val Tyr His Gln Gly Leu Lys Ile Asp
                440                 445                 450 cta gag acc cac tcc ttg tca gtt gtg gtg atc tcc aac atc tgt cag    1627
Leu Glu Thr His Ser Leu Ser Val Val Val Ile Ser Asn Ile Cys Gln
                455                 460                 465 atg cca aat gcc tgg gcg tcc atc ctg tgg tac aac atg ctg acc aac    1675
Met Pro Asn Ala Trp Ala Ser Ile Leu Trp Tyr Asn Met Leu Thr Asn
                470                 475                 480                 485 aat ccc aag aat gtg aac ttc ttc act aag ccg cca att gga acc tgg    1723
Asn Pro Lys Asn Val Asn Phe Phe Thr Lys Pro Pro Ile Gly Thr Trp
                490                 495                 500
```

FIG.3C

```
gac caa gtg gcc gag gtg ctc agc tgg cag ttc tcg tcc acc acc aag     1771
Asp Gln Val Ala Glu Val Leu Ser Trp Gln Phe Ser Ser Thr Thr Lys
            505                 510                 515 cgg ggg ctg agc atc gag cag ctg aca acg ctg gct gag aag ctc cta     1819
Arg Gly Leu Ser Ile Glu Gln Leu Thr Thr Leu Ala Glu Lys Leu Leu
            520                 525                 530 ggg cct ggt gtg aac tac tca ggg tgt cag atc aca tgg gct aac ttc     1867
Gly Pro Gly Val Asn Tyr Ser Gly Cys Gln Ile Thr Trp Ala Asn Phe
            535                 540                 545 tgc aaa gaa aac atg gct ggc aag ggc ttc tcc tac tgg gtc tgg cta     1915
Cys Lys Glu Asn Met Ala Gly Lys Gly Phe Ser Tyr Trp Val Trp Leu
550                 555                 560                 565 gac aat atc atc gac ctt gtg aaa aag tat atc ttg gcc ctt tgg aat     1963
Asp Asn Ile Ile Asp Leu Val Lys Lys Tyr Ile Leu Ala Leu Trp Asn
                570                 575                 580 gaa ggg tac atc atg ggt ttc atc agc aag gag cgg gag cgg gcc atc     2011
Glu Gly Tyr Ile Met Gly Phe Ile Ser Lys Glu Arg Glu Arg Ala Ile
            585                 590                 595 ttg agc act aag ccc cca ggc acc ttc ctg ctg cgc ttc agt gaa agc     2059
Leu Ser Thr Lys Pro Pro Gly Thr Phe Leu Leu Arg Phe Ser Glu Ser
            600                 605                 610 agc aaa gaa gga ggc gtc act ttc act tgg gtg gag aag gac atc agc     2107
Ser Lys Glu Gly Gly Val Thr Phe Thr Trp Val Glu Lys Asp Ile Ser
            615                 620                 625 ggt aag acc cag atc cag tcc gtg gaa cca tac aca aag cag cag ctg     2155
Gly Lys Thr Gln Ile Gln Ser Val Glu Pro Tyr Thr Lys Gln Gln Leu
630                 635                 640                 645 aac aac atg tca ttt gct gaa atc atc atg ggc tat aag atc atg gat     2203
Asn Asn Met Ser Phe Ala Glu Ile Ile Met Gly Tyr Lys Ile Met Asp
                650                 655                 660 gct acc aat atc ctg ttg tct cca ctt gtc tat ctc tat cct gac att     2251
Ala Thr Asn Ile Leu Leu Ser Pro Leu Val Tyr Leu Tyr Pro Asp Ile
            665                 670                 675
```

FIG. 3D

```
ccc aag gag gag gca ttc ggg aag tat tgt cgg cca gag agc cag gag    2299
Pro Lys Glu Glu Ala Phe Gly Lys Tyr Cys Arg Pro Glu Ser Gln Glu
        680                 685                 690 cat cct gaa gct gac cca ggt agc gct gcc cca tac ctg aag acc aag    2347
His Pro Glu Ala Asp Pro Gly Ser Ala Ala Pro Tyr Leu Lys Thr Lys
        695                 700                 705 ttt atc tgt gtg aca cca acg acc tgc agc aat acc att gac ctg ccg    2395
Phe Ile Cys Val Thr Pro Thr Thr Cys Ser Asn Thr Ile Asp Leu Pro
710                 715                 720                 725 atg tcc ccc cgc gct tta gat tca ttg atg cag ttt gga aat aat ggt    2443
Met Ser Pro Arg Ala Leu Asp Ser Leu Met Gln Phe Gly Asn Asn Gly
                730                 735                 740 gaa ggt gct gaa ccc tca gca gga ggg cag ttt gag tcc ctc acc ttt    2491
Glu Gly Ala Glu Pro Ser Ala Gly Gly Gln Phe Glu Ser Leu Thr Phe
            745                 750                 755 gac atg gag ttg acc tcg gag tgc gct acc tcc ccc atg tga             2533
Asp Met Glu Leu Thr Ser Glu Cys Ala Thr Ser Pro Met *
        760                 765                 770 ggagctgaga acggaagctg cagaaagata cgactgaggc gcctacctgc attctgccac   2593
ccctcacaca gccaaacccc agatcatctg aaactactaa ctttgtggtt ccagattttt   2653
tttaatctcc tacttctgct atctttgagc aatctgggca cttttaaaaa tagagaaatg   2713
agtgaatgtg ggtgatctgc ttttatctaa atgcaaataa ggatgtgttc tctgagaccc   2773
atgatcaggg gatg                                                     2787
```

FIG. 3E

```
gctttctcct agggactgtg aggggcgctt ctgactttgg acttgagcac tgcctgggac          60
ctgtgctgag agagcgctag c atg tct cag tgg aat caa gtc caa cag tta          111
                        Met Ser Gln Trp Asn Gln Val Gln Gln Leu
                         1           5                      10 gaa atc aag ttt ttg gag cag gtg gat caa ttc tat gat gac aac ttt          159
Glu Ile Lys Phe Leu Glu Gln Val Asp Gln Phe Tyr Asp Asp Asn Phe
                 15                  20                  25 ccc atg gaa att cgg cat ctg ttg gcc caa tgg att gaa aat caa gac          207
Pro Met Glu Ile Arg His Leu Leu Ala Gln Trp Ile Glu Asn Gln Asp
             30                  35                  40 tgg gag gca gct tct aac aat gaa acc atg gca acg att ctt ctt caa          255
Trp Glu Ala Ala Ser Asn Asn Glu Thr Met Ala Thr Ile Leu Leu Gln
         45                  50                  55 aac ttg tta ata caa ctg gat gaa cag tta ggt cgt gtt tcc aaa gag          303
Asn Leu Leu Ile Gln Leu Asp Glu Gln Leu Gly Arg Val Ser Lys Glu
     60                  65                  70 aaa aac cta ctc ttg ata cac aat cta aaa aga att agg aag gtc ctt          351
Lys Asn Leu Leu Leu Ile His Asn Leu Lys Arg Ile Arg Lys Val Leu
 75                  80                  85                  90 cag gga aaa ttt cat gga aat cca atg cat gta gct gtg gtt att tca          399
Gln Gly Lys Phe His Gly Asn Pro Met His Val Ala Val Val Ile Ser
                 95                 100                 105 aac tgt tta agg gaa gag agg aga ata ttg gct gca gcc aac atg cct          447
Asn Cys Leu Arg Glu Glu Arg Arg Ile Leu Ala Ala Ala Asn Met Pro
             110                 115                 120 gtc cag ggg cct cta gag aaa tcc tta caa agt tct tca gtt tca gaa          495
Val Gln Gly Pro Leu Glu Lys Ser Leu Gln Ser Ser Ser Val Ser Glu
         125                 130                 135 aga cag agg aat gtg gag cac aaa gtg gct gcc att aaa aac agt gtg          543
Arg Gln Arg Asn Val Glu His Lys Val Ala Ala Ile Lys Asn Ser Val
     140                 145                 150 cag atg aca gaa caa gat acc aaa tac tta gaa gat ctg caa gac gaa          591
```

FIG.4A

```
    Gln Met Thr Glu Gln Asp Thr Lys Tyr Leu Glu Asp Leu Gln Asp Glu
    155                 160                 165                 170 ttt gac tac agg tat aaa aca att cag aca atg gat cag agt gac aag    639
    Phe Asp Tyr Arg Tyr Lys Thr Ile Gln Thr Met Asp Gln Ser Asp Lys
                        175                 180                 185 aat agt gcc atg gtg aat cag gaa gtt ttg aca ctg cag gaa atg ctt    687
    Asn Ser Ala Met Val Asn Gln Glu Val Leu Thr Leu Gln Glu Met Leu
                190                 195                 200 aac agc ctc gat ttc aag aga aag gag gct ctc agt aaa atg acc caa    735
    Asn Ser Leu Asp Phe Lys Arg Lys Glu Ala Leu Ser Lys Met Thr Gln
                205                 210                 215 atc atc cat gag aca gac ctg tta atg aac acc atg ctc ata gaa gag    783
    Ile Ile His Glu Thr Asp Leu Leu Met Asn Thr Met Leu Ile Glu Glu
                220                 225                 230 ctg caa gac tgg aag cgg cgg cag caa atc gcc tgc atc ggg ggt cca    831
    Leu Gln Asp Trp Lys Arg Arg Gln Gln Ile Ala Cys Ile Gly Gly Pro
    235                 240                 245                 250 ctc cac aat ggg ctc gac cag ctt cag aac tgc ttt aca cta ttg gca    879
    Leu His Asn Gly Leu Asp Gln Leu Gln Asn Cys Phe Thr Leu Leu Ala
                        255                 260                 265 gaa agt ctt ttc caa ctg aga agg caa ttg gag aaa cta gag gag caa    927
    Glu Ser Leu Phe Gln Leu Arg Arg Gln Leu Glu Lys Leu Glu Glu Gln
                    270                 275                 280 tct acc aaa atg aca tat gaa ggt gat ccc att cca atg caa aga act    975
    Ser Thr Lys Met Thr Tyr Glu Gly Asp Pro Ile Pro Met Gln Arg Thr
                    285                 290                 295 cac atg cta gaa aga gtc acc ttc ttg atc tac aac ctt ttc aag aac    1023
    His Met Leu Glu Arg Val Thr Phe Leu Ile Tyr Asn Leu Phe Lys Asn
                    300                 305                 310 tca ttt gtg gtt gag cga cag cca tgt atg cca acc cac cct cag agg    1071
    Ser Phe Val Val Glu Arg Gln Pro Cys Met Pro Thr His Pro Gln Arg
    315                 320                 325                 330
```

FIG.4B

| | |
|---|---|
| ccg ttg gta ctt aaa acc cta att cag ttc act gta aaa cta agg cta<br>Pro Leu Val Leu Lys Thr Leu Ile Gln Phe Thr Val Lys Leu Arg Leu<br>335 340 345 | 1119 |
| cta ata aaa ttg cca gaa cta aac tat cag gta aag gtt aag gca tca<br>Leu Ile Lys Leu Pro Glu Leu Asn Tyr Gln Val Lys Val Lys Ala Ser<br>350 355 360 | 1167 |
| att gac aag aat gtt tca act cta agc aac cga aga ttt gta ctt tgt<br>Ile Asp Lys Asn Val Ser Thr Leu Ser Asn Arg Arg Phe Val Leu Cys<br>365 370 375 | 1215 |
| gga act aat gtc aaa gcc atg tct att gaa gaa tct tcc aat ggg agt<br>Gly Thr Asn Val Lys Ala Met Ser Ile Glu Glu Ser Ser Asn Gly Ser<br>380 385 390 | 1263 |
| ctc tca gta gaa ttt cga cat ttg caa cca aag gaa atg aag tcc agt<br>Leu Ser Val Glu Phe Arg His Leu Gln Pro Lys Glu Met Lys Ser Ser<br>395 400 405 410 | 1311 |
| gct gga ggt aaa gga aat gag ggc tgt cac atg gtg act gaa gaa ctt<br>Ala Gly Gly Lys Gly Asn Glu Gly Cys His Met Val Thr Glu Glu Leu<br>415 420 425 | 1359 |
| cat tcc ata acg ttt gaa aca cag atc tgc ctc tat ggc ctg acc ata<br>His Ser Ile Thr Phe Glu Thr Gln Ile Cys Leu Tyr Gly Leu Thr Ile<br>430 435 440 | 1407 |
| gat ttg gag acc agc tca ttg cct gtg gtg atg att tcc aat gtc agt<br>Asp Leu Glu Thr Ser Ser Leu Pro Val Val Met Ile Ser Asn Val Ser<br>445 450 455 | 1455 |
| cag tta cct aat gct tgg gca tcc atc att tgg tac aac gtg tca acc<br>Gln Leu Pro Asn Ala Trp Ala Ser Ile Ile Trp Tyr Asn Val Ser Thr<br>460 465 470 | 1503 |
| aac gat tcc cag aac ttg gtt ttc ttt aat aat cct cca cct gcc aca<br>Asn Asp Ser Gln Asn Leu Val Phe Phe Asn Asn Pro Pro Pro Ala Thr<br>475 480 485 490 | 1551 |
| ttg agt caa cta ctg gag gtg atg agc tgg cag ttt tca tcg tac gtt<br>Leu Ser Gln Leu Leu Glu Val Met Ser Trp Gln Phe Ser Ser Tyr Val<br>495 500 505 | 1599 |

FIG. 4C

```
ggt cgt ggt ctt aac tca gat caa ctc cat atg ctg gca gag aag ctt    1647
Gly Arg Gly Leu Asn Ser Asp Gln Leu His Met Leu Ala Glu Lys Leu
            510                 515                 520 aca gtc caa tct agc tac agt gat ggt cac ctc acc tgg gcc aag ttc    1695
Thr Val Gln Ser Ser Tyr Ser Asp Gly His Leu Thr Trp Ala Lys Phe
        52                  530                 535 tgc aag gaa cat tta cct ggt aaa tca ttt acc ttt tgg aca tgg ctt    1743
Cys Lys Glu His Leu Pro Gly Lys Ser Phe Thr Phe Trp Thr Trp Leu
        540                 545                 550 gaa gca ata ttg gat cta att aag aaa cac att ctt ccc ctt tgg att    1791
Glu Ala Ile Leu Asp Leu Ile Lys Lys His Ile Leu Pro Leu Trp Ile
555                 560                 565                 570 gat ggg tat gtc atg ggc ttt gtt agc aaa gag aag gaa cgg ctg ttg    1839
Asp Gly Tyr Val Met Gly Phe Val Ser Lys Glu Lys Glu Arg Leu Leu
                575                 580                 585 cta aag gat aaa atg cct ggc acc ttt tta tta aga ttc agt gaa agc    1887
Leu Lys Asp Lys Met Pro Gly Thr Phe Leu Leu Arg Phe Ser Glu Ser
            590                 595                 600 cat ctc gga gga ata act ttc acc tgg gtg gac cat tct gaa agt ggg    1935
His Leu Gly Gly Ile Thr Phe Thr Trp Val Asp His Ser Glu Ser Gly
        605                 610                 615 gaa gtg aga ttc cac tct gta gaa ccc tac aat aaa ggc cgg ttg tct    1983
Glu Val Arg Phe His Ser Val Glu Pro Tyr Asn Lys Gly Arg Leu Ser
        620                 625                 630 gct ctg cca ttc gct gac atc ctg cga gac tac aaa gtt att atg gct    2031
Ala Leu Pro Phe Ala Asp Ile Leu Arg Asp Tyr Lys Val Ile Met Ala
635                 640                 645                 650 gaa aac att cct gaa aac cct ctg aag tac cta tat cct gac att ccc    2079
Glu Asn Ile Pro Glu Asn Pro Leu Lys Tyr Leu Tyr Pro Asp Ile Pro
                655                 660                 665 aaa gac aaa gcc ttc ggt aaa cac tac agc tct cag cct tgc gaa gtt    2127
Lys Asp Lys Ala Phe Gly Lys His Tyr Ser Ser Gln Pro Cys Glu Val
            670                 675                 680
```

FIG.4D

```
tca aga cca aca gaa agg ggt gac aaa ggt tat gtt cct tct gtt ttt    2175
Ser Arg Pro Thr Glu Arg Gly Asp Lys Gly Tyr Val Pro Ser Val Phe
        685             690             695 atc ccc atc tca aca atc cga agt gat tca aca gag cca cat tct cca    2223
Ile Pro Ile Ser Thr Ile Arg Ser Asp Ser Thr Glu Pro His Ser Pro
        700             705             710 tca gac ctt ctt ccc atg tct cca agt gtg tat gcg gtg ttg aga gaa    2271
Ser Asp Leu Leu Pro Met Ser Pro Ser Val Tyr Ala Val Leu Arg Glu
715             720             725             730 aac ctg agt ccc aca aca att gaa act gca atg aag tct cct tat tct    2319
Asn Leu Ser Pro Thr Thr Ile Glu Thr Ala Met Lys Ser Pro Tyr Ser
            735             740             745 gct gaa tga caggataaac tctgacgcac caagaaagga agcaaatgaa            2368
Ala Glu * aaagtttaaa gactgttctt tgcccaataa ccacatttta tttcttcagc tttgtaaata  2428
ccaggttcta ggaaatgttt gacatctgaa gctctcttca cactcccgtg gcactcctca  2488
attgggagtg ttgtgactga aatgcttgaa accaaagctt cagataaact tgcaagataa  2548
gacaacttta agaaccagt gttaataaca atattaacag                        2588
```

FIG.4E

```
atcttatttt tcttttttggt ggtggtggtg gaagggggga ggtgctagca gggccagcct      60
tgaactcgct ggacagagct acagacctat ggggcctgga agtgcccgct gagaaaggga     120
gaagacagca gaggggttgc cgaggcaacc tccaagtccc agatc atg tct ctg tgg    177
                                                  Met Ser Leu Trp
                                                    1
```

```
ggt ctg gtc tcc aag atg ccc cca gaa aaa gtg cag cgg ctc tat gtc      225
Gly Leu Val Ser Lys Met Pro Pro Glu Lys Val Gln Arg Leu Tyr Val
 5               10                  15                  20 gac ttt ccc caa cac ctg cgg cat ctt ctg ggt gac tgg ctg gag agc      273
Asp Phe Pro Gln His Leu Arg His Leu Leu Gly Asp Trp Leu Glu Ser
                 25                  30                  35 cag ccc tgg gag ttc ctg gtc ggc tcc gac gcc ttc tgc tgc aac ttg      321
Gln Pro Trp Glu Phe Leu Val Gly Ser Asp Ala Phe Cys Cys Asn Leu
             40                  45                  50 gct agt gcc cta ctt tca gac act gtc cag cac ctg cag gcc tcg gtg      369
Ala Ser Ala Leu Leu Ser Asp Thr Val Gln His Leu Gln Ala Ser Val
         55                  60                  65 gga gag cag ggg gag ggg agc acc atc ttg caa cac atc agc acc ctt      417
Gly Glu Gln Gly Glu Gly Ser Thr Ile Leu Gln His Ile Ser Thr Leu
 70                  75                  80 gag agc ata tat cag agg gac ccc ctg aag ctg gtg gcc act ttc aga      465
Glu Ser Ile Tyr Gln Arg Asp Pro Leu Lys Leu Val Ala Thr Phe Arg
 85                  90                  95                 100 caa ata ctt caa gga gag aaa aaa gct gtt atg gaa cag ttc cgc cac      513
Gln Ile Leu Gln Gly Glu Lys Lys Ala Val Met Glu Gln Phe Arg His
                105                 110                 115 ttg cca atg cct ttc cac tgg aag cag gaa gaa ctc aag ttt aag aca      561
Leu Pro Met Pro Phe His Trp Lys Gln Glu Glu Leu Lys Phe Lys Thr
            120                 125                 130 ggc ttg cgg agg ctg cag cac cga gta ggg gag atc cac ctt ctc cga      609
Gly Leu Arg Arg Leu Gln His Arg Val Gly Glu Ile His Leu Leu Arg
        135                 140                 145 gaa gcc ctg cag aag ggg gct gag gct ggc caa gtg tct ctg cac agc      657
```

FIG.5A

```
                Glu Ala Leu Gln Lys Gly Ala Glu Ala Gly Gln Val Ser Leu His Ser
                            150                 155                 160 ttg ata gaa act cct gct aat ggg act ggg cca agt gag gcc ctg gcc              705
Leu Ile Glu Thr Pro Ala Asn Gly Thr Gly Pro Ser Glu Ala Leu Ala
165                 170                 175                 180 atg cta ctg cag gag acc act gga gag cta gag gca gcc aaa gcc cta              753
Met Leu Leu Gln Glu Thr Thr Gly Glu Leu Glu Ala Ala Lys Ala Leu
                185                 190                 195 gtg ctg aag agg atc cag att tgg aaa cgg cag cag cag ctg gca ggg              801
Val Leu Lys Arg Ile Gln Ile Trp Lys Arg Gln Gln Gln Leu Ala Gly
                200                 205                 210 aat ggc gca ccg ttt gag gag agc ctg gcc cca ctc cag gag agg tgt              849
Asn Gly Ala Pro Phe Glu Glu Ser Leu Ala Pro Leu Gln Glu Arg Cys
            215                 220                 225 gaa agc ctg gtg gac att tat tcc cag cta cag cag gag gta ggg gcg              897
Glu Ser Leu Val Asp Ile Tyr Ser Gln Leu Gln Gln Glu Val Gly Ala
230                 235                 240 gct ggt ggg gag ctt gag ccc aag acc cgg gca tcg ctg act ggc cgg              945
Ala Gly Gly Glu Leu Glu Pro Lys Thr Arg Ala Ser Leu Thr Gly Arg
245                 250                 255                 260 ctg gat gaa gtc ctg aga acc ctc gtc acc agt tgc ttc ctg gtg gag              993
Leu Asp Glu Val Leu Arg Thr Leu Val Thr Ser Cys Phe Leu Val Glu
                265                 270                 275 aag cag ccc ccc cag gta ctg aag act cag acc aag ttc cag gct gga             1041
Lys Gln Pro Pro Gln Val Leu Lys Thr Gln Thr Lys Phe Gln Ala Gly
                280                 285                 290 gtt cga ttc ctg ttg ggc ttg agg ttc ctg ggg gcc cca gcc aag cct             1089
Val Arg Phe Leu Leu Gly Leu Arg Phe Leu Gly Ala Pro Ala Lys Pro
                295                 300                 305 ccg ctg gtc agg gcc gac atg gtg aca gag aag cag gcg cgg gag ctg             1137
Pro Leu Val Arg Ala Asp Met Val Thr Glu Lys Gln Ala Arg Glu Leu
310                 315                 320
```

FIG.5B

| | | | | | | | | | | | | | | | |
|---|---|---|---|---|---|---|---|---|---|---|---|---|---|---|---|
| agt | gtg | cct | cag | ggt | cct | ggg | gct | gga | gca | gaa | agc | act | gga | gaa | atc |
| Ser | Val | Pro | Gln | Gly | Pro | Gly | Ala | Gly | Ala | Glu | Ser | Thr | Gly | Glu | Ile |
| 325 | | | | 330 | | | | | 335 | | | | | 340 | |

1185

| atc | aac | aac | act | gtg | ccc | ttg | gag | aac | agc | att | cct | ggg | aac | tgc | tgc |
|---|---|---|---|---|---|---|---|---|---|---|---|---|---|---|---|
| Ile | Asn | Asn | Thr | Val | Pro | Leu | Glu | Asn | Ser | Ile | Pro | Gly | Asn | Cys | Cys |
| | | | | 345 | | | | | 350 | | | | | 355 | |

1233

| tct | gcc | ctg | ttc | aag | aac | ctg | ctt | ctc | aag | aag | atc | aag | cgg | tgt | gag |
|---|---|---|---|---|---|---|---|---|---|---|---|---|---|---|---|
| Ser | Ala | Leu | Phe | Lys | Asn | Leu | Leu | Leu | Lys | Lys | Ile | Lys | Arg | Cys | Glu |
| | | | 360 | | | | | 365 | | | | | 370 | | |

1281

| cgg | aag | ggc | act | gag | tct | gtc | aca | gag | gag | aag | tgc | gct | gtg | ctc | ttc |
|---|---|---|---|---|---|---|---|---|---|---|---|---|---|---|---|
| Arg | Lys | Gly | Thr | Glu | Ser | Val | Thr | Glu | Glu | Lys | Cys | Ala | Val | Leu | Phe |
| | | | 375 | | | | | 380 | | | | | 385 | | |

1329

| tct | gcc | agc | ttc | aca | ctt | ggc | ccc | ggc | aaa | ctc | ccc | atc | cag | ctc | cag |
|---|---|---|---|---|---|---|---|---|---|---|---|---|---|---|---|
| Ser | Ala | Ser | Phe | Thr | Leu | Gly | Pro | Gly | Lys | Leu | Pro | Ile | Gln | Leu | Gln |
| | | 390 | | | | | 395 | | | | | 400 | | | |

1377

| gcc | ctg | tct | ctg | ccc | ctg | gtg | gtc | atc | gtc | cat | ggc | aac | caa | gac | aac |
|---|---|---|---|---|---|---|---|---|---|---|---|---|---|---|---|
| Ala | Leu | Ser | Leu | Pro | Leu | Val | Val | Ile | Val | His | Gly | Asn | Gln | Asp | Asn |
| 405 | | | | | 410 | | | | | 415 | | | | | 420 |

1425

| aat | gcc | aaa | gcc | act | atc | ctg | tgg | gac | aat | gcc | ttc | tct | gag | atg | gac |
|---|---|---|---|---|---|---|---|---|---|---|---|---|---|---|---|
| Asn | Ala | Lys | Ala | Thr | Ile | Leu | Trp | Asp | Asn | Ala | Phe | Ser | Glu | Met | Asp |
| | | | | 425 | | | | | 430 | | | | | 435 | |

1473

| cgc | gtg | ccc | ttt | gtg | gtg | gct | gag | cgg | gtg | ccc | tgg | gag | aag | atg | tgt |
|---|---|---|---|---|---|---|---|---|---|---|---|---|---|---|---|
| Arg | Val | Pro | Phe | Val | Val | Ala | Glu | Arg | Val | Pro | Trp | Glu | Lys | Met | Cys |
| | | | 440 | | | | | 445 | | | | | 450 | | |

1521

| gaa | act | ctg | aac | ctg | aag | ttc | atg | gct | gag | gtg | ggg | acc | aac | cgg | ggg |
|---|---|---|---|---|---|---|---|---|---|---|---|---|---|---|---|
| Glu | Thr | Leu | Asn | Leu | Lys | Phe | Met | Ala | Glu | Val | Gly | Thr | Asn | Arg | Gly |
| | | | 455 | | | | | 460 | | | | | 465 | | |

1569

| ctg | ctc | cca | gag | cac | ttc | ctc | ttc | ctg | gcc | cag | aag | atc | ttc | aat | gac |
|---|---|---|---|---|---|---|---|---|---|---|---|---|---|---|---|
| Leu | Leu | Pro | Glu | His | Phe | Leu | Phe | Leu | Ala | Gln | Lys | Ile | Phe | Asn | Asp |
| | | | 470 | | | | | 475 | | | | | 480 | | |

1617

| aac | agc | ctc | agt | atg | gag | gcc | ttc | cag | cac | cgt | tct | gtg | tcc | tgg | tcg |
|---|---|---|---|---|---|---|---|---|---|---|---|---|---|---|---|
| Asn | Ser | Leu | Ser | Met | Glu | Ala | Phe | Gln | His | Arg | Ser | Val | Ser | Trp | Ser |
| 485 | | | | | 490 | | | | | 495 | | | | | 500 |

1665

FIG.5C

```
cag ttc aac aag gag atc ctg ctg ggc cgt ggc ttc acc ttt tgg cag    1713
Gln Phe Asn Lys Glu Ile Leu Leu Gly Arg Gly Phe Thr Phe Trp Gln
            505             510             515 tgg ttt gat ggt gtc ctg gac ctc acc aaa cgc tgt ctc cgg agc tac    1761
Trp Phe Asp Gly Val Leu Asp Leu Thr Lys Arg Cys Leu Arg Ser Tyr
            520             525             530 tgg tct gac cgg ctg atc att ggc ttc atc agc aaa cag tac gtt act    1809
Trp Ser Asp Arg Leu Ile Ile Gly Phe Ile Ser Lys Gln Tyr Val Thr
            535             540             545 agc ctt ctt ctc aat gag ccc gac gga acc ttt ctc ctc cgc ttc agc    1857
Ser Leu Leu Leu Asn Glu Pro Asp Gly Thr Phe Leu Leu Arg Phe Ser
            550             555             560 gac tca gag att ggg ggc atc acc att gcc cat gtc atc cgg ggc cag    1905
Asp Ser Glu Ile Gly Gly Ile Thr Ile Ala His Val Ile Arg Gly Gln
565             570             575             580 gat ggc tct cca cag ata gag aac atc cag cca ttc tct gcc aaa gac    1953
Asp Gly Ser Pro Gln Ile Glu Asn Ile Gln Pro Phe Ser Ala Lys Asp
            585             590             595 ctg tcc att cgc tca ctg ggg gac cga atc cgg gat ctt gct cag ctc    2001
Leu Ser Ile Arg Ser Leu Gly Asp Arg Ile Arg Asp Leu Ala Gln Leu
            600             605             610 aaa aat ctc tat ccc aag aag ccc aag gat gag gct ttc cgg agc cac    2049
Lys Asn Leu Tyr Pro Lys Lys Pro Lys Asp Glu Ala Phe Arg Ser His
            615             620             625 tac aag cct gaa cag atg ggt aag gat ggc agg ggt tat gtc cca gct    2097
Tyr Lys Pro Glu Gln Met Gly Lys Asp Gly Arg Gly Tyr Val Pro Ala
            630             635             640 acc atc aag atg acc gtg gaa agg gac caa cca ctt cct acc cca gag    2145
Thr Ile Lys Met Thr Val Glu Arg Asp Gln Pro Leu Pro Thr Pro Glu
645             650             655             660 ctc cag atg cct acc atg gtg cct tct tat gac ctt gga atg gcc cct    2193
Leu Gln Met Pro Thr Met Val Pro Ser Tyr Asp Leu Gly Met Ala Pro
            665             670             675
```

FIG. 5D

| | | | | | | | | | | | | | | | |
|---|---|---|---|---|---|---|---|---|---|---|---|---|---|---|---|
| gat | tcc | tcc | atg | agc | atg | cag | ctt | ggc | cca | gat | atg | gtg | ccc | cag | gtg | 2241 |
| Asp | Ser | Ser | Met 680 | Ser | Met | Gln | Leu | Gly 685 | Pro | Asp | Met | Val | Pro 690 | Gln | Val | |

| tac | cca | cca | cac | tct | cac | tcc | atc | ccc | ccg | tat | caa | ggc | ctc | tcc | cca | 2289 |
| Tyr | Pro | Pro 695 | His | Ser | His | Ser | Ile 700 | Pro | Pro | Tyr | Gln | Gly 705 | Leu | Ser | Pro | |

| gaa | gaa | tca | gtc | aac | gtg | ttg | tca | gcc | ttc | cag | gag | cct | cac | ctg | cag | 2337 |
| Glu | Glu | Ser 710 | Val | Asn | Val | Leu | Ser 715 | Ala | Phe | Gln | Glu | Pro 720 | His | Leu | Gln | |

| atg | ccc | ccc | agc | ctg | ggc | cag | atg | agc | ctg | ccc | ttt | gac | cag | cct | cac | 2385 |
| Met | Pro | Pro | Ser | Leu | Gly | Gln | Met | Ser | Leu | Pro | Phe | Asp | Gln | Pro | His | |
| 725 | | | | | 730 | | | | | 735 | | | | | 740 | |

| ccc | cag | ggc | ctg | ctg | ccg | tgc | cag | cct | cag | gag | cat | gct | gtg | tcc | agc | 2433 |
| Pro | Gln | Gly | Leu | Leu 745 | Pro | Cys | Gln | Pro | Gln 750 | Glu | His | Ala | Val | Ser 755 | Ser | |

| cct | gac | ccc | ctg | ctc | tgc | tca | gat | gtg | acc | atg | gtg | gaa | gac | agc | tgc | 2481 |
| Pro | Asp | Pro | Leu | Leu 760 | Cys | Ser | Asp | Val | Thr 765 | Met | Val | Glu | Asp | Ser 770 | Cys | |

| ctg | agc | cag | cca | gtg | aca | gcg | ttt | cct | cag | ggc | act | tgg | att | ggt | gaa | 2529 |
| Leu | Ser | Gln | Pro | Val 775 | Thr | Ala | Phe | Pro | Gln 780 | Gly | Thr | Trp | Ile | Gly 785 | Glu | |

| gac | ata | ttc | cct | cct | ctg | ctg | cct | ccc | act | gaa | cag | gac | ctc | act | aag | 2577 |
| Asp | Ile | Phe | Pro | Pro | Leu | Leu | Pro | Pro | Thr | Glu | Gln | Asp | Leu | Thr | Lys | |
| | 790 | | | | 795 | | | | | 800 | | | | | | |

| ctt | ctc | ctg | gag | ggg | caa | ggg | gag | tcg | ggg | gga | ggg | tcc | ttg | ggg | gca | 2625 |
| Leu | Leu | Leu | Glu | Gly | Gln | Gly | Glu | Ser | Gly | Gly | Gly | Ser | Leu | Gly | Ala | |
| 805 | | | | 810 | | | | | 815 | | | | | | 820 | |

| cag | ccc | ctc | ctg | cag | ccc | tcc | cac | tat | ggg | caa | tct | ggg | atc | tca | atg | 2673 |
| Gln | Pro | Leu | Leu | Gln | Pro | Ser | His | Tyr | Gly | Gln | Ser | Gly | Ile | Ser | Met | |
| | | | | 825 | | | | | 830 | | | | | 835 | | |

| tcc | cac | atg | gac | cta | agg | gcc | aac | ccc | agt | tgg | tga | tcccagctgg | | | | 2719 |
| Ser | His | Met | Asp 840 | Leu | Arg | Ala | Asn | Pro 845 | Ser | Trp | * | | | | | |

FIG.5E

```
agggagaacc caaagagaca gctcttctac taccccccaca gacctgctct ggacacttgc  2779
tcatgccctg ccaagcagca gatggggagg gtgccctcct atccccacct actcctgggt  2839
caggaggaaa agactaacag gagaatgcac agtgggtgga gccaatccac tccttccttt  2899
ctatcattcc cctgcccacc tccttccagc actgactgga agggaagttc aggctctgag  2959
acacgcccca acatgcctgc acctgcagcg cgcacacgca cgcacacaca catacagagc  3019
tctctgaggg tgatggggct gagcagg                                      3046
```

FIG.5F

```
cccttctgt agg atg gta gca cac aac cag gtg gca gcc gac aat gca              49
            Met Val Ala His Asn Gln Val Ala Ala Asp Asn Ala
            1               5                   10 gtc tcc aca gca gca gag ccc cga cgg cgg cca gaa cct tcc tcc tct            97
Val Ser Thr Ala Ala Glu Pro Arg Arg Arg Pro Glu Pro Ser Ser Ser
        15                  20                  25 tcc tcc tcc tcg ccc gcg gcc ccc gcg cgc ccg cgg ccg tgc ccc gcg           145
Ser Ser Ser Ser Pro Ala Ala Pro Ala Arg Pro Arg Pro Cys Pro Ala
        30                  35                  40 gtc ccg gcc ccg gcc ccc ggc gac acg cac ttc cgc aca ttc cgt tcg           193
Val Pro Ala Pro Ala Pro Gly Asp Thr His Phe Arg Thr Phe Arg Ser
45                  50                  55                  60 cac gcc gat tac cgg cgc atc acg cgc gcc agc gcg ctc ctg gac gcc           241
His Ala Asp Tyr Arg Arg Ile Thr Arg Ala Ser Ala Leu Leu Asp Ala
                    65                  70                  75 tgc gga ttc tac tgg ggg ccc ctg agc gtg cac ggg gcg cac gag cgg           289
Cys Gly Phe Tyr Trp Gly Pro Leu Ser Val His Gly Ala His Glu Arg
                80                  85                  90 ctg cgc gcc gag ccc gtg ggc acc ttc ctg gtg cgc gac agc cgc cag           337
Leu Arg Ala Glu Pro Val Gly Thr Phe Leu Val Arg Asp Ser Arg Gln
            95                  100                 105 cgg aac tgc ttt ttc gcc ctt agc gtg aag atg gcc tcg gga ccc acg           385
Arg Asn Cys Phe Phe Ala Leu Ser Val Lys Met Ala Ser Gly Pro Thr
        110                 115                 120 agc atc cgc gtg cac ttt cag gcc ggc cgc ttt cac ctg gat ggc agc           433
Ser Ile Arg Val His Phe Gln Ala Gly Arg Phe His Leu Asp Gly Ser
125                 130                 135                 140 cgc gag agc ttc gac tgc ctc ttc gag ctg ctg gag cac tac gtg gcg           481
Arg Glu Ser Phe Asp Cys Leu Phe Glu Leu Leu Glu His Tyr Val Ala
                    145                 150                 155 gcg ccg cgc cgc atg ctg ggg gcc ccg ctg cgc cag cgc cgc gtg cgg           529
Ala Pro Arg Arg Met Leu Gly Ala Pro Leu Arg Gln Arg Arg Val Arg
                160                 165                 170
```

FIG.6A

```
ccg ctg cag gag ctg tgc cgc cag cgc atc gtg gcc acc gtg ggc cgc      577
Pro Leu Gln Glu Leu Cys Arg Gln Arg Ile Val Ala Thr Val Gly Arg
        175                 180                 185 gag aac ctg gct cgc atc ccc ctc aac ccc gtc ctc cgc gac tac ctg      625
Glu Asn Leu Ala Arg Ile Pro Leu Asn Pro Val Leu Arg Asp Tyr Leu
        190                 195                 200 agc tcc ttc ccc ttc cag att tga ccggcagcgc cgccgtgca cgcagcatta     679
Ser Ser Phe Pro Phe Gln Ile  *
205                 210 actgggatgc cgtgttattt tgttattact tgcctggaac catgtgggta ccctccccgg    739
cctgggttgg agggagcgga tgggtgtagg ggcgaggcgc ctcccgccct cggctggaga    799
cgaggccgca gacccttct cacctcttga gggggtcctc cccctcctgg tgctccctct    859
gggtccccct ggttgttgta gcagcttaac tgtatctgga gccaggacc              908
```

FIG.6B

```
atg gtc acc cac agc aag ttt ccc gcc gcc ggg atg agc cgc ccc ctg       48
Met Val Thr His Ser Lys Phe Pro Ala Ala Gly Met Ser Arg Pro Leu
 1               5                  10                  15 gac acc agc ctg cgc ctc aag acc ttc agc tcc aag agc gag tac cag       96
Asp Thr Ser Leu Arg Leu Lys Thr Phe Ser Ser Lys Ser Glu Tyr Gln
                    20                  25                  30 ctg gtg gtg aac gca gtg cgc aag ctg cag gag agc ggc ttc tac tgg      144
Leu Val Val Asn Ala Val Arg Lys Leu Gln Glu Ser Gly Phe Tyr Trp
                35                  40                  45 agc gca gtg acc ggc ggc gag gcg aac ctg ctc ctc agc gcc gag ccc      192
Ser Ala Val Thr Gly Gly Glu Ala Asn Leu Leu Leu Ser Ala Glu Pro
        50                  55                  60 gcc ggc acc ttt ctg atc cgc gac agc tcg gac cag cgc cac ttc ttc      240
Ala Gly Thr Phe Leu Ile Arg Asp Ser Ser Asp Gln Arg His Phe Phe
 65                  70                  75                  80 acg ctc agc gtc aag acc cag tct ggg acc aag aac ctg cgc atc cag      288
Thr Leu Ser Val Lys Thr Gln Ser Gly Thr Lys Asn Leu Arg Ile Gln
                    85                  90                  95 tgt gag ggg ggc agc ttc tct ctg cag agc gat ccc cgg agc acg cag      336
Cys Glu Gly Gly Ser Phe Ser Leu Gln Ser Asp Pro Arg Ser Thr Gln
                100                 105                 110 ccc gtg ccc cgc ttc gac tgc gtg ctc aag ctg gtg cac cac tac atg      384
Pro Val Pro Arg Phe Asp Cys Val Leu Lys Leu Val His His Tyr Met
            115                 120                 125 ccg ccc cct gga gcc ccc tcc ttc ccc tcg cca cct act gaa ccc tcc      432
Pro Pro Pro Gly Ala Pro Ser Phe Pro Ser Pro Thr Glu Pro Ser
        130                 135                 140 tcc gag gtg ccc gag cag ccg tct gcc cag cca ctc cct ggg agt ccc      480
Ser Glu Val Pro Glu Gln Pro Ser Ala Gln Pro Leu Pro Gly Ser Pro
145                 150                 155                 160 ccc aga aga gcc tat tac atc tac tcc ggg ggc gag aag atc ccc ctg      528
Pro Arg Arg Ala Tyr Tyr Ile Tyr Ser Gly Gly Glu Lys Ile Pro Leu
                165                 170                 175
```

FIG.7A

```
gtg ttg agc cgg ccc ctc tcc tcc aac gtg gcc act ctt cag cat ctc      576
Val Leu Ser Arg Pro Leu Ser Ser Asn Val Ala Thr Leu Gln His Leu
            180                 185                 190 tgt cgg aag acc gtc aac ggc cac ctg gac tcc tat gag aaa gtc acc      624
Cys Arg Lys Thr Val Asn Gly His Leu Asp Ser Tyr Glu Lys Val Thr
            195                 200                 205 cag ctg ccg ggg ccc att cgg gag ttc ctg gac cag tac gat gcc ccg      672
Gln Leu Pro Gly Pro Ile Arg Glu Phe Leu Asp Gln Tyr Asp Ala Pro
            210                 215                 220 ctt taa gggg                                                          682
Leu *
225
```

FIG.7B

```
aattcggcac gagggggggc agcagcggac gccgctaacg gcctccctcg gcgctgacag    60
gctgggccgg cgcccggctc gcttgggtgt tcgcgtcgcc acttcggctt ctcggccggt   120
cgggcccctc ggcccgggct tgcggcgcgc gtcggggctg agggctgctg cggcgcaggg   180
agaggcctgg tcctcgctgc cgagggatgt gagtgggagc tgagcccaca ctggagggcc   240
cccgagggcc cagcctggag gtcgttcaga gccgtgcccg ccccggggct tcgcagacct   300
tgacccgccg ggtaggagcc gccctgcgg gctcgagggc gcgctctggt cgcccgatct    360
gtgtagccgg tttcagaagc aggcaacagg aacaagatgt gaactgtttc tcttctgcag   420
aaaaagaggc tcttcctcct cctcccgcga cggcaaatgt tctgaaaaag actctgc atg  480
                                                              Met
                                                                1
```

| | | | | | | | | | | | | | | |
|---|---|---|---|---|---|---|---|---|---|---|---|---|---|---|
| gga | atg | gcc | tgc | ctt | acg | atg | aca | gaa | atg | gag | gga | aca | tcc | acc tct | 528
| Gly | Met | Ala | Cys | Leu | Thr | Met | Thr | Glu | Met | Glu | Gly | Thr | Ser | Thr Ser |
| | | | 5 | | | | 10 | | | | 15 | | | |

| tct | ata | tat | cag | aat | ggt | gat | att | tct | gga | aat | gcc | aat | tct | atg aag | 576 |
| Ser | Ile | Tyr | Gln | Asn | Gly | Asp | Ile | Ser | Gly | Asn | Ala | Asn | Ser | Met Lys |
| | | 20 | | | | | 25 | | | | | 30 | | |

| caa | ata | gat | cca | gtt | ctt | cag | gtg | tat | ctt | tac | cat | tcc | ctt | ggg aaa | 624 |
| Gln | Ile | Asp | Pro | Val | Leu | Gln | Val | Tyr | Leu | Tyr | His | Ser | Leu | Gly Lys |
| 35 | | | | | 40 | | | | | 45 | | | | |

| tct | gag | gca | gat | tat | ctg | acc | ttt | cca | tct | ggg | gag | tat | gtt | gca gaa | 672 |
| Ser | Glu | Ala | Asp | Tyr | Leu | Thr | Phe | Pro | Ser | Gly | Glu | Tyr | Val | Ala Glu |
| 50 | | | | | 55 | | | | | 60 | | | | 65 |

| gaa | atc | tgt | att | gct | gct | tct | aaa | gct | tgt | ggt | atc | aca | cct | gtg tat | 720 |
| Glu | Ile | Cys | Ile | Ala | Ala | Ser | Lys | Ala | Cys | Gly | Ile | Thr | Pro | Val Tyr |
| | | | | 70 | | | | | 75 | | | | | 80 |

| cat | aat | atg | ttt | gct | tta | atg | agt | gaa | aca | gaa | agg | atc | tgg | tat cca | 768 |
| His | Asn | Met | Phe | Ala | Leu | Met | Ser | Glu | Thr | Glu | Arg | Ile | Trp | Tyr Pro |
| | | | 85 | | | | | 90 | | | | | 95 | |

| ccc | aac | cat | gtc | ttc | cat | ata | gat | gag | tca | acc | agg | cat | aat | gta ctc | 816 |
| Pro | Asn | His | Val | Phe | His | Ile | Asp | Glu | Ser | Thr | Arg | His | Asn | Val Leu |
| | | | 100 | | | | 105 | | | | | 110 | | |

| tac | aga | ata | aga | ttt | tac | ttt | cct | cgt | tgg | tat | tgc | agt | ggc | agc aac | 864 |
| Tyr | Arg | Ile | Arg | Phe | Tyr | Phe | Pro | Arg | Trp | Tyr | Cys | Ser | Gly | Ser Asn |
| | 115 | | | | | 120 | | | | | 125 | | | |

| aga | gcc | tat | cgg | cat | gga | ata | tct | cga | ggt | gct | gaa | gct | cct | ctt ctt | 912 |

FIG.8A

```
Arg Ala Tyr Arg His Gly Ile Ser Arg Gly Ala Glu Ala Pro Leu Leu
130                 135                 140                 145 gat gac ttt gtc atg tct tac ctc ttt gct cag tgg cgg cat gat ttt       960
Asp Asp Phe Val Met Ser Tyr Leu Phe Ala Gln Trp Arg His Asp Phe
                150                 155                 160 gtg cac gga tgg ata aaa gta cct gtg act cat gaa aca cag gaa gaa      1008
Val His Gly Trp Ile Lys Val Pro Val Thr His Glu Thr Gln Glu Glu
                165                 170                 175 tgt ctt ggg atg gca gtg tta gat atg atg aga ata gcc aaa gaa aac      1056
Cys Leu Gly Met Ala Val Leu Asp Met Met Arg Ile Ala Lys Glu Asn
                180                 185                 190 gat caa acc cca ctg gcc atc tat aac tct atc agc tac aag aca ttc      1104
Asp Gln Thr Pro Leu Ala Ile Tyr Asn Ser Ile Ser Tyr Lys Thr Phe
195                 200                 205 tta cca aaa tgt att cga gca aag atc caa gac tat cat att ttg aca      1152
Leu Pro Lys Cys Ile Arg Ala Lys Ile Gln Asp Tyr His Ile Leu Thr
210                 215                 220                 225 agg aag cga ata agg tac aga ttt cgc aga ttt att cag caa ttc agc      1200
Arg Lys Arg Ile Arg Tyr Arg Phe Arg Arg Phe Ile Gln Gln Phe Ser
                230                 235                 240 caa tgc aaa gcc act gcc aga aac ttg aaa ctt aag tat ctt ata aat      1248
Gln Cys Lys Ala Thr Ala Arg Asn Leu Lys Leu Lys Tyr Leu Ile Asn
                245                 250                 255 ctg gaa act ctg cag tct gcc ttc tac aca gag aaa ttt gaa gta aaa      1296
Leu Glu Thr Leu Gln Ser Ala Phe Tyr Thr Glu Lys Phe Glu Val Lys
                260                 265                 270 gaa cct gga agt ggt cct tca ggt gag gag att ttt gca acc att ata      1344
Glu Pro Gly Ser Gly Pro Ser Gly Glu Glu Ile Phe Ala Thr Ile Ile
275                 280                 285 ata act gga aac ggt gga att cag tgg tca aga ggg aaa cat aaa gaa      1392
Ile Thr Gly Asn Gly Gly Ile Gln Trp Ser Arg Gly Lys His Lys Glu
290                 295                 300                 305
```

FIG.8B

```
agt gag aca ctg aca gaa cag gat tta cag tta tat tgc gat ttt tct    1440
Ser Glu Thr Leu Thr Glu Gln Asp Leu Gln Leu Tyr Cys Asp Phe Ser
            310             315             320 aat att att gat gtc agt att aag caa gca aac caa gag ggt tca aat    1488
Asn Ile Ile Asp Val Ser Ile Lys Gln Ala Asn Gln Glu Gly Ser Asn
            325             330             335 gaa agc cga gtt gta act atc cat aag caa gat ggt aaa aat ctg gaa    1536
Glu Ser Arg Val Val Thr Ile His Lys Gln Asp Gly Lys Asn Leu Glu
            340             345             350 att gaa ctt agc tca tta agg gaa gct ttg tct ttc gtg tca tta att    1584
Ile Glu Leu Ser Ser Leu Arg Glu Ala Leu Ser Phe Val Ser Leu Ile
            355             360             365 gat gga tat tat aga tta act gca gat gca cat cat tac ctc tgt aaa    1632
Asp Gly Tyr Tyr Arg Leu Thr Ala Asp Ala His His Tyr Leu Cys Lys
370             375             380             385 gaa gta gca cct cca gcc gtg ctt gaa aat ata caa agc aac tgt cat    1680
Glu Val Ala Pro Pro Ala Val Leu Glu Asn Ile Gln Ser Asn Cys His
            390             395             400 ggc cca att tcg atg gat ttt gcc att agt aaa ctg aag aaa gca ggt    1728
Gly Pro Ile Ser Met Asp Phe Ala Ile Ser Lys Leu Lys Lys Ala Gly
            405             410             415 aat cag act gga ctg tat gta ctt cga tgc agt cct aag gac ttt aat    1776
Asn Gln Thr Gly Leu Tyr Val Leu Arg Cys Ser Pro Lys Asp Phe Asn
            420             425             430 aaa tat ttt ttg act ttt gct gtc gag cga gaa aat gtc att gaa tat    1824
Lys Tyr Phe Leu Thr Phe Ala Val Glu Arg Glu Asn Val Ile Glu Tyr
            435             440             445 aaa cac tgt ttg att aca aaa aat gag aat gaa gag tac aac ctc agt    1872
Lys His Cys Leu Ile Thr Lys Asn Glu Asn Glu Glu Tyr Asn Leu Ser
450             455             460             465 ggg aca aag aag aac ttc agc agt ctt aaa gat ctt ttg aat tgt tac    1920
Gly Thr Lys Lys Asn Phe Ser Ser Leu Lys Asp Leu Leu Asn Cys Tyr
            470             475             480
```

FIG.8C

```
cag atg gaa act gtt cgc tca gac aat ata att ttc cag ttt act aaa    1968
Gln Met Glu Thr Val Arg Ser Asp Asn Ile Ile Phe Gln Phe Thr Lys
            485             490             495 tgc tgt ccc cca aag cca aaa gat aaa tca aac ctt cta gtc ttc aga    2016
Cys Cys Pro Pro Lys Pro Lys Asp Lys Ser Asn Leu Leu Val Phe Arg
            500             505             510 acg aat ggt gtt tct gat gta cca acc tca cca aca tta cag agg cct    2064
Thr Asn Gly Val Ser Asp Val Pro Thr Ser Pro Thr Leu Gln Arg Pro
515             520             525 act cat atg aac caa atg gtg ttt cac aaa atc aga aat gaa gat ttg    2112
Thr His Met Asn Gln Met Val Phe His Lys Ile Arg Asn Glu Asp Leu
530             535             540             545 ata ttt aat gaa agc ctt ggc caa ggc act ttt aca aag att ttt aaa    2160
Ile Phe Asn Glu Ser Leu Gly Gln Gly Thr Phe Thr Lys Ile Phe Lys
            550             555             560 ggc gta cga aga gaa gta gga gac tac ggt caa ctg cat gaa aca gaa    2208
Gly Val Arg Arg Glu Val Gly Asp Tyr Gly Gln Leu His Glu Thr Glu
            565             570             575 gtt ctt tta aaa gtt ctg gat aaa gca cac aga aac tat tca gag tct    2256
Val Leu Leu Lys Val Leu Asp Lys Ala His Arg Asn Tyr Ser Glu Ser
            580             585             590 ttc ttt gaa gca gca agt atg atg agc aag ctt tct cac aag cat ttg    2304
Phe Phe Glu Ala Ala Ser Met Met Ser Lys Leu Ser His Lys His Leu
            595             600             605 gtt tta aat tat gga gta tgt gtc tgt gga gac gag aat att ctg gtt    2352
Val Leu Asn Tyr Gly Val Cys Val Cys Gly Asp Glu Asn Ile Leu Val
610             615             620             625 cag gag ttt gta aaa ttt gga tca cta gat aca tat ctg aaa aag aat    2400
Gln Glu Phe Val Lys Phe Gly Ser Leu Asp Thr Tyr Leu Lys Lys Asn
            630             635             640 aaa aat tgt ata aat ata tta tgg aaa ctt gaa gtt gct aaa cag ttg    2448
Lys Asn Cys Ile Asn Ile Leu Trp Lys Leu Glu Val Ala Lys Gln Leu
            645             650             655
```

FIG.8D

```
gca tgg gcc atg cat ttt cta gaa gaa aac acc ctt att cat ggg aat      2496
Ala Trp Ala Met His Phe Leu Glu Glu Asn Thr Leu Ile His Gly Asn
        660                 665                 670 gta tgt gcc aaa aat att ctg ctt atc aga gaa gaa gac agg aag aca      2544
Val Cys Ala Lys Asn Ile Leu Leu Ile Arg Glu Glu Asp Arg Lys Thr
    675                 680                 685 gga aat cct cct ttc atc aaa ctt agt gat cct ggc att agt att aca      2592
Gly Asn Pro Pro Phe Ile Lys Leu Ser Asp Pro Gly Ile Ser Ile Thr
690                 695                 700                 705 gtt ttg cca aag gac att ctt cag gag aga ata cca tgg gta cca cct      2640
Val Leu Pro Lys Asp Ile Leu Gln Glu Arg Ile Pro Trp Val Pro Pro
                710                 715                 720 gaa tgc att gaa aat cct aaa aat tta aat ttg gca aca gac aaa tgg      2688
Glu Cys Ile Glu Asn Pro Lys Asn Leu Asn Leu Ala Thr Asp Lys Trp
            725                 730                 735 agt ttt ggt acc act ttg tgg gaa atc tgc agt gga gga gat aaa cct      2736
Ser Phe Gly Thr Thr Leu Trp Glu Ile Cys Ser Gly Gly Asp Lys Pro
        740                 745                 750 cta agt gct ctg gat tct caa aga aag cta caa ttt tat gaa gat agg      2784
Leu Ser Ala Leu Asp Ser Gln Arg Lys Leu Gln Phe Tyr Glu Asp Arg
    755                 760                 765 cat cag ctt cct gca cca aag tgg gca gaa tta gca aac ctt ata aat      2832
His Gln Leu Pro Ala Pro Lys Trp Ala Glu Leu Ala Asn Leu Ile Asn
770                 775                 780                 785 aat tgt atg gat tat gaa cca gat ttc agg cct tct ttc aga gcc atc      2880
Asn Cys Met Asp Tyr Glu Pro Asp Phe Arg Pro Ser Phe Arg Ala Ile
                790                 795                 800 ata cga gat ctt aac agt ttg ttt act cca gat tat gaa cta tta aca      2928
Ile Arg Asp Leu Asn Ser Leu Phe Thr Pro Asp Tyr Glu Leu Leu Thr
            805                 810                 815 gaa aat gac atg tta cca aat atg agg ata ggt gcc ctg ggg ttt tct      2976
Glu Asn Asp Met Leu Pro Asn Met Arg Ile Gly Ala Leu Gly Phe Ser
        820                 825                 830
```

FIG.8E

```
ggt gcc ttt gaa gac cgg gat cct aca cag ttt gaa gag aga cat ttg    3024
Gly Ala Phe Glu Asp Arg Asp Pro Thr Gln Phe Glu Glu Arg His Leu
    835             840                 845 aaa ttt cta cag caa ctt ggc aag ggt aat ttt ggg agt gtg gag atg    3072
Lys Phe Leu Gln Gln Leu Gly Lys Gly Asn Phe Gly Ser Val Glu Met
850             855                 860                 865 tgc cgg tat gac cct cta cag gac aac act ggg gag gtg gtc gct gta    3120
Cys Arg Tyr Asp Pro Leu Gln Asp Asn Thr Gly Glu Val Val Ala Val
                870                 875                 880 aaa aag ctt cag cat agt act gaa gag cac cta aga gac ttt gaa agg    3168
Lys Lys Leu Gln His Ser Thr Glu Glu His Leu Arg Asp Phe Glu Arg
            885                 890                 895 gaa att gaa atc ctg aaa tcc cta cag cat gac aac att gta aag tac    3216
Glu Ile Glu Ile Leu Lys Ser Leu Gln His Asp Asn Ile Val Lys Tyr
        900                 905                 910 aag gga gtg tgc tac agt gct ggt cgg cgt aat cta aaa tta att atg    3264
Lys Gly Val Cys Tyr Ser Ala Gly Arg Arg Asn Leu Lys Leu Ile Met
    915                 920                 925 gaa tat tta cca tat gga agt tta cga gac tat ctt caa aaa cat aaa    3312
Glu Tyr Leu Pro Tyr Gly Ser Leu Arg Asp Tyr Leu Gln Lys His Lys
930             935                 940                 945 gaa cgg ata gat cac ata aaa ctt ctg cag tac aca tct cag ata tgc    3360
Glu Arg Ile Asp His Ile Lys Leu Leu Gln Tyr Thr Ser Gln Ile Cys
                950                 955                 960 aag ggt atg gag tat ctt ggt aca aaa agg tat atc cac agg gat ctg    3408
Lys Gly Met Glu Tyr Leu Gly Thr Lys Arg Tyr Ile His Arg Asp Leu
            965                 970                 975 gca acg aga aat ata ttg gtg gag aac gag aac aga gtt aaa att gga    3456
Ala Thr Arg Asn Ile Leu Val Glu Asn Glu Asn Arg Val Lys Ile Gly
        980                 985                 990 gat ttt ggg tta acc aaa gtc ttg cca caa gac aaa gaa tac tat aaa    3504
Asp Phe Gly Leu Thr Lys Val Leu Pro Gln Asp Lys Glu Tyr Tyr Lys
    995                 1000                1005
```

FIG.8F

```
gta aaa gaa cct ggt gaa agt ccc ata ttc tgg tat gct cca gaa tca    3552
Val Lys Glu Pro Gly Glu Ser Pro Ile Phe Trp Tyr Ala Pro Glu Ser
1010                1015                1020                1025 ctg aca gag agc aag ttt tct gtg gcc tca gat gtt tgg agc ttt gga    3600
Leu Thr Glu Ser Lys Phe Ser Val Ala Ser Asp Val Trp Ser Phe Gly
                1030                1035                1040 gtg gtt ctg tat gaa ctt ttc aca tac att gag aag agt aaa agt cca    3648
Val Val Leu Tyr Glu Leu Phe Thr Tyr Ile Glu Lys Ser Lys Ser Pro
            1045                1050                1055 cca gcg gaa ttt atg cgt atg att ggc aat gac aaa caa gga cag atg    3696
Pro Ala Glu Phe Met Arg Met Ile Gly Asn Asp Lys Gln Gly Gln Met
        1060                1065                1070 atc gtg ttc cat ttg ata gaa ctt ttg aag aat aat gga aga tta cca    3744
Ile Val Phe His Leu Ile Glu Leu Leu Lys Asn Asn Gly Arg Leu Pro
        1075                1080                1085 aga cca gat gga tgc cca gat gag atc tat atg atc atg aca gaa tgc    3792
Arg Pro Asp Gly Cys Pro Asp Glu Ile Tyr Met Ile Met Thr Glu Cys
1090                1095                1100                1105 tgg aac aat aat gta aat caa cgc ccc tcc ttt agg gat cta gct ctt    3840
Trp Asn Asn Asn Val Asn Gln Arg Pro Ser Phe Arg Asp Leu Ala Leu
                1110                1115                1120 cga gtg gat caa ata agg gat aac atg gct gga tga aagaaatgac        3886
Arg Val Asp Gln Ile Arg Asp Asn Met Ala Gly  *
                1125                1130 cttcattctg agaccaaagt agatttacag aacaaagttt tatatttcac attgctgtgg    3946
actattatta catatatcat tattatataa atcatgatgc tagccagcaa agatgtgaaa    4006
atatctgctc aaaactttca aagtttagta agttttcttt catgaggcca ccagtaaaag    4066
acattaatga gaattcctta gcaaggattt tgtaagaagt ttcttaaaca ttgtcagtta    4126
acatcactct tgtctggcaa aagaaaaaaa atagacttt tcaactcagc tttttgagac    4186
ctgaaaaaat tattatgtaa attttgcaat gttaaagatg cacagaatat gtatgtatag    4246
tttttaccac agtggatgta taataccttg gcatcttgtg tgatgtttta cacacatgag    4306
ggctggtgtt cattaatact gttttctaat ttttccatag ttaatctata attaattact    4366
tcactataca aacaaattaa gatgttcaga taattgaata agtaccttg tgtccttgtt    4426
catttatatc gctggccagc attataagca ggtgtatact tttagcttgt agttccatgt    4486
actgtaaata tttttcacat aaagggaaca aatgtctagt tttatttgta taggaaattt    4546
```

FIG.8G

```
ccctgaccct aaataataca ttttgaaatg aaacaagctt acaaagatat aatctatttt   4606
attatggttt cccttgtatc tatttgtggt gaatgtgttt tttaaatgga actatctcca   4666
aattttcta agactactat gaacagtttt cttttaaaat tttgagatta agaatgccag    4726
gaatattgtc atcctttgag ctgctgactg ccaataacat tcttcgatct ctgggattta   4786
tgctcatgaa ctaaatttaa gcttaagcca taaaatagat tagattgttt tttaaaaatg   4846
gatagctcat taagaagtgc agcaggttaa gaatttttc ctaaagactg tatatttgag    4906
gggtttcaga attttgcatt gcagtcatag aagagattta ttttcctttt agaggggaaa   4966
tgaggtaaat aagtaaaaaa gtatgcttgt taatttatt caagaatgcc agtagaaaat    5026
tcataacgtg tatctttaag aaaaatgagc atacatctta aatcttttca attaaggtcg   5086
acgcggccgc ggtcgacgcg gccgcgaatt c                                  5117
```

FIG.8H

```
gacgcgggcg cggaaggagc gcggccggag gtcctcagga agaagccgcg gggactggct     60
gcgcttgaca ggctgcactt ggatgggagc acctggtgcc tcgggactgc tccgatgccc    120
gggtctgtgc tgaatgtgta atatgcggaa ctatattgaa acattacaac catcttttga    180
tggcaacacc ctgaggacct cccttttcca gatggggaaa ctgaggccca gaattgctaa    240
gtggcttgct tgagttgaca cagggagctc caggactcac cctcagctga gccacctgcc    300
gggagc atg cct ctg cgc cac tgg ggg atg gcc agg ggc agt aag ccc       348
       Met Pro Leu Arg His Trp Gly Met Ala Arg Gly Ser Lys Pro
       1               5                   10 gtt ggg gat gga gcc cag ccc atg gct gcc atg gga ggc ctg aag gtg     396
Val Gly Asp Gly Ala Gln Pro Met Ala Ala Met Gly Gly Leu Lys Val
15              20                  25                  30 ctt ctg cac tgg gct ggt cca ggc ggc ggg gag ccc tgg gtc act ttc     444
Leu Leu His Trp Ala Gly Pro Gly Gly Gly Glu Pro Trp Val Thr Phe
            35                  40                  45 agt gag tca tcg ctg aca gct gag gaa gtc tgc atc cac att gca cat     492
Ser Glu Ser Ser Leu Thr Ala Glu Glu Val Cys Ile His Ile Ala His
        50                  55                  60 aaa gtt ggt atc act cct cct tgc ttc aat ctc ttt gcc ctc ttc gat     540
Lys Val Gly Ile Thr Pro Pro Cys Phe Asn Leu Phe Ala Leu Phe Asp
65              70                  75 gct cag gcc caa gtc tgg ttg ccc cca aac cac atc cta gag atc ccc     588
Ala Gln Ala Gln Val Trp Leu Pro Pro Asn His Ile Leu Glu Ile Pro
    80                  85                  90 aga gat gca agc ctg atg cta tat ttc cgc ata agg ttt tat ttc cgg     636
Arg Asp Ala Ser Leu Met Leu Tyr Phe Arg Ile Arg Phe Tyr Phe Arg
95              100                 105                 110 aac tgg cat ggc atg aat cct cgg gaa ccg gct gtg tac cgt tgt ggg     684
Asn Trp His Gly Met Asn Pro Arg Glu Pro Ala Val Tyr Arg Cys Gly
                115                 120                 125 ccc cca gga acc gag gca tcc tca gat cag aca gca cag ggg atg caa     732
Pro Pro Gly Thr Glu Ala Ser Ser Asp Gln Thr Ala Gln Gly Met Gln
            130                 135                 140 ctc ctg gac cca gcc tca ttt gag tac ctc ttt gag cag ggc aag cat     780
```

FIG.9A

```
Leu Leu Asp Pro Ala Ser Phe Glu Tyr Leu Phe Glu Gln Gly Lys His
        145             150                 155 gag ttt gtg aat gac gtg gca tca ctg tgg gag ctg tcg acc gag gag        828
Glu Phe Val Asn Asp Val Ala Ser Leu Trp Glu Leu Ser Thr Glu Glu
160             165                 170 gag atc cac cac ttt aag aat gag agc ctg ggc atg gcc ttt ctg cac        876
Glu Ile His His Phe Lys Asn Glu Ser Leu Gly Met Ala Phe Leu His
175             180                 185                 190 ctc tgt cac ctc gct ctc cgc cat ggc atc ccc ctg gag gag gtg gcc       924
Leu Cys His Leu Ala Leu Arg His Gly Ile Pro Leu Glu Glu Val Ala
                195                 200                 205 aag aag acc agc ttc aag gac tgc atc ccg cgc tcc ttc cgc cgg cat        972
Lys Lys Thr Ser Phe Lys Asp Cys Ile Pro Arg Ser Phe Arg Arg His
            210                 215                 220 atc cgg cag cac agc gcc ctg acc cgg ctg cgc ctt cgg aac gtc ttc       1020
Ile Arg Gln His Ser Ala Leu Thr Arg Leu Arg Leu Arg Asn Val Phe
            225                 230                 235 cgc agg ttc ctg cgg gac ttc cag ccg ggc cga ctc tcc cag cag atg       1068
Arg Arg Phe Leu Arg Asp Phe Gln Pro Gly Arg Leu Ser Gln Gln Met
        240                 245                 250 gtc atg gtc aaa tac cta gcc aca ctc gag cgg ctg gca ccc cgc ttc       1116
Val Met Val Lys Tyr Leu Ala Thr Leu Glu Arg Leu Ala Pro Arg Phe
255             260                 265                 270 ggc aca gag cgt gtg ccc gtg tgc cac ctg agg ctg ctg gcc cag gcc       1164
Gly Thr Glu Arg Val Pro Val Cys His Leu Arg Leu Leu Ala Gln Ala
                275                 280                 285 gag ggg gag ccc tgc tac atc cgg gac agt ggg gtg gcc cct aca gac       1212
Glu Gly Glu Pro Cys Tyr Ile Arg Asp Ser Gly Val Ala Pro Thr Asp
            290                 295                 300 cct ggc cct gag tct gct gct ggg ccc cca acc cac gag gtg ctg gtg       1260
Pro Gly Pro Glu Ser Ala Ala Gly Pro Pro Thr His Glu Val Leu Val
            305                 310                 315
```

FIG.9B

```
aca ggc act ggt ggc atc cag tgg tgg cca gta gag gag gag gtg aac        1308
Thr Gly Thr Gly Gly Ile Gln Trp Trp Pro Val Glu Glu Glu Val Asn
    320                 325                 330 aag gag gag ggt tct agt ggc agc agt ggc agg aac ccc caa gcc agc        1356
Lys Glu Glu Gly Ser Ser Gly Ser Ser Gly Arg Asn Pro Gln Ala Ser
335                 340                 345                 350 ctg ttt ggg aag aag gcc aag gct cac aag gca ttc ggc cag ccg gca        1404
Leu Phe Gly Lys Lys Ala Lys Ala His Lys Ala Phe Gly Gln Pro Ala
                355                 360                 365 gac agg ccg cgg gag cca ctg tgg gcc tac ttc tgt gac ttc cgg gac        1452
Asp Arg Pro Arg Glu Pro Leu Trp Ala Tyr Phe Cys Asp Phe Arg Asp
            370                 375                 380 atc acc cac gtg gtg ctg aaa gag cac tgt gtc agc atc cac cgg cag        1500
Ile Thr His Val Val Leu Lys Glu His Cys Val Ser Ile His Arg Gln
        385                 390                 395 gac aac aag tgc ctg gag ctg agc ttg cct tcc cgg gct gcg gcg ctg        1548
Asp Asn Lys Cys Leu Glu Leu Ser Leu Pro Ser Arg Ala Ala Ala Leu
    400                 405                 410 tcc ttc gtg tcg ctg gtg gac ggc tat ttc cgc ctg acg gcc gac tcc        1596
Ser Phe Val Ser Leu Val Asp Gly Tyr Phe Arg Leu Thr Ala Asp Ser
415                 420                 425                 430 agc cac tac ctg tgc cac gag gtg gct ccc cca cgg ctg gtg atg agc        1644
Ser His Tyr Leu Cys His Glu Val Ala Pro Pro Arg Leu Val Met Ser
                435                 440                 445 atc cgg gat ggg atc cac gga ccc ctg ctg gag cca ttt gtg cag gcc        1692
Ile Arg Asp Gly Ile His Gly Pro Leu Leu Glu Pro Phe Val Gln Ala
            450                 455                 460 aag ctg cgg ccc gag gac ggc ctg tac ctc att cac tgg agc acc agc        1740
Lys Leu Arg Pro Glu Asp Gly Leu Tyr Leu Ile His Trp Ser Thr Ser
        465                 470                 475 cac ccc tac cgc ctg atc ctc aca gtg gcc cag cgt agc cag gca cca        1788
His Pro Tyr Arg Leu Ile Leu Thr Val Ala Gln Arg Ser Gln Ala Pro
    480                 485                 490
```

FIG.9C

```
gac ggc atg cag agc ttg cgg ctc cga aag ttc ccc att gag cag cag      1836
Asp Gly Met Gln Ser Leu Arg Leu Arg Lys Phe Pro Ile Glu Gln Gln
495             500             505             510 gac ggg gcc ttc gtg ctg gag ggc tgg ggc cgg tcc ttc ccc agc gtt      1884
Asp Gly Ala Phe Val Leu Glu Gly Trp Gly Arg Ser Phe Pro Ser Val
                515             520             525 cgg gaa ctt ggg gct gcc ttg cag ggc tgc ttg ctg agg gcc ggg gat      1932
Arg Glu Leu Gly Ala Ala Leu Gln Gly Cys Leu Leu Arg Ala Gly Asp
            530             535             540 gac tgc ttc tct ctg cgt cgc tgt tgc ctg ccc caa cca gga gaa acc      1980
Asp Cys Phe Ser Leu Arg Arg Cys Cys Leu Pro Gln Pro Gly Glu Thr
        545             550             555 tcc aat ctc atc atc atg cgg ggg gct cgg gcc agc ccc agg aca ctc      2028
Ser Asn Leu Ile Ile Met Arg Gly Ala Arg Ala Ser Pro Arg Thr Leu
    560             565             570 aac ctc agc cag ctc agc ttc cac cgg gtt gac cag aag gag atc acc      2076
Asn Leu Ser Gln Leu Ser Phe His Arg Val Asp Gln Lys Glu Ile Thr
575             580             585             590 cag ctg tcc cac ttg ggc cag ggc aca agg acc aac gtg tat gag ggc      2124
Gln Leu Ser His Leu Gly Gln Gly Thr Arg Thr Asn Val Tyr Glu Gly
                595             600             605 cgc ctg cga gtg gag ggc agc ggg gac cct gag gag ggc aag atg gat      2172
Arg Leu Arg Val Glu Gly Ser Gly Asp Pro Glu Glu Gly Lys Met Asp
            610             615             620 gac gag gac ccc ctc gtg cct ggc agg gac cgt ggg cag gag cta cga      2220
Asp Glu Asp Pro Leu Val Pro Gly Arg Asp Arg Gly Gln Glu Leu Arg
        625             630             635 gtg gtg ctc aaa gtg ctg gac cct agt cac cat gac atc gcc ctg gcc      2268
Val Val Leu Lys Val Leu Asp Pro Ser His His Asp Ile Ala Leu Ala
    640             645             650 ttc tac gag aca gcc agc ctc atg agc cag gtc tcc cac acg cac ctg      2316
Phe Tyr Glu Thr Ala Ser Leu Met Ser Gln Val Ser His Thr His Leu
655             660             665             670
```

FIG. 9D

```
gcc ttc gtg cat ggc gtc tgt gtg cgc ggc cct gaa aat agc atg gtg        2364
Ala Phe Val His Gly Val Cys Val Arg Gly Pro Glu Asn Ser Met Val
                675             680             685 aca gag tac gtg gag cac gga ccc ctg gat gtg tgg ctg cgg agg gag        2412
Thr Glu Tyr Val Glu His Gly Pro Leu Asp Val Trp Leu Arg Arg Glu
                690             695             700 cgg ggc cat gtg ccc atg gct tgg aag atg gtg gtg gcc cag cag ctg        2460
Arg Gly His Val Pro Met Ala Trp Lys Met Val Val Ala Gln Gln Leu
                705             710             715 gcc agc gcc ctc agc tac ctg gag aac aag aac ctg gtt cat ggt aat        2508
Ala Ser Ala Leu Ser Tyr Leu Glu Asn Lys Asn Leu Val His Gly Asn
                720             725             730 gtg tgt ggc cgg aac atc ctg ctg gcc cgg ctg ggg ttg gca gag ggc        2556
Val Cys Gly Arg Asn Ile Leu Leu Ala Arg Leu Gly Leu Ala Glu Gly
735             740             745             750 acc agc ccc ttc atc aag ctg agt gat cct ggc gtg ggc ctg ggc gcc        2604
Thr Ser Pro Phe Ile Lys Leu Ser Asp Pro Gly Val Gly Leu Gly Ala
                755             760             765 ctc tcc agg gag gag cgg gtg gag agg atc ccc tgg ctg gcc ccc gaa        2652
Leu Ser Arg Glu Glu Arg Val Glu Arg Ile Pro Trp Leu Ala Pro Glu
                770             775             780 tgc cta cca ggt ggg gcc aac agc cta agc acc gcc atg gac aag tgg        2700
Cys Leu Pro Gly Gly Ala Asn Ser Leu Ser Thr Ala Met Asp Lys Trp
                785             790             795 ggg ttt ggc gcc acc ctc ctg gag atc tgc ttt gac gga gag gcc cct        2748
Gly Phe Gly Ala Thr Leu Leu Glu Ile Cys Phe Asp Gly Glu Ala Pro
                800             805             810 ctg cag agc cgc agt ccc tcc gag aag gag cat ttc tac cag agg cag        2796
Leu Gln Ser Arg Ser Pro Ser Glu Lys Glu His Phe Tyr Gln Arg Gln
815             820             825             830 cac cgg ctg ccc gag ccc tcc tgc cca cag ctg gcc aca ctc acc agc        2844
His Arg Leu Pro Glu Pro Ser Cys Pro Gln Leu Ala Thr Leu Thr Ser
                835             840             845
```

FIG.9E

```
cag tgt ctg acc tat gag cca acc cag agg cca tca ttc cgc acc atc         2892
Gln Cys Leu Thr Tyr Glu Pro Thr Gln Arg Pro Ser Phe Arg Thr Ile
            850             855             860 ctg cgt gac ctc acc cgc gtg cag ccc cac aat ctt gct gac gtc ttg         2940
Leu Arg Asp Leu Thr Arg Val Gln Pro His Asn Leu Ala Asp Val Leu
            865             870             875 act gtg aac cgg gac tca ccg gcc gtc gga cct act act ttc cac aag         2988
Thr Val Asn Arg Asp Ser Pro Ala Val Gly Pro Thr Thr Phe His Lys
            880             885             890 cgc tat ttg aaa aag atc cga gat ctg ggc gag ggt cac ttc ggc aag         3036
Arg Tyr Leu Lys Lys Ile Arg Asp Leu Gly Glu Gly His Phe Gly Lys
895             900             905             910 gtc agc ttg tac tgc tac gat ccg acc aac gac ggc act ggc gag atg         3084
Val Ser Leu Tyr Cys Tyr Asp Pro Thr Asn Asp Gly Thr Gly Glu Met
            915             920             925 gtg gcg gtg aaa gcc ctc aag gca gac tgc ggc ccc cag cac cgc tcg         3132
Val Ala Val Lys Ala Leu Lys Ala Asp Cys Gly Pro Gln His Arg Ser
            930             935             940 ggc tgg aag cag gag att gac att ctg cgc acg ctc tac cac gag cac         3180
Gly Trp Lys Gln Glu Ile Asp Ile Leu Arg Thr Leu Tyr His Glu His
            945             950             955 atc atc aag tac aag ggc tgc tgc gag gac caa ggc gag aag tcg ctg         3228
Ile Ile Lys Tyr Lys Gly Cys Cys Glu Asp Gln Gly Glu Lys Ser Leu
            960             965             970 cag ctg gtc atg gag tac gtg ccc ctg ggc agc ctc cga gac tac ctg         3276
Gln Leu Val Met Glu Tyr Val Pro Leu Gly Ser Leu Arg Asp Tyr Leu
975             980             985             990 ccc cgg cac agc atc ggg ctg gcc cag ctg ctg ctc ttc gcc cag cag         3324
Pro Arg His Ser Ile Gly Leu Ala Gln Leu Leu Leu Phe Ala Gln Gln
                995             1000            1005 atc tgc gag ggc atg gcc tat ctg cac gcg cac gac tac atc cac cga         3372
Ile Cys Glu Gly Met Ala Tyr Leu His Ala His Asp Tyr Ile His Arg
            1010            1015            1020
```

FIG.9F

```
gac cta gcc gcg cgc aac gtg ctg ctg gac aac gac agg ctg gtc aag    3420
Asp Leu Ala Ala Arg Asn Val Leu Leu Asp Asn Asp Arg Leu Val Lys
        1025                1030                1035 atc ggg gac ttt ggc cta gcc aag gcc gtg ccc gaa ggc cac gag tac    3468
Ile Gly Asp Phe Gly Leu Ala Lys Ala Val Pro Glu Gly His Glu Tyr
        1040                1045                1050 tac cgc gtg cgc gag gat ggg gac agc ccc gtg ttc tgg tat gcc cca    3516
Tyr Arg Val Arg Glu Asp Gly Asp Ser Pro Val Phe Trp Tyr Ala Pro
1055                1060                1065                1070 gag tgc ctg aag gag tat aag ttc tac tat gcg tca gat gtc tgg tcc    3564
Glu Cys Leu Lys Glu Tyr Lys Phe Tyr Tyr Ala Ser Asp Val Trp Ser
                1075                1080                1085 ttc ggg gtg acc ctg tat gag ctg ctg acg cac tgt gac tcc agc cag    3612
Phe Gly Val Thr Leu Tyr Glu Leu Leu Thr His Cys Asp Ser Ser Gln
                1090                1095                1100 agc ccc ccc acg aaa ttc ctt gag ctc ata ggc att gct cag ggt cag    3660
Ser Pro Pro Thr Lys Phe Leu Glu Leu Ile Gly Ile Ala Gln Gly Gln
        1105                1110                1115 atg aca gtt ctg aga ctc act gag ttg ctg gaa cga ggg gag agg ctg    3708
Met Thr Val Leu Arg Leu Thr Glu Leu Leu Glu Arg Gly Glu Arg Leu
        1120                1125                1130 cca cgg ccc gac aaa tgt ccc tgt gag gtc tat cat ctc atg aag aac    3756
Pro Arg Pro Asp Lys Cys Pro Cys Glu Val Tyr His Leu Met Lys Asn
        1135                1140                1145                1150 tgc tgg gag aca gag gcg tcc ttt cgc cca acc ttc gag aac ctc ata    3804
Cys Trp Glu Thr Glu Ala Ser Phe Arg Pro Thr Phe Glu Asn Leu Ile
                1155                1160                1165 ccc att ctg aag aca gtc cat gag aag tac caa ggc cag gcc cct tca    3852
Pro Ile Leu Lys Thr Val His Glu Lys Tyr Gln Gly Gln Ala Pro Ser
        1170                1175                1180 gtg ttc agc gtg tgc tga ggcacaatgg cagccctgcc tgggaggact           3900
Val Phe Ser Val Cys *
        1185
```

FIG.9G

```
ggaccaggca gtggctgcag agggagcctc ctgctccctg ctccaggatg aaaccaagag   3960
ggggatgtca gcctcaccca caccgtgtgc cttactcctg tctagagacc ccacctctgt   4020
gaacttattt ttctttcttg gccgtgagcc taaccatgat cttgagggac ccaacatttg   4080
taggggcact aatccagccc ttaaatcccc cagcttccaa acttgaggcc caccatctcc   4140
accatctggt aataaactca tgttttctct gctggg                             4176
```

FIG.9H

|       | DAY1 | | DAY2 | | DAY3 | | DAY5 | | C |
|-------|------|---|------|---|------|---|------|---|---|
|       | N | T | N | T | N | T | N | T | C |
| STAT4 | | | | | | | | — | |
| SOCS3 | | | | | | | | — | |
| GAPDH | — | — | — | — | — | — | — | — | — |

FIG.16

METHOD FOR IDENTIFYING A COMPOUND TO BE TESTED FOR AN ABILITY TO REDUCE IMMUNE REJECTION BY DETERMINING STAT4 AND STAT6 PROTEINS

This application is a continuation of U.S. application Ser. No. 09/549,654, filed Apr. 14, 2000, now abandoned, which application is incorporated by reference in its entirety.

1. INTRODUCTION

The present invention relates to methods and compositions for reducing immune rejection, for example, transplant- or autoimmune disorder-related immune rejection. The present invention also relates to methods and compositions for monitoring transplant acceptance and for monitoring an autoimmune disorder in a subject mammal. The present invention still further relates to methods for identifying compounds that can reduce immune rejection.

The present invention is based, in part, on the discovery, demonstrated herein, that immune rejection can be monitored by determining the amount of particular members of the Jak/Stat signal transduction pathway present within an affected tissue (that is, a transplant cell, tissue, organ, or organ system, or a cell, tissue, organ, or organ system that is, or is suspected of, being affected by an autoimmune disorder). The present invention is further based, in part, on the discovery, demonstrated herein, that immune rejection can be reduced and tolerance can be induced by modulating the amount of these particular members of the Jak/Stat signal transduction pathway present, expressed or active within an affected tissue. In particular, the results presented herein demonstrate that immune rejection can be monitored by determining the amount of Stat1 mRNA or protein, Stat2 mRNA or protein, Stat3 mRNA, protein Stat4 mRNA or protein, Stat6 mRNA or protein, SOCS1 mRNA or protein, or SOCS3 mRNA or protein present, e.g., present in an affected tissue.

2. BACKGROUND OF THE INVENTION

Ongoing advances in transplantation, including new immunosuppressive agents and improvements in histocompatibility matching, organ procurement, and surgical techniques, are gradually improving the outcome of clinical transplantation (Hariharan et al, 2000. N Engl J Med 342:605–12). However, chronic allograft rejection remains the prime determinant of long-term graft survival (Paul. L. C., 1999, Kidney International 56:783–793).

Tissue transplantation between genetically nonidentical individuals results in immunological rejection of the tissue through T cell-dependent mechanisms. To prevent allograft rejection, immunosuppressive agents such as calcineurin phosphatase inhibitors and glucocorticosteroids which directly or indirectly interfere with IL-2 signaling are administered to transplant recipients (see, e.g., Borel, J. F., 1989, Pharmacol. Rev. 42:260–372; Morris, P. J., 1991, Curr. Opin. Immunol. 3:748–751; Sigal et al., 1992, Ann. Rev. Immunol. 10:519–560; and L'Azou et al., 1999, Arch. Toxicol. 73:337–345). The most commonly used immunosuppressive agents today are cyclosporin A, FK506, and rapamycin. These immunosuppressive agents act indiscriminately on all T cells by impairing T cell receptor ("TCR") signal transduction. Further, since the effect of the immunosuppressive agents is short-lasting, transplant recipients normally require life-long treatment of immunosuppressive agents to prevent transplant rejection. As a result of the long-term nonspecific immunosuppression, these immunosuppressive agents have many serious adverse effects. For example, the administration of cyclosporin A or FK506 to a transplant recipient results in degenerative changes in renal tubules. Transplant recipients receiving long-term immunosuppressive treatment have a high risk of developing infections and tumors. For example, patients receiving immunotherapy are at higher risk of developing lymphomas, skin tumors and brain tumors (see, e.g., Fellstrom et al., 1993, Immunol. Rev. 134:83–98).

An alternative to immunosuppressive agents for the prevention of allograft rejection is the blockage of specific receptors involved in T cell costimulation. T cell activation requires both TCR-mediated signal transduction and simultaneously delivered costimulatory signals. These costimulatory signals are contributed, in part, by the activation of the costimulatory molecule CD28, which is expressed on resting T cells, by CD80 (B7-1) or CD86 (B7-2) expressed on antigen presenting cells (APCs). The activation of the costimulatory molecule CD40, which is expression on antigen presenting cells (i.e., B cells, dendritic cells, and macrophages), by CD40 ligand ("CD40L"), which is expressed on activated T cells, contributes to the upregulation of T cell activation by inducing the expression of B7-1 and B7-2 on antigen presenting cells and the production of certain chemokines and cytokines such as IL-8, MIP-1α, TNF-α, and IL-12 (Cella et al., 1996, J. Exp. Med. 184:747–752: and Caux et al., 1994, J. Exp. Med. 180:1263–1272). The CD40/CD40L interaction also results in the differentiation of T cells to T helper ("TH") type 1 cells in part due to the expression of cytokines such as IL-12 by dendritic cells and macrophages.

CTLA-4 is normally expressed as a membrane-bound receptor on T cells and has been shown to downregulate T cell activation by competing with CD28 for B7-1 and B7-2. The administration of soluble CTLA-4Ig is believed to prevent allograft rejection by competing with CD28 for B7-1 and B7-2. Soluble CTLA-4Ig has been administered to transplant recipients to disrupt the CD28/B7 interaction so that T cell costimulation is blocked and allograft rejection does not occur (Zheng et al., 1999, J. Immunol. 162:4983–4990; Lenschow et al., 1996, Ann. Rev. Immunol. 14:233–258). Unfortunately, CTLA-4Ig has variable efficacy, and typically does not prevent development of chronic rejection.

Anti-CD40L (anti-CD154) monoclonal antibodies have also been administered to transplant recipients to prevent allograft rejection. These antibodies function by blocking the interaction of CD40 on antigen presenting cells (APC) and CD40L on activated T cells. It has recently been shown that graft survival achieved through the use of anti-CD40L monoclonal antibodies results in a significant inhibition of TH1 type cytokines (i.e., IL-2, IL-12, TNFα, and IFNγ), and an increase in the levels of the TH2 type cytokines (i.e., IL-4, and IL-10) in the graft sections (Hancock et al., 1996, Proc. Natl. Acad. Sci. USA 93:13967–13972). Although the administration of anti-CD40L monoclonal antibodies has been shown to result in permanent graft survival when given to mice in combination with donor-specific spleen cells, adverse side effects such as coagulation have also been shown to be associated with the administration of anti-CD40L monoclonal antibodies. Initial clinical trials in adult renal transplant recipients receiving anti-CD40L monoclonal antibody plus glucocorticoids were halted because of thromboembolic complications (Vincent, J., Biogen News, press release, Nov. 2, 1999, www.prnewswire.com), though the extent to which thromoboembolism was attributable to monoclonal antibodies versus non-specific factors in the antibody formulation is unclear (Kawai et al., 2000, Nature Med. 6:114; and Kirk et al., 2000, Nature Med. 6:114). Further, in the primate renal allograft study, concomitant use of mainstream immunosuppressive agents such as FK-506, methylprednisolone and mycophenolate mofetil diminished the efficacy of CD40L (CD154) mAb, though the exact contribution of each of the individual drugs to this reduction in efficacy was not determined (Kirk, A. D., 1999, Nature Medicine 5:686–693.). The results presented herein demonstrate that some, but not all, combinations of CD154 mAb and immunosuppressive agents are antagonistic, and that strategies for design of clinical trials based on use of CD154 mAb can be logically developed by taking into account the extent to which a given drug inhibits induction of CD154.

In addition, no satisfactory methods presently exist for monitoring whether a transplant graft is being accepted or rejected by a recipient. In general, signs of cellular damage within the transplant tissue can be assayed. Alternatively, for tissues such as kidney or liver, physiological function of the transplant tissue can be assayed. Often, however, by the time overt signs of either cellular damage or a decrease in physiological function are detected, the tissue graft is already beyond rescue. This is particularly true in the case of such organ transplants as heart transplants, with which the first overt signs of rejection are often complete failure of the heart's function.

Accordingly, there is a need for improved, safer immunomodulatory treatments that have long-lasting effects for the prevention of transplant rejection. In particular, there is a need for treatments that are more specific and less toxic than the currently available therapeutic agents. Further, there is also a great need for an improved method for monitoring acceptance of transplant tissue in subject mammals that have undergone a transplant.

2.1. Jak/STAT Signal Transduction

Signal transduction pathways represent molecular solutions to the fact that such molecules as polypeptide hormones, growth factors and cytokines cannot cross the cell membrane, but must activate intracellular signaling molecules to elicit a response in target cells. Among such signal transduction pathways is the Jak/Stat signal transduction pathway. See, e.g., Heim, M. H., 1999, J. Recept. & Sig. Trans. Res. 19:75–120; and Leonard, W. J. & O'Shea, J. J., 1998, Ann. Rev. Immunol. 16:293–322.

While the pathway was originally discovered as part of a study of interferon-induced intracellular signalling, to date, several dozen polypeptide ligands have been identified that activate the Jak/Stat pathway. Defects in the Jak/Stat pathway have been identified in a number of diseases, including leukemias, lymphomas, inherited immunodeficiency syndromes, breast cancer and a form of dwarfism caused by constitutively activation of a Stat by a mutant fibroblast growth factor-receptor.

Stats (Signal transducers and activators of transcription) are phosphoproteins that are transcription factors, and that are activated in response to cytokines, growth factors and interferons. Stats are activated by receptor-associated Janus kinases ("Jaks"), which include Jak1, Jak2, Tyk2, and Jak3. Specifically, a ligand-induced receptor aggregation results in the transphorphorylation and activation of the catalytic activity of the associated Jak. The activated Jak phosphorylates the receptors at multiple sites. Stats are recruited to the multimeric complex consisting of the phosphorylated receptor and catalytically active Jak. The catalytically active Jak phosphorylates tyrosine residues in the carboxy-terminus of the Stats. The phosphorylated Stats form homodimers and heterodimers (Darnell, J. E., 1997, Science 277:1630–1635; and Leonard et al., 1998, Ann. Rev. Immunol. 16:293–322; and Darnell et al., 1994, Science 264:1415–1421). The dimerization of Stats is believed to trigger the dissociation of Stats from the receptor complex and their translocation to the nucleus. In the nucleus, Stat dimers bind to their cognate DNA regulatory elements, which binding results in increased transcription, i.e., transactivation. Thus, the Jak/Stat system provides a method of both signal amplification and transduction.

Seven Stat genes (Stat1, Stat2, Stat3, Stat4, Stat5A, Stat5B, and Stat6) and several Stat isoforms have been discovered, the isoforms resulting from alternative splicing or posttranslational processing (for review see, e.g., Leonard et al., 1998, Ann. Rev. Immunol. 16:293–322). Different Stats are activated in response to different cytokines and growth factors. For example, Stat4 has been shown be activated in response to IL-12 induced signal transduction (Thierfelder et al., 1996, Nature 382:171–174; and Kaplan et al., 1996, Nature 382:174–177). Stat6 has been shown to be activated in response to IL-4 and IL-13 induced signal transduction (Takeda et al., 1996, Nature 380:627–630). Certain transcription factors activated in response to a given cytokine have been shown to be important in TH1 and/or TH2 differentiation. Stat4 has been shown to be important in TH1 differentiation and Stat6 has been shown to be important in TH2 differentiation (see, e.g., Romagnani, S., 1997, Immunology Today 18:263–266; Ray, A. and Cohn, L., 1999, J. Clin. Invest. 104(8):985–993).

With respect to TH1 and TH2, the majority of mature T lymphocytes can be divided into two distinct phenotypes: $CD8^+$ cytotoxic T lymphocytes (CTLs), which display the CD8 marker on their cell surface, and $CD4^+$ helper T lymphocytes (T helper or TH cells), which display the CD4 marker on their cell surface. TH cells are involved in both humoral (i.e., antibody) and cell-mediated forms of immune response. TH cells have been further categorized into two distinct subpopulations, termed TH1 and TH2 cell subpopulations. These two subpopulations of TH cells have been categorized on the basis of their restricted cytokine profiles and different functions. For example, TH1 cells are known to produce IL-2, IL-12, tumor necrosis factor $\beta$ ("TNF-$\beta$"), and interferon-$\alpha$ ("IFN-$\alpha$"). TH2 cells are known to produce IL-4, IL-5, IL-10 and IL-13. Inappropriate immune responses have been shown to be associated with various diseases and disorders. For example, an inappropriate TH2-like response has shown to be associated with atopic conditions, such as asthma and allergy (see, e.g. , Holgate, S. T., 1997, Lancet 350(suppl. II):5–9; Ray, A. and Cohn, L, supra; Oettgen, H. C. and Geha, R. S., 1999, J. Clin. Invest. 104(7):829–835). Further, an inappropriate TH 1-like response has been shown to associated with the pathogenesis of autoimmune diseases such multiple sclerosis, pancreases of insulin-dependent diabetes patients, thyroid glands of Hashimoto's thyroiditis, and gut of Crohn's disease patients.

2.2. Negative Regulators of the Jak/STAT Signaling Pathway

Three protein families have been discovered that negatively regulate cytokine-induced Jak/Stat signaling, tyrosine phosphatases SHP1 and SHP2, the suppressors of cytokine signaling ("SOCS"), and protein inhibitors of activated Stats (PIAS). SHP1 and SHP2 bind to phosphorylated tyrosine residues on receptors or Jaks, and inactivate signaling by dephosphorylating them (Haque et al., 1998, J. Biol. Chem.

273:33898–33896; and You et al., 1999, Mol. Cell. Biol. 19:2416–2424).

The SOCS family of proteins have been shown to inhibit the Jak/Stat pathway by inhibiting the activity of the Jaks (Hilton et al., Proc. Natl. Acad. Sci. USA 95:114–119; and Hilton, 1999, Cell. and Mol. Life Sci. 55:1658–1577). The nature of the interaction between the different receptors, Jaks, and the SOCS is unclear (Hilton, D. J., 1999, Cell. Mol. Sci. 55:1568–1577). SOCS1 have been shown to directly interact with all the Jaks and Tyk2. CIS (Cytokine inducible SH2 containing protein), a member of the SOCS family, on the other hand, was shown to interact with the EPO receptor or the β chain of the IL-3 receptor in a phosphorylation dependent manner, indicating it may act by competing with Stat molecules for binding to receptors (Yoshimura et al., 1995, EMBO J. 14:2816–2826). SOCS1 expression inhibits IL-6, LIF, oncostatin M, IFN-γ, IFN-β, IFN-α, thrombopoeitin, and growth hormone (GH) induced Jak/Stat signaling. SOCS3 expression inhibits IFN-γ, IFN-β, IFN-α, GH and leptin.

Four members of the PIAS family have been identified, PIAS1, PIAS3, PIASxα, and PIASxβ. PIAS1 was found to bind only to activated Stat1, and PIAS3 to only activated Stat3 (Liu et al., 1998, Proc. Natl. Acad. Sci. USA 95:10626–10631; and Chung et al., 1997, Science 278:1803–1805). PIAS-mediated inhibition of the Jak/Stat signaling pathway, unlike SOCS-mediated inhibition of the Jak/Stat signaling pathway, is very specific. However, unlike some of the SOCS which are elevated rapidly in response to cytokines, the PIAS levels in the cells are more or less constant.

3. SUMMARY OF THE INVENTION

The present invention relates to methods and compositions for reducing immune rejection, for example, transplant- or autoimmune disorder-related immune injury or rejection. The present invention also relates to methods and compositions for monitoring transplant acceptance and for monitoring an autoimmune disorder in a subject mammal. The present invention still further relates to methods for identifying compounds that can reduce immune injury.

The present invention is based, in part, on the discovery, demonstrated herein, that immune rejection can be monitored by determining the amount of particular members of the Jak/Stat signal transduction pathway present within an affected tissue (that is, a transplant cell, tissue, organ, or organ system, or a cell, tissue, organ, or organ system that is, or is suspected of, being affected by an autoimmune disorder). In particular, the results presented herein demonstrate that immune rejection can be monitored by determining the amount of Stat4 mRNA or protein, Stat6 mRNA or protein, SOCS1 mRNA or protein, or SOCS3 mRNA or protein, present in an affected tissue. The results presented herein also demonstrate that immune rejection can be monitored by determining the amount of Stat1 mRNA or protein, Stat2 mRNA or protein, or Stat3 mRNA or protein present, e.g., present in an affected tissue. The present invention is further based, in part, on the discovery, demonstrated herein, that immune rejection can be reduced and tolerance can be induced by modulating the amount of these particular members of the Jak/Stat signal transduction pathway present, expressed or active within an affected tissue.

Thus, in one aspect, the invention relates to methods for monitoring acceptance of a transplant in a subject mammal that has undergone a transplant, wherein said method comprises: determining the amount of at least one of the following: (i) Stat4 mRNA or Stat4 protein, (ii) Stat6 mRNA or Stat6 protein, (iii) SOCS1 mRNA or SOCS1 protein, or (iv) SOCS3 mRNA or SOCS3 protein, present in a transplant sample from the subject. In alternate embodiments, such methods comprise determining the amount of at least two, at least three, or each of (i) to (iv) present in the transplant sample. In certain embodiments, the amount of mRNA is determined, and can, for example, be determined via use of nucleic acid microarrays. In other embodiments, the amount of protein is determined, while in still other embodiments, the amount of mRNA and protein is determined. With respect to Stat6, when the amount of Stat6 is being determined, it is preferable that the amount of Stat6 protein be determined. In any such embodiment wherein a Stat protein amount is determined, the amount determined can be the total amount of the Stat protein present in a sample or, alternatively, can be the amount of phosphorylated Stat protein present in the sample.

In a preferred embodiment, a method for monitoring acceptance of a transplant in a subject mammal that has undergone a transplant comprises determining the amount of Stat4 and Stat6 mRNA or Stat4 and Stat6 protein present in a transplant sample from the subject. Such an embodiment can further comprise determining the ratio of Stat4 to Stat6 amounts.

The methods for monitoring acceptance of a transplant in a subject mammal that has undergone a transplant can further comprise assaying the transplant sample for evidence of lymphocyte infiltration or tissue damage (cell injury) using standard techniques. For example, histological techniques well known to those of skill in the art can be utilized to evaluate internationally recognized and used diagnostic criteria for the evaluation of graft rejection, which include features specific for each organ involved. For example, immunohistologic evaluation of such tissues, via, e.g., use of labeled antibody techniques to localize and quantitate gene expression. The evaluation of such criteria can, therefore, be enhanced by, for example, localization of Stat4, Stat6, SOCS1 and/or SOCS3 proteins, and/or detection of corresponding mRNAs via, e.g., in situ hybridization.

Such methods can also further comprise comparing the amount or ratio determined to that present in a control sample, for example, a corresponding pre-transplant subject sample or a subject blood sample. In instances wherein the amount of Stat4, SOCS1, or SOCS3 mRNA or protein in the transplant sample is greater than, or the amount of Stat6 mRNA or protein in the transplant sample is less than, that of the control sample, such a result indicates that acceptance of the transplant has not occurred, has not been induced or is not being maintained. In instances wherein the amount of Stat4, SOCS1, or SOCS3 mRNA or protein in the transplant sample is less than, or the amount of Stat6 mRNA or protein in the transplant sample is equal to or greater than that of the control sample, such a result indicates that acceptance of the transplant has occurred, is being induced or is being maintained. In instances wherein the ratio of Stat4 to Stat6 in the transplant sample is greater than or equal to that in the control sample, such a result indicates that acceptance of the transplant has not occurred, has not been induced or is not being maintained. In instances wherein the ratio of Stat4 to Stat6 in the transplant sample is less than that in the control sample, such a result indicates that acceptance of the transplant has occurred, has been induced or is being maintained.

In another aspect, the invention relates to methods for monitoring acceptance of a transplant in a subject mammal that has undergone a transplant, wherein said method comprises: determining the amount of at least one of the following: (i) Stat1 mRNA or Stat1 protein, (ii) Stat2 mRNA or Stat2 protein, or (iii) Stat3 mRNA or Stat3 protein, present in a cell sample from the subject. In alternate embodiments, such methods comprise determining the amount of at least two or each of (i) to (iii) present in the sample. In certain embodiments, the amount of mRNA is determined, and can, for example, be determined via use of nucleic acid microarrays. In other embodiments, the amount of protein is determined, while in still other embodiments, the amount of mRNA and protein is determined. In any such embodiment wherein a Stat protein amount is determined, the amount determined can be the total amount of the Stat protein present in a sample or, alternatively, can be the amount of phosphorylated Stat protein present in the sample.

In a particular embodiment of such Stat 1-, Stat 2-, and/or Stat 3-related methods, the cell sample is a transplant sample obtained within 2 to 3 days post-transplantation. In an alternative embodiment of such Stat 1-, Stat 2-, and/or Stat 3-related methods, the cell sample is a subject blood sample.

Such Stat 1-, Stat-2, and/or Stat 3-related methods can also further comprise comparing the amount determined to that present in a control sample, for example, a corresponding pre-transplant subject sample or, in the case of embodiments wherein the cell sample is a transplant sample obtained within 2–3 days post-transplantation, a subject blood sample. In instances wherein the amount of Stat1, Stat2, or Stat3 mRNA or protein in the cell sample is greater than that of the control sample, such a result indicates that acceptance of the transplant has not occurred, has not been induced or is not being maintained. In instances wherein the amount of Stat1, Stat2, or Stat3 mRNA or protein in the transplant sample is less than that of the control sample, such a result indicates that acceptance of the transplant has occurred, is being induced or is being maintained.

In another aspect, the invention relates to methods for monitoring an autoimmune disorder in a subject mammal, wherein said method comprises: determining the amount of at least one of the following: (i) Stat4 mRNA or Stat4 protein, (ii) Stat6 mRNA or Stat6 protein, (iii) SOCS1 mRNA or SOCS1 protein, or (iv) SOCS3 mRNA or SOCS3 protein, present in a sample from a subject mammal being treated for or suspected of exhibiting the autoimmune disorder, wherein the sample is obtained from a tissue affected by the disorder. In alternate embodiments, such methods comprise determining the amount of at least two, at least three, or each of (i) to (iv) present in the sample. In certain embodiments, the amount of mRNA is determined, and can, for example, be determined via use of nucleic acid microarrays. In other embodiments, the amount of protein is determined, while in still other embodiments, the amount of mRNA and protein is determined. With respect to Stat6, when the amount of Stat6 is being determined, it is preferable that the amount of Stat6 protein be determined. In any such embodiment wherein a Stat protein amount is determined, the amount determined can be the total amount of the Stat protein present in a sample or, alternatively, can be the amount of phosphorylated Stat protein present in the sample.

In a preferred embodiment, a method for monitoring an autoimmune disorder in a subject mammal comprises determining the amount of Stat4 and Stat6 mRNA or Stat4 and Stat6 protein present in a sample from the subject mammal being treated for or suspected of exhibiting the autoimmune disorder, wherein the sample is obtained from a tissue affected by the disorder. Such an embodiment can further comprise determining the ratio of Stat4 to Stat6 amounts.

The methods for monitoring an autoimmune disorder in a subject mammal can further comprise assaying the sample for evidence of leukocyte infiltration or tissue damage (cell injury) using standard techniques. For example, histological techniques well known to those of skill in the art can be utilized. Alternatively, standard techniques can be utilized to assay (e.g., in serum) for the presence of autoimmune antibodies associated with the particular autoimmune disorder of interest. There are internationally used diagnostic criteria for evaluation of graft rejection, with features specific for each organ. The immunohistologic evaluation of such tissues, i.e., use of unlabeled-antibody techniques to localize and quantitate gene expression, can be enhanced by localization of Stat4 and Stat6 proteins, or detection of corresponding mRNAs by in situ hybridization.

Such methods for monitoring an autoimmune disorder in a subject mammal can further comprise comparing the amount or ratio determined to that present in a control sample, for example, a corresponding tissue not affected by the disorder or a subject blood sample. In instances wherein the amount of Stat4, SOCS1, or SOCS3 mRNA or protein in the sample is greater than, or the amount of Stat6 mRNA or protein in the sample is less than, that of the control sample, such a result indicates that the subject mammal exhibits or continues to exhibit the disorder. In instances wherein the amount of Stat4, SOCS1, or SOCS3 mRNA or protein in the sample is less than, or the amount of Stat6 mRNA or protein in the sample is equal to or greater than that of the control sample, such a result indicates that the subject mammal does not exhibit the disorder or that treatment for the disorder is effective. In instances wherein the ratio of Stat4 to Stat6 in the sample is greater than or equal to that in the control sample, such a result indicates that the subject mammal exhibits or continues to exhibit the disorder. In instances wherein the ratio of Stat4 to Stat6 in the transplant sample is less than that in the sample, such a result indicates that the subject mammal does not exhibit the disorder or that treatment for the disorder is effective.

The methods for monitoring transplant acceptance or monitoring an autoimmune disorder can be performed with kits designed for carrying out such methods. As such, the present invention also relates to kits for monitoring transplant acceptance and autoimmune disorders.

In yet another aspect, the present invention relates to a method for identifying a compound to be tested for an ability to reduce immune rejection, said method comprises: (a) contacting an activated T cell sample with a test compound; (b) determining the amount of at least one of the following: (i) Stat1 mRNA or Stat1 protein, (ii) Stat2 mRNA or Stat2 protein, (iii) Stat3 mRNA or Stat3 protein, (iv) Stat4 mRNA or Stat4 protein, (v) Stat6 mRNA or Stat6 protein; (vi) SOCS1 mRNA or SOCS1 protein, or (vii) SOCS3 mRNA or SOCS3 protein, present in (a); and (c) comparing the amount(s) in (a) to that/those present in a corresponding control activated T cell sample that has not been contacted with the test compound, so that if the amount of (i), (ii), (iii), (iv), (vi), or (vii) is decreased, or the amount of (v) is increased, relative to the amount in the control sample, a compound to be tested for an ability to reduce immune rejection is identified. In alternate embodiments, such methods comprise determining the amount of at least two, at least three, at least four, at least five, at least six, or each of (i) to (vii) present in the activated T cell sample and comparing the amounts to those present in the control sample.

In certain embodiments, the amount of mRNA is determined, in other embodiments, the amount of protein is determined, while in still other embodiments, the amount of mRNA and protein is determined. With respect to Stat6, when the amount of Stat6 is being determined, it is preferable that the amount of Stat6 protein be determined. In any such embodiment wherein a Stat protein amount is determined, the amount determined can be the total amount of the Stat protein present in a sample or, alternatively, can be the amount of phosphorylated Stat protein present in the sample.

In a preferred embodiment of a method for identifying a compound to be tested for an ability to reduce immune rejection, said method comprises: (a) contacting an activated T cell sample with a test compound; (b) determining the amount of Stat4 mRNA and Stat6 mRNA or Stat4 protein and Stat6 protein present in the sample; and (c) comparing the amounts in (b) to those present in a corresponding control activated T cell sample that has not been contacted with the test compound, so that if the amount of Stat4 is decreased or the amount of Stat6 is increased relative to the amount in the control sample, a compound to be tested for an ability to reduce immune rejection is identified.

In another preferred embodiment of a method for identifying a compound to be tested for an ability to reduce immune rejection, said method comprises: (a) contacting an activated T cell sample with a test compound; (b) determining the ratio of Stat4 mRNA to Stat6 mRNA or Stat4 protein to Stat6 protein present in the sample; and (c) comparing the ratio in (b) to that present in a corresponding control activated T cell sample that has not been contacted with the test compound, so that if the ratio in the sample is decreased relative to that in the control sample, a compound to be tested for an ability to reduce immune rejection is identified.

In another aspect, the present invention relates to a method for identifying a compound to be tested for an ability to reduce immune rejection, said method comprises: (a) contacting a resting T cell sample, a T cell activator and a test compound; (b) determining the amount of at least one of the following: (i) Stat1 mRNA or Stat1 protein, (ii) Stat2 mRNA or Stat2 protein, (iii) Stat3 mRNA or Stat3 protein, (iv) Stat4 mRNA or Stat4 protein, (v) Stat6 mRNA or Stat6 protein; (vi) SOCS1 mRNA or SOCS1 protein, or (vii) SOCS3 mRNA or SOCS3 protein, present in (a); and (c) comparing the amount(s) in (a) to that/those present in a corresponding resting T cell sample that has been contacted with the T cell activator, but has not been contacted with the test compound, so that if the amount of (i), (ii), (iii), (iv), (vi), or (vii) is decreased, or the amount of (v) is increased, relative to the amount in the control sample, a compound to be tested for an ability to reduce immune rejection is identified. In alternate embodiments, such methods comprise determining the amount of at least two, at least three, at least four, at least five, at least six, or each of (i) to (vii) present in the activated T cell sample and comparing the amounts to those present in the control sample.

In certain embodiments of such methods, the amount of mRNA is determined, in other embodiments, the amount of protein is determined, while in still other embodiments, the amount of mRNA and protein is determined. With respect to Stat6, when the amount of Stat6 is being determined, it is preferable that the amount of Stat6 protein be determined. In any such embodiment wherein a Stat protein amount is determined, the amount determined can be the total amount of the Stat protein present in a sample or, alternatively, can be the amount of phosphorylated Stat protein present in the sample. Further, in certain embodiments, the resting T cell is a primary T cell, and in other embodiments, the resting T cell is a T cell line.

In a preferred embodiment of a method for identifying a compound to be tested for an ability to reduce immune rejection, said method comprises: (a) contacting a resting T cell sample, a T cell activator and a test compound; (b) determining the amount of Stat4 mRNA and Stat6 mRNA or Stat4 protein and Stat6 protein present in the sample; and (c) comparing the amounts in (b) to those present in a corresponding control resting T cell sample that has been contacted with the T cell activator, but has not been contacted with the test compound, so that if the amount of Stat4 is decreased or the amount of Stat6 is increased relative to the amount in the control sample, a compound to be tested for an ability to reduce immune rejection is identified.

In another preferred embodiment of a method for identifying a compound to be tested for an ability to reduce immune rejection, said method comprises: (a) contacting a resting T cell sample, a T cell activator and a test compound; (b) determining the ratio of Stat4 mRNA to Stat6 mRNA or Stat4 protein to Stat6 protein present in the sample; and (c) comparing the ratio in (b) to that present in a corresponding control resting T cell sample that has been contacted with a T cell activator, but has not been contacted with the test compound, so that if the ratio in (a) is decreased relative to that in the control sample, a compound to be tested for an ability to reduce immune rejection is identified.

In another aspect, the present invention relates to a method for identifying a compound to be tested for an ability to reduce immune rejection, comprising: (a) contacting a T cell sample, a cytokine and a test compound, wherein the T cell sample is responsive to the cytokine; (b) determining the amount of at least one of the following: (i) Stat1 mRNA or Stat1 protein, (ii) Stat2 mRNA or Stat2 protein, (iii) Stat3 mRNA or Stat3 protein, (iv) Stat4 mRNA or Stat4 protein, (v) Stat6 mRNA or Stat6 protein; (vi) SOCS1 mRNA or SOCS1 protein, or (vii) SOCS3 mRNA or SOCS3 protein, present in (a); and (c) comparing the amount(s) in (a) to that/those present in a corresponding control T cell sample that has been contacted with the cytokine, but has not been contacted with the test compound, so that if the amount of (i), (ii), (iii), (iv), (vi), or (vii) is decreased, or the amount of (v) is increased, relative to the amount in the control sample, a compound to be tested for an ability to reduce immune rejection is identified. In preferred embodiments, the cytokine is IL-2, IL-4, IL-12, or IL-13.

In certain embodiments of such methods, the amount of mRNA is determined, in other embodiments, the amount of protein is determined, while in still other embodiments, the amount of mRNA and protein is determined. With respect to Stat6, when the amount of Stat6 is being determined, it is preferable that the amount of Stat6 protein be determined. In any such embodiment wherein a Stat protein amount is determined, the amount determined can be the total amount of the Stat protein present in a sample or, alternatively, can be the amount of phosphorylated Stat protein present in the sample.

In a preferred embodiment of such a method for identifying a compound to be tested for an ability to reduce immune rejection, said method comprises: (a) contacting a T cell sample, a cytokine and a test compound, wherein the T cell sample is responsive to the cytokine; (b) determining the amount of Stat4 and Stat6 mRNA or Stat4 and Stat6 protein present in the sample; and (c) comparing the amounts in (a) to those present in a corresponding control T cell sample that has been contacted with the cytokine, but has not been contacted with the test compound, so that if the amount of Stat4 is decreased or the amount of Stat6 is increased relative to the amounts in the control sample, a compound to be tested for an ability to reduce immune rejection is identified.

In another preferred embodiment of such a method for identifying a compound to be tested for an ability to reduce immune rejection, said method comprises: (a) contacting a T cell sample, a cytokine and a test compound, wherein the T cell sample is responsive to the cytokine; (b) determining the ratio of Stat4 mRNA to Stat6 mRNA or Stat4 mRNA to Stat6 protein present in the sample; and (c) comparing the ratio to in (a) to that present in a corresponding control T cell sample that has been contacted with the cytokine, but has not been contacted with the test compound, so that if the ratio in the sample is decreased relative to that in the control sample, a compound to be tested for an ability to reduce immune rejection is identified.

In yet another aspect, the present invention relates to methods for reducing immune rejection in a subject mammal, said methods comprising: administering to a subject mammal in need of such a reduction a concentration of a compound sufficient to decrease the level of Stat4 mRNA or protein in the subject relative to that observed in the subject in the absence of the compound, wherein said compound does not induce platelet aggregation and does not affect NF-κB activation in CD40L$^+$ cells.

Alternatively, such methods for reducing immune rejection in a subject mammal can comprise: administering to a subject mammal in need of such a reduction a concentration of a compound sufficient to increase the level of Stat6 mRNA or protein in the subject relative to that observed in the subject in the absence of the compound, wherein said compound does not induce platelet aggregation and does not affect NF-κB activation in CD40L$^+$ cells.

Such methods for reducing immune rejection in a subject mammal can also comprise: administering to a subject mammal in need of such a reduction a concentration of a compound sufficient to decrease the level of Stat4 mRNA or protein and maintain or increase the level of Stat6 mRNA or protein in the subject relative to that observed in the subject in the absence of the compound, wherein said compound does not induce platelet aggregation and does not affect NF-κB activation in CD40L$^+$ cells.

The methods of the present invention for reducing immune rejection can be utilized, e.g., for reducing immune rejection in a subject mammal that has undergone a transplant. For example, such methods can induce tolerance in a subject mammal that has undergone a transplant. The methods of the present invention for reducing immune rejection can also be utilized, e.g., for reducing immune rejection in a subject mammal exhibiting an autoimmune disorder.

3.1. Definitions

As used herein, the term "transplant" includes any cell, organ, organ system or tissue which can elicit an immune response in a recipient subject mammal. In general, therefore, a transplant includes an allograft or a xenograft cell, organ, organ system or tissue. An allograft refers to a graft (cell, organ, organ system or tissue) obtained from a member of the same species as the recipient. A xenograft refers to a graft (cell, organ, organ system or tissue) obtained from a member of a different species as the recipient.

The term "immune rejection," as used herein, is intended to refer to immune responses involved in transplant rejection, as well as to the concomitant physiological result of such immune responses, such as for example, interstitial fibrosis, chronic graft artheriosclerosis, or vasculitis. The term "immune rejection," as used herein, is also intended to refer to immune responses involved in autoimmune disorders, and the concomitant physiological result of such immune responses, including T cell-dependent infiltration and direct tissue injury; T cell-dependent recruitment and activation of macrophages and other effector cells; and T cell-dependent B cell responses leading to autoantibody production.

The term "transplant rejection," as used herein, refers to T cell-mediated rejection of transplant cells, organs, organ systems or tissue. In general, such transplant rejection generally includes accelerated, acute and chronic rejection. It is intended that the term, as used herein, also refer to graft versus host disease, and the physiological results of such a disorder.

The term "reducing immune rejection," is meant to encompass prevention or inhibition of immune rejection, as well as delaying the onset or the progression of immune rejection. The term is also meant to encompass prolonging survival of a transplant in a subject mammal, or reversing failure of a transplant in a subject. Further, the term is meant to encompass ameliorating a symptom of an immune rejection, including, for example, ameliorating an immunological complication associated with immune rejection, such as for example, interstitial fibrosis, chronic graft atherosclerosis, or vasculitis. The term is also meant to encompass induction of tolerance in a subject mammal that has undergone a transplant.

The term "tolerance," as used herein, refers to a state wherein the immune system of a transplant recipient subject mammal is non-responsive to the transplant. This state is considered donor transplant-specific, and, as such, is distinguished from nonspecific immunosuppression. Operatively, the term as used herein, refers to permanent acceptance of a graft without ongoing immunosuppression, wherein, for example, challenge with a second graft of donor origin (especially when the second graft is of the same tissue as the first graft) should be accepted, and challenge with a third party graft should be rejected.

The term "autoimmune rejection," as used herein, refers to immune responses involved in autoimmune disorders, and the concomitant physiological result of such immune responses.

The term "activated T cell," as used herein, refers to a T cell that expresses antigens indicative of T-cell activation (that is, T cell activation markers). Examples of T cell activation markers include, but are not limited to, CD25, CD26, CD30, CD38, CD69, CD70, CD71, ICOS, OX-40 and 4-1BB. The expression of activation markers can be measured by techniques known to those of skill in the art, including, for example, western blot analysis, northern blot analysis, RT-PCR, immunofluorescence assays, and fluorescence activated cell sorter (FACS) analysis.

The term "resting T cell," as used herein, refers to a T cell that does not express T-cell activation markers. Resting T cells include, but are not limited to, T cells which are CD25$^{31}$, CD69$^-$, ICOS$^-$, SLAM$^-$, and 4-1BB$^-$. The expression of these markers can be measured by techniques known to those of skill in the art, including, for example, western blot analysis, northern blot analysis, RT-PCR, immunofluorescence assays, and fluorescence activated cell sorter (FACS) analysis.

The term "T cell activator," as used herein, refers to any compound or factor that is a T cell receptor stimulatory factor, that is, induces T cell receptor signalling. Preferably, the compound or factor also induces co-stimulatory pathways. Non-limiting examples of T cell activators include, but are not limited to, anti-CD3, antibodies (preferably monoclonal antibodies) either alone or in conjunction with anti-CD28 antibodies (preferably monoclonal antibodies), or mitogens such as, for example, phorbol 12-myristate 13-acetate (PMA), phytohemagglutinin (PHA) or concanavalin-A (Con-A).

4. BRIEF DESCRIPTION OF THE DRAWINGS

FIG. 1. Human Stat1 nucleic acid and amino acid sequences (SEQ ID NOs:1, 2, respectively).

FIG. 2. Human Stat2 nucleic acid and amino acid sequences (SEQ ID NOs:3, 4, respectively).

FIG. 3. Human Stat3 nucleic acid and amino acid sequences (SEQ ID NOs:5, 6, respectively).

FIG. 4. Human Stat4 nucleic acid and amino acid sequences (SEQ ID NOs:7, 8, respectively).

FIG. 5. Human Stat6 nucleic acid and amino acid sequences (SEQ ID NOs:9, 10, respectively).

FIG. 6. Human SOCS1 nucleic acid and amino acid sequences (SEQ ID NOs:11, 12, respectively).

FIG. 7. Human SOCS3 nucleic acid and amino acid sequences (SEQ ID NOs:13, 14, respectively).

FIG. 8. Human Jak2 nucleic acid and amino acid sequences (SEQ ID NOs:15, 16 respectively).

FIG. 9. Human Tyk2 nucleic acid and amino acid sequences (SEQ ID NOs:17, 18 respectively).

FIG. 10. Effects of immunosuppressants on CD154 mAb-induced cardiac allograft survival. Murine recipients were followed for up to 100 days post-transplant, and mean (±SD) cardiac allograft survival are shown (n=6/group). Statistical analysis (Mann-Whitney U test) showed that CD154 mAb or combined CD154 and rapamycin (CD154RPM) induced highly significant prolongation of allograft survival ($p<0.001$) compared to recipients treated with IgG, combined CD154 and cyclosporin A (CD154/CsA), or CD154 plus methylprednisolone (CD154/MP).

Figure 11A:
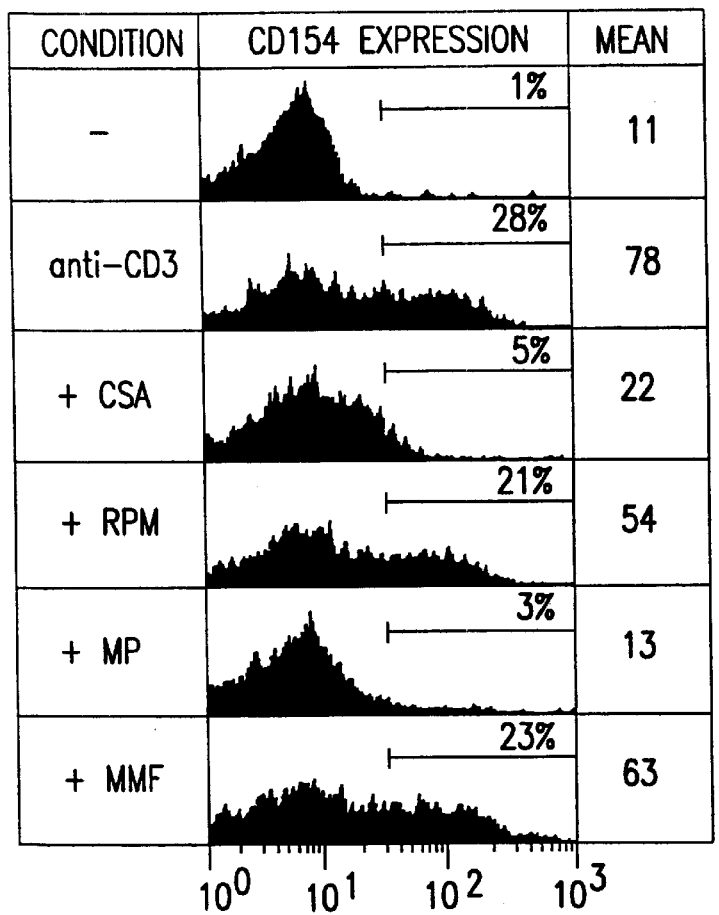
Figure 11B:
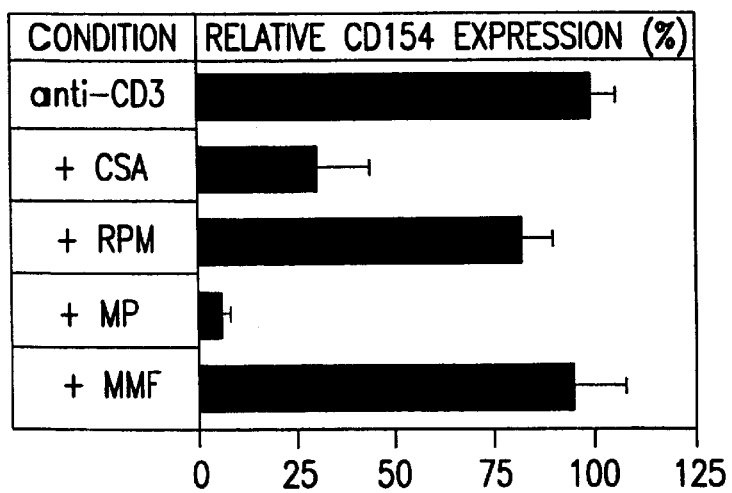

FIGS. 11A–11B. Contrasting effects of immunosuppressive agents on activation-induced CD154 expression by CD4+ T cells, as determined by dual color flow cytometry after 7 hr of culture. Except for the control sample depicted in the uppermost section of Panel A, all culture plates were pre-coated with CD3 mAb. Representative individual samples are shown in panel A, in which the histograms depict CD154 expression by gated CD4+ T cells. The percentage of CD154+ cells and the mean channel fluorescence of CD154 staining are indicated. Panel B shows the average activation-induced CD154 expression determined from 3 independent experiments. Percent CD154 expression (mean±SD) was calculated relative to the percentage of CD4+ CD154+ cells observed in the absence of immunosuppressive drugs. Cyclosporin A (CsA) and methylprednisolone (MP) significantly inhibited activation-induced CD154 expression ($p<0.01$).

Figure 12A:
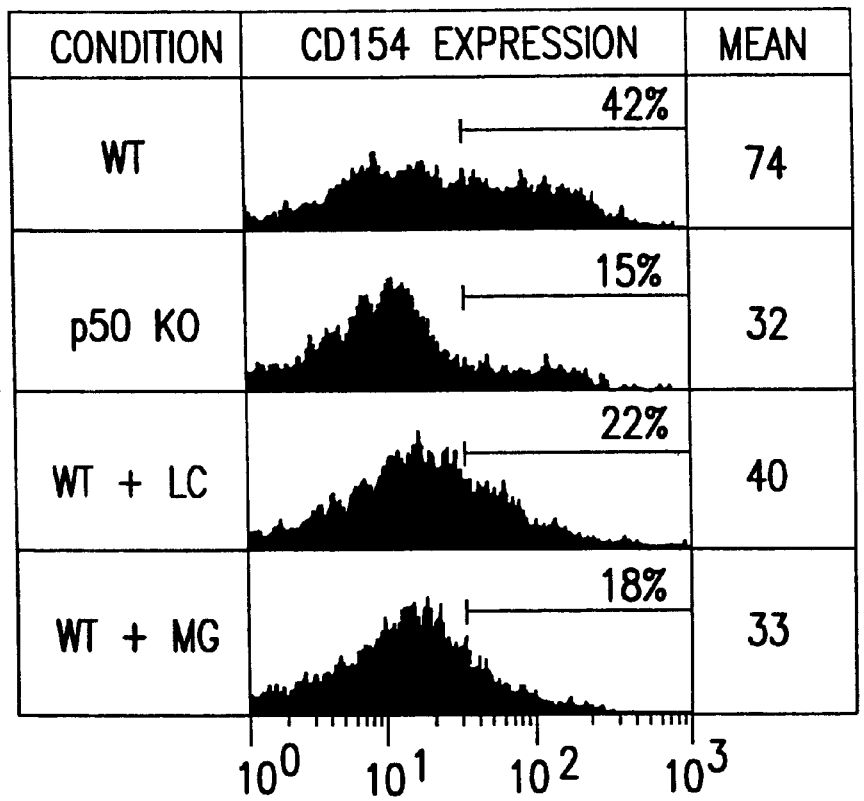
Figure 12B:
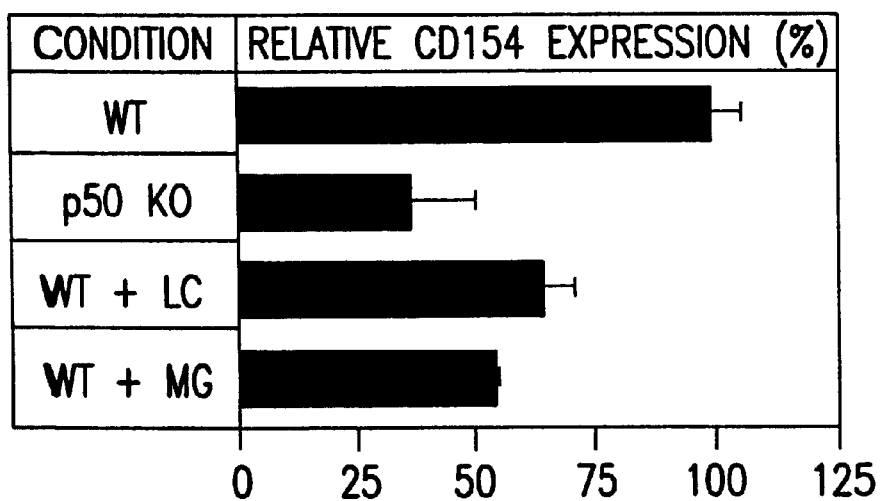

FIGS. 12A–12B. Critical role for NF-κB in activation-induced CD154 expression by CD4+ T cells in vitro. The experimental design and data presentation arc identical to that shown in FIG. 10: splenic cells were derived from either NFκB/p50 KO or control wild-type (WT) mice: Genetic deletion of NFκB/p50 inhibited activation-induced CD154 expression ($p<0.02$). Inhibition of NF-κB p50 in WT mice by the proteasome antagonists lactacystin (LC) and MG-273 (MG) also significantly blocked activation-induced CD154 expression ($p<0.04$).

Figure 13:
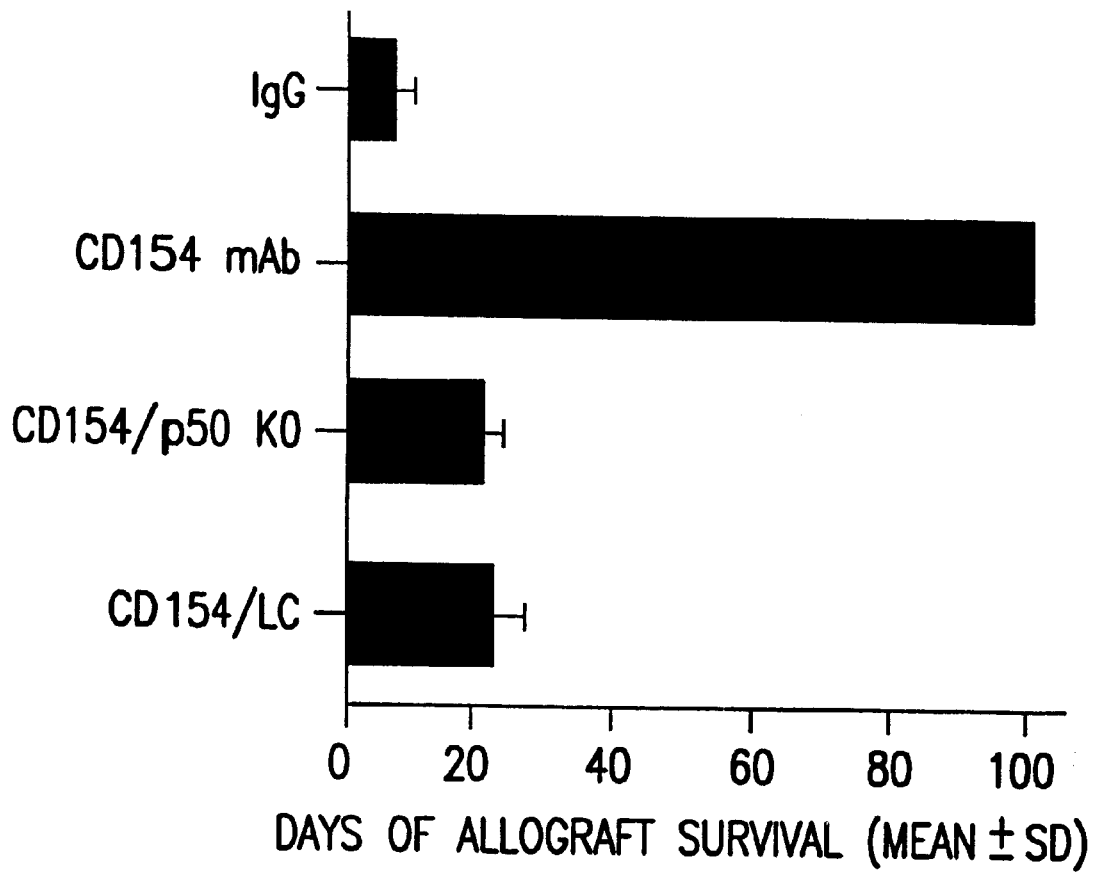

FIG. 13. Permanent cardiac allograft survival using CD154 mAb is NF-κB-dependent. Mice were followed for up to 100 days post-transplant and mean (±SD) cardiac allograft survival are shown (n=6/group). Statistical analysis (Mann-Whitney U test) showed that use of NF-κB/p50 KO mice as recipients, or administration of a lactacystin-derived (LC) proteasome inhibitor to wild-type mice, significantly impaired the efficacy of CD154 mAb therapy ($p<0.001$).

Figure 14A:
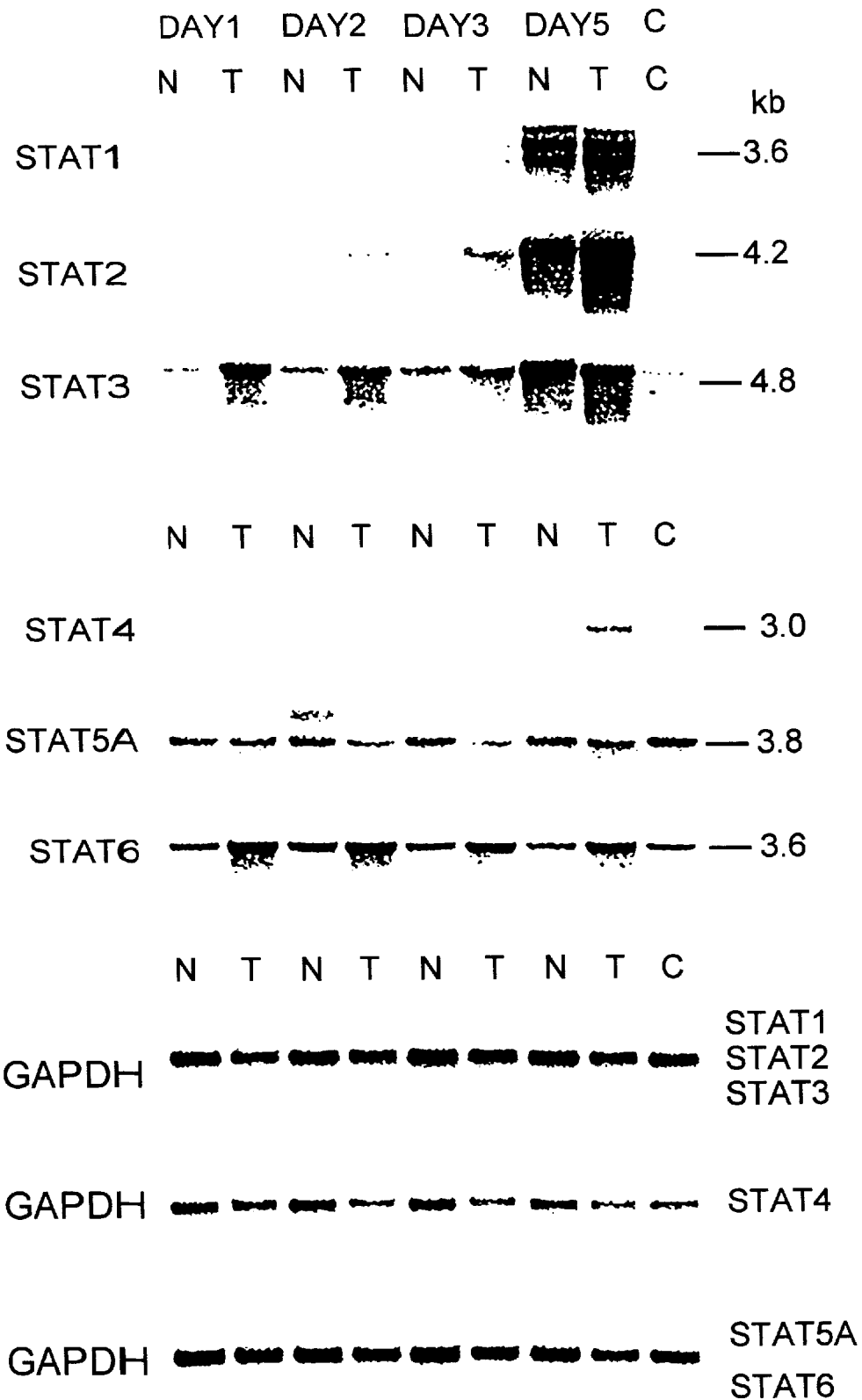
Figure 14B:
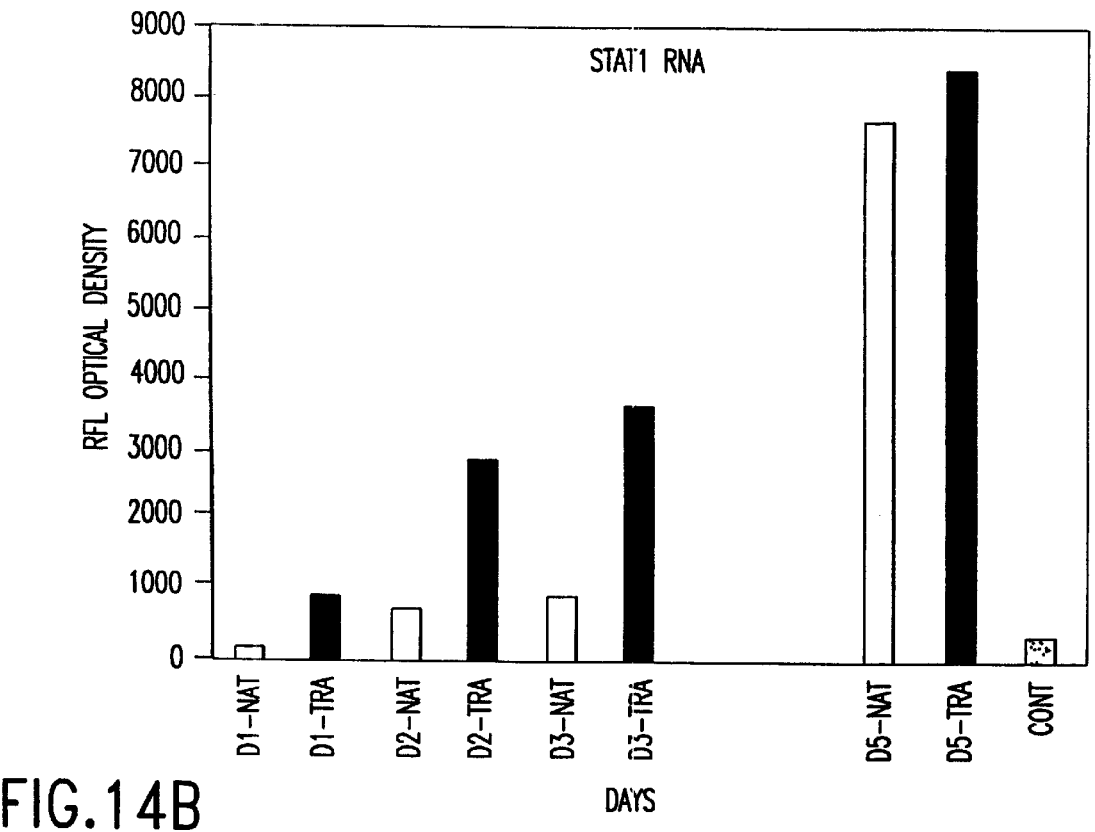
Figure 14C:
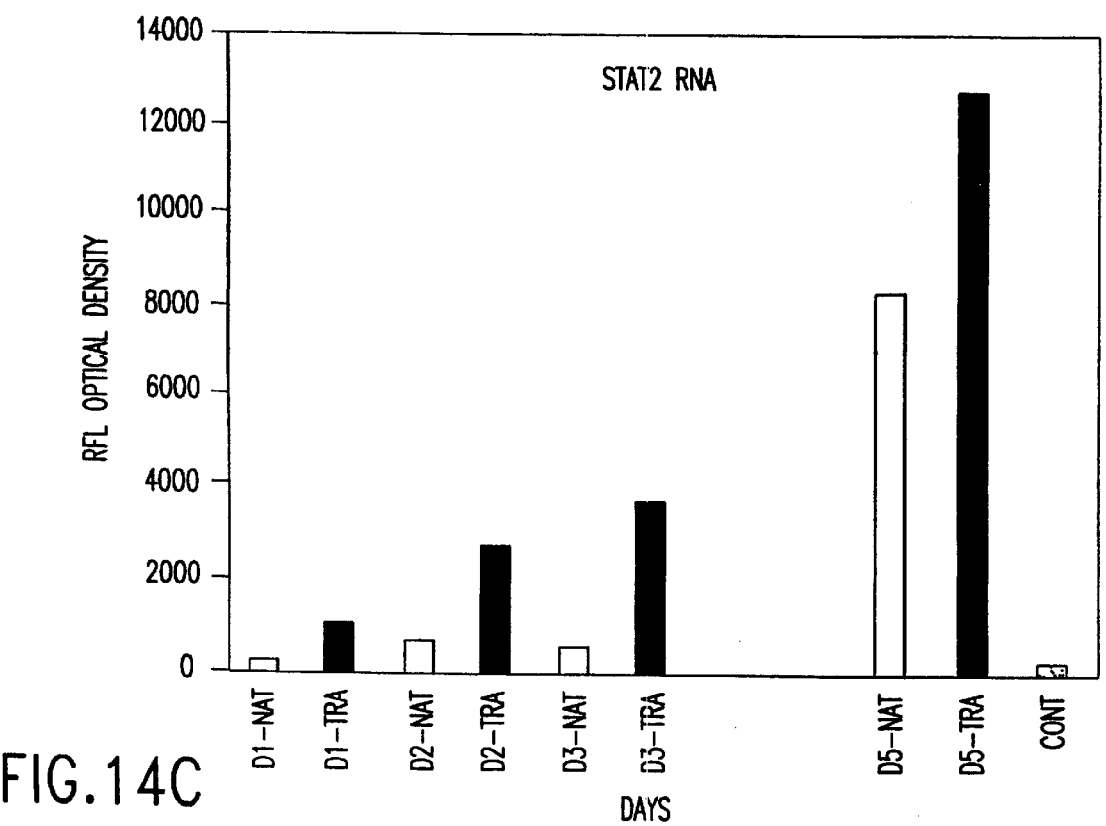
Figure 14D:
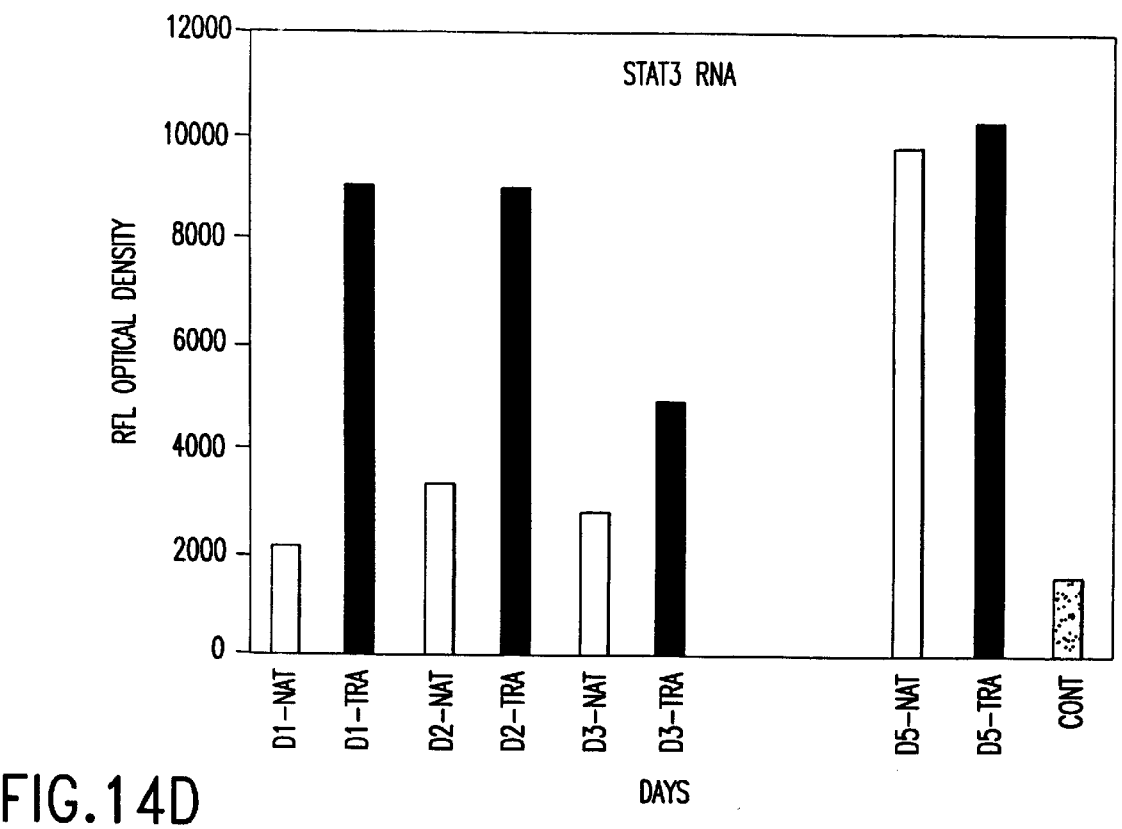
Figure 14E:
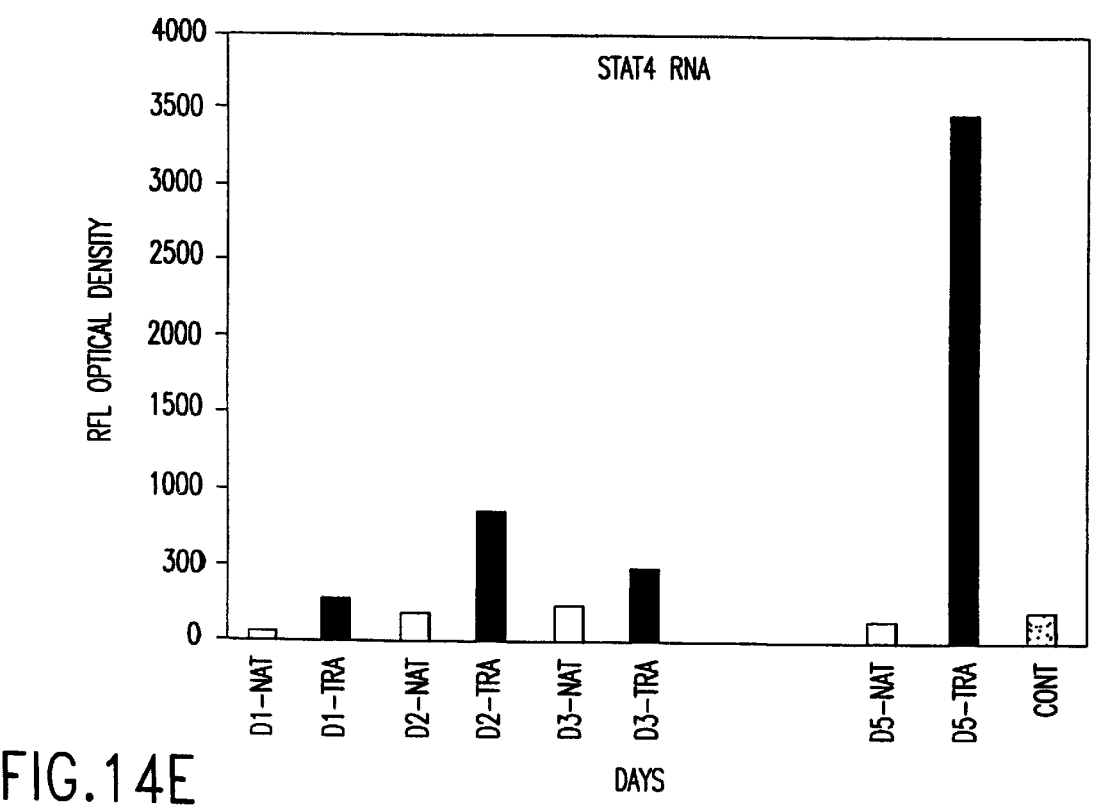
Figure 14F:
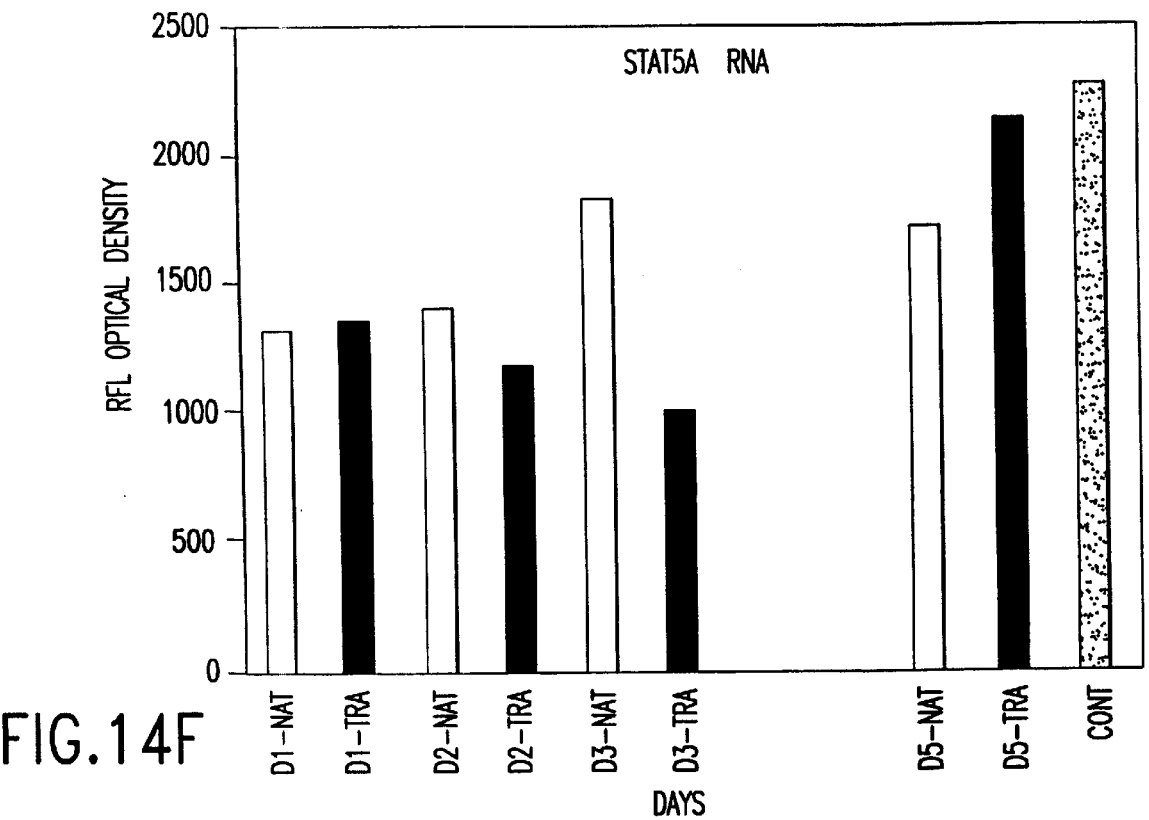
Figure 14G:
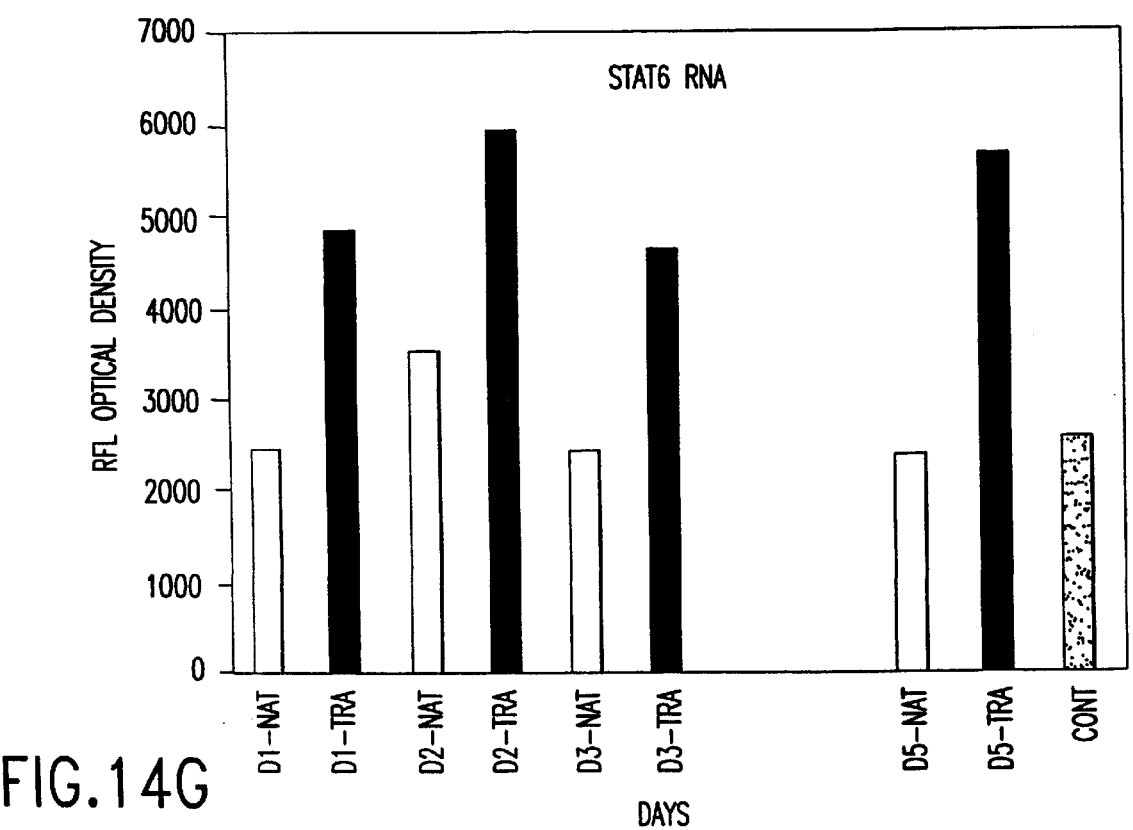

FIG. 14A. Kinetics of Stat RNA expression in heart allografts. Post-transplantation expression of Stats at day 1, day 2, day 3, day 5 were studied using RNA obtained from transplanted (Balb/c), native (B6/129), and control (B6/129) hearts of 8–10 weeks old female mice. Equal amounts of heart RNA (25 μg) were loaded onto each lane of three 1.2% agarose-fornaldehyde gels. Hybridizations were done with probes specific to the transcriptional activation domains and 3'-untranslated regions of the Stats. The Stat probes described in the Materials and Methods Section of Section 8, below, were used for all the hybridizations. The locations of probes are shown underneath the cDNA line drawings next to the hybridization patterns. Murine GAPDH cDNA fragment was used as a control. The Stats and SOCS listed on the right of the GAPDH hybridization patterns indicate the probes used with the particular membranes. Designations: C, control heart (B6/129); N, native heart; T, transplanted heart. These data demonstrate that in the allografts Stats 1 and 2 increase progresssively, peaking at day 5, whereas Stat3 rises to a plateau level by day 1. All 3 Stats increase within native control hearts by day 5.

FIGS. 14B–14G. Kinetics of Stat RNA expression in heart allografts. The Stat levels were normalized against the GAPDH values. Normalized Stat levels are graphed as relative optical density (relative to other Stats). Closed, open, and gray bars indicate Stat RNA levels in transplant, native, and control hearts, respectively. Designations: D1, day 1; D2, day 2; D3, day 3; D5, day5; NAT, native; TRA, transplant; CONT, control.

Figure 15:
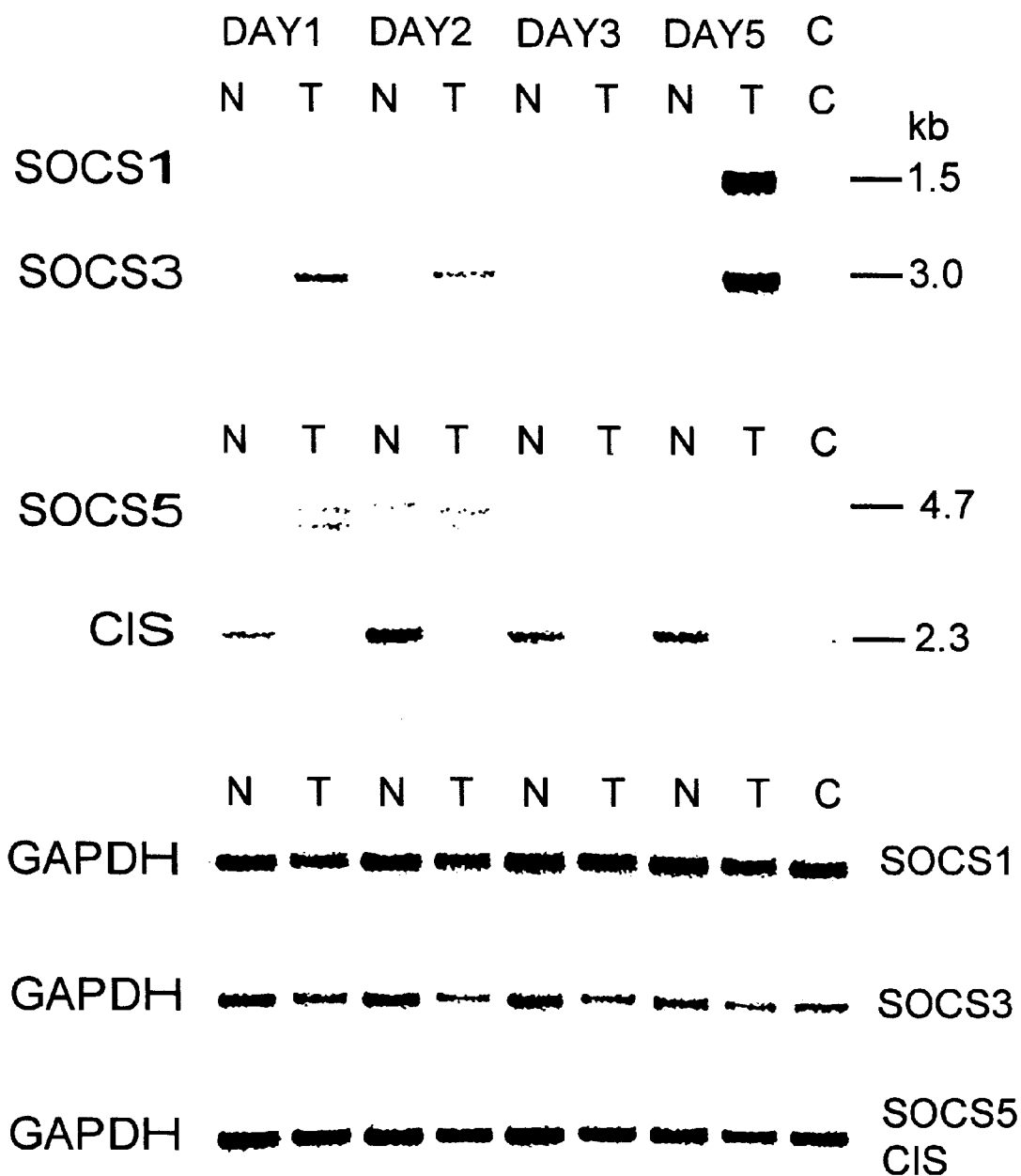

FIG. 15. Kinetics of SOCSCIS RNA expression in heart allografts. Post-transplantation expression of SOCS/CIS RNA at day 1, day 2, day 3, and day 5 post-transplantation were studied by deprobing and rehybridizing the same membranes initially used for studying the Stat RNA expression studies described above in FIG. 14A. Hybridizations were done with probes specific to the 3'-untranslated regions of the SOCS. The SOCS and CIS probes described in the Materials and Methods Section of Section 8, below, were used for all the hybridizations. The locations of probes are shown underneath the cDNA line drawings next to the hybridization patterns. Murine GAPDH cDNA fragment was used as a control. The SOCS/CIS list on the right of the GAPDH hybridization patterns indicate the probes used with the individual membranes. Designations: N, native hearts; T, transplanted hearts; C, control hearts (B6/129). These data demonstrate that SOCS1 is densely expressed in allografts at day 5, with only minor expression in native heart samples. SOCS3 is well-expressed from day 1 in allografts, with a further increase at day 5; no expression was seen in native hearts. SOCS5 is expressed predominantly as a 4.4 kb species, with a minor species at 3.8 kb, in control and native heart samples. However, in allografts, the 2 SOCS5 species are expressed in approximately equal amounts. By contrast, CIS expression remained unchanged in native hearts but decreased in allografts from day 1 onwards.

FIG. 16. The similarity in the expression patterns of Stat4 and SOCS3 RNA in heart allografts. Stat4 and SOCS3 RNA expression in the days that follow the surgery show a high degree of similarity between the patterns of Stat4 and SOCS3 RNAs, albeit differences in their abundance (using Kodak Biomax MR film at 80° C., with intensifying screen, the exposure time for the Stat4 blot was approximately 4 days, and for SOCS3 only 15 hrs).

Figure 17:
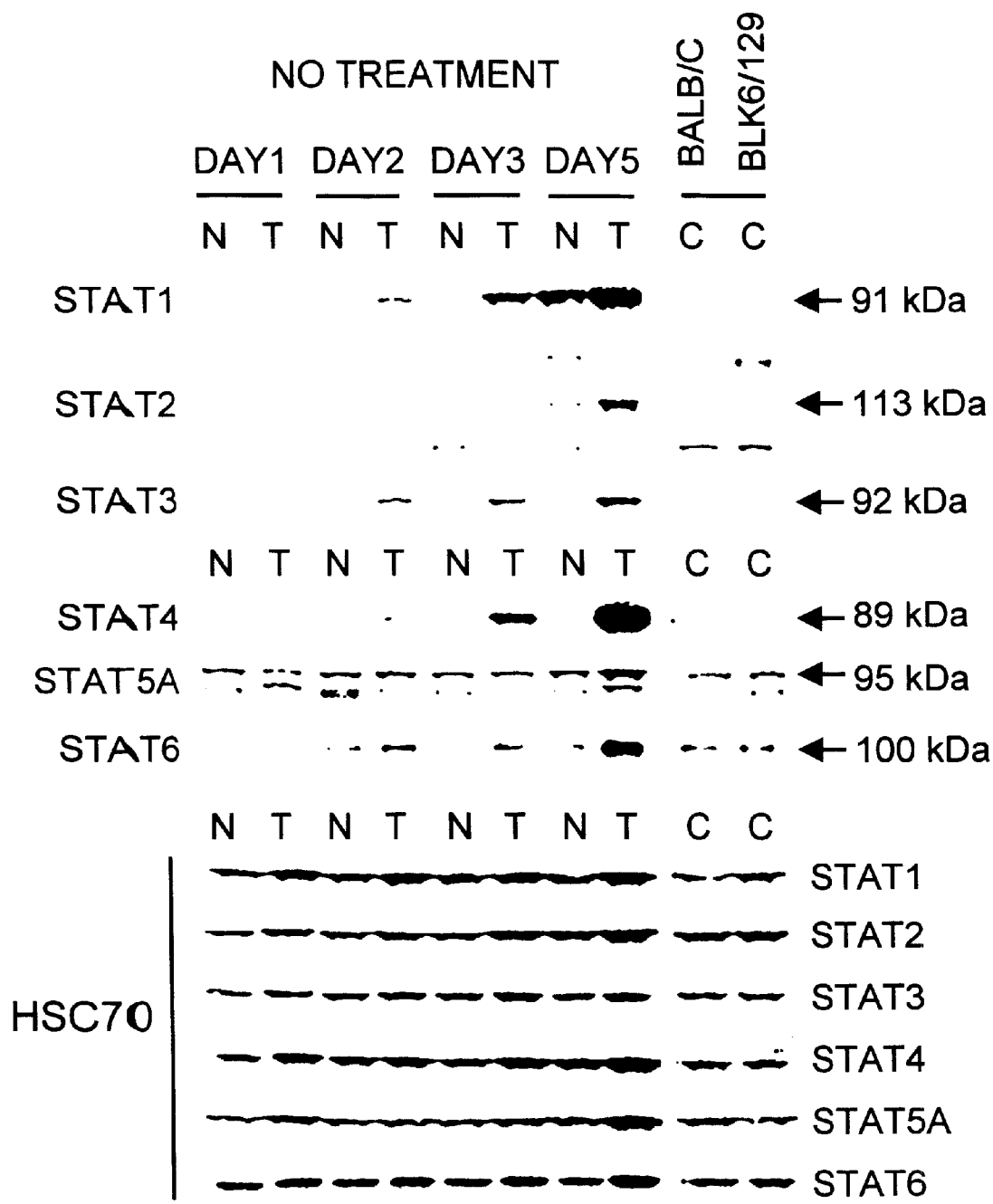

FIG. 17. Stat protein levels following cardiac transplantation. Total proteins from the native and transplant hearts of untreated mice were extracted following transplantation, electrophoresed, transferred onto Immobilon-P membranes and Stat levels analyzed by Western blots as described in Materials and Methods section of Section 8, below. To identify Stats correctly, cell extracts recommended as positive controls by the antibody suppliers were used in the Western blots, together with Precision Protein standards. Designations: N, native hearts; T, transplant hearts; C, control hearts (Balb/c or B6/129), HSC 70, constitutive heat-shock protein. Molecular weights of the Stats are shown on the right. The list on the right of the HSC70 patterns indicates which Stat antibody was used with the individual membranes. These data demonstrate a general agreement with the mRNA data, and show that all of the Stats except Stat5A increase in allografts just prior to rejection (i.e. at day 5), with the greatest and most allograft-specific expression being found for Stat4.

Figure 18:
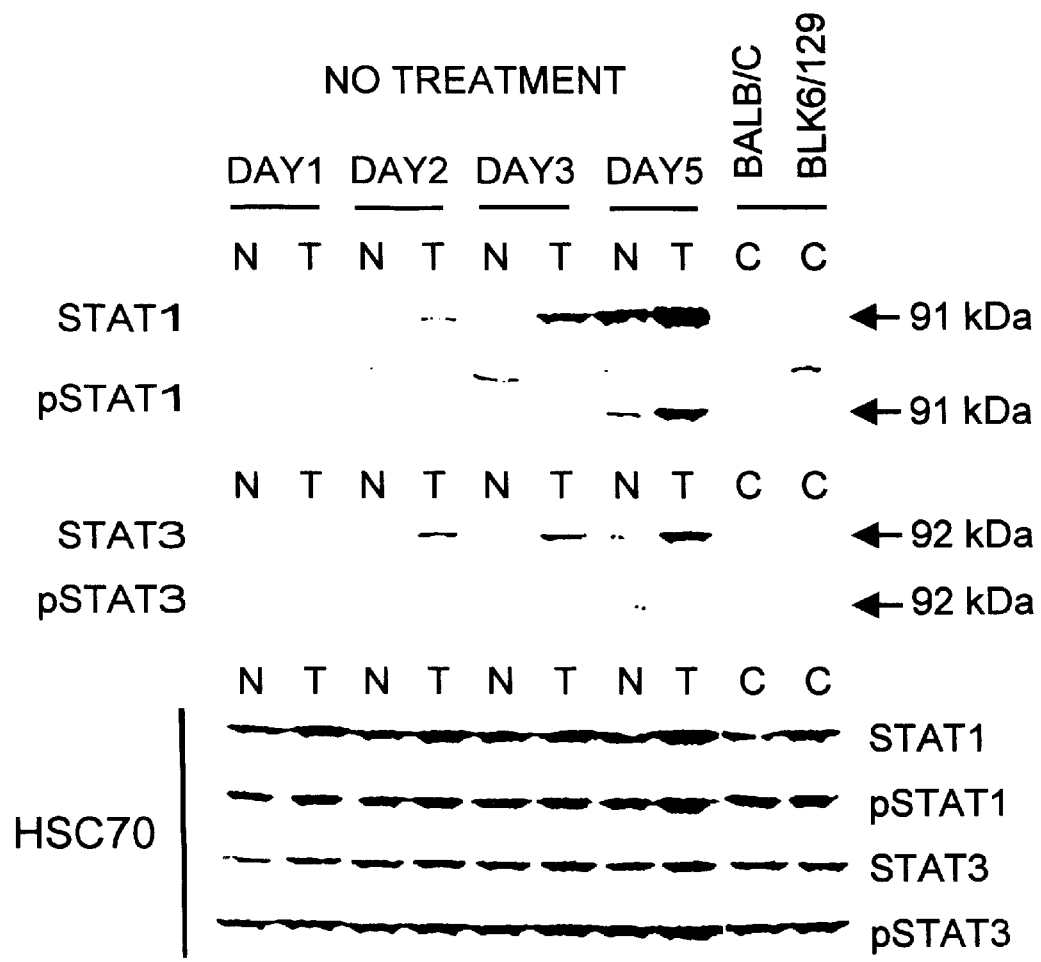

FIG. 18. Phosphorylated Stat levels following cardiac transplantation. Proteins were prepared and Stat levels analyzed by Western blotting as described in Materials and Methods section of Section 8, below. Designations: N, native hearts; T, transplant hearts; C, control hearts (Balb/c or B6/129), HSC 70, constitutive heat-shock protein. Molecular weights of the Stats are shown on the right. These data demonstrate an increase in pStat1 which parallels the rise in Stat1 levels.

Figure 19:
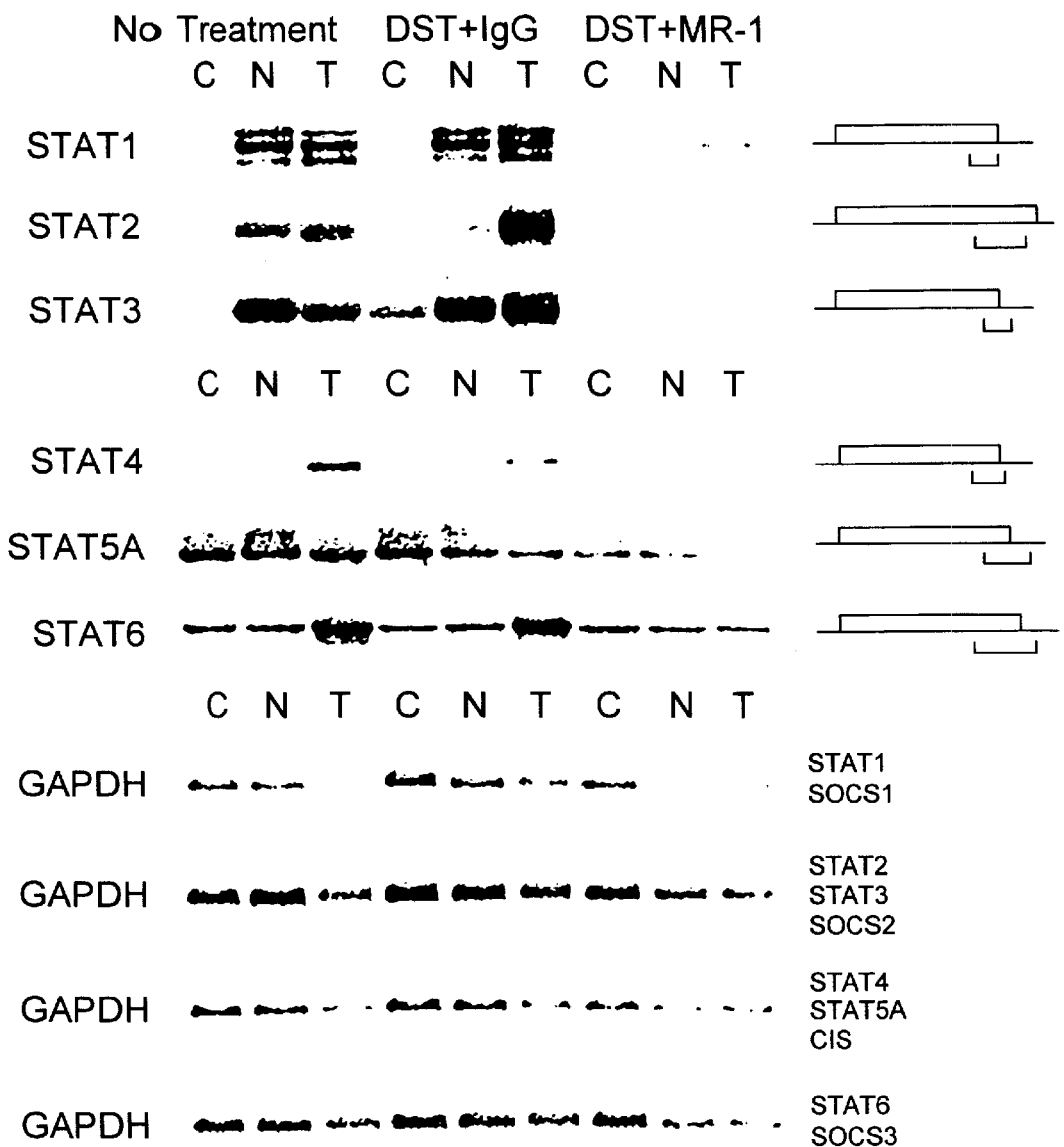

FIG. 19. Stat RNA expression in day 5 post-transplant heart allografts and the effect of anti-CD40L antibody MR-1 on Stat expression. Expression of Stat1, Stat2, Stat3, Stat4, Stat5A and Stat6 RNA was studied using RNA from transplanted (Balb/c) native (B6/129), and control (B6/129) hearts of 8–10 wks old female mice. Equal amounts of heart RNA (25 $\mu$g) were loaded onto each lane of four 1.2% agarose-formaldehyde gels, blotted and analyzed as explained in the Materials and Methods section presented in Section 8, below. The Stat probes described in the Materials and Methods section presented in Section 8 were used for all the hybridizations. Murine GADPH cDNA fragment was used as a control. The size of the Stat RNAs are shown on the right. The Stat and SOCS list on the right of the GAPDH hybridization patterns indicate the probes used with the particular membranes. Designations: C, control heart (B6/129); N, native heart; T, transplanted heart. These data demonstrate that CD40L mAb suppresses expression of each of the Stat mRNA.

Figure 20:
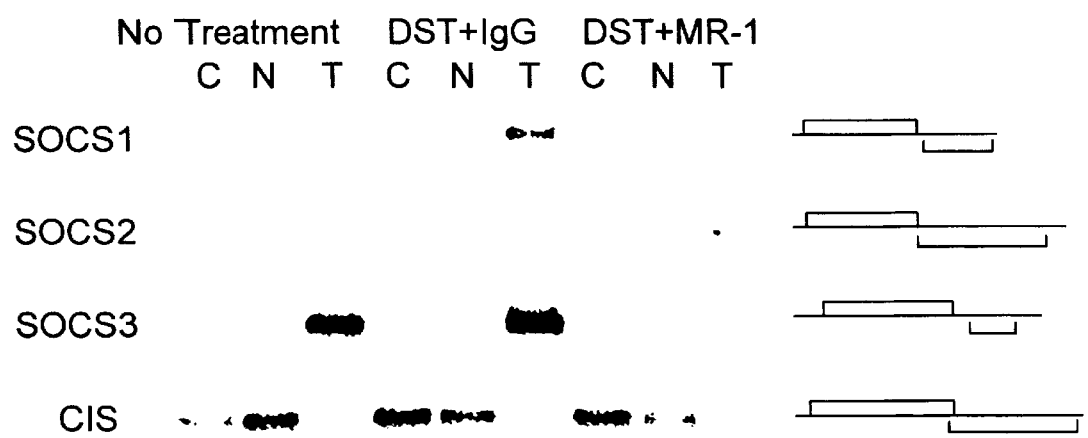

FIG. 20. SOCS/CIS RNA expression in day 5 post-transplant heart allografts and the effect of anti-CD40L antibody MR-1 on SOCS/CIS expression. Expression of SOCS1, SOCS2, SOCS3, and CIS RNA was studied by deprobing and rehybridizing the same membranes initially used for studying the Stat RNA expression. Hybridizations were done with probes specific 3'-untranslated regions of the SOCS. The locations of probes are shown on the right. Designations: C, control heart (B6/129); N, native heart; T, transplanted heart. These data demonstrate that SOCS1 and SOCS3 levels increased during allograft rejection, but CD40L mAb prevented this induction. SOCS2 levels remained constant. CIS levels were decreased in transplants, regardless of CD40L mAb therapy.

Figure 21:
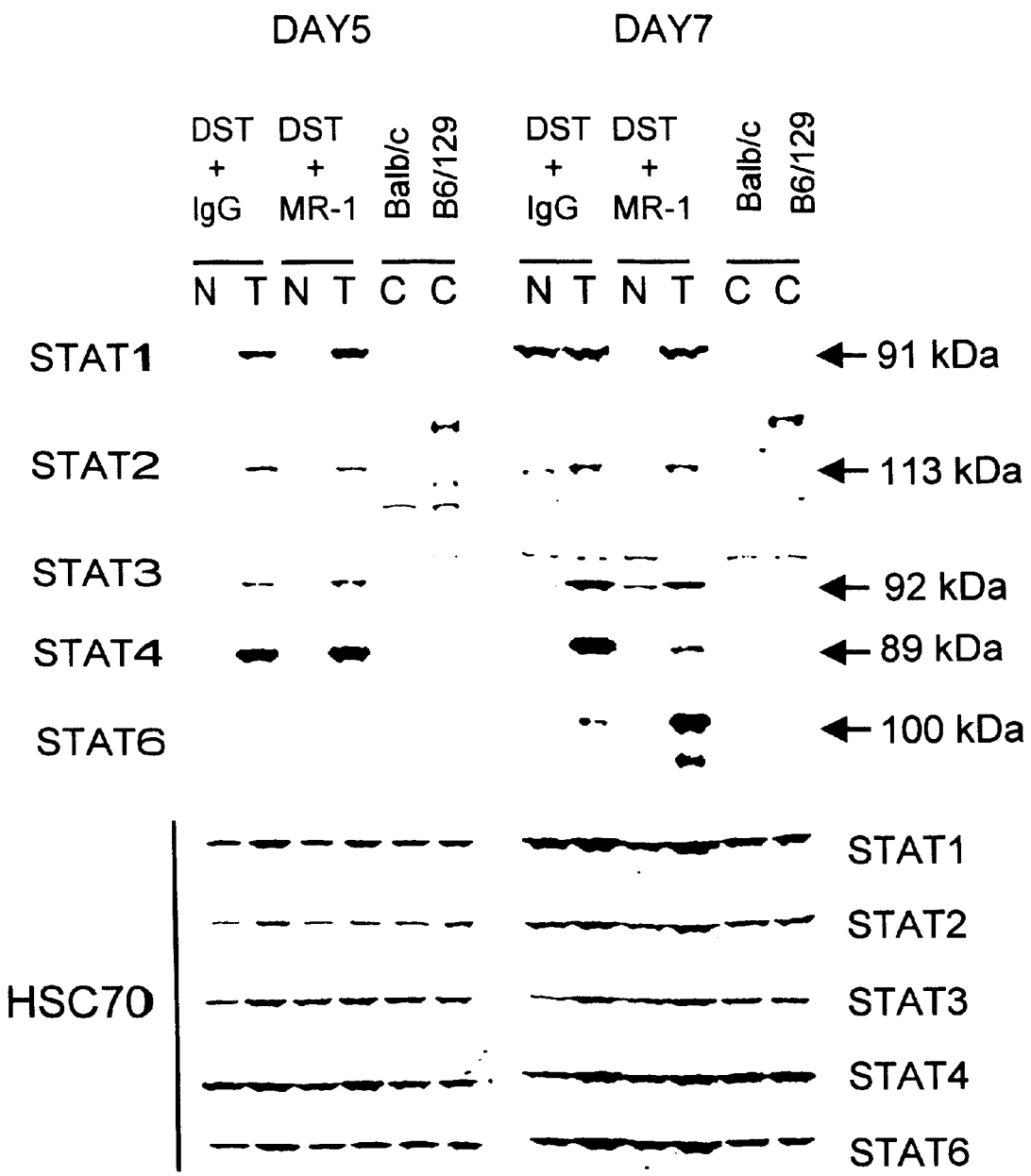

FIG. 21. The effect of treatment with the anti-CD40L monoclonal antibody MR-1 on the levels of Stats. Mice were given a single dose injection (DST plus IgG or DST plus MR-1) the day of the transplant surgery. Proteins were extracted from the native and transplanted hearts of both the IgG and MR-1 treated groups (2 mice/group) 5 days and 7 days following transplant surgery. Designations: C, control heart (B6/129); N, native heart; T, transplanted heart. Molecular weights of the Stats are shown on the right. These data demonstrate that CD40L mAb suppresses intragraft levels of each of the Stat proteins except that of Stat6, which at day 7 in this series was increased post-CD40L mAb therapy.

Figure 22:
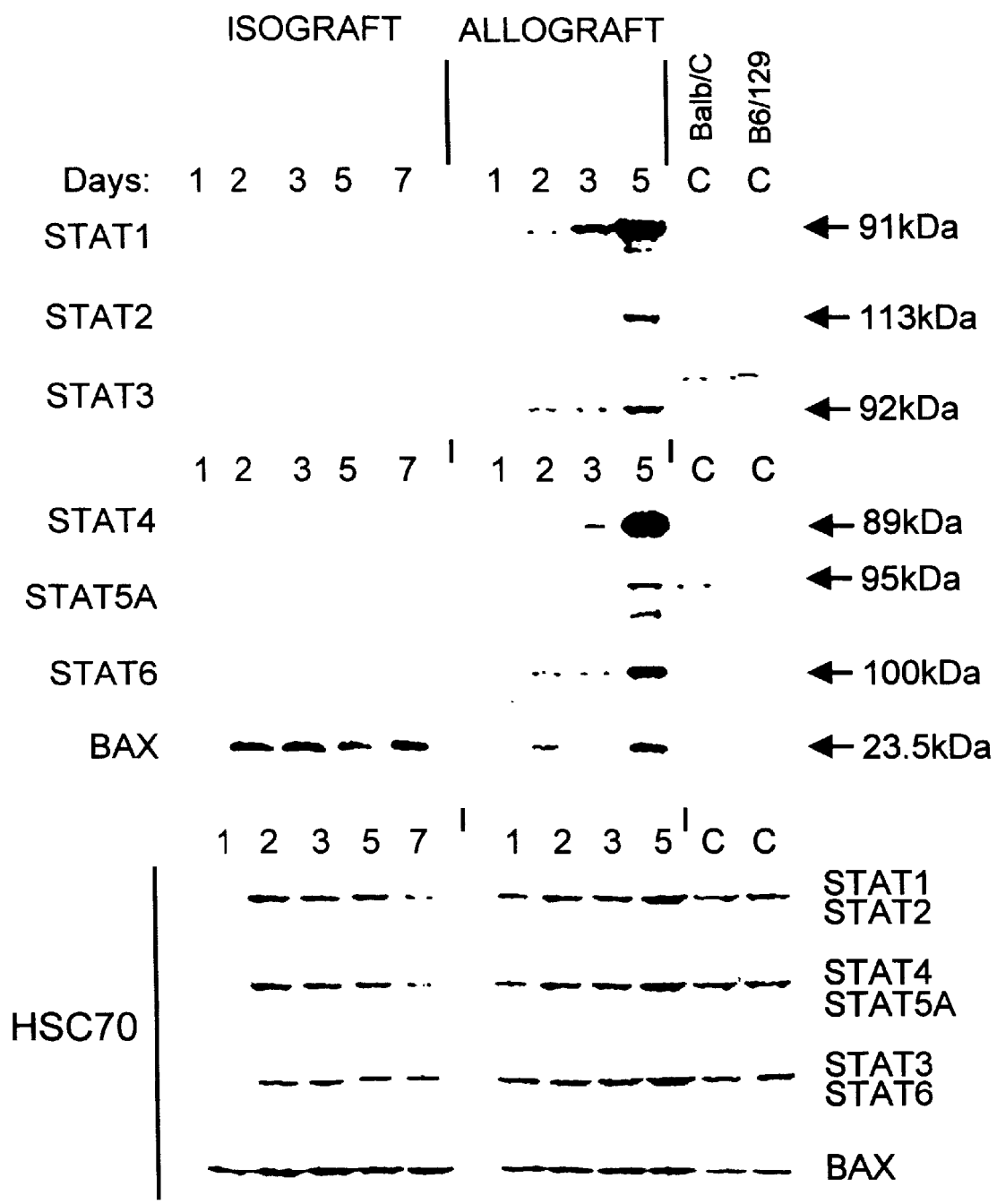

FIG. 22. Stat levels in isografts versus allografts following cardiac transplantation. Stat levels were studied in protein extracts from isografts (both donor and recipient mice were Balb/c) and allografts (donor mice were Balb/c and recipient mice were B6/129). Proteins were prepared and Stat, Bax, and HSC70 levels were analyzed by Western blotting as described in Materials and Methods section of Section 8, below. Designations: N, native hearts; T, transplant hearts; C, control hearts (Balb/c or B6/129), HSC 70, constitutive heat-shock protein. Molecular weights of the Stats are shown on the right. The list on the right of the HSC70 patterns indicates which Stat antibody was used with the individual membranes. These data demonstrate that isografts showed only low levels of Stats, whereas allografts had progressive increases in Stat proteins, peaking at day 5. This pattern of induction was allo-specific and differed from that of an unrelated protein, Bax, which increased in both isografts and allografts.

5. DETAILED DESCRIPTION OF THE INVENTION

5.1. Methods and Compositions for Monitoring Transplant Acceptance and Autoimmune Disorders As demonstrated below, immune rejection can be monitored by determining the amount of particular members of the Jak/Stat signal transduction pathway present within an affected tissue. Specifically, the results presented herein demonstrate that immune rejection can be monitored by determining the amount of Stat4 mRNA or protein, Stat6 mRNA or protein, SOCS1 mRNA or protein, or SOCS3 mRNA or protein present in an affected tissue. In particular, the results presented herein demonstrate that immune rejection can be monitored by determining the amount of Stat4 mRNA or protein, Stat6 mRNA or protein, SOCS1 mRNA or protein, or SOCS3 mRNA or protein, present in an affected tissue. The results presented herein also demonstrate that immune rejection can be monitored by determining the amount of Stat1 mRNA or protein, Stat2 mRNA or protein, or Stat3 mRNA or protein present, e.g., present in an affected tissue.

The term "affected tissue," as used herein, refers to a transplant cell, tissue, organ, or organ system, or a cell, tissue, organ, or organ system. For example, such an affected tissue can include, but is not limited to, heart, liver, kidney, lung, bone marrow, skin, muscle, pancreatic islet, or intestine transplant cells, tissues, organs or organ system. The term "affected tissue," as used herein, also refers to a cell, tissue, organ or organ system that is, or is suspected of, being affected by an autoimmune disorder. For example, such an affected tissue can include, but is not limited to, a cell, tissue, organ, or organ system involved in systemic lupus erythematosus, glomerulonephritis, rheumatoid arthritis, Wegener's granulomatosis, chronic active hepatitis, or vasculitis.

Thus, aspects of the present invention relate to methods and compositions for monitoring such immune rejection. In particular, such methods and compositions can relate, for example, to methods for monitoring acceptance of a transplant in a subject mammal that has undergone a transplant, and can also relate, for example, to methods for monitoring an autoimmune disorder in a subject mammal being treated for or suspected of exhibiting an autoimmune disorder. Such methods and compositions are discussed in detail herein.

In one aspect, the invention relates to methods for monitoring acceptance of a transplant in a subject mammal that has undergone a transplant, wherein said method comprises: determining the amount of at least one of the following: (i) Stat4 mRNA or Stat4 protein, (ii) Stat6 mRNA or Stat6 protein, (iii) SOCS1 mRNA or SOCS1 protein, or (iv) SOCS3 mRNA or SOCS3 protein, present in a transplant sample from the subject. In alternate embodiments, such methods comprise determining the amount of at least two, at least three, or each of (i) to (iv) present in the transplant sample. In certain embodiments, the amount of mRNA is determined, and can, for example, be determined via use of nucleic acid microarrays. In other embodiments, the amount of protein is determined, while in still other embodiments, the amount of mRNA and protein is determined. With respect to Stat6, when the amount of Stat6 is being determined, it is preferable that the amount of Stat6 protein be determined. In any such embodiment wherein a Stat protein amount is determined, the amount determined can be the total amount of the Stat protein present in a sample or, alternatively, can be the amount of phosphorylated Stat protein present in the sample.

In a preferred embodiment, a method for monitoring acceptance of a transplant in a subject mammal that has undergone a transplant comprises determining the amount of Stat4 and Stat6 mRNA or Stat4 and Stat6 protein present in a transplant sample from the subject. Such an embodiment can further comprise determining the ratio of Stat4 to Stat6 amounts.

Such methods can also further comprise comparing the amount or ratio determined to that present in a control sample, for example, a corresponding pre-transplant subject sample (e.g., a sample from a corresponding pre-transplant cell, tissue, organ, or organ system) or a subject blood sample.

In instances wherein the amount of Stat4, SOCS1, or SOCS3 mRNA or protein in the transplant sample is greater than, or the amount of Stat6 mRNA or protein in the transplant sample is less than, that of the control sample, such a result indicates that acceptance of the transplant has not been induced or is not being maintained. Likewise, in instances wherein the ratio of Stat4 to Stat6 in the transplant sample is greater than or equal to that in the control sample, such a result indicates that acceptance of the transplant has not occurred, has not been induced or is not being maintained. Such results suggest a course of action that can include, for example, administration of a high dose of immunosuppressive drugs (e.g., a high dose of corticosteroids, in, for example, the form of a single bolus intravenous injection) and/or administration of compounds to effectuate T cell depletion, including but not limited to administration of anti-CD3 antibodies.

In instances wherein the amount of Stat4, SOCS1, or SOCS3 mRNA or protein in the transplant sample is less than, or the amount of Stat6 mRNA or protein in the transplant sample is equal to or greater than that of the control sample, such a result indicates that acceptance of the transplant has occurred, is being induced or is being maintained. Likewise, in instances wherein the ratio of Stat4 to Stat6 in the transplant sample is less than that in the control sample, such a result indicates that acceptance of the transplant has occurred, has been induced or is being maintained.

The methods for monitoring acceptance of a transplant in a subject mammal that has undergone a transplant can further comprise assaying the transplant sample for evidence of lymphocyte infiltration or tissue damage (cell injury) using standard techniques. For example, histological techniques well known to those of skill in the art can be utilized to evaluate internationally recognized and used diagnostic criteria for the evaluation of graft rejection, which include features specific for each organ involved. For example, for evaluation of heart allograft transplants see, e.g., Billingham, M. E., 1990, J. Heart Transplant. 9(3 Pt 2):272–6. For evaluation of renal allografts see, e.g., Racusen et al., 1999, Kidney Int. 55(2):713–23. In one non-limiting embodiment, immunohistologic evaluation of transplant tissues (such as heart or kidney) can be performed via, e.g., use of labeled antibody techniques to localize and quantitate gene expression. The evaluation of such criteria can, therefore, be enhanced by, for example, localization of Stat4, Stat6, SOCS1 and/or SOCS3 proteins, and/or detection of corresponding mRNAs via, e.g., in situ hybridization.

Additionally, methods for monitoring acceptance of a transplant in a subject mammal that has undergone a transplant can comprise: determining the amount of at least one of the following: (i) Stat1 mRNA or Stat1 protein, (ii) Stat2 mRNA or Stat2 protein, or (iii) Stat3 mRNA or Stat3 protein, present in a cell sample from the subject. In alternate embodiments, such methods comprise determining the amount of at least two or each of (i) to (iii) present in the sample. In certain embodiments, the amount of mRNA is determined, and can, for example, be determined via use of nucleic acid microarrays. In other embodiments, the amount of protein is determined, while in still other embodiments, the amount of mRNA and protein is determined. In any such embodiment wherein a Stat protein amount is determined, the amount determined can be the total amount of the Stat protein present in a sample or, alternatively, can be the amount of phosphorylated Stat protein present in the sample.

In a particular embodiment of such Stat 1-, Stat 2-, and/or Stat 3-related methods, the cell sample is a transplant sample obtained within 2 to 3 days post-transplantation. In an alternative embodiment of such Stat 1-, Stat 2-, and/or Stat 3-related methods, the cell sample is a subject. blood sample.

Such Stat 1-, Stat-2, and/or Stat 3-related methods can also further comprise comparing the amount determined to that present in a control sample, for example, a corresponding pre-transplant subject sample or, in the case of embodiments wherein the cell sample is a transplant sample obtained within 2–3 days post-transplantation, a subject blood sample. In instances wherein the amount of Stat1, Stat2, or Stat3 mRNA or protein in the cell sample is greater than that of the control sample, such a result indicates that acceptance of the transplant has not occurred, has not been induced or is not being maintained. In instances wherein the amount of Stat1, Stat2, or Stat3 mRNA or protein in the transplant sample is less than that of the control sample, such a result indicates that acceptance of the transplant has occurred, is being induced or is being maintained. Such results suggest a course of action that can include, for example, administration of a high dose of immunosuppressive drugs (e.g., a high dose of corticosteroids, in, for example, the form of a single bolus intravenous injection) and/or administration of compounds to effectuate T cell depletion, including but not limited to administration of anti-CD3 antibodies.

Methods for monitoring acceptance of a transplant can be performed at any point post-transplantation. In a preferred embodiment, monitoring is performed daily during the first week post-transplant, followed by weekly monitoring until approximately one month post-transplant, followed by monthly monitoring until approximately one year post-transplant. It is understood, of course, that the frequency of monitoring can, at least in part, depend upon the particular situation (e.g., the nature of the graft, overall health of the recipient subject mammal, the particular immunotherapeutic, immunosuppressive, or immunomodulatory treatment being administered, etc.).

In another aspect, the invention relates to methods for monitoring an autoimmune disorder in a subject mammal, wherein said method comprises: determining the amount of at least one of the following: (i) Stat4 mRNA or Stat4 protein, (ii) Stat6 mRNA or Stat6 protein, (iii) SOCS1 mRNA or SOCS1 protein, or (iv) SOCS3 mRNA or SOCS3 protein, present in a sample from a subject mammal being treated for or suspected of exhibiting the autoimmune disorder, wherein the sample is obtained from a tissue affected by the disorder. In alternate embodiments, such methods comprise determining the amount of at least two, at least three, or each of (i) to (iv) present in the sample. In certain embodiments, the amount of mRNA is determined, in other embodiments, the amount of protein is determined, while in still other embodiments, the amount of mRNA and protein is determined.

In a preferred embodiment, a method for monitoring an autoimmune disorder in a subject mammal comprises determining the amount of Stat4 and Stat6 mRNA or Stat4 and Stat6 protein present in a sample from the subject mammal being treated for or suspected of exhibiting the autoimmune disorder, wherein the sample is obtained from a tissue affected by the disorder. Such an embodiment can further comprise determining the ratio of Stat4 to Stat6 amounts.

Such methods for monitoring an autoimmune disorder in a subject mammal can further comprise comparing the amount or ratio determined to that present in a control sample, for example, a corresponding tissue not affected by the disorder or a subject blood sample.

In instances wherein the amount of Stat4, SOCS1, or SOCS3 mRNA or protein in the sample is greater than, or the amount of Stat6 mRNA or protein in the sample is less than, that of the control sample, such a result indicates that the subject mammal exhibits or continues to exhibit the disorder. Likewise, in instances wherein the ratio of Stat4 to Stat6 in the sample is greater than or equal to that in the control sample, such a result indicates that the subject mammal exhibits or continues to exhibit the disorder. Such results suggest a course of action that can include, for example, the need to increase immunosuppression, as might be undertaken by bolus intravenous steroids (e.g., methylprednisolone) or use of a CD3 mAb such as OKT3.

In instances wherein the amount of Stat4, SOCS1, or SOCS3 mRNA or protein in the sample is less than, or the amount of Stat6 mRNA or protein in the sample is equal to or greater than that of the control sample, such a result indicates that the subject mammal does not exhibit the disorder or that treatment for the disorder is effective. Likewise, in instances wherein the ratio of Stat4 to Stat6 in the transplant sample is less than that in the sample, such a result indicates that the subject mammal does not exhibit the disorder or that treatment for the disorder is effective.

The methods for monitoring an autoimmune disorder in a subject mammal can further comprise assaying the sample for evidence of leukocyte infiltration or tissue damage (cell injury) using standard techniques. For example, histological techniques well known to those of skill in the art can be utilized. Alternatively, standard techniques can be utilized to assay (e.g., in serum) for the presence of autoimmune antibodies associated with the particular autoimmune disorder of interest. For example, there are standard immunohistology methods for detection of autoantibodies directed against a particular tissue (e.g., anti-glomerular basement membrane, anti-parietal cell, anti-thyroid and anti-islet etc.), as well as assays for their detection in serum (e.g. rheumatoid factor assay and anti-double-stranded DNA antibodies). See, e.g., Manual of Clinical Laboratory Immunology (N R Rose, H Friedman, J L Fahey eds. 1986, Am Soc Microbiol, Washington, D.C.; Diagnostic Immunopathology (R B Colvin, et al., eds., 1995, Raven Press, New York).

The methods described herein can be performed using a sample from any subject mammal that has undergone a transplant or either exhibits or is suspected of exhibiting an autoimmune disorder. Preferably, the mammal is a human, however, such subject mammals can also include, but are not limited to, pigs, dogs, cats, horses, cattle, sheep, mice, rats, and rabbits.

It is noted that such methods for monitoring transplant acceptance and for monitoring autoimmunde disorders can be used to determine whether a subject can be effectively treated with a specific agent or class of agents intended to promote transplant acceptance or to treat the autoimmune disorder. Thus, in one embodiment, the present invention provides such methods for determining whether a subject can be effectively treated with an agent for an autoimmune disorder or for reducing immune rejection. Monitoring the influence of agents (e.g., drugs and compounds) on the expression or activity of Stat1, Stat2, Stat3, Stat4, Stat6, SOCS1 or SOCS3 mRNA or polypeptide can, therefore, be applied in basic drug screening, preclinical studies, clinical trials and during therapeutic treatment regimens designed to reduce immune rejection or to ameliorate a symptom of an autoimmune disorder.

The methods described herein comprise determining the amount of Stat1 mRNA or protein, Stat2 mRNA or protein, Stat3 mRNA or protein, Stat4 mRNA or protein, Stat6 mRNA or protein, SOCS1 mRNA or protein, and/or SOCS3 mRNA or protein present in a sample. Standard techniques, as described below, can routinely be utilized to determine these amounts. In general, such methods of the invention can routinely be performed using standard techniques for detecting the presence or absence of a polypeptide or nucleic acid of the invention in a biological sample. This involves obtaining a biological sample from a test subject and contacting the biological sample with a compound or an agent capable of detecting the polypeptide or mRNA such that the presence of a polypeptide or nucleic acid of the invention is detected in the biological sample.

When comparing levels, such comparisons can be either quantitative or qualitative. Thus, in qualitative instances, for example, in instances wherein a control sample is determined to contain none of a given molecule (that is, Stat1, Stat2, Stat3, Stat4, Stat6, SOCS1, SOCS3 mRNA or protein) and the molecule is determined to be present in the test sample (that is, either a transplant or autoimmune sample), the amount of the molecule in the test sample is greater than that present in the control sample. In quantitative instances wherein both the control and test samples are determined to contain a given molecule, using standard techniques, the amount in the test sample can routinely be determined to be greater than, equal to, or less than that of the control sample. Likewise, using standard techniques, the ratio of Stat4 to Stat6 mRNA or protein present in test and control samples can routinely be determined. In general, the amount of a given molecule in test and control samples will differ by at least 2-fold, and in certain instances, 2.5-fold, at least 3-fold, at least 4-fold, at least 5-fold, or at least 10-fold.

With respect to methods for monitoring acceptance of a transplant, such methods can be performed on any transplant from which a sample to be analyzed can be obtained. Such transplants include, but are not limited to, heart, liver, kidney, lung, bone marrow, skin, muscle, pancreatic islet, or intestine transplants.

Likewise, with respect to methods for monitoring autoimmune disorders, such methods can be performed for any autoimmune disorder (or suspected autoimmune disorder) for which a sample of an affected tissue (or a tissue suspected of being affected) can obtained. Such autoimmune disorders include, but are not limited to, systemic lupus erythematosus, glomerulonephritis, rheumatoid arthritis, Wegener's granulomatosis, chronic active hepatitis, and vasculitis Methods for obtaining samples from a recipient transplant subject mammal or from a subject mammal exhibiting or suspected of exhibiting an autoimmune disorder are well known to those of skill in the art. Such methods can include biopsy methods, such as, for example, standard needle or punch biopsy methods. In certain embodiments, a particular subset of the sample can be isolated for the analysis. For example, a particular subset of a transplant or autoimmune disorder sample containing cell types of interest (e.g. leukocyte cell types) can be isolated. Such isolation can performed utilizing standard techniques such as, for example, laser microdissection (see, e.g., Fend et al., 1999, Am. J. Pathol. 154(1):61–6; Schutze et al., 1998, Nat. Biotechnol. 16(8):737–42; and Simone et al., 1998, Trends Genet. 14(7): 272–6).

Stat1, Stat2, Stat3, Stat4, Stat6, SOCS1 and SOCS3 nucleic acid and amino acid sequences are well known to those of skill in the art. For Stat1, see, for example, Schindler et al., 1992, Proc. Natl. Acad. Sci. U.S.A. 89:7836–7839 and Zhong et al., 1994, Science 264:95–98. For Stat2, see, for example, Yan et al., 1995, Nucleic Acids Res. 23(3): 459–463, Bluyssen and Levy, 1997, J. Biol. Chem. 272(7): 4600–4605, and Paulson et al., 1999, J. Biol. Chem. 274 (36):25343–25349. For Stat3, see, for example, Ripperger, 1995, J. Biol. Chem. 270(50):29998–30006, Akira et al., 1994, Cell 77(1):63–71, Zhong et al., 1994, Science 264:95–98, Zhong et al., 1994, Proc. Natl. Acad. Sci. U.S.A. 91:4806–4810. For Stat4, see, for example, Quelle et al., 1995, Mol. Cell. Biol. 15:3336–3343; and Hou et al., 1994, Science 265:1701–1706. For Stat6, see, for example, Yamamoto et al., 1994, Mol. Cell. Biol. 17:4342–4349; Zhang et al., 1994, 91:4806–4810; and Yamamoto et al., 1997, ytogenet. Cell. 77:207–210. For SOCS1 and 3 sequences, see, for example, Starr et al., 1997, Nature, 387:917–921; Minamoto et al., 1997, Biochem., Biophys. Res. Commun. 237:79–83; Masuhara et al., 1997, Biochem, Biophys. Res. Commun. 239:439–446; Naka et al., 1997, Nature 387:924–929; and Endo et al., 1997, Nature 387:921–924. Representative examples of human Stat1, Stat2, Stat3, Stat4, Stat6, SOCS1 and SOCS3 sequences are shown in FIGS. 1-7 (SEQ ID NOs:1–14), respectively.

Further, additional forms, e.g., alleles or species homologs of such sequences can routinely be obtained and detected using the sequences described above in conjunction with standard cloning and hybridization techniques such as those find in Sambrook et al., eds., *Molecular Cloning: A Laboratory Manual*, $2^{nd}$. ed., *Cold Spring Harbor Laboratory*, Cold Spring Harbor Laboratory Press, Cold Spring Harbor, N.Y., 1989.

The methods for monitoring transplant acceptance or monitoring an autoimmune disorder can be performed with kits designed for carrying out such methods. As such, the present invention also relates to kits for monitoring transplant acceptance and autoimmune disorders.

Such kits can be utilized for determining the amount of Stat1, Stat2, Stat3, Stat4, Stat6, SOCS1, and/or SOCS3 mRNA present within a sample (e.g., a transplant sample or a sample obtained from an autoimmune tissue or a tissue suspected of being effected by an autoimmune disorder). Alternatively, such kits can be utilized for determining the amount of Stat1, Stat2, Stat3, Stat4, Stat6, SOCS1, and/or SOCS3 polypeptide present within a sample (e.g., a transplant sample or a sample obtained from an autoimmune tissue or a tissue suspected of being effected by an autoimmune disorder). A kit can be capable of being used to determine the amount of any one, two, three, four, five, six, or seven of Stat1, Stat2, Stat3, Stat4, Stat6, SOCS1, and/or SOCS3 sequences (mRNA or polypeptide).

The kit, for example, can comprise a microarray for determining such amounts, wherein the microarray comprises one or more nucleic acid sequences immobilized onto a solid surface, said nucleic acid sequence or sequences exhibiting complementarity to at least one of Stat1, Stat2, Stat3, Stat4, Stat6, SOCS1, and/or SOCS3 mRNA. The kit can, in addition, comprise a labeled compound or agent capable of detecting the of Stat1, Stat2, Stat3, Stat4, Stat6, SOCS1, and/or SOCS3 polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for use in determining the amount or amounts of mRNA or polypeptide, and can also include directions for monitoring and diagnosis.

For antibody-based kits, the kit can comprise, for example: (1) a first antibody (e.g., attached to a solid support) which binds to a of Stat1, Stat2, Stat3, Stat4, Stat6, SOCS1, and/or SOCS3 polypeptide; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a of Stat1, Stat2, Stat3, Stat4, Stat6, SOCS1, and/or SOCS3 nucleic acid sequence; or (2) a pair of primers useful for amplifying a of Stat1, Stat2, Stat3, Stat4, Stat6, SOCS1, and/or SOCS3 nucleic acid molecule. The kit can also comprise, e.g., a buffering agent, a preservative, or a protein stabilizing agent. The kit can also comprise components necessary for detecting the detectable agent (e.g., an enzyme or a substrate).

For microarray-based kits, such kits can comprise a nucleotide sequence, e.g., an oligonucleotide sequence, immobilized onto the surface of a solid support (e.g., a glass or porous solid support).

The kits can also contain a control sample or a series of control samples (postive control, negative control, or both) which can be assayed and compared to the test sample contained.

Each component of the kit is usually enclosed within an individual container and all of the various containers are within a single package along with instructions for observing and monitoring transplant acceptance or monitoring an autoimmune disorder.

NUCLEIC ACID DETECTION

Preferred agents for detecting an mRNA of interest (that is Stat1, Stat2, Stat3, Stat4, Stat6, SOCS1 or SOCS3 mRNA) are primers or labeled nucleic acid probes capable of hybridizing to the mRNA under stringent hybridization conditions. Nucleic acid probes can be, for example, full-length sequences, such as the nucleic acid sequences depicted in FIGS. 1–7 (SEQ ID NOs:1, 3, 5, 7, 9, 11 and 13), or complements thereof, or portions of such sequences (or complements thereof, such as oligonucleotides of at least about 12, 15, 25 30, 50, 100, 250 or 500 nucleotides in length and sufficient to specifically hybridize under stringent conditions to the mRNA.

In certain embodiments, determination of the amount of Stat1, Stat2, Stat3, Stat4, Stat6, SOCS1 and/or SOCS3 mRNA involves the use of a probe/primer in a polymerase chain reaction (PCR) (see, e.g., U.S. Pat. Nos. 4,683,195 and 4,683,202), such as, for example, anchor PCR, RACE PCR or RT-PCR. Such methods can include the steps of collecting a cell sample, isolating mRNA from the cells of the sample, reverse transcribing the mRNA, contacting the sample with one or more primers which specifically hybridize to the selected sequence under conditions such that hybridization and amplification of the sequence (if present) occurs, and determining the amount of product that is present.

Alternative amplification methods can also routinely be utilized. Such methods can include, for example, self sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), or any other nucleic acid amplification method, followed by the detection/quantitation of the amplified molecules using techniques well known to those of skill in the art. These schemes are especially useful for the detection of nucleic acid molecules if such molecules are present in very low numbers.

As used herein, the term "hybridizes under stringent conditions" is intended to describe conditions for hybridization and washing under which nucleotide sequences at least 60% (preferably at least 75%, more preferably at least 85%, most preferably at least 95%) identical to each other typically remain hybridized to each other. Such stringent conditions are known to those skilled in the art and can be found in Current Protocols in Molecular Biology, John Wiley & Sons, NY (1989), 6.3.1–6.3.6. A preferred, non-limiting example of stringent hybridization conditions are hybridization in 6x sodium chloride/sodium citrate (SSC) at about 45° C., followed by one or more washes in 0.2xSSC, 0.1% SDS at 50–65° C. (preferably 65° C.).

Probes can comprise any readily detectable label moiety. For example, probes utilized herein comprise a radioisotope, a fluorescent compound, an enzyme, or an enzyme co-factor as a label moiety.

In alternate embodiments, the Stat1, Stat2, Stat3, Stat4, Stat6, SOCS1 and/or SOCS3 mRNA sequences can be detected "in situ" directly upon the sample, e.g., the biopsy sample. Techniques for such procedures are well known to those of skill in the art. See, e.g., Nuovo, G. J., 1992, "PCR In Situ Hybridization: Protocols and Applications," Raven Press, NY.

In other embodiments, the amount of Stat1, Stat2, Stat3, Stat4, Stat6, SOCS1 and/or SOCS3 mRNA can be determined by hybridizing nucleic acid arrays, e.g., microarrays. In a specific embodiment of the invention, the expression of one or more of Stat1, Stat2, Stat3, Stat4, Stat6, SOCS1 and SOCS3 is measured or detected using a DNA microarray. A DNA microarray or chip is a microscopic array of DNA fragments or synthetic oligonucleotides, disposed in a defined pattern on a solid support, wherein they are amenable to analysis by standard hybridization methods (see, e.g., Schena, 1996, BioEssays 18: 427).

Microarrays share certain preferred characteristics: The arrays are reproducible, allowing multiple copies of a given array to be produced and easily compared with each other. Preferably the microarrays are small, usually smaller than 5 $cm^2$, and they are made from materials that are stable under binding (e.g., nucleic acid hybridization) conditions. Microarrays contain a surface to which sequences corresponding to gene products (e.g., mRNA, cDNA, cRNA, or complements thereof), can be specifically hybridized or bound at a known position. For practicing the methods of the present invention, the binding sites of the microarray are polynucleotides, preferably DNA polynucleotides, that specifically hybridize to at least a portion of Stat1, Stat2, Stat3, Stat4, Stat6, SOCS1, or SOCS3 mRNA or cDNA, or any combination of such mRNA or cDNA molecules, produced by a subject mammal. That is, a given binding site or unique set of binding sites in the microarray will specifically bind the product (e.g., mRNA or cDNA) of a single gene, e.g., Stat1, Stat2, Stat3, Stat4, Stat6, SOCS1 or SOCS3.

Preferably, the nucleotide sequence of each of the different polynucleotide bound to the surface is in the range of about 15 to about 100 nucleotides in length. Polynucleotides can be synthesized using conventional methods, such as phosphoramidite-based synthesis methods. Alternatively, the binding site polynucleotide sequences can be derived from cDNA or genomic clones.

DNA microarrays can be probed using mRNA, extracted and, optionally, reverse-transcribed and amplified from a sample (e.g., a transplant, autoimmune or control sample). Nucleic acid hybridization and wash conditions are optimally chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., 1996, Genome Research 6:639–645, and Chee et al., 1996, Science 274:610–614) or positive controls. Thus, in a preferred embodiment, a microarray of the invention further comprises a binding site designed to act as a negative control and/or a binding site designed to act as a positive control. For example, a positive control can relate to a constitutively expressed gene sequence, e.g., a ubiquitin sequence, HSC70, or GADPH. A negative control can relate to a gene sequence not expressed in the test cell or tissue being assayed.

Exemplary, non-limiting examples of hybridization conditions that can be utilized with DNA microarrays are as follows: hybridization in 5xSSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1×SSC plus 0.2% SDS) (Shena et al., 1996, Proc. Natl. Acad. Sci. USA, 93:10614–19).

The use of a two-color fluorescence labeling and detection scheme to define alterations in gene expression has been described, e.g., in Shena et al., 1995, Science 270:467–470. An advantage of using mRNA, cRNA, or cDNA labeled with two different fluorophores is that a direct and internally controlled comparison of the mRNA levels corresponding to each arrayed gene in two cell states (e.g., control and transplant) can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a transplant or autoimmune sample cell.

To facilitate detection the mRNA or cDNA are typically labeled with fluorescent dyes that emit at different wavelengths. Examples of fluorescent dyes include, but are not limited to, rhodamine, fluorescein, isothiocyanate, rhodamine, phycoerythrin, phycocyanin, allophycocyanin, o-phthaldehyde and fluorescamine. The fluorescence emissions at each site of a DNA array can be, preferably, detected by scanning confocal laser microscopy. In one embodiment, a separate scan, using the appropriate excitation line, is carried out for each of two fluorophores used. Alternatively, a laser can be used that allows simultaneous specimen illumination at wavelengths specific to the two fluorophores and emissions from the two fluorophores can be analyzed simultaneously (see, e.g., Shalon et al., 1996, Genome Research 6:639–645).

Signals are recorded and, in a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site.

It will be appreciated that when mRNA or cRNA is hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cRNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

Microarrays can be made in a number of ways well known to those of skill in the art. With respect to the nucleic acids of the binding sites, the nucleic acid for the microarray can be generated by synthesis of synthetic polynucleotides or oligonucleotides, e.g., using N-phosphonate or phosphoramidite chemistries (e.g., Froehler et al., 1986, Nucleic Acid Res 14:5399–5407). In some embodiments, synthetic nucleic acids include non-natural bases, e.g., inosine. Additionally, it is possible to vary the charge on the phosphate backbone of the oligonucleotide, for example, by thiolation or methylation, or even to use a peptide rather than a phosphate backbone. The making of such modifications is within the skill of one trained in the art. Further, nucleic acid analogues may be used as binding sites for hybridization. An example of a suitable nucleic acid analogue is peptide nucleic acid (see, e.g., Egholm et al., 1993, Nature 365:566–568; see also U.S. Pat. No. 5,539,083, Cook et al., entitled "Peptide nucleic acid combinatorial libraries and improved methods of synthesis," issued Jul. 23, 1996). In addition, binding (hybridization) sites can also be made from plasmid or phage clones of genes, cDNAs (e.g., expressed sequence tags), or inserts therefrom (Nguyen et al., 1995, Genomics 29:207–209). In yet another embodiment, the polynucleotide of the binding sites is RNA.

The nucleic acid or analogue is attached to a solid support to produce the binding site. Solid supports may be made from glass, silicon, plastic (e.g., polypropylene, nylon, polyester), polyacrylamide, nitrocellulose, cellulose acetate or other materials. In general, non-porous supports, and glass in particular, are preferred. The solid support may also be treated in such a way as to enhance binding of oligonucleotides thereto, or to reduce non-specific binding of unwanted substances thereto. Preferably, the glass support is treated with polylysine or silane to facilitate attachment of oligonucleotides to the slide.

Methods of immobilizing DNA on the solid support may include direct touch, micropipetting (Yershov et al., Proc. Natl. Acad. Sci. USA, 1996, 93:4913–4918), or the use of controlled electric fields to direct a given oligonucleotide to a specific spot in the array (U.S. Pat. No. 5,605,662). In principal, any type of array, for example, dot blots on a nylon hybridization membrane (see Sambrook et al., 1989, *Molecular Cloning—A Laboratory Manual* (2nd Ed.), Vols. 1–3, Cold Spring Harbor Laboratory, Cold Spring Harbor, N.Y.), can used, although, as will be recognized by those of skill in the art, very small arrays are be preferred because hybridization volumes will be smaller. DNA can typically be immobilized at a density of 50, 75, 100, up to 10,000 oligonucleotides per $cm^2$ and preferably at a density of about 1000 oligonucleotides per $cm^2$.

In addition, nucleic acids can be attached to a surface by printing on glass plates (Schena et al., 1995, Science 270:467–470; DeRisi et al., 1996, Nature Genetics 14:457–460; Shalon et al., 1996, Genome Res. 6:639–645; and Schena et al., Proc. Natl. Acad. Sci. USA, 1996, 93(20):10614–19.) As an alternative to immobilizing prefabricated oligonucleotides onto a solid support, it is possible to synthesize oligonucleotides directly on the support (Maskos et al., 1993, Nucl. Acids Res. 21: 2269–70; Fodor et al., 1991, Science 251: 767–73; Lipshutz et al., 1999, Nat. Genet. 21(1 Suppl):20–4; McGall et al., Proc. Natl. Acad. Sci. USA 93: 13555–60, 1996). Other methods for making microarrays, e.g., by masking (Maskos and Southern, 1992, Nuc. Acids Res. 20:1679–1684), may also be used.

PROTEIN DETECTION

Standard techniques can also be utilized for determining the amount of the protein or proteins of interest (that is, Stat1, Stat2, Stat3, Stat4, Stat6, SOCS1 and/or SOCS3 protein) present in a sample. It is to be understood, that such a determination of the amount of a protein present includes determining the total amount of a protein present, and also includes, especially with respect to determining the amount of a Stat protein present, determining the amount of a phosphorylated form of the protein present.

For example, standard techniques can be employed using, e.g., immunoassays such as, for example, Western blot, immunoprecipitation followed by sodium dodecyl sulfate polyacrylamide gel electrophoresis (SDS-PAGE), immunocytochemistry, and the like to determine the amount of the protein or proteins of interest present in a sample. A preferred agent for detecting a protein of interest is an antibody capable of binding to a protein of interest, preferably an antibody with a detectable label.

With respect to determining the amount of a phosphorylated form of a protein of interest that is present in a sample, such a determination can also be performed using standard techniques well known to those of skill in the art. For example, such a determination can include, first, immunoprecipitation with an antibody that is specific for a phosphorylated amino acid residue, e.g., an anti-phosphotyrosine antibody, such that all exhibiting such a phosphorylated residue in a sample will be inmmunoprecipitated. Second, the immunoprecipitated proteins can be contacted with a second antibody that is specific for the particular protein of interest, e.g., Stat1, Stat2, Stat3, Stat4, or Stat6. Alternatively, a phosphorylated protein of interest can be identified and quantitated using an antibody specific for the phosphorylated form of the particular protein itself, e.g, an antibody specific for phosphorylated Stat1 that does not recognize non-phosphorylated Stat1. Such antibodies exist, and are well known to those of skill in the art.

For such detection methods, protein from the sample to be analyzed can easily be isolated using techniques which are well known to those of skill in the art. Protein isolation methods can, for example, be such as those described in Harlow and Lane (Harlow, E. and Lane, D., 1988, "Antibodies: A Laboratory Manual", Cold Spring Harbor Laboratory Press, Cold Spring Harbor, N.Y.).

Preferred methods for the detection of the protein or proteins of interest involve their detection via interaction with a protein-specific antibody. For example, antibodies directed a protein of interest can be utilized as described herein. Antibodies directed against Stat1, Stat2, Stat3, Stat4, Stat6, SOCS1 or SOCS3 protein are well known to those of skill in the art. For example, antibodies directed against Stat1, Stat2, Stat3, Stat4, Stat6, SOCS1 or SOCS3 can be obtained from such companies as Zymed Laboratories, Inc. (South San Francisco, Calif.), Santa Cruz Biotechnology, Inc. (Santa Cruz, Calif.), and Research Diagnostics, Inc., (Flanders, N.J.). Alternatively, such antibodies can be generated utilizing standard techniques well known to those of skill in the art. See, e.g., Section 5.3, below, for a more detailed discussion of such antibody generation techniques. Briefly, such antibodies can be polyclonal, or more preferably, monoclonal. An intact antibody, or a fragment thereof (e.g., Fab or F(ab')$_2$) can, for example, be used.

For example, antibodies, or fragments of antibodies, specific for a protein of interest can be used to quantitatively or qualitatively detect the presence of the protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by removing a histological specimen (e.g., a biopsy specimen) from a patient, and applying thereto a labeled antibody thereto that is directed to a Stat1, Stat2, Stat3, Stat4, Stat6, SOCS1 or SOCS3 protein. The antibody (or fragment) is preferably applied by overlaying the labeled antibody (or fragment) onto a biological sample. Through the use of such a procedure, it is possible to determine not only the presence of the protein of interest, but also its distribution, its presence in lymphocytes within the sample. A wide variety of well-known histological methods (such as staining procedures) can be utilized in order to achieve such in situ detection.

Immunoassays for a protein of interest typically comprise incubating a biological sample, e.g., a biopsy or subject blood sample, of a detectably labeled antibody capable of identifying a protein of interest, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which a Stat1-, Stat2-, Stat3-, Stat4-, Stat6-, SOCS1- or SOCS3-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, ENZYME IMMUNOASSAY, CRC Press, Boca Raton, Fla.; Ishikawa, E. et al., (eds.), 1981, ENZYME IMMUNOASSAY, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope (e.g. $^{125}I$, $^{131}I$, $^{35}S$ or $^{3}H$) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.2. Methods and Compositions for Identifying Compounds That Reduce Immune Rejection As demonstrated below, immune rejection can be reduced and tolerance can be induced by modulating the amount of particular members of the Jak/Stat pathway present, expressed or active within an affected tissue. Specifically, the results presented herein demonstrate that modulation of Stat1, Stat2, Stat3, Stat4, Stat6, SOCS1 and/or SOCS3 levels can reduce immune rejection.

The methods described herein identify compounds that modulate the expression and/or activity of Stat1, Stat2, Stat3, Stat4, Stat6, SOCS1 or SOCS3 sequences in a manner that can reduce immune rejection (either, for example, in a transplant situation or in an autoimmune situation). The compounds identified via such methods are, therefore, useful as lead compounds in the development of therapeutic compositions for the reduction of immune rejection. Such methods are particularly useful in that the effort and great expense involved in testing potential therapeutics in vivo is efficiently focused on those compounds identified via the in vitro and ex vivo methods described herein.

Thus, the present invention relates to a method for identifying a compound to be tested for an ability to reduce immune rejection, said method comprises: (a) contacting an activated T cell sample with a test compound; (b) determining the amount of at least one of the following: (i) Stat1 mRNA or Stat1 protein, (ii) Stat2 mRNA or Stat2 protein, (iii) Stat3 mRNA or Stat3 protein, (iv) Stat4 mRNA or Stat4 protein, (v) Stat6 mRNA or Stat6 protein; (vi) SOCS1 mRNA or SOCS1 protein, or (vii) SOCS3 mRNA or SOCS3 protein, present in (a); and (c) comparing the amount(s) in (a) to that/those present in a corresponding control activated T cell sample that has not been contacted with the test compound, so that if the amount of (i), (ii), (iii), (iv), (vi), or (vii) is decreased, or the amount of (v) is increased, relative to the amount in the control sample, a compound to be tested for an ability to reduce immune rejection is identified. In alternate embodiments, such methods comprise determining the amount of at least two, at least three, at least four, at least five, at least six, or each of (i) to (vii) present in the activated T cell sample and comparing the amounts to those present in the control sample.

In certain embodiments, the amount of mRNA is determined, in other embodiments, the amount of protein is determined, while in still other embodiments, the amount of mRNA and protein is determined. With respect to Stat6, when the amount of Stat6 is being determined, it is preferable that the amount of Stat6 protein be determined. In any such embodiment wherein a Stat protein amount is determined, the amount determined can be the total amount of the Stat protein present in a sample or, alternatively, can be the amount of phosphorylated Stat protein present in the sample.

In a preferred embodiment of a method for identifying a compound to be tested for an ability to reduce immune rejection, said method comprises: (a) contacting an activated T cell sample with a test compound; (b) determining the amount of Stat4 mRNA and Stat6 mRNA or Stat4 protein and Stat6 protein present in the sample; and (c) comparing the amounts in (a) to those present in a corresponding control activated T cell sample that has not been contacted with the test compound, so that if the amount of Stat4 is decreased or the amount of Stat6 is increased relative to the amount in the control sample, a compound to be tested for an ability to reduce immune rejection is identified.

In another preferred embodiment of a method for identifying a compound to be tested for an ability to reduce immune rejection, said method comprises: (a) contacting an activated T cell sample with a test compound; (b) determining the ratio of Stat4 mRNA to Stat6 mRNA or Stat4 protein to Stat6 protein present in the sample; and (c) comparing the ratio in (a) to that present in a corresponding control activated T cell sample that has not been contacted with the test compound, so that if the ratio in (a) is decreased relative to that in the control sample, a compound to be tested for an ability to reduce immune rejection is identified.

In another aspect, the present invention relates to a method for identifying a compound to be tested for an ability to reduce immune rejection, said method comprises: (a) contacting a resting T cell sample, a T cell activator and a test compound; (b) determining the amount of at least one of the following: (i) Stat1 mRNA or Stat1 protein, (ii) Stat2 mRNA or Stat2 protein, (iii) Stat3 mRNA or Stat3 protein, (iv) Stat4 mRNA or Stat4 protein, (v) Stat6 mRNA or Stat6 protein; (vi) SOCS1 mRNA or SOCS1 protein, or (vii)

SOCS3 mRNA or SOCS3 protein, present in (a); and (c) comparing the amount(s) in (a) to that/those present in a corresponding resting T cell sample that has been contacted with the T cell activator, but has not been contacted with the test compound, so that if the amount of (i), (ii), (iii), (iv), (vi), or (vii) is decreased, or the amount of (v) is increased, relative to the amount in the control sample, a compound to be tested for an ability to reduce immune rejection is identified. In alternate embodiments, such methods comprise determining the amount of at least two, at least three, at least four, at least five, at least six, or each of (i) to (vii) present in the activated T cell sample and comparing the amounts to those present in the control sample.

Optionally, such methods can further include comparing the amount or amounts in (a) to a control resting T cell sample that has not been contacted with the T cell activator or with the test compound and/or with a control resting T cell sample that has been contacted with the test compound, but has not been contacted with a T cell activator (and, therefore, remains in the resting state). Such controls provide evidence regarding the specificity and toxicity of the test compound.

In certain embodiments of such methods, the amount of mRNA is determined, in other embodiments, the amount of protein is determined, while in still other embodiments, the amount of mRNA and protein is determined. With respect to Stat6, when the amount of Stat6 is being determined, it is preferable that the amount of Stat6 protein be determined. In any such embodiment wherein a Stat protein amount is determined, the amount determined can be the total amount of the Stat protein present in a sample or, alternatively, can be the amount of phosphorylated Stat protein present in the sample. Further, in certain embodiments, the resting T cell is a primary T cell, and in other embodiments, the resting T cell is a T cell line.

In a preferred embodiment of a method for identifying a compound to be tested for an ability to reduce immune rejection, said method comprises: (a) contacting a resting T cell sample, a T cell activator and a test compound; (b) determining the amount of Stat4 mRNA and Stat6 mRNA or Stat4 protein and Stat6 protein present in the sample; and (c) comparing the amounts in (a) to those present in a corresponding control resting T cell sample that has been contacted with the T cell activator, but has not been contacted with the test compound, so that if the amount of Stat4 is decreased or the amount of Stat6 is increased relative to the amount in the control sample, a compound to be tested for an ability to reduce immune rejection is identified.

In another preferred embodiment of such a method for identifying a compound to be tested for an ability to reduce immune rejection, said method comprises: (a) contacting a resting T cell sample, a T cell activator and a test compound; (b) determining the ratio of Stat4 mRNA to Stat6 mRNA or Stat4 protein to Stat6 protein present in the sample; and (c) comparing the ratio in (a) to that present in a corresponding control resting T cell sample that has been contacted with a T cell activator, but has not been contacted with the test compound, so that if the ratio in the sample is decreased relative to that in the control samples, a compound to be tested for an ability to reduce immune rejection is identified.

In another aspect, the present invention relates to a method for identifying a compound to be tested for an ability to reduce immune rejection, comprising: (a) contacting a T cell sample, a cytokine and a test compound, wherein the T cell sample is responsive to the cytokine; (b) determining the amount of at least one of the following: (i) Stat1 mRNA or Stat1 protein, (ii) Stat2 mRNA or Stat2 protein, (iii) Stat3 mRNA or Stat3 protein, (iv) Stat4 mRNA or Stat4 protein, (v) Stat6 mRNA or Stat6 protein; (vi) SOCS1 mRNA or SOCS1 protein, or (vii) SOCS3 mRNA or SOCS3 protein, present in (a); and (c) comparing the amount(s) in (a) to that/those present in a corresponding control T cell sample that has been contacted with the cytokine, but has not been contacted with the test compound, so that if the amount of (i), (ii), (iii), (iv), (vi), or (vii) is decreased, or the amount of (v) is increased, relative to the amount in the control sample, a compound to be tested for an ability to reduce immune rejection is identified.

Cytokines that can be used as part of these methods include, but are not limited to, IL-2, IL-4, IL-12, or IL-13.

In certain embodiments of such methods, the amount of mRNA is determined, in other embodiments, the amount of protein is determined, while in still other embodiments, the amount of mRNA and protein is determined. With respect to Stat6, when the amount of Stat6 is being determined, it is preferable that the amount of Stat6 protein be determined. In any such embodiment wherein a Stat protein amount is determined, the amount determined can be the total amount of the Stat protein present in a sample or, alternatively, can be the amount of phosphorylated Stat protein present in the sample.

In a preferred embodiment of such a method for identifying a compound to be tested for an ability to reduce immune rejection, said method comprises: (a) contacting a T cell sample, a cytokine and a test compound, wherein the T cell sample is responsive to the cytokine; (b) determining the amount of Stat4 and Stat6 mRNA or Stat4 and Stat6 protein present in the sample; and (c) comparing the amounts in (a) to those present in a corresponding control T cell sample that has been contacted with the cytokine, but has not been contacted with the test compound, so that if the amount of Stat4 is decreased or the amount of Stat6 is increased relative to the amounts in the control sample, a compound to be tested for an ability to reduce immune rejection is identified.

In another preferred embodiment of such a method for identifying a compound to be tested for an ability to reduce immune rejection, said method comprises: (a) contacting a T cell sample, a cytokine and a test compound, wherein the T cell sample is responsive to the cytokine; (b) determining the ratio of Stat4 mRNA to Stat6 mRNA or Stat4 mRNA to Stat6 protein present in the sample; and (c) comparing the ratio to in (a) to that present in a corresponding control T cell sample that has been contacted with the cytokine, but has not been contacted with the test compound, so that if the ratio in the sample is decreased relative to that in the control sample, a compound to be tested for an ability to reduce immune rejection is identified.

Standard methods and compositions for determining the amount of Stat1 mRNA or protein, Stat2 mRNA or protein, Stat3 mRNA or protein, Stat4 mRNA or protein, Stat6 mRNA or protein, SOCS1 mRNA or protein, and SOCS3 mRNA or protein can be utilized. Such methods and compositions are described in detail, above, in Section 5.1.

In addition to the ability to modulate Stat and/or SOCS levels as described herein, it may be desirable, at least in certain instances, that compounds that reduce immune rejection also modulate the expression or activity of such molecules as IL-4, interferon-γ (IFN-γ), IL-12, or IL-13. Thus, the methods described herein for identifying compounds to be tested for an ability to reduce immune rejection can further comprise determining the level of IL-4, IFN-γ or IL-13 in the T cell sample that has been contacted with the test compound, and comparing this level with that of the control T cell sample that has not been contacted with the test compound. Preferred compounds are ones wherein: the level of IL-12 or IFN-γ in the test sample is decreased relative to the corresponding level in the control sample, or wherein the level of IL-4 or IL-13 in the test sample is equal to or greater than the corresponding level in the control sample.

The present methods of identifying compounds that to be tested for an ability to reduce immune rejection, can comprise methods for identifying compounds that modulate the activity of Stat1, Stat2, Stat3, Stat4, Stat6, SOCS1, or SOCS3. Thus, such methods can comprise: (a) contacting a T cell sample with a test compound; (b) determining the activity of at least one of Stat1, Stat2, Stat3, Stat4, Stat6, SOCS1, or SOCS3; and (c) comparing the activity level or levels to that/those in a corresponding control T cell sample that has not been contacted with the test compound, so that if the level of Stat1, Stat2, Stat3, Stat4, SOCS1 or SOCS3 activity in (a) is decreased, or the level of Stat6 activity in (a) is increased, relative to the level of activity in the control sample, a compound to be tested for an ability to reduce immune rejection is identified.

In one preferred embodiment, the activity of Stat4 and Stat6 is determined. Such a preferred embodiment can further include determining the ratio of Stat4 activity to Stat6 activity so that if the ratio in the test sample is decreased relative to that in the control sample, a compound to be tested for an ability to reduce immune rejection is identified.

The T cell sample utilized herein can be an activated T cell sample, a resting T cell sample, or a cytokine-responsive T cell sample, as discussed above. In instances wherein the T cell sample is a resting T cell sample, the T cell sample is contacted with a T cell activator and the test compound. In instances wherein the T cell sample is a cytokine-responsive T cell sample, the T cell sample is contacted with the cytokine and the test compound.

Standard techniques can be utilized to determine the level of Stat1, Stat2, Stat3, Stat4, Stat6, SOCS1 or SOCS3 activity. For example, the activity of Stat1, Stat2, Stat3, Stat4, Stat6, SOCS1 or SOCS3 can be determined by detecting the binding of Stat1, Stat2, Stat3, Stat4, Stat6, SOCS1 or SOCS3 to its cognate DNA binding element, via, for example, an electromobility shift assay ("EMSA"), detecting the expression of a gene whose expression is controlled by a promoter that is responsive to Stat1, Stat2, Stat3, Stat4, Stat6, SOCS1 or SOCS3, detecting the induction of a reporter gene that comprises a regulatory element that is responsive to Stat1, Stat2, Stat3, Stat4, Stat6, SOCS1 or SOCS3, wherein the element is operably linked to a nucleic acid encoding a detectable marker, e.g., luciferase.

Genes whose expression is controlled by a Stat 1-responsive promoter are well known, and include, for example GBP-1, inducible NO synthase (iNOS), ICAM, IRF-1, major histocompatibility complex (MHC) class II transactivator (CIITA). See, e.g., Lew et al., 1991, Mol. Cell. Biol. 11:182–191, Gao et al., 1997, J. Biol. Chem. 272:1226–1230, Caldenhoven et al., 1994, J. Biol. Chem. 269:21146–21154, Sims et al., 1993, Mol. Cell. Biol. 13:690–702, Pine et al., 1994, EMBO J. 13:158–167, Harada et al., 1994, Mol. Cell. Biol. 14:1500–1509, and Piskurich et al., 1999, Mol. Cell. Biol. 19(1):431–40. Thus, expression of such genes in the T cell sample in the presence and absence of a test compound can routinely be determined using standard techniques. Likewise, the structure of Stat 1-responsive promoters are well known (see, e.g., Sims et al., 1993, Mol. Cell. Biol. 13:690–702, Pine et al., 1994, EMBO J. 13:158–167, and Piskurich et al., 1999, Mol. Cell. Biol. 19(1):431–40), making the construction and assay of Stat 1-reporter genes routine.

Genes whose expression is controlled by a Stat 2-responsive promoter are well known, and include, for example IRF-1. See, e.g., Li et al., 1996, J. Biol. Chem. 271(10):5790–5794. Thus, expression of such genes in the T cell sample in the presence and absence of a test compound can routinely be determined using standard techniques. Likewise, the structure of Stat 2-responsive promoters are well known (see, e.g., Ghislain et al., 1996, J. Biol. Chem. 271(21):12408–12413 and Li et al., 1996, J. Biol. Chem. 271(10):5790–5794), making the construction and assay of Stat 2-reporter genes routine.

Genes whose expression is controlled by a Stat 3-responsive promoter are well known, and include, for example alpha-2-macroglobulin, fibrinogen, junb, haptoglobin, matrix metalloproteinase (MMP-1), TIMP-1, and $p21^{WAF/CIP1}$ See, e.g., Wegenka et al., 1993, Mol. Cell. Biol. 13:276–288, Fujitani et al., 1994, Biochem. Bioph. Res. Co. 202:1181–1187, Coffer et al., 1995, Oncogene 10:985–994, Akira et al., 1994, Cell 77:63–71, and Chin et al., 1996, Science 272:719–722. Thus, expression of such genes in the T cell sample in the presence and absence of a test compound can routinely be determined using standard techniques. Likewise, the structure of Stat 3-responsive promoters are well known (see, e.g., Wegenka et al., 1993, Mol. Cell. Biol. 13:276–288 and Chin et al., 1996, Science 272:719–722), making the construction and assay of Stat 3-reporter genes routine.

Genes whose expression is controlled by a Stat 4-responsive promoter are well known, and include, for example interferon-γ and IL-12. See, e.g., Grigorieva et al., 2000, J Biol. Chem. 275(10):7343–7350 and Naeger, L. K. et al., 1999, J. Biol. Chem. 274:1875–1878). Thus, expression of such genes in the T cell sample in the presence and absence of a test compound can routinely be determined using standard techniques. Likewise, the structure of Stat 4-responsive promoters are well known (see, e.g., Grigorieva et al., 2000, J Biol. Chem. 275(10):7343–7350 and Naeger, L. K. et al., 1999, J. Biol. Chem. 274:1875–1878), making the construction and assay of Stat 4-reporter genes routine.

Genes whose expression is controlled by a Stat 6-responsive promoter are well known, and include, for example IL-4, CD23, IL-4 receptor, MHC class II. See, e.g., Tinnell et al., 1998, Int. Immunol. 10(10):1529–38, Linehan et al., 1998, J. Immunol. 161(1):302–10, and Kotanides et al., 1996, J. Biol. Chem. 271(41):25555–25561. Thus, expression of such genes in the T cell sample in the presence and absence of a test compound can routinely be determined using standard techniques. Likewise, the structure of Stat 6-responsive promoters are well known (see, e.g., Curiel, R. E. et al., 1997, Eur. J. Imm. 27:1982–1987, Linehan et al., 1998, J. Immunol. 161(1):302–10, and Kotanides et al., 1996, J. Biol. Chem. 271(41):25555–25561), making the construction and assay of Stat 6-reporter genes routine.

EMSAs can also routinely be utilized to assess Stat1, Stat2, Stat3, Stat4 or Stat6 activity. Such techniques are well known to those of skill in the art. See, e.g., Amici et al., 1995, Cancer Research 55: 14452–4457. Briefly, in a representative, non-limiting example, extracts of cells treated with a test compound are mixed with $^{32}$P-Stat 4 (or Stat1, 2, 3, or 6) element or a control oligonucleotide and poly(dI-dC) (Pharmacia Biotech Inc.) in binding buffer (e.g., Tris-Cl, pH 7.8, 50 mM NaCl, 1 mM EDTA, 0.5 mM dithiothreitol, 5% glycerol). After an approximately 20 minute incubation at room temperature, Stat4 (or Stat1, 2, 3, or 6)-DNA-complexes or control oligonucleotide complexes are analyzed by nondenaturing 4% polyacrylamide gel electrophoresis and autoradiography. The amount of shifted Stat4 (or Stat 1, 2, 3, or 6) probe, an indicator Stat4 (or Stat1, 2, 3, or 6) activity, respectively, can be quantitated by Molecular Dynamics PhosphoImager (MDP) analysis.

The activity of SOCS1 or SOCS3 activity can be determined by, e.g., detecting the expression of a gene whose expression is controlled by SOCS1 or SOCS3. For example, SOCS1 expression inhibits IL-6, LIF, oncostatin M, IFN-γ, IFN-β, IFN-α, thrombopoeitin, and growth hormone (GH) induced Jak/Stat signaling. SOCS3 expression inhibits IFN-γ, IFN-β, IFN-α, GH and leptin. Thus, expression of such genes in the T cell sample in the presence and absence of a test compound can routinely be determined using standard techniques.

The activity of Stat1, Stat2, Stat3, Stat4, Stat6, SOCS1 or SOCS3 can also be assessed by detecting the proliferation of the T cell sample, detecting the effector function of the sample or detecting differentiation of the sample. Techniques known to those of skill in the art can be used for measuring these activities. For example, cellular proliferation can be assayed by $^3$H-thymidine incorporation assays and trypan blue cell counts. The effector function of T-cells can be measured, for example, by a $^{51}$Cr-release assay (see, e.g., Palladino et al., 1987, Cancer Res. 47:5074–5079 and Blachere et al., 1993, J. Immunotherapy 14:352–356).

As set forth above, the methods described herein for identifying compounds to be tested for an ability to reduce immune rejection assay whether a test compound has an effect on the expression and/or activity of Stat 1 mRNA or protein, Stat2 mRNA or protein, Stat3 mRNA or protein, Stat4 mRNA or protein, Stat6 mRNA or protein, SOCS1 mRNA or protein, and/or SOCS3 mRNA or protein produced by a T cell, in particular, an activated T cell, or at a minimum, a T cell that has the ability to respond to exogenous cytokines.

The T cell used as part of the methods can be one that is constitutively activated (e.g., a constitutively activated T cell line), one that has or has gained the ability to respond to cytokines, one that is activated prior to performing the method, or one that is activated concurrently with the method. A T cell to be used as part of the methods described herein can be activated either prior to or simultaneously with contacting the cell with a test compound. With respect to activated, including constitutively activated T cells, activation of such T cells can, in certain instances be further enhanced by addition and contact with a T cell activator.

An activated T cell is one that expresses antigens indicative of T-cell activation (that is, T cell activation markers). Examples of T cell activation markers include, but are not limited to, CD25, CD26, CD30, CD38, CD69, CD70, CD71, ICOS, OX-40 and 4-1BB. The expression of activation markers can be measured by techniques known to those of skill in the art, including, for example, western blot analysis, northern blot analysis, RT-PCR, immunofluorescence assays, and fluorescence activated cell sorter (FACS) analysis. The activated T cell used as part of the present methods can be an activated T cell line or can be a primary cell that has been activated.

Activated T cell lines are well known to those of skill in the art. Examples of activated T cell lines include TH1 cell lines such as AE7, PL17, and OF6, and TH2 cell lines such as D10 and CDC35.

T cell lines that do not express the T cell activation markers required to constitute activation, but nonetheless have the ability to respond to cytokines are also well known to those of skill in the art. Examples of such T cell lines include CTLL-2 and HT-2.

Alternatively, primary T cells can be isolated, the majority of which will be in a resting state, and activated using standard techniques. For example, immune cells can be collected or isolated from blood, or secondary lymphoid organs of the subject, such as but not limited to lymph nodes, tonsils, the spleen, Peyer's patch of the intestine, and bone marrow, by any of the methods known in the art. Immune cells obtained from such sources typically comprise predominantly recirculating lymphocytes and macrophages at various stages of differentiation and maturation. Optionally, standard techniques, such as morphological observation and immunochemical staining, can be used, if desired, to verify the presence of the desired cells, that is, T cells. In a preferred aspect, the immune cells used in the methods of the invention described herein are human peripheral blood compositions lacking red blood cells, e.g., whole blood leukocytes (whole peripheral blood from which the red blood cells and serum have been substantially removed), which can be collected from a human subject by standard techniques, such as by use of a syringe to withdraw the blood, followed by subjecting the blood to Ficoll-Hypaque (Pharmacia) gradient centrifugation. Blood, anticoagulated with preservative-free heparin, usually yields 0.5 to 1×10$^6$ lymphocytes/ml. Separated blood cells (e.g., leukocytes) may be frozen by standard techniques prior to use in the present methods. In a specific embodiment, the immune cells used are purified white blood cells comprising lymphocytes and macrophages.

In one embodiment wherein further purification of T cells is desired, antibodies against specific surface markers can be directly labeled by conjugation of a detectable compound to such antibodies to facilitate detection and separation of T cells. Alternatively, in another embodiment, the primary antibody is detected by detecting binding of a secondary antibody or reagent to the primary antibody. In a further embodiment, the secondary antibody is labeled. Examples of detectable compounds include, but are not limited to, biotin, photobiotin, fluorescein isothiocyanate (FITC), or phycoerythrin (PE), or other compounds known in the art. Cells retaining labeled antibodies are then separated from cells that do not bind such antibodies by techniques known in the art such as, but not limited to, various cell sorting methods (e.g., FACS), affinity chromatography, and panning.

In another embodiment wherein further purification of T cells is desired, T cells are sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150–165). Laser excitation of fluorescent moieties in the individual particles results in a small electrical charge allowing electromagnetic separation of positive and negative particles from a mixture.

In another embodiment wherein further purification of T cells is desired, magnetic beads can be used to separate T cells. T cells may be sorted using a magnetic activated cell sorting (MACS) technique, a method for separating particles based on their ability to bind magnetic beads (0.5–100μ diameter; Dynal, Inc., Lake Success, N.Y.) as un dertaken according to the manufacturer's instructions. A variety of useful modifications can be performed on the magnetic microspheres, including covalent addition of antibody which specifically recognizes a cell-solid phase surface molecule or hapten. A magnetic field is then applied, to physically manipulate the selected beads. The beads are then mixed with the immune cells to allow binding. Cells are then passed through a magnetic field to separate out cells having T cell surface markers.

The isolated resting T cells can then be activated by contacting with a T cell activator. Any T cell activator can be utilized for this purpose. For example, any compound or factor that is a T cell receptor stimulatory factor, that is, induces T cell receptor signalling can be used. Preferably, the compound or factor also induces co-stimulatory pathways. Representative, non-limiting examples of T cell activators include, but are not limited to, anti-CD3 antibodies (preferably monoclonal antibodies) either alone or in conjunction with anti-CD28 antibodies (preferably monoclonal antibodies), or mitogens such as, for example, phorbol 12-myristate 13-acetate (PMA), phytohemagglutinin (PHA), or concanavalin-A (ConA).

Compounds that can be tested and identified methods described herein can include, but are not limited to, compounds obtained from any commercial source, including Aldrich (1001 West St. Paul Ave., Milwaukee, Wis. 53233), Sigma Chemical (P.O. Box 14508, St. Louis, Mo. 63178), Fluka Chemie AG (Industriestrasse 25, CH-9471 Buchs, Switzerland (Fluka Chemical Corp. 980 South 2nd Street, Ronkonkoma, N.Y. 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasago (4 Volvo Drive, Rockleigh, N.J. 07647), SST Corporation (635 Brighton Road, Clifton, N.J. 07012), Ferro (111 West Irene Road, Zachary, La. 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272). Further any kind of natural products may be screened using the methods of the invention, including microbial, fungal, plant or animal extracts.

Furthermore, diversity libraries of test compounds, including small molecule test compounds, may be utilized. For example, libraries may be commercially obtained from Specs and BioSpecs B. V. (Rijswijk, The Netherlands), Chembridge Corporation (San Diego, Calif.), Contract Service Company (Dolgoprudny, Moscow Region, Russia), Comgenex USA Inc. (Princeton, N.J.), Maybridge Chemicals Ltd. (Cornwall PL34 OHW, United Kingdom), and Asinex (Moscow, Russia).

Still further, combinatorial library methods known in the art, can be utilize, including, but not limited to: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des.12:145). combinatorial libraries of test compounds, including small molecule test compounds, can be utilized, and may, for example, be generated as disclosed in Eichler & Houghten, 1995, Mol. Med. Today 1:174–180; Dolle, 1997, Mol. Divers. 2:223–236; and Lam, 1997, Anticancer Drug Des. 12:145–167.

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994. J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Bio/Techniques 13:412–421), or on beads (Lam, 1991, Nature 354:82–84), chips (Fodor, 1993, Nature 364:555–556), bacteria (U.S. Pat. No. 5,223,409), spores (U.S. Pat. Nos. 5,571,698; 5,403,484; and 5,223, 409), plasmids (Cull et al., 1992, Proc. Natl. Acad. Sci. USA 89:1865–1869) orphage (Scott and Smith, 1990, Science 249:386–390; Devlin, 1990, Science 249:404–406; Cwirla et al., 1990, Proc. Natl. Acad. Sci. USA 87:6378–6382; and Felici, 1991, J. Mol. Biol. 222:301–310).

Among the test compounds that can be tested are compounds, including small organic molecule compounds that act as protein tyrosine kinase inhibitors, including, but not limited to, the tyrphostin class of protein tyrosine kinase inhibitors (see, e.g., Gazit et al. 1989, J. Medicinal Chem. 32:2344–2352; and Levitski, 1992, FASEB J. 6:3275). Among such tyrphostin compounds that can be tested are A25 (available, e.g., from CalBiochem) or AG-490 (B42) (Meydan, N. et al., 1996, Nature 379:645–648) or derivatives thereof. Further, among the compounds that can be tested are compounds that interfere with SH2 domain interactions (see, e.g., U.S. Pat. No. 5,710,129; 5,776,902; and 5,580,97, or derivatives of compounds therein), e.g., SH2-mediated Stat 4/IL-12 receptor-$\beta_2$ interactions. Still further, among the compounds that can be tested are compounds that interfere with Jak 2/IL-12 receptor-$\beta_2$ interactions and/or ones that interfere with Tyk 2/IL-12 receptor-$\beta_1$, interactions.

Upon identification of compounds to be tested for an ability to reduce immune rejection, the compounds can be further investigated. In particular, for example, the compounds identified via the present methods can be further tested in vivo in accepted animal models of transplant or autoimmune disorders. Further, the compounds identified can also be analyzed with respect to their specificity. In particular, the compounds can be tested for an effect on platelet aggregation and/or on NF-κB activation. Techniques for such additional compound investigation are described below.

Accepted animal models can be utilized to determine whether the compounds identified via the methods described herein. Such models can include both transplant-related models as well as autoimmune disorder models.

For example, the ability of a compound to reduce immune rejection, including the ability of the compound to induce tolerance in a subject mammal that has undergone a transplant can include, but are not limited to, a murine allograft model in which an allogeneic heart is transplanted into a subject mouse recipient (Hancock et al., 1998, Nature Medicine 4:1392–1396). In addition, primate models can also be tested. Such models include, for example, a primate renal allograft model (Kirk et al., 1997, Proc. Natl. Acad. Sci. USA 94:8789–8794). In addition, a graft versus host disease (GVHD) model can be used (see, e.g., Guillen et al., 1986, Laboratory Investigation 55:35–42). In such models, chronic and acute GVHD is made to result from introduction of donor cells into a host exhibiting disparate MHC alleles. The GVHD results, therefore, from the donor cells' response to such the host's disparate MHC alleles.

The ability of a compound to reduce immune rejection can also be tested in such autoimmune disorder models as, first, an experimental allergic encephalomyelitis (EAE) model. EAE is an experimental autoimmune disease of the central nervous system (CNS) (Zamvil et al., 1990, Ann. Rev, Immunol. 8:579) and is a disease model for the human autoimmune condition, multiple sclerosis (MS). EAE is an example of a cell-mediated autoimmune disorder that is mediated via T cells. No direct evidence exists for an autoantibody requirement in disease progression. EAE is readily induced in mammalian species by immunizations of myelin basic protein purified from the CNS or an encephalitogenic proteolipid (PLP). SJL/J mice are a susceptible strain of mice (H-2') and, upon induction of EAE, these mice develop an acute paralytic disease and an acute cellular infiltrate is identifiable within the CNS.

In addition, a collagen-induced arthritis (CIA) model can be utilized to determine whether the compound of interest reduce immune rejection. CIA is an animal model for the human autoimmune disease rheumatoid arthritis (RA) (Trenthom et al., 1977, J. Exp. Med., 146:857). This disease can be induced in many species by the administration of heterologous type II collagen (Courtenay et al., 1980, Nature 283:665; Cathcart et at, 1986, Lab. Invest., 54:26). With respect to animal models of arthritis see, in addition, e.g., Holmdahl, R., 1999, Curr. Biol. 15:R528–530.

Still further, animal models for type 1 diabetes, thyroid autoimmunity or systemic lupus erythematosus, including glomerulonephritis can be utilized to determine whether the compound of interest reduces immune rejection (see, e.g., Flanders et al., 1999, Autoimmunity 29:235–246; Krogh et al., 1999, Biochimie 81:511–515; and Foster, N. H., 1999, Semin. Nephrol. 19:12–24, respectively).

In addition, it is preferred that compounds to be utilized as therapeutic according to the methods described herein not induce platelet aggregation. Therefore, it is preferable that compounds identified via the methods described herein that are to be tested for an ability to reduce immune rejection be further tested for an ability to induce platelet aggregation. In vitro and ex vivo assays for platelet aggregation are well known and compounds of interest can easily be tested via such assays.

Specifically, such assays include, but are not limited to the turbidometric method, in which aggregation is measured as an increase in transmission of visible light through a stirred or agitated platelet suspension. See, e.g., Chanarin, L., 1989, Laboratory Haematology, Chapter 30, Churchill, Livingstone, London; and Schmidt, R. M. (ed), 1979, CRC Handbook Series in Clinical Laboratory Science, CRC Press, Inc.: Boca Raton, Fla.

Platelet aggregation can also be assayed via methods such as those described in U.S. Pat. No. 5,976,532. For example, in a non-limiting example of such a method, the platelet concentration in platelet-rich plasma obtained (PRP) obtained from blood samples is adjusted to 200,000 to 300,000/mm$^3$. In an in vitro assay, the PRP is aliquoted and incubated in the presence or absence of a compound of interest for a period of time (e.g., 15 minutes at 37° C.) prior to the addition of a platelet inducing agonist (e.g., ADP, thrombin, collagen, epinephrine, and ristocetin). In an ex vivo assay, the PRP obtained from individuals treated with the compound of interest or a placebo is aliquoted and incubated in the presence of a platelet inducing agonist (e.g., ADP, thrombin, collagen, epinephrine, and ristocetin). Platelet aggregation is measured by assessing an increase in the transmission of visible light through a platelet suspension using a spectrophotometer.

It is also preferred that compounds to be utilized as therapeutic according to the methods described herein not affect NF-κB activation, in particular, NF-κB activation in CD40L$^+$ cells. Therefore, it is preferable that compounds identified via the methods described herein that are to be tested for an ability to reduce immune rejection be further tested for possible effect on NF-κB activation in CD40L+ cells. In such tests, a CD40L$^+$ cell is contacted with the compound of interest, and its effect on NF-κB activation, if any is assayed, and compared to the level of NF-κB activation in a corresponding control CD40L$^+$ cell that has not been contacted with the compound.

Standard techniques can be utilized to test for NF-κB activation. For example, the activity of NF-κB can be assessed by detecting the binding of NF-κB to its cognate DNA binding element in an electromobility shift assay (EMSA), detecting the expression of a gene whose expression is controlled by a promoter that is responsive to NF-κB, detecting the induction of the expression of a reporter gene construct that comprises a regulatory element that is responsive to NF-κB is operably linked to a nucleic acid encoding a detectable marker, e.g., luciferase.

Genes whose expression is controlled by an NF-κB-responsive promoter are well known, and include, for example granulocyte/macrophage colony-stimulating factor (GM-CSF), granulocyte colony-stimulating factor (G-CSF), IL-2, IL-6, IL-8, tumor necrosis factor-α (TNF-α), and intercellular cell adhesion molecule 1 (ICAM-1). See, e.g., Baeuerle and Henkel, 1994, Ann. Rev. Immunol. 12:141–179. Thus, expression of such genes in CD40L$^+$ cells in the presence and absence of a compound of interest can routinely be determined using standard techniques. Expression can be determined using standard techniques. Preferably, the compound being tested will not increase such expression and, most preferably, will have no effect on such expression. Likewise, the structure of NF-κB-responsive promoters are well known (see, e.g., Baeuerle and Henkel, 1994, Ann. Rev. Immunol. 12:141–179; and Thanos et al., 1995, Cell 80:529–532), making the construction and assay of NF-κB reporter genes routine. Thus, the induction and expression of such reporter genes in CD40L$^+$ cells in the presence and absence of a compound of interest can routinely be determined using standard techniques. Preferably, the compound being tested will not induce expression of the reporter gene.

EMSAs can also routinely be utilized to assess NF-κB activity. Such techniques are well known to those of skill in the art. See, e.g., Amici et al., 1995, Cancer Research 55: 14452–4457. Briefly, in a representative, non-limiting example, extracts of cells treated with a test composition or control composition are mixed with $^{32}$P-NF-κB element or a control oligonucleotide and poly(dI-dC) (Pharmacia Biotech Inc.) in binding buffer (e.g., Tris-Cl, pH 7.8, 50 mM NaCl, 1 mM EDTA, 0.5 mM dithiothreitol, 5% glycerol). After an approximately 20 minute incubation at room temperature, NF-κB-DNA-complexes or control oligonucleotide complexes are analyzed by non-denaturing 4% polyacrylamide gel electrophoresis and autoradiography. The amount of shifted NF-κB probe, an indicator NF-κB activity, respectively, can be quantitated by Molecular Dynamics PhosphoImager (MDP) analysis.

Further, the effect, if any, of the compound of interest on NF-κB activation can also be tested by assaying for a cellular response, for example, cellular differentiation, or cell proliferation. Cellular proliferation can be assayed by, for example, $^3$H-thymidine incorporation assays and trypan blue cell counts. Preferably, the compound will have no effect on such cellular responses.

5.3. Methods and Compositions for Reducing Immune Rejection

Described herein are methods and compositions for reducing immune rejection in a subject mammal. In particular, such methods comprise administration of compounds that serve to reduce the amount or activity of Stat1 mRNA or protein, Stat2 mRNA or protein, Stat4 mRNA or protein, SOCS1 mRNA or protein or SOCS3 mRNA or protein, and/or increase the amount or activity of Stat6 mRNA or protein. The compounds utilized herein are ones that neither induce platelet aggregation nor affect NF-κB activation.

Immune rejection in any subject mammal that has undergone a transplant, or that exhibits or is suspected of exhibiting an autoimmune disorder can be reduced using the methods presented herein. Preferably, the mammal is a human, however, such subject mammals can also include, but are not limited to, other primates, including monkeys, as well as pigs, dogs, cats, horses, cattle, sheep, mice, rats, and rabbits.

The term "reducing immune rejection," is meant to encompass prevention or inhibition of immune rejection, as well as delaying the onset or the progression of immune rejection. The term is also meant to encompass prolonging survival of a transplant in a subject mammal, or reversing failure of a transplant in a subject. Further, the term is meant to encompass ameliorating a symptom of an immune rejection, including, for example, ameliorating an immunological complication associated with immune rejection, such as for example, interstitial fibrosis, chronic graft atherosclerosis, or vasculitis. The term is also meant to encompass induction of tolerance in a subject mammal that has undergone a transplant.

Specifically, the present invention relates to methods for reducing immune rejection in a subject mammal, said methods comprising: administering to a subject mammal in need of such a reduction a concentration of a compound sufficient to reduce the level or activity of Stat4 mRNA or protein in the subject relative to that observed in the subject in the absence of the compound, wherein said compound does not induce platelet aggregation and does not affect NF-κB activation in CD40L+ cells.

The present invention also relates to methods for reducing immune rejection in a subject mammal, said methods comprising: administering to a subject mammal in need of such a reduction a concentration of a compound sufficient to reduce the level or activity of Stat1 mRNA or protein, Stat2 mRNA or protein, or Stat3 mRNA or protein in the subject relative to that observed in the subject in the absence of the compound, wherein said compound does not induce platelet aggregation and does not affect NF-κB activation in CD40L+ cells.

Such methods can also include methods for reducing immune rejection in a subject mammal, comprising administering to the subject mammal in need of such a reduction a concentration of a compound sufficient to decrease the level or activity of Stat4 mRNA or protein in the subject relative to that observed in the subject in the absence of the compound, and wherein the level or activity of Stat6 mRNA or protein in the subject is maintained or increased relative to that observed in the subject in the absence of the compound. Further, the compound administered is one that does not induce platelet aggregation or affect NF-κB activation in CD-40L+ cells.

Alternatively, such methods for reducing immune rejection in a subject mammal can comprise: administering to a subject mammal in need of such a reduction a concentration of a compound sufficient to increase the level or activity of Stat6 mRNA or protein in the subject relative to that observed in the subject in the absence of the compound, wherein said compound does not induce platelet aggregation and does not affect NF-κB activation in CD40L+ cells.

Such methods for reducing immune rejection in a subject mammal can also comprise: administering to a subject mammal in need of such a reduction a concentration of a compound sufficient to decrease the level or activity of Stat4 mRNA or protein and maintain or increase the level or activity of Stat6 mRNA or protein in the subject subject relative to that observed in the subject in the absence of the compound, wherein said compound does not induce platelet aggregation and does not affect NF-κB activation in CD40L+ cells.

Generally, practice of these methods does not solely entail administration of compositions that are considered signal 2-type blockers (see, e.g., Gummert J. F., et al., 1999, J. Am. Soc. Nephrol. 10: 1366), that is, compounds (e.g., CD40L antibodies) that act to inhibit CD40/CD40L (CD154) interactions or B7/CD28 interactions.

It is noted, however, that embodiments of the present invention further include combinatorial immune reduction therapy utilizing compositions as taught herein in conjunction with immunosuppressive or immunomodulatory drug therapies, as described in detail, below.

The methods of the present invention for reducing immune rejection can be utilized, e.g., for reducing immune rejection in a subject mammal that has undergone a transplant. For example, such methods can induce tolerance in a subject mammal that has undergone a transplant. Such methods can be used to reduce immune reject in a transplant situation involving any cell, organ, organ system or tissue which can elicit an immune response in a recipient subject mammal. In general, therefore, a transplant includes an allograft, or a xenograft cell, organ, organ system or tissue. An allograft refers to a graft (cell, organ, organ system or tissue) obtained from a member of the same species as the recipient. A xenograft refers to a graft (cell, organ, organ system or tissue) obtained from a member of a different species as the recipient. In particular, the transplant can, for example, be an allograft heart, liver, kidney, lung, bone marrow, skin, muscle, pancreatic islet, intestine or cornea transplant.

The methods of the present invention for reducing immune rejection can also be utilized, e.g., for reducing immune rejection in a subject mammal exhibiting an autoimmune disorder. Thus, the present invention can treat an autoimmune disorder affecting any body cell, tissue, organ or organ system, including but not limited to cutaneous, cardiac, pericardial, endocardial, vascular lining or wall, blood, blood-forming (e.g., marrow or spleen), endocrine (e.g., pancreatic or thyroid), gastrointestinal (e.g., bowel), respiratory (e.g., lung), renal, central nervous system, peripheral nervous system, muscular or skeletal joint (e.g., articular cartilage or synovial) tissue. The methods and compositions of the present invention can, therefore, be utilized to treat any autoimmune disorder including, but not limited to atopic dermatitis, contact dermatitis, eczematous dermatitides, seborrheic dermatitis, Lichen planus, Pemphilgus, bullous pemphigus, Epidermolysis bullosa, Alopecia areata, urticaria, angioedemas, erythema, eosinophilias, migraine, lupus, including cutaneous lupus (discoid lupus erythematosus), extracutaneous lupus, including systemic lupus erythematosus, acute lupus, lupus annularis, lupus discretus, lupus lymphaticus, lupus papillomatis, lupus psoriasis, lupus vulgaris, lupus sclerosis, neonatal lupus erythematosus, and drug-induced lupus; antiphospholipid syndrome (APS), hemolytic anemia (HA), idiopathic thrombocytopenia (ITP), thyroiditis, diabetes mellitus (DM), inflammatory bowel disease, e.g., Crohn's disease or ulcerative cholitis, rhinitis, uveitis, nephrotic syndrome, demyelinating diseases such as multiple sclerosis (MS), myasthenia gravis (MG), and arthritis, e.g., rheumatoid arthritis, non-rheumatoid inflammatory arthritis, arthritis associated with Lyme disease, or osteoarthritis.

The compounds utilized as part of these methods include, but are not limited to, ones identified via the methods described above. A number of different points along the Jak/Stat pathway can be targeted by the compounds utilized as part of the methods for reducing immune rejection described herein. Administration methods, including gene therapy methods, and pharmaceutical preparations by which such compounds can routinely be utilized as part of methods for reducing immune rejection are taught below.

For example, compounds that specifically downregulate Stat4 mRNA or protein levels or activity, while not affecting NF-κB activation or platelet aggregation can be utilized as part of these methods. In addition, compounds that specifically downregulate Stat1 mRNA or protein levels or activity, while not affecting NF-κB activation or platelet aggregation can be utilized as part of these methods. Also, compounds that specifically downregulate Stat2 mRNA or protein levels or activity, while not affecting NF-κB activation or platelet aggregation can be utilized as part of these methods. In addition, compounds that specifically downregulate Stat3 mRNA or protein levels or activity, while not affecting NF-κB activation or platelet aggregation can be utilized as part of these methods. In addition, compounds that specifically downregulate SOCS1 mRNA or protein evels or activity, while not affecting NF-κB activation or platelet aggregation can be utilized as part of these methods. Likewise, compounds that specifically downregulate SOCS3 mRNA or protein levels or activity, while not affecting NF-κB activation or platelet aggregation can be utilized as part of these methods. In addition, compounds or methods that specifically increase Stat 6 mRNA or protein levels or activity, while not affecting NF-κB activation or platelet aggregation can be utilized as part of these methods. Representative, non-limiting examples of such compounds are described in detail below.

First, such compounds can include, for example, antisense, ribozyme, or triple helix compounds that can downregulate the expression or Stat1, Stat2, Stat3, Stat4, SOCS1 or SOCS3. Such compounds are described in detail in the subsection below.

Second, such compounds can include, for example, antibody compositions that can downregulate the expression or activity of Stat1, Stat2, Stat3, Stat4, SOCS1 or SOCS3. Such compounds are described in detail in the subsection below.

Further, among such compounds are ones, including ones administered via gene therapy techniques, that serve to upregulate Stat6 expression or activity, and compounds that act in maintaining Stat6 expression or activity levels as Stat4 activity or expression levels are decreased.

Compositions can include, for example ones can be utilized that compete with Stat4 for binding to the IL-12 receptor $\beta_2$ ("IL-12R$\beta_2$"). Examples of such compounds include, but are note limited to limited to, peptide compositions as in Naeger, L. K. et al., 1999, J. Biol. Chem. 274:1875–1878. Additional examples of compounds that can be utilized include compounds, such as small organic compounds that act as inhibitors of SH2 domain-mediated interactions such as SH2-mediated Stat4/IL-12R$\beta_2$ interactions. One example of such an embodiment involves a composition of the invention comprises one or more peptides that bind to the Stat4 SH2 domain which prevent Stat4 from binding to the IL-12R$\beta_2$, or that comprise one or more dominant-negative Stat4 polypeptides (e.g., a Stat4 polypeptide lacking its SH2 domain or a Stat4 polypeptide lacking its DNA binding domain). Examples of such polypeptides include, but are not limited to, (using the standard one-letter amino acid code) phospho-YLPSNID peptides (Naeger, L. K. et al., 1999, J. Biol. Chem. 274:1875–1878).

In specific embodiments, Stat1 antisense oligonucleotides, Stat2 antisense oligonucleotides, Stat3 antisense oligonucleotides, or any combination thereof, are administered to reduce immune rejection. In other embodiments one or more anti-Stat1 antibodies, anti-Stat2 antibodies, or anti-Stat3 antibodies are administered to reduce immune rejection. In other embodiments, one or more peptides that compete with Jak1 or Tyk2 for binding to the IFN-α receptor or IFN-β receptor are administered to reduce immune rejection. In yet another embodiment, one or more peptides that compete with Jak1 or Jak2 for binding to the IFN-γ receptor are administered to reduce immune rejection. In other embodiments, one or more peptides that compete with Stat1 or Stat2 for binding to the IFN-α receptor or IFN-β receptor are administered to reduce immune rejection. In other embodiments, one or more peptides that compete with Stat1 for binding to the IFN-γ receptor are administered to reduce immune rejection. In yet other embodiments, one or more dominant-negative Stat1 polypeptides (e.g., a Stat1 polypeptide lacking its SH2 domain or a Stat1 polypeptide lacking its DNA binding domain), dominant-negative Stat2 polypeptides (e.g., a Stat2 polypeptide lacking its SH2 domain or a Stat2 polypeptide lacking its DNA binding domain), or dominant-negative Stat3 polypeptides (e.g., a Stat3 polypeptide lacking its SH2 domain or a Stat3 polypeptide lacking its DNA binding domain) are administered to reduce immune rejection.

Jak2 is involved in activation of Stat4 protein. In view of this, another composition that can be utilized as part of the methods of the invention comprises a composition that reduces the expression or activity of Jak2, while not affecting NF-κB activation or platelet aggregation. In one embodiment, therefore, one or more peptides that compete with Jak2 for binding to the IL-12R$\beta_2$ can be utilized. In other embodiments, such compounds include Jak2 antisense molecules, triple helix molecules or ribozyme molecules that serve to downregulate the expression of Jak2. Representative antisense compositions are described in detail below. Such compounds also include antibodies or fragments thereof that specifically bind to and inhibit the activity of Jak2.

Tyk2 is also involved in activation of Stat4 protein. In view of this, another composition that can be utilized as part of the methods of the invention comprises a composition that reduces the expression or activity of Tyk2, while not affecting NF-κB activation or platelet aggregation. In another embodiment, a composition of the invention comprises one or more peptides that compete with Tyk2 for binding to the IL-12R$\beta_1$. In other embodiments, such compounds include Tyk2 antisense molecules, triple helix molecules or ribozyme molecules that serve to downregulate the expression of Tyk2. Representative antisense compositions are described in detail below.

In yet another embodiment, a composition that can be utilized as part of these methods comprises one or more small molecules that decrease or downregulate Stat4 expression or activity, while not affecting NF-κB activation or platelet aggregation. For example, among the compounds that can be utilized as part of these methods are protein tyrosine kinase inhibitors, including, but not limited to the tyrphostin class of protein tyrosine kinase inhibitors. Preferable tyrphostin compositions are ones that inhibit or downregulate Stat4 activity by (without wishing to be bound by any particular mechanism) inhibiting Jak2 or Tyk2 protein tyrosine kinase activity without deleterious effects on normal hematopoiesis. In specific embodiments, the tyrphostin is AG-490 (B42), although it is preferred that this particular tyrphostin not be utilized for treatment of autoimmune disorders, specifically multiple sclerosis (MS).

ANTISENSE, RIBOZYME, TRIPLE-HELIX COMPOSITIONS

Representative, non-limiting examples of Stat1 antisense molecules include the following: 5'-GCT GAA GCT CGA ACC ACT GTG ACA TCC-3' (SEQ ID NO:19); and 5'-AAG TTC GTA CCA CTG AGA CAT CCT GCC (SEQ ID NO:20).

Representative, non-limiting examples of Stat2 antisense molecules include the following: 5'-CAT CTC CCA CTG CGC CAT TTG GAC TCT TCA -3' (SEQ ID NO:21); and 5'-CAG CAT TTC CCA CTG CGC CAT TTG GGC-3' (SEQ ID NO:22).

Representative, non-limiting examples of Stat3 antisense molecules include the following: 5'-CTG GTT CCA CTG AGC CAT CCT GCT GCA TCAG-3' (SEQ ID NO:23); and 5'-CTG TAG CTG ATT CCA TTG GGC CAT CCT-3' (SEQ ID NO:24).

Representative, non-limiting examples of Stat4 antisense molecules include the following: 5'-GAT TCC ACT GAG ACA TGC TGC TCT CTC TCT C-3' (SEQ ID NO:25); and 5'-GAC TTG ATT CCA CTG AGA CAT GCT AGC-3' (SEQ ID NO:26).

Representative, non-limiting examples of Jak2 antisense molecules include the following: 5'-GCC AGG CCA TTC CCA TCT AGA GCT TTT TTC-3' (SEQ ID NO:27); and 5'-CGT AAG GCA GGC CAT TCC CAT GCA GAG-3' (SEQ ID NO:28).

Representative, non-limiting examples of Tyk2 antisense molecules include the following: 5'-CCC ACA CAG AGG CAT GGT CCC CAC CAT TCA-3' (SEQ ID NO:29); and 5'-GGC CAT CCC CCA GTG GCG CAG AGG CAT GCT CCC-3' (SEQ ID NO:30).

Representative, non-limiting examples of SOCS1 antisense molecules include the following: 5'-CCT GGT TGC GTG CTA CCA TCC TAC TCG AGG GGC-3' (SEQ ID NO:31); and 5'-CAC CTG GTT GTG TGC TAC CAT CCT ACT-3' (SEQ ID NO:32).

Representative, non-limiting examples of SOCS3 antisense molecules include the following: 5'-GCT GTG GGT GAC CAT GGC GCA CGG AGC CAG CG-3' (SEQ ID NO:33); and 5'-GGC GGG AAA CTT GCT GTG GGT GAC CAT-3' (SEQ ID NO:34).

In addition, standard techniques can be utilized to produce antisense, triple helix, or ribozyme molecules for use as part of the methods described herein. First, standard techniques can be utilized for the production of antisense nucleic acid molecules, i.e., molecules which are complementary to a sense nucleic acid encoding a polypeptide of interest (e.g., Stat1, Stat2, Stat3, Stat4, Jak2, Tyk2, SOCS1, or SOCS3), e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of interest. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Antisense nucleic acid molecules administered to a subject or generated in situ such that they hybridize with or bind to cellular mRNA encoding the polypeptide of interest to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue, e.g., transplant or autoimmune lesion, site. Alternatively, antisense nucleic acid molecules can be modified to target selected cells and then administered systemically. For example, for systemic administration, antisense molecules can be modified such that they specifically bind to receptors or antigens expressed on a selected cell, e.g., T cell, surface, e.g., by linking the antisense nucleic acid molecules to peptides or antibodies which bind to cell surface receptors or antigens. The antisense nucleic acid molecules can also be delivered to cells using vectors, e.g., gene therapy vectors, described below. To achieve sufficient intracellular concentrations of the antisense molecules, vector constructs in which the antisense nucleic acid molecule is placed under the control of a strong pol II or pol III promoter are preferred.

An antisense nucleic acid molecule of interest can be an α-anomeric nucleic acid molecule. An a-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

Ribozymes are catalytic RNA molecules with ribonuclease activity which are capable of cleaving a single-stranded nucleic acid, such as an mRNA, to which they have a complementary region, and can also be generated using standard techniques. Thus, ribozymes (e.g., hammerhead ribozymes (described in Haselhoff and Gerlach (1988) *Nature* 334:585–591)) can be used to catalytically cleave mRNA transcripts to thereby inhibit translation of the protein encoded by the mRNA. A ribozyme having specificity for a nucleic acid molecule encoding a polypeptide of interest can be designed based upon the nucleotide sequence of a cDNA disclosed herein. For example, a derivative of a *Tetrahymena* L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of interest can be used to select a catalytic RNA having a specific ribonuclease activity from a pool of RNA molecules. See, e.g., Bartel and Szostak (1993) *Science* 261:1411–1418.

Triple helical structures can also be generated using well known techniques. For example, expression of a polypeptide of interest can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569–84; Helene (1992) *Ann. N.Y. Acad. Sci.* 660:27–36; and Maher (1992) *Bioassays* 14(12):807–15.

In various embodiments, nucleic acid compositions can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93: 14670–675.

PNAs can, for example, be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) *Nucleic Acids Res.* 17:5973–88). PNA monomers are then coupled in a stepwise manner to produce a chimeric molecule with a 5' PNA segment and a 3' DNA segment (Finn et al. (1996) *Nucleic Acids Res.* 24(17):3357–63). Alternatively, chimeric molecules can be synthesized with a 5' DNA segment and a 3' PNA segment (Peterser et al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958–976) or intercalating agents (see, e.g., Zon (1988) *Pharm. Res.* 5:539–549). To this end, the oligonucleotide may be conjugated to another molecule, e.g., a peptide, hybridization triggered cross-linking agent, transport agent, hybridization-triggered cleavage agent, etc.

ANTIBODY COMPOSITIONS

In one embodiment, anti-Stat1 antibodies, anti-Stat2 antibodies, anti-Stat3 antibodies, anti-Stat4 antibodies, anti-SOCS1 antibodies or anti-SOCS3 antibodies are administered to a mammal, preferably a human, to reduce immune rejection. In another embodiment, any combination of anti-Stat1 antibodies, anti-Stat2 antibodies, anti-Stat3 antibodies, anti-Stat4, anti-SOCS1 antibodies and anti-SOCS3 antibodies are administered to a mammal, preferably a human, to reduce immune rejection. In a preferred embodiment, anti-Stat1 antibodies, anti-Stat2 antibodies, anti-Stat3 antibodies, anti-Stat4 antibodies, anti-SOCS1 antibodies or anti-SOCS3 antibodies are administered to a mammal, preferably a human, in combination with other types of treatments (e.g., immunosuppressive agents) to reduce immune rejection. In yet another preferred embodiment, any combination of anti-Stat1 antibodies, anti-Stat2 antibodies, anti-Stat3 antibodies, anti-Stat4, anti-SOCS1 antibodies and anti-SOCS3 antibodies are administered to a mammal, preferably a human, in combination with other types of treatments (e.g., immunosuppressive agents) to reduce immune rejection.

Anti-Stat1 antibodies, anti-Stat2 antibodies, anti-Stat3 antibodies, anti-Stat4 antibodies, anti-SOCS1 antibodies, anti-SOCS3 antibodies, or any combination thereof can be administered to a mammal, preferably a human, using various delivery systems are known to those of skill in the art. For example, anti-Stat1 antibodies, anti-Stat2 antibodies, anti-Stat3 antibodies, anti-Stat4 antibodies, anti-SOCS1 antibodies, anti-SOCS3 antibodies, or any combination thereof can be administered by encapsulation in liposomes, microparticles or microcapsules. See, e.g., U.S. Pat. No. 5,762,904, U.S. Pat. No. 6,004,534, and PCT Publication WO 99/52563. In addition, anti-Stat1 antibodies, anti-Stat2 antibodies, anti-Stat3 antibodies, anti-Stat4 antibodies, anti-SOCS1 antibodies, anti-SOCS3 antibodies, or any combination thereof can be administered using recombinant cells capable of expressing the antibodies, or retroviral, other viral vectors or non-viral vectors capable of expressing the antibodies.

Anti-Stat1 antibodies, anti-Stat2 antibodies, anti-Stat3 antibodies, anti-Stat4, anti-SOCS1 antibodies and anti-SOCS3 antibodies can be obtained from any known source. For example, anti-Stat1 antibodies, anti-Stat2 antibodies, anti-Stat3 antibodies, anti-Stat4, anti-SOCS1 antibodies and anti-SOCS3 antibodies can be obtained from Santa Cruz Biotechnology, Inc. (Santa Cruz, Calif.), Research Diagnostics, Inc. (Flanders, N.J.) or Zymed Laboratories (South San Francisco, Calif.). Alternatively, anti-Stat1 antibodies, anti-Stat2 antibodies, anti-Stat3 antibodies, anti-Stat4, anti-SOCS1 antibodies and anti-SOCS3 antibodies can be produced by any method known in the art for the synthesis of antibodies, in particular, by chemical synthesis or preferably, by recombinant expression techniques.

Antibodies of the invention include, but are not. limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, 1 gM, IgD, IgA and IgY), class (e.g., $IgG_1$, $IgG_2$, $IgG_3$, $IgG_4$, $IgA_1$ and $IgA_2$) or subclass of immunoglobulin molecule. Examples of immunologically active portions of immunoglobulin molecules include F(ab) and $F(ab')_2$ fragments which can be generated by treating the antibody with an enzyme such as pepsin or papain.

An isolated Stat1, Stat2, Stat3, Stat4, SOCS1 or SOCS3, or a fragment thereof, can be used as an immunogen to generate antibodies using standard techniques for polyclonal and monoclonal antibody preparation. The full-length Stat1, Stat2, Stat3, Stat4, SOCS1 or SOCS3 polypeptide or protein can be used or, alternatively, the invention provides antigenic peptide fragments of Stat1, Stat2, Stat3, Stat4, SOCS1 or SOCS3 for use as immunogens. An antigenic peptide comprises at least 8 (preferably 10, 15, 20, or 30) amino acid residues of the amino acid sequence of Stat1, Stat2, Stat3, Stat4, SOCS1 or SOCS3, and encompasses an epitope of Stat1, Stat2, Stat3, Stat4, SOCS1 or SOCS3 such that an antibody raised against the peptide forms a specific immune complex with Stat1, Stat2, Stat3, Stat4, SOCS1 or SOCS3.

The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. Alternatively, antibodies specific for a protein or polypeptide of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those on the desired Stat1, Stat2, Stat3, Stat4, SOCS1 or SOCS3 protein or polypeptide, and preferably at most 20%, yet more preferably at most 10%, and most preferably at most 5% (by dry weight) of the sample is contaminating antibodies. A purified antibody composition means that at least 99% of the antibodies in the composition are directed against the desired Stat1, Stat2, Stat3, Stat4, SOCS1 or SOCS3 protein or polypeptide.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against Stat 1, Stat2, Stat3, Stat4, SOCS1 or SOCS3 polypeptide can be identified and isolated by screening a recombinant combinatorial immunoglobulin library (e.g., an antibody phage display library) with Stat1, Stat2, Stat3, Stat4, SOCS1 or SOCS3. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant antibodies, such as chimeric and humanized monoclonal antibodies, comprising both human and non-human portions, can be made using standard recombinant DNA techniques. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Fremont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) Bio/technology 12:899–903).

As described herein, anti-Stat1, anti-Stat2, anti-Stat3, anti-Stat4, anti-SOCS1 or anti-SOCS3 antibodies can be used diagnostically to monitor protein levels within affected tissue (e.g., a transplant cell, tissue, organ or organ system, or a cell, tissue, organ or organ system that is, or is suspected of being affected by an autoimmune disorder) as part of a clinical testing procedure, e.g., to, for example, determine transplant rejection or the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Further, as described herein, anti-Stat1 antibodies, anti-Stat2 antibodies, anti-Stat3 antibodies, anti-Stat4 antibodies, anti-SOCS1 antibodies, anti-SOCS3 antibodies, or any combination thereof can be conjugated to a therapeutic moiety and administered to a mammal, preferably a human, to reduce or prevent immune rejection. Examples of therapeutic moieties that can be conjugated to antibodies include, but are not limited to, a cytotoxin, a therapeutic agent or a radioactive metal ion. A cytotoxin or cytotoxic agent includes any agent that is detrimental to cells such as taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The antibodies can also be conjugated a drug moiety that modifies a given biological response. For example, a drug moiety may be a protein or polypeptide possessing a desired biological activity. Such proteins may include, for example, a toxin such as abrin, ricin A, pseudomonas exotoxin, or diphtheria toxin; and a lymphokine such as IL-4 or IL-13.

The invention also provides kits comprising an anti-Stat1 antibody, an anti-Stat2 antibody, an anti-Stat3 antibody, an anti-Stat4 antibody, an anti-SOCS1 antibody, an anti-SOCS3 antibody, or any combination thereof conjugated to a detectable substance, and instructions for use. Still another aspect of the invention is a pharmaceutical composition comprising an anti-Stat1 antibody, an anti-Stat2 antibody, an anti-Stat3 antibody, an anti-Stat4 antibody, an anti-SOCS1 antibody, an anti-SOCS3 antibody and a pharmaceutically acceptable carrier. In preferred embodiments, the pharmaceutical composition contains an anti-Stat1 antibody, an anti-Stat2 antibody, an anti-Stat3 antibody, an anti-Stat4 antibody, an anti-SOCS1 antibody, or an anti-SOCS3 antibody, a therapeutic moiety, and a pharmaceutically acceptable carrier.

In instances wherein an anti-Stat1 antibody, an anti-Stat2 antibody, an anti-Stat3 antibody, an anti-Stat4 antibody, an anti-SOCS1 antibody, an anti-SOCS3 antibody is to be utilized as a therapeutic, characterization of the antibody can routinely be assayed and ascertained via the methods presented herein. For example, the fact that lymphocytes and animal models for transplants and autoimmune disorders are readily available, coupled with the availability of multiple assays for Stat and SOCS expression and activity provide for routine testing and analysis (e.g., for in vitro and in vivo testing and analysis) of such antibodies. The antibodies described herein can be tested, for example, for their ability to modulate the expression and/or activity of Stat1, Stat2, Stat3, Stat4, Stat6, SOCS1, SOCS3, or any combination thereof, and for their specificity and toxicity.

GENE THERAPY TECHNIQUES

Gene therapy refers to therapy performed by the administration to a subject of an expressed or expressible nucleic acid. Any of the methods for gene therapy available in the art can be used according to the present invention. Exemplary methods are described below.

In one embodiment, Stat4 antisense oligonucleotides are administered to reduce immune rejection by way of gene therapy. In another embodiment, nucleic acid molecules comprising sequences encoding one or more anti-Stat4 antibodies are administered to reduce immune rejection, by way of gene therapy. In another embodiment, nucleic acid molecules comprising sequences encoding one or more peptides that compete with Jak2 for binding to the IL-12 receptor $\beta_2$ ("IL-12R$\beta_2$") are administered to immune rejection, by way of gene therapy. In another embodiment, nucleic acid molecules comprising sequences encoding one or more peptides that compete with Tyk2 for binding to the IL-12R$\beta_1$ are administered to reduce immune rejection, by way of gene therapy. In another embodiment, nucleic acid molecules comprising sequences encoding one or more peptides that compete with Stat4 for binding to the IL-12R$\beta_2$ are administered to reduce immune rejection, by way of gene therapy. In another embodiment, nucleic acid molecules comprising sequences encoding one or more peptides that bind to the Stat4 SH2 domain which prevent Stat4 from binding to the IL-12R$\beta_2$ are administered to reduce immune rejection, by way of gene therapy. In yet another embodiment, nucleic acid molecules comprising sequences encoding one or more dominant-negative Stat4 polypeptides (e.g., a Stat4 polypeptide lacking its SH2 domain or a Stat4 polypeptide lacking its DNA binding domain) are administered to reduce immune rejection, by way of gene therapy.

In specific embodiments, Stat1 antisense oligonucleotides, Stat2 antisense oligonucleotides, Stat3 antisense oligonucleotides, or the combination thereof are administered to reduce immune rejection by way of gene therapy. In other embodiments, nucleic acid molecules comprising sequences encoding one or more anti-Stat1 antibodies, anti-Stat2 antibodies, or anti-Stat3 antibodies are administered to reduce immune rejection, by way of gene therapy. In other embodiments, nucleic acid molecules comprising sequences encoding one or more peptides that compete with Jak1 or Tyk2 for binding to the IFN-α receptor or IFN-β receptor are administered to reduce immune rejection, by way of gene therapy. In yet another embodiment, nucleic acid molecules comprising sequences encoding one or more peptides that compete with Jak1 or Jak2 for binding to the IFN-γ receptor are administered to reduce immune rejection, by way of gene therapy. In other embodiments, nucleic acid molecules comprising sequences encoding one or more peptides that compete with Stat1 or Stat2 for binding to the IFN-α receptor or IFN-β receptor are administered to reduce immune rejection, by way of gene therapy. In other embodiments, nucleic acid molecules comprising sequences encoding one or more peptides that compete with Stat1 for binding to the IFN-γ receptor are administered to reduce immune rejection, by way of gene therapy. In yet other embodiments, nucleic acid molecules comprising sequences encoding one or more dominant-negative Stat1 polypeptides (e.g., a Stat1 polypeptide lacking its SH2 domain or a Stat1 polypeptide lacking its DNA binding domain), dominant-negative Stat2 polypeptides (e.g., a Stat2 polypeptide lacking its SH2 domain or a Stat2 polypeptide lacking its DNA binding domain), or dominant-negative Stat3 polypeptides (e.g., a Stat3 polypeptide lacking its SH2 domain or a Stat3 polypeptide lacking its DNA binding domain) are administered to reduce immune rejection, by way of gene therapy.

For general reviews of the methods of gene therapy, see Goldspiel et al., 1993, *Clinical Pharmacy* 12:488–505; Wu and Wu, 1991, *Biotherapy* 3:87–95; Tolstoshev, 1993, *Ann. Rev. Pharmacol. Toxicol.* 32:573–596; Mulligan, 1993, *Science* 260:926–932; and Morgan and Anderson, 1993, *Ann. Rev. Biochem.* 62:191–217; May, 1993, TIBTECH 11(5): 155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In one aspect, a composition of the invention comprises nucleic acid sequences encoding one or more anti-Stat 1, anti-Stat 2, anti-Stat 3, anti-Stat 4, anti-SOCS1, or anti-SOCS 3 antibodies or fragments thereof, said nucleic acid sequences being part of expression vectors that express one or more anti-Stat 1, anti-Stat 2, anti-Stat 3, anti-Stat 4, anti-SOCS1, or anti-SOCS 3 antibodies or fragments thereof in a suitable host. In particular, such nucleic acid sequences have promoters operably linked to the anti-Stat 1, anti-Stat 2, anti-Stat 3, anti-Stat 4, anti-SOCS1, or anti-SOCS 3 antibodies or fragments thereof, said promoter being inducible or constitutive, and, optionally, tissue-specific.

In another aspect, a composition of the invention comprises nucleic acid sequences encoding dominant-negative Stat1, Stat2, Stat3,Stat4, SOCS1, or SOCS3 polypeptides, said nucleic acid sequences being part of expression vectors that express dominant-negative Stat1, Stat2, Stat3,Stat4, SOCS1, or SOCS3 polypeptides in a suitable host. In particular, such nucleic acid sequences have promoters operably linked to the dominant-negative Stat1, Stat2, Stat3, Stat4, SOCS1, or SOCS3, said promoter being inducible or constitutive, and, optionally, tissue-specific. In another particular embodiment, nucleic acid molecules are used in which the dominant-negative Stat 1, Stat2, Stat3,Stat4, SOCS1, or SOCS3 coding sequences and any other desired sequences are flanked by regions that promote homologous recombination at a desired site in the genome, thus providing for intrachromosomal expression of the dominant-negative Stat1, Stat2, Stat3,Stat4, SOCS1, or SOCS3 nucleic acids (Koller and Smithies, 1989, *Proc. Natl. Acad. Sci. USA* 86:8932–8935; Zijlstra et al., 1989, *Nature* 342:435–438).

In another aspect of the invention, a composition of the invention comprises nucleic acid molecules comprising sequences encoding one or more peptides that compete with Tyk2 for binding to the IL-12Rβ$_1$, said nucleic acid sequences being part of expression vectors that express one or more peptides in a suitable host. In another aspect of the invention, a composition of the invention comprises nucleic acid sequences nucleic acid molecules comprising sequences encoding one or more peptides that compete with Stat4 for binding to the IL-12Rβ$_2$, said nucleic acid sequences being part of expression vectors that express one or more peptides in a suitable host. In yet another aspect of the invention, a composition of the invention comprises nucleic acid molecules comprising sequences encoding one or more peptides that bind to the Stat4 SH2 domain which prevent Stat4 from binding to the IL-12Rβ$_2$, said nucleic acid sequences being part of expression vectors that express one or more peptides in a suitable host. In particular a embodiment of the invention, the nucleic acid sequences encoding peptides of the invention have promoters operably linked to said nucleic acid sequences, said promoter being inducible or constitutive, and, optionally, tissue-specific.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequence is directly administered in vivo, where it is expressed to produce the encoded product. This can be accomplished by any of numerous methods known in the art, e.g., by constructing it as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, *J. Biol. Chem.* 262:4429–4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, *Proc. Natl. Acad. Sci. USA* 86:8932–8935; Zijlstra et al., 1989, *Nature* 342:435–438).

In one embodiment, viral vectors that contain Stat4 antisense oligonucleotides are used (see Miller et al., 1993, *Meth. Enzymol.* 217:581–599). In another embodiment, viral vectors that contain nucleic acids encoding one or more anti-Stat4 antibodies are used. In another embodiment, viral vectors that contain nucleic acids encoding one or more peptides that compete with Jak2 for binding to the IL-12 receptor $\beta_2$ ("IL-12R$\beta_2$") are used. In another embodiment, viral vectors that contain nucleic acids encoding one or more peptides that compete with Tyk2 for binding to the IL-12R$\beta_1$ are used. In another embodiment, viral vectors that contain nucleic acids encoding one or more peptides that compete with Stat4 for binding to the IL-12R$\beta_2$ are used. In another embodiment, viral vectors that contain nucleic acids encoding one or more peptides that bind to the Stat4 SH2 domain which prevent Stat4 from binding to the IL-12R$\beta_2$ are used. In yet another embodiment, viral vectors that contain nucleic acids encoding dominant-negative Stat4 polypeptides (e.g., Stat4 lacking its SH2 domain or Stat4 lacking its DNA binding domain) are used. For example, a retroviral vector can be used. These retroviral vectors have been modified to delete retroviral sequences that are not necessary for packaging of the viral genome and integration into host cell DNA. The nucleic acid sequences encoding the Stat1, Stat2, Stat3, Stat4, SOCS1 or SOCS3 antibodies, or polypeptides or peptides of the invention to be used in gene therapy are cloned into one or more vectors, which facilitates delivery of the gene into a patient. More detail about retroviral vectors can be found in Boesen et al., 1994, *Biotherapy* 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, *J. Clin. Invest.* 93:644–651; Kiem et al., 1994, *Blood* 83:1467–1473; Salmons and Gunzberg, 1993, *Human Gene Therapy* 4:129–141; and Grossman and Wilson, 1993, *Curr. Opin. in Genetics and Devel.* 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, *Current Opinion in Genetics and Development* 3:499–503 present a review of adenovirus-based gene therapy. Bout et al., 1994, *Human Gene Therapy* 5:3–10 demonstrated the use of adenovirus vectors to transfer genes to the respiratory epithelia of rhesus monkeys. Other instances of the use of adenoviruses in gene therapy can be found in Rosenfeld et al., 1991, *Science* 252:431–434; Rosenfeld et al., 1992, *Cell* 68:143–155; Mastrangeli et al., 1993, *J. Clin. Invest.* 91:225–234; PCT Publication WO94/12649; and Wang, et al., 1995, *Gene Therapy* 2:775–783. In a preferred embodiment, adenovirus vectors are used.

Adeno-associated virus (AAV) has also been proposed for use in gene therapy (Walsh et al., 1993, *Proc. Soc. Exp. Biol. Med.* 204:289–300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, *Meth. Enzymol.* 217:599–618; Cohen et al., 1993, *Meth. Enzymol.* 217:618–644; Cline, 1985, *Pharmac. Ther.* 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In one embodiment in which recombinant cells are used in gene therapy, nucleic acid sequences encoding Stat1, Stat2, Stat3, Stat4, SOCS1 or SOCS3 antibodies, or polypeptides or peptides of the invention are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, 1992, *Cell* 71:973–985; Rheinwald, 1980, *Meth. Cell Bio.* 21A:229; and Pittelkow and Scott, 1986, *Mayo Clinic Proc.* 61:771).

Promoters that may be used to control the expression of nucleic acid sequences encoding Stat1, Stat2, Stat3, Stat4, SOCS1 or SOCS3 antibodies, or polypeptides or peptides of the invention include, but are not limited to, the SV40 early promoter region (Bernoist and Chambon, 1981, *Nature* 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. USA 78:1441–1445), the regulatory sequences of the metallothionein gene (Brinster et al., 1982, Nature 296:39–42); prokaryotic expression vectors such as the β-lactamase promoter (Villa-Kamaroff et al., 1978, Proc. Natl. Acad. Sci. USA 75:3727–3731), or the tac promoter (DeBoer et al., 1983, Proc. Natl. Acad. Sci. USA 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlau f et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

PHARMACEUTICAL COMPOSITIONS

The nucleic acid molecules, polypeptides, antibodies and small molecules (also referred to herein as "active compounds") described herein can be incorporated into pharmaceutical compositions suitable for administration. Such compositions typically comprise the active compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of interest (e.g., Stat1, Stat2, Stat3, Stat4, Stat6, SOS 1, or SOCS3). Such methods comprise formulating a pharmaceutically acceptable carrier with an agent which modulates expression or activity of a polypeptide or nucleic acid of interest (e.g., Stat1, Stat2, Stat3, Stat4, Stat6, SOS 1, or SOCS3). Such compositions can further include additional active agents. Thus, the invention further includes methods for preparing a pharmaceutical composition by formulating a pharmaceutically acceptable carrier with an agent which modulates expression or activity of a polypeptide or nucleic acid of interest and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Intravenous administration is preferred. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (more preferably, 0.1 to 20 mg/kg, 0.1–10 mg/kg, or 0.1 to to 1.0 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 0.1 to 1.0 mg/kg, 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a representative, non-limiting example, a subject is treated at the time of transplantation, or when diagnosed as exhibiting a reoccurrence of rejection, or an occurrence of a rejection (e.g., an autoimmune rejection) with one to several (for example, between 3 and 7) doses of an appropriate modulator of Stat1, Stat2, Stat3, Stat4, Stat6, SOS 1, and/or SOCS3 for a maximum of one week. In a preferred embodiment of such an example, treatment would further comprise additional administration approximately once per month for about 3 to 6 months. The preferred route of administration is intravenous bolus injection. It will also be appreciated that the effective dosage of the modulator used for treatment may increase or decrease over the course of a particular treatment. Changes in dosage may result and become apparent from the results of diagnostic assays as described herein.

Preferably, administration of modulator is by intravenous injection, and can also be are or near the site of the cells or tissue to be treated, e.g., administration is at or near the site of the transplant or autoimmune disorder lesion.

In addition to those compounds described above, the present invention encompasses agents and use of agents which modulate expression or activity of a nucleic acid or polypeptide of interest. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

In one embodiment, one or more compositions for modulation of Stat1, Stat2, Stat3, Stat4, Stat6, SOCS1, or SOCS3 can be used combinatorially. For example, compositions for decreasing expression or activity of Stat4 can be utilized in combination (either simultaneously or serially) with compositions or techniques for increasing expression or activity of Stat6 can be utilized.

In another embodiment, one or more compositions of the present invention that modulate expression or activity of Stat1, Stat2, Stat3, Stat4, Stat6, SOCS1 or SOCS3 can be administered to a mammal, preferably a human, in combination with one or more standard immunosuppressive or immunomodulatory compounds to reduce or prevent immune rejection resulting from an autoimmune disorder or an allograft. Examples of immunosuppressive agents include, but are not limited to, azathioprine, corticosteriods (e.g., prednisone), cyclosporine, OKT3 (anti-CD3 monoclonal human antibody), mycophenolate mofetil, rapamycin (sirolimus), mizoribine, deoxyspergualin, macrolide antibiotics such as, for example, FK506 (tacrolimus), brequinar, malononitriloamindes.(e.g., leflunamide), and anti-IL-2R antibodies (e.g., anti-Tac monoclonal antibody and BT 536). See, e.g., Grummet et al., 1999, J. Am. Soc. Nephrol. 10:1366–1388; and Norman and Wadi, eds., 1998, "Primer on Transplantation," Am. Soc. Tx. Phys, $1^{st}$ ed.).

Immunosuppressive agents may be administered at high doses initially and then tapered off over time to reduce or prevent immune rejection. For example, one or more compositions of the invention in combination with an initial dose of cyclosporine ranging from between 5 and 10 mg/kg per day, an initial dose of 10 mg/kg per day prednisone, or an initial dose of 10 mg/kg per day mycophenolate mofetil may be administered to animal to reduce or prevent immune rejection. Alternatively, one or more compositions of the invention in combination with an initial dose of cyclosporine ranging from between 5 and 10 mg/kg per day, an initial dose of 10 mg/kg per day prednisone, and an initial dose of 10 mg/kg per day mycophenolate mofetil may be administered to animal to reduce or prevent immune rejection. Preferably, corticosteroids are not administered children.

In yet another embodiment, one or more compositions of the present invention that modulate expression or activity of Stat1, Stat2, Stat3, Stat4, Stat6, SOCS1 or SOCS3 can be administered to a mammal, preferably a human, in combination with one or more standard autoimmune therapeutic agents used for treating a particular autoimmune disorder. For example, one or more compositions of the present invention may be administered in combination with one or more conventional anti-lupus therapeutic agents or drugs such as, for example, salicylates, corticosteroids, and immunosuppresants.

In another embodiment, one or more compositions of the present invention for modulating the expression or activity of Stat1, Stat2, Stat3, Stat4, Stat6, SOCS1, or SOCS3 are administered to a mammal, preferably a human, in combination with one or more T cell-targeted or B cell-targeted agents. Examples of such agents include, but are limited to, CTLA-4Ig, IL-2 antagonists (e.g., anti-IL-2 receptor antibodies and IL-2 toxin conjugates), B7 monoclonal antibodies, anti-CD40L monoclonal antibodies, CD4 antagonists (e.g., anti-CD4 monoclonal antibodies), CD3 antagonists (e.g., anti-CD3 monoclonal antibodies), and IL-12 antagonists (e.g., anti-IL-12 monoclonal antibodies and IL-12 toxin conjugates) to reduce or prevent immune rejection an autoimmune disorder or an allograft.

In order that the invention described herein may be more fully understood, the following examples are set forth. It should be understood that these examples are for illustrative purposes only and are not to be construed as limiting this invention in any manner.

6. EXAMPLE: QUANTITATIVE ANALYSIS OF NF-κB AND IκB PROTEINS IN MOUSE CARDIAC ALLOGRAFTS

NF-κB proteins are transcription factors complexed with IκB proteins in the cytoplasm but which upon cell activation are released, translocate to the nucleus and bind κB motifs in the promoters of many genes, in particular of the promoters of genes whose expression is involved the immune response. Since NF-κB plays an important role in the transcription of genes involved in immune responses, the expression levels of NF-κB and IκB proteins and their localization were determined in mouse cardiac allografts. The data generated and analyzed represents the first comprehensive analysis of NF-κB and IκB protein expression, phosphorylation, and localization as detected by Western blotting and immunohistology in serially harvested allografts (BALB/c→B6), isoftafts and native hearts from recipients treated with IgG (rejection by day 8) or CD40 ligand monoclonal antibody ("CD40L mAb"; permanent survival).

Heterotopic cardiac allografting was performed with anastomoses to the abdominal aorta and vena cava (Hancock et al., 1998, Nature Medicine 4:1392–1396), using BALB/c donors and B6/129 wild-type or other Balb/c wild-type mice as recipients. Recipients were treated with hamster IgG or hamster anti-mouse (CD40L mAb; 250 μg, administered intravenously) plus DST ($5 \times 10^6$ splenic mononuclear cells) at the time of transplantation (Hancock et al., 1998, Nature Medicine 4:1392–1396). The protein expression, phosphorylation and localization of NF-κB and IκB were detected by Western blot analysis and immunohistology using serially harvested allografts, isografts and native hearts from recipients treated with IgG (rejection by day 8) or CD40L mAb (permanent survival).

The following tissue-specific expression patterns in the basal cardiac state relative to other organs were detected: low p50; low p52; low p65; low C-rel; low relB; low IkBa; high IkBb; low IkBe; low BCL-3 and high p105. The level of NF-κB proteins was significantly increased (2–4 fold) upon allografting and these levels were only modestly affected by CD40L mAb. Significant increases in the levels of IκBa (greater than 2 fold) and IκBe (greater than 6 fold) proteins were also detected in cardiac allografts. In contrast, a significant decrease in the level of IκBb protein, low to undetectable levels of p105 protein, and trace levels of BCL-3 were detected in cardiac allografts, but were only modestly affected by CD40L mAb. Thus, these results demonstrate that in cardiac allografts the NF-κB regulatory apparatus is highly activated at the protein level and is only modestly affected by CD40L mAb.

Cardiac samples principally express p105 and IκBb, but these are down-regulated during rejection, presumably through the action of the proteasome. By contrast, cardiac allograft rejection is associated primarily with expression by infiltrating leukocytes of p65, p50 and c-rel NF-κB proteins, plus IκBa and IκBc proteins.

The results, therefore, suggest that monitoring of the levels of NF-κB and IκB proteins in biopsies from transplant recipients may be of diagnostic and/or prognostic significance.

7. EXAMPLE: DIFFERENTIAL EFFECTS OF IMMUNOSUPPRESSIVE AGENTS ON ANTI-CD40L ANTIBODY-MEDIATED TOLERANCE INDUCTION

The data presented herein demonstrate that concomitant use of the immunosuppressive agents cyclosporin A or methylprednisolone, but not rapamycin, blocks CD154 mAb efficacy in experimental allograft recipients. Indeed, the differential effects of these agents on CD154 mAb-induced tolerance correlates with their capacity to inhibit activation-induced CD154 expression on CD4+ T cells. Full expression of CD154 expression was found to require NF-κB activation, and CD154 mAb was ineffective in NF-κB/p50 deficient allograft recipients or control mice in which NF-κB activation was blocked by a proteasome inhibitor. Hence, these data indicate that strategies to use CD154 mAb clinically must take into account the effects of immunosuppressive agents on CD154 induction, which appears to be at least partially NF-κB dependent, and suggest that ligation of surface-expressed CD154 provides an important signal that modulates T cell activation.

Materials & Methods
Media and Reagents:
Cell culture media, serum and supplements were purchased from Gibco BRL (Rockville. Md.) and all mAbs were from PharMingen (San Diego, Calif.). Cyclosporin A (catalog C-3662, Sigma. St. Louis. Mo.) was prepared as a 5 mg/ml stock solution in 0.9% saline; rapamycin (catalog 380-004-M001, Alexis, San Diego. Calif.) as a 1 mg/ml stock solution in ethanol: 6α-methylprednisolone (catalog M-0369, Sigma) as a 5 mg/ml stock solution in 80% ethanol; mycophenolate mofetil (catalog M-5255, Sigma) as a 20 mM stock solution in DMSO; and the 3 proteasome inhibitors (Grisham, M. B., et al., 1999, Methods Enzymol 300:345–63), clasto-lactacystin β-lactone (catalog 426102, Calbiochem, San Diego, Calif.) and its derivative PS-519 (Proscript, Cambridge, Mass.), and dipeptide-boronate (MG-273. ProScript), each as a 10 mM stock solution in DMSO.

Mice:

BALB/c ($H-2^d$) and B6/129 ($H-2^b$) mice were obtained from Jackson Labs (Bar Harbor, Me.), and NF-κB/p50 knockout (p50 KO) B6/129 mice ($H-2^b$) (Sha, W. C. et al., 1995, Cell 80:321–30.) were provided by Dr. David Baltimore (MIT, Cambridge, Mass.), and were housed under specific pathogen-free conditions.

Cardiac Transplantation:

Heterotopic cardiac allografting was performed with anastomoses to the abdominal aorta and vena cava (Hancock, W. W. et al., 1998, Nature Medicine 4:1392–1396), using BALB/c donors and B6/129 wild-type or NF-κB/p50 KO mice as recipients (n=6/group). Recipients were treated with hamster IgG or hamster anti-mouse CD154 mAb (250 μg, i.v.) plus DST ("donor specific transfusion"; $5 \times 10^6$ splenic mononuclear cells) at the time of transplantation (Hancock, W. W. et al., 1998, Nature Medicine 4:1392–1396). Additional groups of allografted wild-type mice were treated with CD154 mAb/DST plus (i) rapamycin (0.2 mg/kg/d i.p.) or (ii) cyclosporin A (10 mg/kg/d i.p.) on day 0 and every other day until day 14; (iii) methylprednisolone (1 mg/kg i.p.) on day 0, 1 and 2; and (iv) PS-519 (1 mg/kg/d i.p.) daily from the time of transplantation. Graft survival was monitored by daily palpation, and rejection was confirmed by laparotomy and histologic evaluation.

Measurement of Activation-induced CD154 Expression:

Six-well plates (Costar) were pre-coated overnight with 1 μg/ml of rat anti-mouse CD3 mAb (2C11). After washing with media (RPMI supplemented with 10% fetal bovine serum, 50 U/ml penicillin, 50 μg/ml streptomycin, 2 mM glutamine and 50 μM 2-mercaptoethanol) one ml of media containing 2× final drug concentration was added to each well. After testing of a range of concentrations of each agent, the optimal final physiologic drug concentrations for the data to be reported were 125 ng/ml cyclosporin A, 20 ng/ml rapamycin. 100 μg/ml methylprednisolone, 1 μM mycophenolate mofetil, 10 μm lactacystin and 10 μM MG-273. Cells were obtained from mechanically disrupted spleens and, after collection by centrifugation and washing once with media, one ml aliquots containing two million viable splenocytes were added to each well. Cultures were incubated at 37° C. in 5% $CO_2$ for 7 hr. and were then diluted two-fold with chilled media containing 0.1% sodium azide (FACS media). Cells were collected by centrifugation at 4° C., resuspended in FACS media containing 1 μg Fc Block (PharMingen) and incubated on ice for 15 min. Samples were then split and either a mixture of 1 μg each of FITC-conjugated CD4-specific mAb and PE-conjugated control hamster IgG mAb or FITC-conjugated CD4-specific mAb and PE-conjugated CD154-specific mAb were added. After a 30 min incubation on ice, cells were washed twice and analyzed on a Becton Dickinson FACScan using Cell Quest software. Viable CD4+ lymphocytes were gated using a combination of forward/side scatter and CD4 staining.

Statistics

Flow cytometry data was analyzed using student t-test and cardiac allograft survival was evaluated by the two-tailed Mann-Whitney U test using the program InStat (GraphPad Software, San Diego. Calif.); $p < 0.05$ indicated a significant result.

Results

Given the apparent efficacy of CD154 mAb in inducing long-term cardiac allograft survival in various mouse strains (Larsen, C. P. et. al., 1996, Nature 381:434–438; Hancock. W. W. et al., 1996 Proc. Natl. Acad. Sci. USA. 93:13967–13972), without development of transplant arteriosclerosis or other sequelae of chronic rejection (Hancock, W. W. et al., 1998, Nature Medicine 4:1392–1396), investigators have begun clinical testing. As human allograft recipients presently derive significant benefit from conventional immunosuppressant therapy, initial CD154 mAb trial designs have included pharmacologic immunosuppression. However, conventional immunosuppression with glucocorticoids or cyclosporin A has prevented the success of otherwise potent experimental approaches for tolerance induction, such as that seen with intrathymic injection of donor MHC antigen in rodents (Perico, N. et al.,1995, J. Amer. Soc. Nephrol. 5:1618–1623). Likewise, CD154 mAb-induced prolongation of renal allograft survival in the initial primate studies was diminished by concomitant use of either glucocorticoids or FK506 (Kirk, A. D. et. Al, 1999, Nature Medicine 5:686–693): FK-506, like cyclosporin A, blocks activation of the calcium-dependent serine phosphatase calcineurin.

To understand the potential for inhibitory effects of immunosuppressive agents on the therapeutic efficacy of CD154 mAb, the effectiveness of CD154 mAb was investigated in conjunction with adjunct therapies in a completely MHC-mismatched ($H2^{d \rightarrow b} 2^b$) mouse cardiac allograft model. The results of concomitant administration of cyclosporin A, methylprednisolone or rapamycin on allograft survival in mice treated with CD154 mAb plus DST are summarized in FIG. 10. Whereas CD154 mAb therapy induced permanent cardiac allograft survival (>100 days), the effects of CD154 mAb were blocked by addition of cyclosporin A or methylprednisolone ($p < 0.001$ vs. CD154 mAb/DST alone), but not by rapamycin (FIG. 10).

Given these markedly contrasting differences in effects of standard immunosuppressive agents on the efficacy of CD154 mAb therapy, and recent evidence that CCD154 may signal to T cells (Blair, P. J. et al., 2000, J Exp Med 191:651–660), it was hypothesized that inhibition of CD154 expression was involved. Accordingly, the in vitro effects of standard immunosuppressive agents on the expression of CD154 by activated T cells were tested in vitro. It was found that whereas resting CD4+ splenic cells lacked CD154 expression, 25–30% of cells expressed the molecule within 7 hours of activation with plate-bound CD3 mAb (FIG. 11A). This upregulation was markedly suppressed by therapeutic doses of cyclosporin A or methylprednisolone but not by rapamycin or mycophenolate mofetil (FIG. 11a). Analysis of three separate experiments showed >90% suppression by methylprednisolone ($p < 0.01$) and >70% suppression by cyclosporin A ($p < 0.01$) whereas the effects of rapamycin (<20% inhibition) and mycophenolate mofetil (<10% inhibition) were not statistically distinguishable from control activated cells (FIG. 11B). Thus, pharmacologic immunosuppressives that reduce the efficacy of CD154 mAb in vivo also inhibit activation-induced CD154 expression in vitro.

Since the allograft response is highly T cell-dependent, immunosuppressants must modulate one or more aspects of the T cell response. As reviewed in this context (Gummert, J. F. et al., 1999, J. Am. Soc. Nephrol. 10:1366–1380), full T cell activation requires three signals: signal 1 is the triggering of the T cell antigen receptor, signal 2 is costimulation through CD28 and related molecules, and signal 3 is provided by cytokines. Cyclosporin A, like FK-506, blocks activation of calcineurin, an early event in T cell activation, just downstream of signal 1. Calcineurin dephosphorylates the transcription factor, nuclear factor of activated T cells (NFAT), and though it is well known that NFAT is essential to the transcription of IL-2 and (FN-γ (Ullman, K. S. et al., 1990, Anna Rev Immunol 8:421–52), it is less appreciated that NFATp-binding sites are also present in the CD154 promoter (Schubert, L. A.,et al., 1995, J. Biol Chem 270:29624–7). It was found here that CD154 induction on murine CD4+ T cells was markedly inhibited by cyclosporin A, as was reported for human T cells (Fuleihan. R., et al., 1994., J. Clin Invest 93:1315–20).

In contrast to cyclosporin A, the macrolide rapamycin blocks a relatively late stage of T cell activation, as the target of rapamycin ("TOR"), is downstream of signal 3, cytokine receptor activation. Notably, though rapamycin is known to block various CD28-mediated events, and costimulation though CD28 can augment CD154 expression (Klaus. S. J., et al., 1994, J. Immunol 152:5643–5652), it was found here that rapamycin had no significant inhibitory effect on CD154 induction, suggesting that the effects of CD28 costimulation on CD154 expression are not critical. Hence, our data suggest that the contrasting efficacies of rapamycin and other immunophilin-binding agents such as cyclosporin A or FK506 in trials of CD154 mAb correlate with their capacities to block CD154 induction and may reflect inhibition of late and early T cell activation events, respectively.

The immunosuppressive agent mycophenolate mofetil blocks the final stage of T cell activation. T cell proliferation, which requires de novo synthesis of purine and pyrimidine nucleotides. Mycophenolate mofetil is converted within lymphocytes to its active metabolite, mycophenolic acid, which is a reversible inhibitor of a key enzyme in the de-novo purine synthesis pathway, inosine monophosphate dehydrogenase (Gummert, J. F. et al., 1999, J. Am. Soc. Nephrol. 10:1366–1380). Mycophenolate mofetil was notable in the current studies for its complete lack of effect on CD154 expression by T cells, consistent with an antagonistic function at late stages of T cell activation. Accordingly, use of CD154 mAb with mycophenolate mofetil and/or rapamycin may be particularly efficacious in the management of transplant recipients.

Methylprednisolone resulted in almost complete inhibition of CD154 induction in mouse CD4+ T cells, consistent with a single previous report of the effects of dexamethasone on human CD4+ T cells in which activation was induced by a non-TCR-dependent mechanism (PMA/ionomycin) (Bischof, F. et al., 1998, Cell Immunol 187:3844). Glucocorticoids enter target cells, bind cytoplasmic receptors and form complexes which translocate to the nucleus and bind specific response elements in the promoters of target genes (Gummert, J. F. et al., 1999, J. Am. Soc. Nephrol. 10:1366–1380). In addition to inhibiting late events in T cell activation including proliferation and cytokine production, glucocorticoids block early events such as the activation of transcription factors AP-1 and NF-κKB. Indeed, ligand-bound glucocorticoid receptors bind Rel A and NF-κB p50 subunits in vitro (Epinat, J. C. et al., 1999, Oncogene 18:6896–6909), affecting the transactivation potential of RelA/p65, and also enhance transcription of the NF-κB antagonist IκB-α. Thus. we considered whether NF-κB activation was required for CD154 expression.

Compared with the responses in normal CD3 mAb-activated CD4+ T cells, CD154 induction was consistently inhibited by about 65% in NF-κB/p50 KG cells (FIG. 12) (p<0.02). Since activation of NF-κB requires the signal-coupled phosphorylation and proteolysis of IκB-α through the 26S proteasome (Lin, Y. C., et al., 1995, Proc Natl Acad Sci USA 92:552–6; Traenckner, E. B. et al., 1995, EMBO J 14:2876–83), we also tested the effects of 2 different types of proteasome inhibitors on CD154 induction by activated T cells (FIG. 12). Lactacystin irreversibly blocks proteasome activity by acylating a threonine residue in the active site of the mammalian proteasome subunit X, whereas dipeptide boronates, such as MG-273, act by irreversible inhibition of proteasomal chymotryptic activity (Grisham, M. B. et al., 1999, Methods Enzymol 300:345–63). Use of either agent in vitro significantly decreased CD154 expression by CD3-stimulated CD4+ cells (p<0.05) (FIG. 12). Together, these data indicate that NF-κB activation is required for optimal induction of CD154 by activated T cells.

To assess the validity of these in vitro data as guides to the in vivo efficacy of CD154 mAb therapy, CD154 mAb-induced cardiac allograft survival in normal vs. NF-κB/p50 KO mice, as well as in wild-type mice treated with a proteasome inhibitor; all experiments involved the same $H2^d \rightarrow H2^b$ MHC disparity. As anticipated from the in vitro data using spleen cells from NF-κB/p50 KO mice was evaluated, the efficacy of CD154 mAb therapy in vivo was abrogated in NF-κB/p50 KG mice (p<0.001) (FIG. 13). Moreover, administration of a proteasome inhibitor to wild-type mice also blocked the effects of CD154 mAb therapy in vivo (p<0.001) (FIG. 13). In this light, even agents such as the calcineurin-inhibitors, cyclosporin A and FK-506, which are known to inhibit NF-κB activation (Epinat, J. C. et al., 1999, Oncogene 18:6896–6909), may exert their effects on CD154 induction and CD154 mAb therapy as consequences of NF-κB inhibition.

The first conclusion of these in vitro and in vivo studies is that CD154 mAb fails to prolong allograft survival under conditions that diminish upregulation of CD154 upon CD4+ T cell activation. Indeed, the flow cytometric assay of CD154 expression provides a ready approach to evaluating potential clinical utility of CD154 mAb in combination with other immunosuppressive agents, and predicting those combinations which are likely to be successful (e.g. CD154 mAb plus rapamycin or mycophenolate mofetil) or not (e.g. CD154 mAb plus cyclosporin A or glucocorticoids). These studies further suggest that agents blocking early stages of T cell activation, thereby suppressing CD154 induction, will not be useful adjuncts to CD154 mAb therapy.

A second conclusion from the data is that NP-κB is required for CD154 induction, a finding that has not been previously described. Interestingly, the phenotype of NF-κB/p50KO is one of moderate immunodeficiency associated with defective antibody responses (Sha, W. C. et al.,1995, Cell, 80:321–30). These data indicate, therefore, that much of this phenotype may relate to defects in CD154 induction, which is key to development of B cell responses.

In addition, these findings provide an alternate interpretation for recent experimental data emphasizing an important role for CD40/CD154 interactions in the development of apoptosis in vivo, and which have suggested that concomitant use of cyclosporin A prevents tolerance induction by impairing activation-induced cell death (Li, X. C. et al., 1999, J. Immunol 163:2500–2 507; Wells. A. D. et al., 1999 Nat Med 5:1303–7). These data are more consistent with models suggesting that CD154mAb functions by stimulating CD154-dependent events (Blair, P. J. et al., 2000, J Exp Med 191:651–660), at least transiently. Further, these data demonstrate, for the first time, that NF-κB is required for CD154 induction.

8. EXAMPLE: Post-Transplantation Stat and SOCS Levels and Their Involvement in Immune Reduction and Tolerance Induction This Example presents the first data that has been generated on the post-transplantation levels of Stat and SOCS members post-transplantation. Using a vascularized cardiac transplant model, the levels of Stats (Stats 1–6) and SOCS (inhibitors of Stats) were measured during rejection and tolerance (via CD40L antibody treatment). During rejection, a rapid upregulation of Stat1, Stat2 and Stat3 mRNA was observed, followed by upregulation of these Stats in the animals' own hearts, indicating a systemic expression pattern. In contrast, RNA and protein analysis demonstrate that changes in Stat4 and Stat6 expression are confined to the transplant tissue. Specifically, Stat4 mRNA, however, was upregulated only later, and only in the transplant heart. Likewise, Stat6 mRNA was upregulated locally in the transplant tissue. Treatment with CD40L monoclonal antibody (MR-1) resulted in the downregulation of all the Stats, with the exception of Stat6, which was upregulated upon MR-1 treatment. Thus, reduction of immune rejection, via induction of tolerance, was accompanied by a downregulation of Stat4 and an increase in Stat6 levels. Cardiac transplants in Stat6 knockout mice were rejected despite treatment with MR-1. These results indicate that an immune deviation from TH1 (mediated by IL-12 and Stat4) to TH2 (mediated by IL-4 and Stat6) is a prerequisite in the induction of tolerance, and that Stat4 and Stat6, at a minimum, are citrical signals in graft survival. Further, these results indicate that Stat6, at a minimum, is a prerequisite in the induction of tolerance.

Materials & Methods

Cloning by RT-PCR:

5 μg of IL-6 (Pharmingen, San Diego, Calif.) was injected intravenously to a B6/129 strain female mouse. The heart, liver and spleen from the mouse was collected 1 hr after the intravenous injection of IL-6. Total RNA from these three organs were prepared using the acid-guanidine thiocyanate-phenol-chloroform method (Promega, Madison, Wis.). The RNA was then dissolved in water, quantitated, and a portion of the RNA was combined in equal amounts, and 1 μg of the combined RNA was used in a 50 μl reaction volume for the synthesis of first-strand cDNA. The ProStar Ultra HF RT-PCR System (Stratagene, La Jolla, Calif.) reagents were used both for the first-strand cDNA generation and for the subsequent steps during the amplification of the cDNA template. The following upstream and downstream primers were used:

Stat1: 5'-GAACTTTCAGCTGTTACTTTCC-3' (SEQ ID NO:35)

5'-CTGTGCTCATCATACTGTC-3' (SEQ ID NO:36)

Stat2: 5'-GTGTTACAGTCACTCCCACTG-3 (SEQ ID NO:37)

5'-CCTCAGGCAAATCTGACTCTG-3' (SEQ ID NO:38)

Stat3: 5'-GAAAGTACTGTAGGCCCGAG-3' (SEQ ID NO:39)

5'-CTGGAACCACAAAGTTAGGAG-3' (SEQ ID NO:40)

Stat4: 5'-GAAGTGAGATTCCACTCTGTAG-3' (SEQ ID NO:41)

5'-CACTCTCCAGTTTCATCTGC-3' (SEQ ID NO:42)

Stat5A: 5'-CGAAAGCAGTTGACGGATACG-3' (SEQ ID NO:43)

5'-CTCCAACTTAGTTGCCTAAACC-3' (SEQ ID NO:44)

Stat5B: 5'-CAAGCCGTTAGAAGCAGGAG-3' (SEQ ID NO:45)

5'CCATGGTTCACAACCTACAG-3' (SEQ ID NO:46)

Stat6: 5'-GATGAGGCTTTCCGGAGTCAC-3' (SEQ ID NO:47)

5'-CAGTTGTATCACATTCGAGC-3' (SEQ ID NO:48)

SOCS1: 5'-CTGTGCCGCAGCATTAAGTG-3' (SEQ ID NO:49)

5'-GTTTATTACCTAAACTGGCTG-3' (SEQ ID NO:50)

SOCS2: 5'-CCAGGTATAAGTATTTCTCTC-3' (SEQ ID NO:51)

5'-GGCCATTTGATCTTGAGCAGC-3' (SEQ ID NO:52)

SOCS3: 5'-GCAGATTGGCTTCTTCCTCAG-3' (SEQ ID NO:53)

5'-GGCATTTAAGGCGAGTCTCC-3' (SEQ ID NO:54)

SOCS5: 5'-GGAGCTTACTCGCAGTAGGCTC-3' (SEQ ID NO:55)

5'-GTAGGAGTCTCTCCGTGCAAGC-3' (SEQ ID NO:56)

CIS: 5'-CCAACTCTGACTGAGCCAGG-3' (SEQ ID NO:57)

5'-CATCCATACGCAGGTGGATG-3' (SEQ ID NO:58)

Amplification reactions included 5 μl 10× Ultra HF PCR buffer, 1 μl dNTP (40 mM) mix, 0.5 μl upstream primer (approximately 500 ng/ul), 0.5 μl downstream primer (~500 ng/μl), 1 μl first-strand cDNA reaction, 41 μl H$_2$O, 1 μl Pfu Turbo DNA polymerase (2.5 U/μl). The same PCR program was used for all the amplifications: samples were heated for 1 min at 95° C., followed by 40 cycles of 1 min at 95° C., 1 min at 58° C., 2 min at 68° C., and final extension at 68° C. for 5 min. The PCR samples were then loaded onto agarose or acrylamide gels, the cDNA fragments were isolated and cloned directly into SfrI cut PCR-Script (Stratagene). Sequence analysis of the plasmids were performed by Tufts Core Facility (Boston, Mass.). The length of the cloned fragments were as follows: Stat1 (334 bp); Stat2 (694 bp); Stat3 (373 bp); Stat4 (442 bp); stat 5A (634 bp); Stat 5B (458 bp); Stat6 (894 bp); SOCS1 (381 bp); SOCS 2 (266 bp); SOCS3 (381 bp); SOCS 5 (558 bp); and CIS (688 bp).

Cardiac Transplantation:

Heterotopic cardiac allografting was performed with anastomoses to the abdominal aorta and vena cava, using BALB/c donors and B6/129 wild-type or Stat-6 KO mice as recipients (n=6/group). See, Hancock et al., 1998, Nature Med. 4:1392–1396. Recipients were intravenously administered donor specific transfusion ("DST"; 5×10$^6$ splenic mononuclear cells) ("DST+IgG") plus 250 μg hamster anti-mouse CD40L mAb (CD154 mAb ; BioExpress, West Lebanon, N.H.) and DST ("DST+MR-1") or control hamster IgG ("DST+IgG") at the time of transplantation. Graft survival was monitored by daily palpation and rejection was confirmed by laparotomy and histologic evaluation.

RNA Isolations and Northern Blot Analysis:

Total RNA from native or transplanted hearts of Balb/c or B6/129 mice was prepared using the acid-guanidine thiocyanate-phenol-chloroform method (Chomezynski, P. and Sacchi, N., 1987, Anal. Biochem. 162:156–159). 25 μg of RNA was loaded onto each lane of 1.2% agarose-formaldehyde gels. The 0.24 kB RNA ladder (GIBCO-BRL, Rockville, Md.) was used as a size control. After electrophoresis the RNA was blotted overnight onto Nytran Supercharge membranes (Schleicher & Schuell, Keene, N.H.) with 20×SSC and cross-linked onto the membranes by irradiation with UV light using a Stratalinker (Stratagene). $^{32}$P-labeled probes were prepared by using the Multiprime DNA labelling system and $^{32}$P-dCTP (both from Amersham Pharmacia Biotech, Piscataway, N.J.). Hybridizations with the $^{32}$P-labeled probes were done at 68° C. in roller bottles using ExpressHyb Solution (Clontech Laboratories, Palo Alto, Calif.). For re-use, the membranes were deprobed in 0.5% SDS at 95–100° C. and exposed to film to assure complete removal of previous hybridization signals.

The nucleotide sequences of the probes utilized are presented below:

Stat1 (SEQ ID NO:59):
gaactttcagctgttactttccca-gatattattcgcaactacaaagtcatg-gctgccgagaacataccagagaatcccctgaa gtatctgtaccccaatattga-caaagaccacgcctttgggaagtattattccagaccaaaggaagcaccagaacc gatgga gcttgacgacctaagcgaactggata-catcaagactgagttgatttctgtgtctgaagtccaccttctagacttcagacca cagacaacctgcttcccatgtctcca-gaggagtttgatgagatgtcccggatagtgggccccgaatttgacagtatgatgagcacac Stat2 (SEQ ID NO:60):
gtgttacagtcactcccactgaca-gagatcatccgccactaccaggttcttgccgaagagaacatccccgagaacccact ccgcttcctctatcccgaatccctcgg-gacgaagcttttgggtgttactaccaggaaaaagttaatttggaagaacaggag gaatatttgaaacataaactcattgt-gatctctaacagacaggtggacgagctgcagcagcctctggagctcaaacaggat tcagagtccttagaagtgaatgca-gagctcttgttagcacacgaccaggagttgccattgatgatgcagactgggctggtt tgggcacagagctgaaagtggacccat-actgagtacagccccacaagtcctgctggagccagcccacaagtcctg ctg-gagccagccccacaagtcctgctggagc-cagccccacaagtcctgctggagccagcccacaagtcctgctggag cagccccacaagtcctgctggagccagc-ccacaagtcctgctggagccagcccacaagtcagctggagccagc ccca-caagtcctgctggagctagcccca-caagtcctgctggagccagccccacaagtcctgctggagctagccccacaa gtccagctggagccagcacacttgctg-cagcagccatcagagtcagatttgcctgagg Stat3 (SEQ ID NO:61):
gaaagtactgtaggcccgagagccag-gagcaccccgaagccgacccaggtagtgctgccccgtacctgaagaccaag ttcatctgtgtgacaccaacgacctg-cagcaataccattgacctgccgatgtcccccccgcactttagattcattgatgcagttt ggaaataacggtgaaggtgctgagccct-cagcaggagggcagttgagtcgctcacgtttgacatggatctgacctcgga gtgt-gctacctccccatgtgaggagct-gaaaccagaagctgcagagacgtgacttgagacacctgccccgtgctccac ccctaagcagccgaaccccatatcgtctgaaactcctaactttgtggttccag Stat4 (SEQ ID NO:62):
gaagtgagattccactctgtagaac-cctacaacaaagggagactgtcggctctggccttcgctgacatcctgcgagaetac aaggttatcatggctgaaaacatccct-gaaaaccctctgaagtacctctaccctgacattcccaaagacaaagcctttggca aacactacagctcccagccgtgc-gaagtctcaagaccaaccgaacggggagacaaagggttacgtcccctctgtttttatc cccatttaacaatccgaagcgattc-cacggagccacaatctccttcagaccttctccccatgtctccaagtgcatatgctgt gctgagagaaaacctgagcccaacga-caattgaaactgcaatgaattccccatattctgctgaatgacggtgcaaacgga cactttaaagaaggaagcagatgaaactggagagtg Stat5A (SEQ ID NO:63):
cgaaagcagttgacggatacgtgaagc-cacagatcaagcaagtggtccctgagttcgtcaatgcatccacagatgccgg agccagcgccacctacatggaccag-gctccttccccagtcgtgtgccctcaacctcactacaacatgtacccacccaacc ctgaccctgtccttgaccaagatggc-gagtttgacctggatgagagcatggatgttgccaggcacgtggaagaactttac gccggcccatggacagtctcgacgc-ccgcctctccccacctgctggtctcttcacctccgctagaagctccctgtcctgaa cgctggactccatgcttctcttggaaac-caccttcagtgtaaggagcccacgtcagttgtagtatctctgttcataccaacaat ggctttgcacgttcacagggctacct-tgcccacacagtctctgggtttgtggctaaagcggtggtgaccttttggtcagacct caagggccccccagggcctctcgtgtaa-gagctgaacctatcattgctgacaaacctatttctccggtgtccttttttctgtcca atg-gccatttcagtgaaattctagaaaag-gcagggaggcaggtttaggcaactaagttggag Stat 5B (SEQ ID NO:64):
caagccaagccgttagaagcaggagc-ccctggccagtgcctggtcacggagctgagctgtgtttagatgtgttggctgct gcgtggtgaaggaagacccgtctcca-gaaaagcaatttaggcalaaagggattccgtttgatggcagagtcccagtgcta gaaaggtagcgaaggtggaca cttacagtctcaactcatcgtcgtaaat-gtcctcgtaacgacattgattcttctacctg gataac-cttttgtttgtttgtttgtttttgttfgttttftccccctgtaaccattttttttttctgacaag aaaacattttaattfctctaag caagaagcatttttcaaataccatgtct-gtgacccaaagttaaaaatggatgataattcatgtaaatgttgcaacatagcaac ctgaacctgcacgcgattcgggctctgtaggttgtgaaccatgg Stat6 (SEQ ID NO:65):
gatgaggctttccggagtcactataagc-ccgaacagatggggaaggacgggaggggttatgtctctactactatcaagat gactgtggaaagggaccagcccttc-ctactccagagccccagatgcctgccatggtgccaccttatgatcttggaatgg cccctgatgcttccatgcaactcagct-cagatatggggtatcctccacagtccatccactcatttcagagcctagaagagtc catgagtgtactgccatcttttcag-gagcctcacctgcaaatgccccccaa-catgagccagataaccatgcctttgaccag cctcaccccccagggtctgctg-cagtgccagtcccaggaacatgctgtgtccagccctgaacccatgctttggtcag atgtg actatggtagaggacagttgcctaact-cagcctgtgggaggtttcccccaaggcacctgggtcagtgaagacatgtaccc tccctgctgcctcccactgaacaggac-ctcaccaagcttctcctggagaaccaaggggagggaggagggtccttagga agccagcccctcctgaaaccatctcct-tatgggcaatcagggatctcactgtcccacctggacctaaggaccaacccag ctggtgatcccagctggagaagccca-gaaacaaagcctcttctgtctctatggaccagctctggacacctgctcatgcagg tgccttccgtctcaactgttccttggt-taagagaaaagaactggctgggagaccatgtggtgtatggaactgctgtgctctgt cctacctgccatatcagggc-cccccttttccagcactgggtgcaaagg-gatgagtggggtgttaatgctcgaatgtgatac aactg SOCS1 (SEQ ID NO:66):
ctgtgccgcagcattaagtgggggcgc-cttattatttcttattattaattattattattttctggaaccacgtgggagccctccc cgcctgggtcggagggagtggttgtg-gagggtgagatgcctcccacttctggctggagacctcatcccacctctcaggg gtgggggtgctcccctcctggtgctc-cctccgggtccccctggttgtagcagcttgtgtctggggccaggacctgaattc cactcctacctctccatgtttacatat-tcccagtatctttgcacaaaccaggggtcggggagggtctctggcttcattttctgc tgtgcagaatatcctatttttatattttacagccagtttaggtaataaac SOCS2 (SEQ ID NO:67):
ccaggtataag-tatttctctctcttttttcgttttttttt-taaaaaaaaaaaaacacatgcctcatatagactatctccgaatgcagct atgt-gaaagagaacccagaggccctcctctggataactgcgcagaattctctcttaagg acagttgggctcagtctaactta aaggtgtgaagatgtagctaggtattt-taaagttcccttaggtagttttagctgaatgatgctttctttcctatggctgctcaag atcaaatggcc SOCS3 (SEQ ID NO:68):
gcagattggcttcttcctcaggccctc-
cactcccgcagagtagagctggcaggacctggaattcgtctgaggggaggggg
gagctgccacctgctttcccccctc-
ccccagctccagcttctttcaagtggagccagccggcctggcctggtgggacaata
cctttgacaagcggactctcccctc-
cccttcctccacaccccctctgcttcccaagggaggtggggacacctccaagtgtt
gaacttagaactgcaaggggaatct-
tcaaactttcccgctggaacttgtttgcgctttgatttggtttgatcaagagcaggca
cctggggaaggatggaa-
gagaaaagggtgtgtgaagggtttttat-
gctggccaaagaaataaccactcccactgccca acctaggtgaggagtggtg-
gctcctggctctggggagagtggcaagggggtgacctgaagagagctatactggt
gccag                 gctcctctccatggggcagctaat-
gaaacctcgcagatcccttgcacccca-
gaaccctccccgttgtgaagaggcagtag catttagaagggagacagatgag-
gctggtgagctggccgccttttccaacaccgaagggaggcagatcaacagatgag
ccatcttggagcccaggtttccctg-
gagcagatggagggttctgctttgtctctcctatgtggggctaggagactcgcctt
aaatgcc
    SOCS5 (SEQ ID NO:69):
    ggagcttactcgcagtag-
gctctcgctcttctaatcaatg-
gataaagtggggaaaatgtggaacaacttaaaatacagatgc cagaatctct-
tcagccacgagggaggaagccgtaatgagaacgtggagatgaaccccaacag
atgtccgtctgtcaaag agaaaagcatcagtctgggagag-
gcagctccccagcaagagagcagtccct-
taagagaaaatgttgccttacagctggg actgagcccttccaagaccttttccag-
gcggaaccaaaactgtgccgcagagatccctcaagtggttgaaatcagcatcg
agaaagacagtgactcgggtgccac-
cccaggaacgaggcttgcacggagagactcctac
    CIS (SEQ ID NO:70):
    ccaactctgactgagccaggcaccct-
gctctgcctcacacagtcacatcctggagggaacacagtccccagctggacttg
gggttctgctgtcctttcttcagtcatc-
ctggtgcctgcatgcatgtgacagctggaccagagaatgccagcaagaacaag
gcaggtggaggagggattgtcaca-
caactctgaggtcaacgcctctaggtacaatatggctctttgtggtgagccatgtat
cagagcgagacaggcaggac-
ctcgtctctccacagaggctggacctag-
gtctccactcacttgcctgccctgccacctg asctgtgtctattctcccagccctg-
gtttctcagtctgctgagtagggcaggccccctacccatgtatagaatagcgagcct
gtttctgggagaatatcagccagaggt-
tgatcatgccaaggcccttatggggacgcagactgggctaggggactacac
agttatacagtatttatttatttat-
tctccttgcaggggttggggggtggaat-
gatggcgtgagccatcccacttctctgccctgt gctctgggtggtccagagac-
ccccaggtctggttcttccctgtggagaccccccatcccaaaacattgttgggccc
aaagta gtctcgaatgtcctgggcccatccacctgcgtatggatg
Western Blotting:

Hearts obtained from mice were frozen in liquid nitrogen and homogenized with Tissue Tearor (model 985370, Biospec Products, Inc.) in 800 μl lysis buffer containing 4% SDS, 125 mM Tris-HCl, pH 6.8, and protease inhibitors Antipain, Benzamidin, BeStatin, Chymostatin, Leupeptin, Pefabloc C, Pepstatin A, PMSF, TLCK, TPCK. The protease inhibitors were prepared and used as suggested by the manufacturer, Roche Molecular Biochemicals, Indianapolis, IN. Following homogenization, the DNA in the samples was sheared by sonication for 30 sec at 5 Watts (RMS) output power, with a Virtis sonicator (model Virsonic 60, Virtis Company, Gardiner, N.Y.). Samples were then heated at 95° C. for minutes and centrifuged at 14,000×g for 30 minutes, to get rid of particulate material. Protein concentrations in the extracts were determined using DC Protein Assay (Bio-Rad Laboratories, Hercules, Calif.). The protein concentration in all the samples was equalized to 10 mg/ml by adding lysis buffer, and 1 vol. 2×Sample buffer (20% Glycerol, 0.005% Bromophenol blue) was added to yield samples with a protein concentration of 5 mg/ml. The samples were kept at −80° C. until use. Prior to loading onto 10% SDS-polyacrylamide gels, 2.5% β-mercaptoethanol was added to every sample (100 μg) followed by heating to 95° C. for 10 min. After electrophoresis, proteins were transferred onto Immobilon-P membranes (Millipore Corporation, Bedford, Mass. 01730) for 2.5 hrs at 100 V, using a Hoefer Transphor Electrophoresis unit. The Transfer buffer consisted of 12 mM Tris base, 96 mM Glycine, and 200 ml Methanol in 1 liter. After the transfer, the membranes were placed in roller bottles and rotated for 1 hr (at 4° C.) in a Blocking solution (1×PBS +0.1% Tween-20+5% non-fat dry milk+0.02% sodium azide), the membranes were rinsed once with the Rinse solution (1×PBS+0.1% Tween-20) and rolled overnight with the primary antibody in the Blocking solution. After washing times in the Rinse solution (15, 10, 5 minutes), the blots were incubated for 1 hour with the secondary antibody conjugated to horseradish peroxidase, followed by another set of washes with the Rinse solution and one final wash in 1×TBS (10 mM Tris-HCl, pH 8.0, 150 mM NaCl). Chemiluminescence was performed by using the Luminol Reagent (Santa Cruz Biotechnology, Inc., Santa Cruz, Calif.) and detection was with Biomax MR film (Eastman Kodak Company, Rochester, N.Y.). All the antibodies were used at 1:1000 dilution. Stat1, phospo-Stat1, Stat3, phospho-Stat3, Stat4, and Stat5A were from UpState Biotechnology (Lake Placid, N.Y.). Stat2, Stat6, HSC70, and the secondary antibodies were from Santa Cruz Biotechnology.

Quantification of RNA and Protein

Quantification of the RNA and protein bands on the Kodak Biomax MR film was performed on a Macintosh Performa 6300CD computer using the public domain NIH Image program (developed at the U.S. National Institutes of Health and available on the Internet).

Results

STAT and SOCS RNA Levels in Heart Allografts During the 5 Days Following Transplantation Hearts from Balb/c mice were transplanted into B6/129 female mice using a vascularized mouse cardiac allograft model. The heart transplant resulted with animals having two hearts: their own hearts and a second functional heart grafted adjacent to the kidneys. To determine the kinetics of Stat and SOCS RNA expression following cardiac allograft surgery, total RNA was prepared from the animals' own hearts (native), the transplanted hearts and from the hearts of healthy controls (designated as "N", "T", and "C", respectively) one, two, three, and five days post-transplantation. RNA (25 μg/lane) was then electrophoresed on three identical gels, transferred to Nytran Supercharge membranes and the membranes were hybridized with Stat probes, SOCS probes, and a GAPDH probe as a control (FIGS. 14–16).

As shown in FIGS. 14A and 14B–G, increases of approximately 5-fold in Stat1, Stat2 and Stat3 RNA levels were detected in the transplanted hearts relative to the control hearts as early as one day post-transplantation, and were more evident by the second day. During the first two days, the increase appeared to be localized to only the transplanted tissue. By the third day, and much more strongly by the fifth day, higher levels of Stat1, 2, and 3 RNA were also detected in the native hearts.

Stat4 RNA levels, almost undetectable the first three days post-transplantation, increased significantly (approximately 60-fold) in the transplanted hearts at around day five post-transplantation, but not earlier. Stat5A RNA levels did not change in the native and transplanted hearts during the five days following the transplant surgery. An increase in Stat6 RNA expression was detected in transplanted hearts as early as day one post-transplantation (approximately 2-fold), and remained at approximately the same level during the five days following transplantation. The fact that increases in Stat4 and Stat6 RNA expression were only detected in the transplanted hearts by day five post-transplantation suggests that the up-regulation of the expression of these two Stats was localized to the transplanted hearts (FIGS. 14A, 14B–G).

An increase in SOCS1 RNA expression levels in the transplanted hearts began to increase by day two post-transplantation and by day five post-transplantation SOCS1 RNA expression in the transplanted hearts had increased approximately 300-fold (FIG. 15). Between days 1 and 3, there was an approximately 6-fold difference in such SOCS1 RNA levels, and between days 3 and 5, there was an approximately 25-fold difference in such SOCS1 RNA levels. At approximately 38-fold, the SOCS1 RNA increase in native hearts was much less pronounced (FIG. 15).

A considerably high level of SOCS3 RNA expression was detected in the transplanted hearts as early as one day post-transplantation (approximately 100-fold increase), and reached an approximately 230-fold increase at five days post-transplantation. (FIG. 15). However, SOCS3 RNA expression remained low in native hearts, and was hardly detectable in the native hearts five days following the transplant surgery. As shown in FIG. 16, Stat4 and SOCS3 RNA expression patterns were found to be quite similar to each other, both of them being expressed only in the transplanted hearts, and both of them being significantly up-regulated at approximately day 5 post-transplantation.

Two species of SOCS5 RNA were detected (4.4 kb and 3.8 kb) in the naive and transplanted hearts. The shorter species 3.8 kb SOCS5 RNA species was much more abundant in the transplanted hearts than in naive hearts or in control hearts. The level of CIS RNA expression detected in naive hearts remained almost unchanged relative to the control hearts, while a lower level of CIS RNA expression was detected in the transplanted hearts relative to the naive hearts or control hearts (FIG. 15).

STAT Protein Levels in Heart Allografts and Native Hearts During the 5 Days Post-transplantation To determine the effect of cardiac allografts on Stat and SOCS protein expression, protein extracts were prepared from transplanted and native hearts at day one, day two, day three, and day five, post-transplantation. In the transplanted hearts an increase in Stat1 protein levels relative to the control hearts was detected as early as one day post-transplantation, increased steadily, and by day five post-transplantation Stat1 protein levels were approximately 17-fold higher (FIG. 17). In the native hearts an increase in Stat1 protein levels began increasing at day two post-transplantation and by day five post-transplantation Stat1 levels were 15-fold higher.

An increase in Stat2 protein expression levels in the transplanted hearts was initially detected three days post-transplantation, and by day five post-transplantation had increased sharply by approximately 27-fold. In native hearts an increase in Stat2 protein levels was detected by day three post-transplantation and by day five post-transplantation a 10-fold increase in the levels of Stat2 protein was detected.

An increase in Stat3 protein levels in the transplanted hearts was detected as early as day two post-transplantation and by day five post-transplantation the levels of Stat3 protein in the transplanted hearts exhibited an approximately 3.5-fold increase. In the native hearts a 2-fold increase in the levels of Stat3 protein was detectable only by day five post-transplantation.

Stat4 levels began increasing around one day post-transplantation in the transplanted heart, with a dramatic increase (approximately 16-fold) between day 2 and day 5 post-transplantation. Stat4 was detected only in the transplant tissue, not in the native heart tissue (FIG. 17).

Stat5A protein levels did not change in the transplanted or native hearts relative to the control hearts.

Stat6 is normally made at a low level in hearts (see, e.g., FIG. 17, control lanes). As was observed with Stat4, Stat6 expression, however, only increased (aproximately 1.5–3.5-fold) in transplanted hearts.

Phosphorylated Forms of Stat1 and Stat3 During Graft Rejection

To determine whether the levels of phosphorylated Stat1 and phosphorylated Stat3 protein parallel that of the newly synthesized Stat1 and Stat3 in the native and transplanted hearts following cardiac allograft surgery, the levels of these Stats and their phosphorylated forms were analyzed (FIG. 18). As shown in FIG. 18, an increase in phosphorylated Stat1 protein levels paralleled the increase in the total Stat1 protein levels detected both in native and transplanted hearts on days three and five post-transplantation. In contrast, the level of phosphorylated Stat3 protein detected in native and transplanted hearts over the five day post-transplantation period did not parallel the increase in the total Stat3 protein levels detected during this period. Ijn particular, although there was a steady increase of total Stat3 over the five day period, there was no major change in the levels of phosphorylated Stat3 protein detected over this same period, with the exception of the appearance of a slightly higher molecular weight form of phosphorylated Stat3 protein.

The Effect of Anti-CD40L Monoclonal Antibody MR-1 on the Stat and SOCS RNA Levels in 5-day Post-Transplant Hearts To determine how Stat and SOCS RNA expression levels are affected in cardiac allografts when tolerance has been induced, six mice having undergone cardiac transplant surgery were divided into three groups. One group of mice were intravenously administered DST ("donor specific transfusion") +MR-1 anti-CD40L antibody which has been shown to induce tolerance), on the day of the transplant surgery. The second group of mice were intravenously administered DST+IgG as control on the day of the transplant surgery and the third group received no treatment. The animals were sacrificed five days post-transplantation and total RNA was prepared from the animals' own hearts (native), the transplanted hearts and from the hearts of healthy controls (designated as "N", "T", and "C", respectively). The RNA (25 $\mu$g /lane) was electrophoresed on four identical gels and the Northern blots were hybridized to Stat probes, SOCS probes and a GAPDH probe as a control. (FIGS. 19, 20)

Stat1, Stat2, and Stat3 mRNA were found to be expressed at some level in the normal heart (see control lanes of the no treatment group). Five days post-transplantation, the transplant allograft tissue exhibited a dramatic upregulation of Stat1, Stat2 (approximately 45-fold), and Stat3 (approximately 6-fold) mRNAs. This upregulation was found to be systemic in nature in that the increases were also observed in the native heart tissue (approximately 43-fold, 48-fold, and 5.5-fold, respectively). Treatment with DST+ IgG caused minimal changes n the transplant Stat RNA levels, but the single does of DST+MR-1 resulted in lower levels of Stat1, Stat2, and Stat3 mRNAs (62%, 76%, and 50% lower than the animals that received no treatment).

Stat4 mRNA was found only in the transplanted heart tissue, as a local signal, and was not detected in the control or native hearts (FIG. 19; see the control and native lanes of the no treatment group). Stat4 mRNA was significantly reduced (approximately 6-fold) in transplants obtained from MR-1-treated animals.

Only minimal differences in Stat 5A mRNA expression in transplant tissue of the group that received no treatment and the controls (approximately 1.4-fold increase) were observed. MR-1 treatment, however, lowered the Stat 5 A expression level by 70%. MR-1 treatment resulted in Stat 5A levels that were 60% lower than control heart levels. Stat 5B mRNA levels were too low to be detected (data not shown).

Stat6 mRNA is normally expressed at some level in the heart, and five days post-transplantation, Stat6 mRNA levels doubled only in the transplanted, not native, hearts. Upon MR-1 treatment, however, Stat6 mRNA levels were down-regulated to pre-transplantation (control) levels.

The same membranes were used to determine the mRNA expression levels of SOCS1, SOCS 2, SOC, and CIS (FIG. 20). SOCS1 and SOCS3 mRNA levels were almost undetectable in control hearts. SOCS1 and SOCS3 mRNA levels were increased five days post-transplantation in transplant tissue in both DST+IgG treated mice and untreated mice (some low level of SOCS1 expression was also detected in the native hearts of the untreated groups). Treatment with DST+MR-1 resulted in a 93% and 73% reduction in the level of SOCS1 and SOCS3 mRNA expression, respectively, relative to that in transplanted hearts of untreated mice.

SOCS 2 RNA levels remained unchanged in the control, native, and transplanted hearts in the three experimental groups. Interestingly, CIS levels were 50% higher in the transplanted hearts of mice, regardless of treatment.

The Effect of Anti-CD40L Monoclonal Antibody MR-1 on Stat Protein Levels in 5-day and 7-day Post-Transplant Hearts To determine how Stat protein levels are affected in cardiac allografts when tolerance has been induced, the day of the surgery mice were intravenously administered a single dose of either DST+IgG or DST+MR-1, and the Stat protein levels were analyzed five and seven days post-transplantation. As shown in FIG. 21, at day 5 post-transplantation thee were minimal changes in the Stat levels between IgG and MR-1 treated animals, but a day 7 post-transplantation, there was significant changes in such levels. Stat1 and Stat2 levels were reduced 64% and 52%, respectively, in native hearts of MR-1 treated animals. Stat3 levels were reduced in the transplant tissue by 29%. The most dramatic change at day 7 post-transplantation was the amount of Stat4 reduction (approximately 63%) in the transplanted hearts. Stat6, on the other hand, tended to increase about 2-fold upon MR-1 treatment.

Stat and Bax Protein Levels in Isografts and Allografts

The level of Stat1, Stat2, Stat3, Stat4, Stat5A, and Stat6 were compared in isografts and allografts to exclude the possibility that the observed changes in Stats were due to the surgery and the healing process that follows the surgery. As shown in FIG. 22, between day 1 and day 2 post-transplantation, the isografts showed a small increase in different Stats. The low levels, however, of Stat1, Stat2, and Stat5A remained constant between days 2 and 7 post-transplantation, and Stat3 and Stat6 levels declined between these days. In allografts, on the other hand, all of the Stats reached high levels by day 5. Bax, an unrelated protein, showed a very different profile, with its levels increasing in both isografts and allografts.

Transplantation in Stat6 Knockout Mice

Stat6 is activated by IL-4 and IL-13, and Stat6 knock-out animals have been shown to be deective in TH2 differentiation (Kaplan, M. H. et al., 1996, Imm. 4:313–319; Takeda, K. et al., 1996, Nature 380:627–630; and Shimoda, K. et al., 1996, Nature 380:630–633). The results presented herein indicate that induction of tolerance, by causing lower Stat4 and higher Stat6 levels, shifts the differentiation of T cells toward the TH2 lineage.

To assess the importance of Stat6 and the TH2 response in MR-1 mediated tolerance induction, hearts from B6/129 background mice were transplanted into three Stat6 (−/−) mice with a Balb/c background. The day of the surgery the animals were injected with MR-1 and splenocytes from the donor animals. In normal animals, such a transplant results in indefinite graft survival. Stat6 (−/−) animals, however, readily rejected the transplanted hearts at day 11. This result points out the importance of Stat6 in the induction of tolerance, e.g., the induction of tolerance via MR-1 administration.

The contents of all references, patents and published patent applications cited throughout this application are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound to be tested for an ability to reduce immune rejection, comprising:

(a) contacting an activated T cell sample with a test compound;

(b) determining the amount of:

(i) Stat4 protein, and
(ii) Stat6 protein, present in (a); and
(c) comparing the amounts in (a) to those present in a corresponding control activated T cell sample that has not been contacted with the test compound, so that if the amount of (i) is decreased, and the amount of (ii) is maintained or increased, relative to the amount in the control sample, a compound to be tested for an ability to reduce immune rejection is identified.

2. A method for identifying a compound to be tested for an ability to reduce immune rejection, comprising:

(a) contacting an activated T cell sample with a test compound;
(b) determining the ratio Stat4 protein to Stat6 present in the sample; and
(c) comparing the ratio (a) to that present in a corresponding control activated T cell that has not been contacted with the test compound, so that if the ratio in the sample is decreased relative to that in the control sample, a compound to be tested for an ability to reduce immune rejection is identified.

3. A method for identifying a compound to be tested for an ability to reduce immune rejection, comprising:

(a) contacting a resting T cell sample with a T cell activator and a test compound;
(b) determining the amount of:
(i) Stat4 protein, and
(ii) Stat6 protein, present in (a); and
(c) comparing the amounts in (a) to those present in a corresponding control activated T cell sample that has not been contacted with the test compound, so that if the amount of (i) is decreased and the amount of (ii) is maintained or increased, relative to the amount in the control sample, a compound to be tested for an ability to reduce immune rejection is identified.

4. The method of claim 3, wherein the resting T cell is a primary T cell.

5. The method of claim 3, wherein the resting T cell is a T cell line.

6. A method for identifying a compound to be tested for an ability to reduce immune rejection, comprising:

(a) contacting a resting T cell sample with a T cell activator and a test compound;
(b) determining the ratio of Stat4 protein to Stat6 protein present in the sample; and
(c) comparing the ratio to in (a) to that present in a corresponding control activated T cell sample that has not been contacted with the test compound, so that if the ratio in the sample is decreased relative to that in the control sample, a compound to be tested for an ability to reduce immune rejection is identified.

7. A method for identifying a compound to be tested for an ability to reduce immune rejection, comprising:

(a) contacting a T cell sample with a cytokine and a test compound, wherein the T cell sample is activated by the cytokine;
(b) determining the amount of:
(i) Stat4 protein, and
(ii) Stat6 protein, present in (a); and
(c) comparing the amounts in (a) to those present in a corresponding control T cell sample that has not been contacted with the test compound, so that if the amount of (i) is decreased, and the amount of (ii) is maintained or increased, relative to the amount in the control sample, a compound to be tested for an ability to reduce immune rejection is identified.

8. The method of claim 7, wherein the T cell is a T cell line.

9. The method of claim 7, wherein the cytokine is IL-2, IL-4, IL-12, or IL-13.

* * * * *

SEQUENCE LISTING

<160> NUMBER OF SEQ ID NOS: 70

<210> SEQ ID NO 1
<211> LENGTH: 4003
<212> TYPE: DNA
<213> ORGANISM: Homo sapiens
<220> FEATURE:
<221> NAME/KEY: CDS
<222> LOCATION: (197)...(2449)

<400> SEQUENCE: 1
attaaacctc tcgccgagcc cctccgcaga ctctgcgccg gaaagtttca tttgctgtat       60

-continued

```
gccatcctcg agagctgtct aggttaacgt tcgcactctg tgtatataac ctcgacagtc      120
ttggcaccta acgtgctgtg cgtagctgct cctttggttg aatccccagg cccttgttgg      180
ggcacaaggt ggcagg atg tct cag tgg tac gaa ctt cag cag ctt gac tca     232
               Met Ser Gln Trp Tyr Glu Leu Gln Gln Leu Asp Ser
                 1               5                  10 aaa ttc ctg gag cag gtt cac cag ctt tat gat gac agt ttt ccc atg       280
Lys Phe Leu Glu Gln Val His Gln Leu Tyr Asp Asp Ser Phe Pro Met
         15                  20                  25 gaa atc aga cag tac ctg gca cag tgg tta gaa aag caa gac tgg gag       328
Glu Ile Arg Gln Tyr Leu Ala Gln Trp Leu Glu Lys Gln Asp Trp Glu
     30                  35                  40 cac gct gcc aat gat gtt tca ttt gcc acc atc cgt ttt cat gac ctc       376
His Ala Ala Asn Asp Val Ser Phe Ala Thr Ile Arg Phe His Asp Leu
 45                  50                  55                  60 ctg tca cag ctg gat gat caa tat agt cgc ttt tct ttg gag aat aac       424
Leu Ser Gln Leu Asp Asp Gln Tyr Ser Arg Phe Ser Leu Glu Asn Asn
                 65                  70                  75 ttc ttg cta cag cat aac ata agg aaa agc aag cgt aat ctt cag gat       472
Phe Leu Leu Gln His Asn Ile Arg Lys Ser Lys Arg Asn Leu Gln Asp
             80                  85                  90 aat ttt cag gaa gac cca atc cag atg tct atg atc att tac agc tgt       520
Asn Phe Gln Glu Asp Pro Ile Gln Met Ser Met Ile Ile Tyr Ser Cys
         95                 100                 105 ctg aag gaa gaa agg aaa att ctg gaa aac gcc cag aga ttt aat cag       568
Leu Lys Glu Glu Arg Lys Ile Leu Glu Asn Ala Gln Arg Phe Asn Gln
    110                 115                 120 gct cag tcg ggg aat att cag agc aca gtg atg tta gac aaa cag aaa       616
Ala Gln Ser Gly Asn Ile Gln Ser Thr Val Met Leu Asp Lys Gln Lys
125                 130                 135                 140 gag ctt gac agt aaa gtc aga aat gtg aag gac aag gtt atg tgt ata       664
Glu Leu Asp Ser Lys Val Arg Asn Val Lys Asp Lys Val Met Cys Ile
                145                 150                 155 gag cat gaa atc aag agc ctg gaa gat tta caa gat gaa tat gac ttc       712
Glu His Glu Ile Lys Ser Leu Glu Asp Leu Gln Asp Glu Tyr Asp Phe
            160                 165                 170 aaa tgc aaa acc ttg cag aac aga gaa cac gag acc aat ggt gtg gca       760
Lys Cys Lys Thr Leu Gln Asn Arg Glu His Glu Thr Asn Gly Val Ala
        175                 180                 185 aag agt gat cag aaa caa gaa cag ctg tta ctc aag aag atg tat tta       808
Lys Ser Asp Gln Lys Gln Glu Gln Leu Leu Leu Lys Lys Met Tyr Leu
    190                 195                 200 atg ctt gac aat aag aga aag gaa gta gtt cac aaa ata ata gag ttg       856
Met Leu Asp Asn Lys Arg Lys Glu Val Val His Lys Ile Ile Glu Leu
205                 210                 215                 220 ctg aat gtc act gaa ctt acc cag aat gcc ctg att aat gat gaa cta       904
Leu Asn Val Thr Glu Leu Thr Gln Asn Ala Leu Ile Asn Asp Glu Leu
                225                 230                 235 gtg gag tgg aag cgg aga cag cag agc gcc tgt att ggg ggg ccg ccc       952
Val Glu Trp Lys Arg Arg Gln Gln Ser Ala Cys Ile Gly Gly Pro Pro
            240                 245                 250 aat gct tgc ttg gat cag ctg cag aac tgg ttc act ata gtt gcg gag      1000
Asn Ala Cys Leu Asp Gln Leu Gln Asn Trp Phe Thr Ile Val Ala Glu
        255                 260                 265 agt ctg cag caa gtt cgg cag cag ctt aaa aag ttg gag gaa ttg gaa      1048
Ser Leu Gln Gln Val Arg Gln Gln Leu Lys Lys Leu Glu Glu Leu Glu
    270                 275                 280 cag aaa tac acc tac gaa cat gac cct atc aca aaa aac aaa caa gtg      1096
Gln Lys Tyr Thr Tyr Glu His Asp Pro Ile Thr Lys Asn Lys Gln Val
285                 290                 295                 300
```

-continued

| | |
|---|---|
| tta tgg gac cgc acc ttc agt ctt ttc cag cag ctc att cag agc tcg<br>Leu Trp Asp Arg Thr Phe Ser Leu Phe Gln Gln Leu Ile Gln Ser Ser<br>305 310 315 | 1144 |
| ttt gtg gtg gaa aga cag ccc tgc atg cca acg cac cct cag agg ccg<br>Phe Val Val Glu Arg Gln Pro Cys Met Pro Thr His Pro Gln Arg Pro<br>320 325 330 | 1192 |
| ctg gtc ttg aag aca ggg gtc cag ttc act gtg aag ttg aga ctg ttg<br>Leu Val Leu Lys Thr Gly Val Gln Phe Thr Val Lys Leu Arg Leu Leu<br>335 340 345 | 1240 |
| gtg aaa ttg caa gag ctg aat tat aat ttg aaa gtc aaa gtc tta ttt<br>Val Lys Leu Gln Glu Leu Asn Tyr Asn Leu Lys Val Lys Val Leu Phe<br>350 355 360 | 1288 |
| gat aaa gat gtg aat gag aga aat aca gta aaa gga ttt agg aag ttc<br>Asp Lys Asp Val Asn Glu Arg Asn Thr Val Lys Gly Phe Arg Lys Phe<br>365 370 375 380 | 1336 |
| aac att ttg ggc acg cac aca aaa gtg atg aac atg gag gag tcc acc<br>Asn Ile Leu Gly Thr His Thr Lys Val Met Asn Met Glu Glu Ser Thr<br>385 390 395 | 1384 |
| aat ggc agt ctg gcg gct gaa ttt cgg cac ctg caa ttg aaa gaa cag<br>Asn Gly Ser Leu Ala Ala Glu Phe Arg His Leu Gln Leu Lys Glu Gln<br>400 405 410 | 1432 |
| aaa aat gct ggc acc aga acg aat gag ggt cct ctc atc gtt act gaa<br>Lys Asn Ala Gly Thr Arg Thr Asn Glu Gly Pro Leu Ile Val Thr Glu<br>415 420 425 | 1480 |
| gag ctt cac tcc ctt agt ttt gaa acc caa ttg tgc cag cct ggt ttg<br>Glu Leu His Ser Leu Ser Phe Glu Thr Gln Leu Cys Gln Pro Gly Leu<br>430 435 440 | 1528 |
| gta att gac ctc gag acg acc tct ctg ccc gtt gtg gtg atc tcc aac<br>Val Ile Asp Leu Glu Thr Thr Ser Leu Pro Val Val Val Ile Ser Asn<br>445 450 455 460 | 1576 |
| gtc agc cag ctc ccg agc ggt tgg gcc tcc atc ctt tgg tac aac atg<br>Val Ser Gln Leu Pro Ser Gly Trp Ala Ser Ile Leu Trp Tyr Asn Met<br>465 470 475 | 1624 |
| ctg gtg gcg gaa ccc agg aat ctg tcc ttc ttc ctg act cca cca tgt<br>Leu Val Ala Glu Pro Arg Asn Leu Ser Phe Phe Leu Thr Pro Pro Cys<br>480 485 490 | 1672 |
| gca cga tgg gct cag ctt tca gaa gtg ctg agt tgg cag ttt tct tct<br>Ala Arg Trp Ala Gln Leu Ser Glu Val Leu Ser Trp Gln Phe Ser Ser<br>495 500 505 | 1720 |
| gtc acc aaa aga ggt ctc aat gtg gac cag ctg aac atg ttg gga gag<br>Val Thr Lys Arg Gly Leu Asn Val Asp Gln Leu Asn Met Leu Gly Glu<br>510 515 520 | 1768 |
| aag ctt ctt ggt cct aac gcc agc ccc gat ggt ctc att ccg tgg acg<br>Lys Leu Leu Gly Pro Asn Ala Ser Pro Asp Gly Leu Ile Pro Trp Thr<br>525 530 535 540 | 1816 |
| agg ttt tgt aag gaa aat ata aat gat aaa aat ttt ccc ttc tgg ctt<br>Arg Phe Cys Lys Glu Asn Ile Asn Asp Lys Asn Phe Pro Phe Trp Leu<br>545 550 555 | 1864 |
| tgg att gaa agc atc cta gaa ctc att aaa aaa cac ctg ctc cct ctc<br>Trp Ile Glu Ser Ile Leu Glu Leu Ile Lys Lys His Leu Leu Pro Leu<br>560 565 570 | 1912 |
| tgg aat gat ggg tgc atc atg ggc ttc atc agc aag gag cga gag cgt<br>Trp Asn Asp Gly Cys Ile Met Gly Phe Ile Ser Lys Glu Arg Glu Arg<br>575 580 585 | 1960 |
| gcc ctg ttg aag gac cag cag ccg ggg acc ttc ctg ctg cgg ttc agt<br>Ala Leu Leu Lys Asp Gln Gln Pro Gly Thr Phe Leu Leu Arg Phe Ser<br>590 595 600 | 2008 |
| gag agc tcc cgg gaa ggg gcc atc aca ttc aca tgg gtg gag cgg tcc<br>Glu Ser Ser Arg Glu Gly Ala Ile Thr Phe Thr Trp Val Glu Arg Ser | 2056 |

```
                 605                 610                 615                 620
cag aac gga ggc gaa cct gac ttc cat gcg gtt gaa ccc tac acg aag                2104
Gln Asn Gly Gly Glu Pro Asp Phe His Ala Val Glu Pro Tyr Thr Lys
                         625                 630                 635 aaa gaa ctt tct gct gtt act ttc cct gac atc att cgc aat tac aaa                2152
Lys Glu Leu Ser Ala Val Thr Phe Pro Asp Ile Ile Arg Asn Tyr Lys
            640                 645                 650 gtc atg gct gct gag aat att cct gag aat ccc ctg aag tat ctg tat                2200
Val Met Ala Ala Glu Asn Ile Pro Glu Asn Pro Leu Lys Tyr Leu Tyr
                655                 660                 665 cca aat att gac aaa gac cat gcc ttt gga aag tat tac tcc agg cca                2248
Pro Asn Ile Asp Lys Asp His Ala Phe Gly Lys Tyr Tyr Ser Arg Pro
        670                 675                 680 aag gaa gca cca gag cca atg gaa ctt gat ggc cct aaa gga act gga                2296
Lys Glu Ala Pro Glu Pro Met Glu Leu Asp Gly Pro Lys Gly Thr Gly
685                 690                 695                 700 tat atc aag act gag ttg att tct gtg tct gaa gtt cac cct tct aga                2344
Tyr Ile Lys Thr Glu Leu Ile Ser Val Ser Glu Val His Pro Ser Arg
                    705                 710                 715 ctt cag acc aca gac aac ctg ctc ccc atg tct cct gag gag ttt gac                2392
Leu Gln Thr Thr Asp Asn Leu Leu Pro Met Ser Pro Glu Glu Phe Asp
            720                 725                 730 gag gtg tct cgg ata gtg ggc tct gta gaa ttc gac agt atg atg aac                2440
Glu Val Ser Arg Ile Val Gly Ser Val Glu Phe Asp Ser Met Met Asn
        735                 740                 745 aca gta tag agcatgaatt tttttcatct tctctggcga cagttttcct                        2489
Thr Val  *
750 tctcatctgt gattccctcc tgctactctg ttccttcaca tcctgtgttt ctagggaaat              2549 gaaagaaagg ccagcaaatt cgctgcaacc tgttgatagc aagtgaattt ttctctaact              2609 cagaaacatc agttactctg aagggcatca tgcatcttac tgaaggtaaa attgaaaggc              2669 attctctgaa gagtgggttt cacaagtgaa aaacatccag atacacccaa agtatcagga              2729 cgagaatgag ggtcctttgg gaaggagaa gttaagcaac atctagcaaa tgttatgcat               2789 aaagtcagtg cccaactgtt ataggttgtt ggataaatca gtggttattt agggaactgc              2849 ttgacgtagg aacggtaaat ttctgtggga gaattcttac atgttttctt tgctttaagt              2909 gtaactggca gttttccatt ggtttacctg tgaaatagtt caaagccaag tttatataca              2969 attatatcag tcctctttca aaggtagcca tcatggatct ggtaggggga aaatgtgtat              3029 tttattacat ctttcacatt ggctatttaa agacaaagac aaattctgtt tcttgagaag              3089 agaatattag cttactgtt tgttatggct taatgacact agctaatatc aatagaagga               3149 tgtacatttc caaattcaca agttgtgttt gatatccaaa gctgaataca ttctgctttc              3209 atcttggtca catacaatta tttttacagt tctcccaagg gagttaggct attcacaacc              3269 actcattcaa aagttgaaat taaccataga tgtagataaa ctcagaaatt taattcatgt              3329 ttcttaaatg ggctactttg tcctttttgt tattagggtg gtatttagtc tattagccac              3389 aaaattggga aggagtaga aaaagcagta actgacaact tgaataatac accagagata               3449 atatgagaat cagatcattt caaaactcat ttcctatgta actgcattga gaactgcata              3509 tgtttcgctg atatatgtgt ttttcacatt tgcgaatggt tccattctct ctcctgtact              3569 ttttccagac acttttttga gtggatgatg tttcgtgaag tatactgtat ttttaccttt              3629 ttccttcctt atcactgaca caaaaagtag attaagagat gggtttgaca aggttcttcc              3689 cttttacata ctgctgtcta tgtggctgta tcttgttttt ccactactgc taccacaact              3749
```

-continued

```
atattatcat gcaaatgctg tattcttctt tggtggagat aaagatttct tgagttttgt   3809
tttaaaatta aagctaaagt atctgtattg cattaaatat aatatcgaca cagtgctttc   3869
cgtggcactg catacaatct gaggcctcct ctctcagttt ttatatagat ggcgagaacc   3929
taagtttcag ttgattttac aattgaaatg actaaaaaac aaagaagaca acattaaaaa   3989
caatattgtt tcta                                                      4003
```

<210> SEQ ID NO 2
<211> LENGTH: 750
<212> TYPE: PRT
<213> ORGANISM: Homo sapiens

<400> SEQUENCE: 2

```
Met Ser Gln Trp Tyr Glu Leu Gln Gln Leu Asp Ser Lys Phe Leu Glu
 1               5                  10                  15

Gln Val His Gln Leu Tyr Asp Asp Ser Phe Pro Met Glu Ile Arg Gln
                20                  25                  30

Tyr Leu Ala Gln Trp Leu Glu Lys Gln Asp Trp Glu His Ala Ala Asn
            35                  40                  45

Asp Val Ser Phe Ala Thr Ile Arg Phe His Asp Leu Leu Ser Gln Leu
        50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Lys Met Tyr Leu Met Leu Asp Asn
        195                 200                 205

Lys Arg Lys Glu Val Val His Lys Ile Ile Glu Leu Leu Asn Val Thr
210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
290                 295                 300

Thr Phe Ser Leu Phe Gln Gln Leu Ile Gln Ser Ser Phe Val Val Glu
305                 310                 315                 320
```

-continued

```
Arg Gln Pro Cys Met Pro Thr His Pro Gln Arg Pro Leu Val Leu Lys
            325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
            355                 360                 365

Asn Glu Arg Asn Thr Val Lys Gly Phe Arg Lys Phe Asn Ile Leu Gly
370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
            405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
            435                 440                 445

Glu Thr Thr Ser Leu Pro Val Val Val Ile Ser Asn Val Ser Gln Leu
450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
            485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
            515                 520                 525

Pro Asn Ala Ser Pro Asp Gly Leu Ile Pro Trp Thr Arg Phe Cys Lys
            530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
            565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
            610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
            645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
            675                 680                 685

Glu Pro Met Glu Leu Asp Gly Pro Lys Gly Thr Gly Tyr Ile Lys Thr
            690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
            725                 730                 735

Ile Val Gly Ser Val Glu Phe Asp Ser Met Met Asn Thr Val
```

<210> SEQ ID NO 3
<211> LENGTH: 3291
<212> TYPE: DNA
<213> ORGANISM: Homo sapiens
<220> FEATURE:
<221> NAME/KEY: CDS
<222> LOCATION: (58)...(2613)

<400> SEQUENCE: 3

```
aagtcgcgac cagagccatt ggagggcgcg gggactgcaa ccctaatcag agcccaa atg      60
                                                                 Met
                                                                  1 gcg cag tgg gaa atg ctg cag aat ctt gac agc ccc ttt cag gat cag        108
Ala Gln Trp Glu Met Leu Gln Asn Leu Asp Ser Pro Phe Gln Asp Gln
              5                  10                  15 ctg cac cag ctt tac tcg cac agc ctc ctg cct gtg gac att cga cag        156
Leu His Gln Leu Tyr Ser His Ser Leu Leu Pro Val Asp Ile Arg Gln
         20                  25                  30 tac ttg gct gtc tgg att gaa gac cag aac tgg cag gaa gct gca ctt        204
Tyr Leu Ala Val Trp Ile Glu Asp Gln Asn Trp Gln Glu Ala Ala Leu
     35                  40                  45 ggg agt gat gat tcc aag gct acc atg cta ttc ttc cac ttc ttg gat        252
Gly Ser Asp Asp Ser Lys Ala Thr Met Leu Phe Phe His Phe Leu Asp
 50                  55                  60                  65 cag ctg aac tat gag tgt ggc cgt tgc agc cag gac cca gag tcc ttg        300
Gln Leu Asn Tyr Glu Cys Gly Arg Cys Ser Gln Asp Pro Glu Ser Leu
                 70                  75                  80 ttg ctg cag cac aat ttg cgg aaa ttc tgc cgg gac att cag ccc ttt        348
Leu Leu Gln His Asn Leu Arg Lys Phe Cys Arg Asp Ile Gln Pro Phe
             85                  90                  95 tcc cag gat cct acc cag ttg gct gag atg atc ttt aac ctc ctt ctg        396
Ser Gln Asp Pro Thr Gln Leu Ala Glu Met Ile Phe Asn Leu Leu Leu
        100                 105                 110 gaa gaa aaa aga att ttg atc cag gct cag agg gcc caa ttg gaa caa        444
Glu Glu Lys Arg Ile Leu Ile Gln Ala Gln Arg Ala Gln Leu Glu Gln
    115                 120                 125 gga gag cca gtt ctc gaa aca cct gtg gag agc cag caa cat gag att        492
Gly Glu Pro Val Leu Glu Thr Pro Val Glu Ser Gln Gln His Glu Ile
130                 135                 140                 145 gaa tcc cgg atc ctg gat tta agg gct atg atg gag aag ctg gta aaa        540
Glu Ser Arg Ile Leu Asp Leu Arg Ala Met Met Glu Lys Leu Val Lys
                150                 155                 160 tcc atc agc caa ctg aaa gac cag cag gat gtc ttc tgc ttc cga tat        588
Ser Ile Ser Gln Leu Lys Asp Gln Gln Asp Val Phe Cys Phe Arg Tyr
            165                 170                 175 aag atc cag gcc aaa ggg aag aca ccc tct ctg gac ccc cat cag acc        636
Lys Ile Gln Ala Lys Gly Lys Thr Pro Ser Leu Asp Pro His Gln Thr
        180                 185                 190 aaa gag cag aag att ctg cag gaa act ctc aat gaa ctg gac aaa agg        684
Lys Glu Gln Lys Ile Leu Gln Glu Thr Leu Asn Glu Leu Asp Lys Arg
    195                 200                 205 aga aag gag gtg ctg gat gcc tcc aaa gca ctg cta ggc cga tta act        732
Arg Lys Glu Val Leu Asp Ala Ser Lys Ala Leu Leu Gly Arg Leu Thr
210                 215                 220                 225 acc cta atc gag cta ctg ctg cca aag ttg gag gag tgg aag gcc cag        780
Thr Leu Ile Glu Leu Leu Leu Pro Lys Leu Glu Glu Trp Lys Ala Gln
                230                 235                 240 cag caa aaa gcc tgc atc aga gct ccc att gac cac ggg ttg gaa cag        828
Gln Gln Lys Ala Cys Ile Arg Ala Pro Ile Asp His Gly Leu Glu Gln
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 245 |     |     |     |     | 250 |     |     |     |     | 255 |     |      |
| ctg | gag | aca | tgg | ttc | aca | gct | gga | gca | aag | ctg | ttg | ttt | cac | ctg | agg | 876  |
| Leu | Glu | Thr | Trp | Phe | Thr | Ala | Gly | Ala | Lys | Leu | Leu | Phe | His | Leu | Arg |      |
|     |     | 260 |     |     |     |     | 265 |     |     |     |     | 270 |     |     |     |      |
| cag | ctg | ctg | aag | gag | ctg | aag | gga | ctg | agt | tgc | ctg | gtt | agc | tat | cag | 924  |
| Gln | Leu | Leu | Lys | Glu | Leu | Lys | Gly | Leu | Ser | Cys | Leu | Val | Ser | Tyr | Gln |      |
|     | 275 |     |     |     |     | 280 |     |     |     |     | 285 |     |     |     |     |      |
| gat | gac | cct | ctg | acc | aaa | ggg | gtg | gac | cta | cgc | aac | gcc | cag | gtc | aca | 972  |
| Asp | Asp | Pro | Leu | Thr | Lys | Gly | Val | Asp | Leu | Arg | Asn | Ala | Gln | Val | Thr |      |
| 290 |     |     |     |     | 295 |     |     |     |     | 300 |     |     |     |     | 305 |      |
| gag | ttg | cta | cag | cgt | ctg | ctc | cac | aga | gcc | ttt | gtg | gta | gaa | acc | cag | 1020 |
| Glu | Leu | Leu | Gln | Arg | Leu | Leu | His | Arg | Ala | Phe | Val | Val | Glu | Thr | Gln |      |
|     |     |     | 310 |     |     |     |     | 315 |     |     |     |     | 320 |     |     |      |
| ccc | tgc | atg | ccc | caa | act | ccc | cat | cga | ccc | ctc | atc | ctc | aag | act | ggc | 1068 |
| Pro | Cys | Met | Pro | Gln | Thr | Pro | His | Arg | Pro | Leu | Ile | Leu | Lys | Thr | Gly |      |
|     |     | 325 |     |     |     |     | 330 |     |     |     |     | 335 |     |     |     |      |
| agc | aag | ttc | acc | gtc | cga | aca | agg | ctg | ctg | gtg | aga | ctc | cag | gaa | ggc | 1116 |
| Ser | Lys | Phe | Thr | Val | Arg | Thr | Arg | Leu | Leu | Val | Arg | Leu | Gln | Glu | Gly |      |
|     | 340 |     |     |     |     | 345 |     |     |     |     | 350 |     |     |     |     |      |
| aat | gag | tca | ctg | act | gtg | gaa | gtc | tcc | att | gac | agg | aat | cct | cct | caa | 1164 |
| Asn | Glu | Ser | Leu | Thr | Val | Glu | Val | Ser | Ile | Asp | Arg | Asn | Pro | Pro | Gln |      |
| 355 |     |     |     |     | 360 |     |     |     |     | 365 |     |     |     |     |     |      |
| tta | caa | ggc | ttc | cgg | aag | ttc | aac | att | ctg | act | tca | aac | cag | aaa | act | 1212 |
| Leu | Gln | Gly | Phe | Arg | Lys | Phe | Asn | Ile | Leu | Thr | Ser | Asn | Gln | Lys | Thr |      |
| 370 |     |     |     | 375 |     |     |     |     | 380 |     |     |     |     | 385 |     |      |
| ttg | acc | ccc | gag | aag | ggg | cag | agt | cag | ggt | ttg | att | tgg | gac | ttt | ggt | 1260 |
| Leu | Thr | Pro | Glu | Lys | Gly | Gln | Ser | Gln | Gly | Leu | Ile | Trp | Asp | Phe | Gly |      |
|     |     |     |     | 390 |     |     |     |     | 395 |     |     |     |     | 400 |     |      |
| tac | ctg | act | ctg | gtg | gag | caa | cgt | tca | ggt | ggt | tca | gga | aag | ggc | agc | 1308 |
| Tyr | Leu | Thr | Leu | Val | Glu | Gln | Arg | Ser | Gly | Gly | Ser | Gly | Lys | Gly | Ser |      |
|     |     |     | 405 |     |     |     |     | 410 |     |     |     |     | 415 |     |     |      |
| aat | aag | ggg | cca | cta | ggt | gtg | aca | gag | gaa | ctg | cac | atc | atc | agc | ttc | 1356 |
| Asn | Lys | Gly | Pro | Leu | Gly | Val | Thr | Glu | Glu | Leu | His | Ile | Ile | Ser | Phe |      |
|     |     | 420 |     |     |     |     | 425 |     |     |     |     | 430 |     |     |     |      |
| acg | gtc | aaa | tat | acc | tac | cag | ggt | ctg | aag | cag | gag | ctg | aaa | acg | gac | 1404 |
| Thr | Val | Lys | Tyr | Thr | Tyr | Gln | Gly | Leu | Lys | Gln | Glu | Leu | Lys | Thr | Asp |      |
|     | 435 |     |     |     |     | 440 |     |     |     |     | 445 |     |     |     |     |      |
| acc | ctc | cct | gtg | gtg | att | att | tcc | aac | atg | aac | cag | ctc | tca | att | gcc | 1452 |
| Thr | Leu | Pro | Val | Val | Ile | Ile | Ser | Asn | Met | Asn | Gln | Leu | Ser | Ile | Ala |      |
| 450 |     |     |     |     | 455 |     |     |     |     | 460 |     |     |     |     | 465 |      |
| tgg | gct | tca | gtt | ctc | tgg | ttc | aat | ttg | ctc | agc | cca | aac | ctt | cag | aac | 1500 |
| Trp | Ala | Ser | Val | Leu | Trp | Phe | Asn | Leu | Leu | Ser | Pro | Asn | Leu | Gln | Asn |      |
|     |     |     |     | 470 |     |     |     |     | 475 |     |     |     |     | 480 |     |      |
| cag | cag | ttc | ttc | tcc | aac | ccc | ccc | aag | gcc | ccc | tgg | agc | ttg | ctg | ggc | 1548 |
| Gln | Gln | Phe | Phe | Ser | Asn | Pro | Pro | Lys | Ala | Pro | Trp | Ser | Leu | Leu | Gly |      |
|     |     |     | 485 |     |     |     |     | 490 |     |     |     |     | 495 |     |     |      |
| cct | gct | ctc | agt | tgg | cag | ttc | tcc | tcc | tat | gtt | ggc | cga | ggc | ctc | aac | 1596 |
| Pro | Ala | Leu | Ser | Trp | Gln | Phe | Ser | Ser | Tyr | Val | Gly | Arg | Gly | Leu | Asn |      |
|     |     | 500 |     |     |     |     | 505 |     |     |     |     | 510 |     |     |     |      |
| tca | gac | cag | ctg | agc | atg | ctg | aga | aac | aag | ctg | ttc | ggg | cag | aac | tgt | 1644 |
| Ser | Asp | Gln | Leu | Ser | Met | Leu | Arg | Asn | Lys | Leu | Phe | Gly | Gln | Asn | Cys |      |
|     | 515 |     |     |     |     | 520 |     |     |     |     | 525 |     |     |     |     |      |
| agg | act | gag | gat | cca | tta | ttg | tcc | tgg | gct | gac | ttc | act | aag | cga | gag | 1692 |
| Arg | Thr | Glu | Asp | Pro | Leu | Leu | Ser | Trp | Ala | Asp | Phe | Thr | Lys | Arg | Glu |      |
| 530 |     |     |     |     | 535 |     |     |     |     | 540 |     |     |     |     | 545 |      |
| agc | cct | cct | ggc | aag | tta | cca | ttc | tgg | aca | tgg | ctg | gac | aaa | att | ctg | 1740 |
| Ser | Pro | Pro | Gly | Lys | Leu | Pro | Phe | Trp | Thr | Trp | Leu | Asp | Lys | Ile | Leu |      |
|     |     |     |     | 550 |     |     |     |     | 555 |     |     |     |     | 560 |     |      |
| gag | ttg | gta | cat | gac | cac | ctg | aag | gat | ctc | tgg | aat | gat | gga | cgc | atc | 1788 |

```
                                              -continued

Glu Leu Val His Asp His Leu Lys Asp Leu Trp Asn Asp Gly Arg Ile
            565                 570                 575 atg ggc ttt gtg agt cgg agc cag gag cgc cgg ctg ctg aag aag acc      1836
Met Gly Phe Val Ser Arg Ser Gln Glu Arg Arg Leu Leu Lys Lys Thr
580                 585                 590 atg tct ggc acc ttt cta ctg cgc ttc agt gaa tcg tca gaa ggg ggc      1884
Met Ser Gly Thr Phe Leu Leu Arg Phe Ser Glu Ser Ser Glu Gly Gly
            595                 600                 605 att acc tgc tcc tgg gtg gag cac cag gat gat gac aag gtg ctc atc      1932
Ile Thr Cys Ser Trp Val Glu His Gln Asp Asp Asp Lys Val Leu Ile
610                 615                 620                 625 tac tct gtg caa ccg tac acg aag gag gtg ctg cag tca ctc ccg ctg      1980
Tyr Ser Val Gln Pro Tyr Thr Lys Glu Val Leu Gln Ser Leu Pro Leu
                630                 635                 640 act gaa atc atc cgc cat tac cag ttg ctc act gag gag aat ata cct      2028
Thr Glu Ile Ile Arg His Tyr Gln Leu Leu Thr Glu Glu Asn Ile Pro
            645                 650                 655 gaa aac cca ctg cgc ttc ctc tat ccc cga atc ccc cgg gat gaa gct      2076
Glu Asn Pro Leu Arg Phe Leu Tyr Pro Arg Ile Pro Arg Asp Glu Ala
        660                 665                 670 ttt ggg tgc tac tac cag gag aaa gtt aat ctc cag gaa cgg agg aaa      2124
Phe Gly Cys Tyr Tyr Gln Glu Lys Val Asn Leu Gln Glu Arg Arg Lys
    675                 680                 685 tac ctg aaa cac agg ctc att gtg gtc tct aat aga cag gtg gat gaa      2172
Tyr Leu Lys His Arg Leu Ile Val Val Ser Asn Arg Gln Val Asp Glu
690                 695                 700                 705 ctg caa caa ccg ctg gag ctt aag cca gag cca gag ctg gag tca tta      2220
Leu Gln Gln Pro Leu Glu Leu Lys Pro Glu Pro Glu Leu Glu Ser Leu
                710                 715                 720 gag ctg gaa cta ggg ctg gtg cca gag cca gag ctc agc ctg gac tta      2268
Glu Leu Glu Leu Gly Leu Val Pro Glu Pro Glu Leu Ser Leu Asp Leu
            725                 730                 735 gag cca ctg ctg aag gca ggg ctg gat ctg ggg cca gag cta gag tct      2316
Glu Pro Leu Leu Lys Ala Gly Leu Asp Leu Gly Pro Glu Leu Glu Ser
        740                 745                 750 gtg ctg gag tcc act ctg gag cct gtg ata gag ccc aca cta tgc atg      2364
Val Leu Glu Ser Thr Leu Glu Pro Val Ile Glu Pro Thr Leu Cys Met
    755                 760                 765 gta tca caa aca gtg cca gag cca gac caa gga cct gta tca cag cca      2412
Val Ser Gln Thr Val Pro Glu Pro Asp Gln Gly Pro Val Ser Gln Pro
770                 775                 780                 785 gtg cca gag cca gat ttg ccc tgt gat ctg aga cat ttg aac act gag      2460
Val Pro Glu Pro Asp Leu Pro Cys Asp Leu Arg His Leu Asn Thr Glu
                790                 795                 800 cca atg gaa atc ttc aga aac tgt gta aag att gaa gaa atc atg ccg      2508
Pro Met Glu Ile Phe Arg Asn Cys Val Lys Ile Glu Glu Ile Met Pro
            805                 810                 815 aat ggt gac cca ctg ttg gct ggc cag aac acc gtg gat gag gtt tac      2556
Asn Gly Asp Pro Leu Leu Ala Gly Gln Asn Thr Val Asp Glu Val Tyr
        820                 825                 830 gtc tcc cgc ccc agc cac ttc tac act gat gga ccc ttg atg cct tct      2604
Val Ser Arg Pro Ser His Phe Tyr Thr Asp Gly Pro Leu Met Pro Ser
    835                 840                 845 gac ttc tag gaaccacatt tcctctgttc ttttcatatc tctttgccct              2653
Asp Phe *
850 tcctactcct catagcatga tattgttctc caaggatggg aatcaggcat gtgtcccttc    2713 caagctgtgt taactgttca aactcaggcc tgtgtgactc cattggggtg agaggtgaaa    2773
```

```
gcataacatg ggtacagagg ggacaacaat gaatcagaac agatgctgag ccataggtct    2833
aaataggatc ctggaggctg cctgctgtgc tgggaggtat aggggtcctg ggggcaggcc    2893
agggcagttg acaggtactt ggagggctca gggcagtggc ttctttccag tatggaagga    2953
tttcaacatt ttaatagttg gttaggctaa actggtgcat actggcattg gccttggtgg    3013
ggagcacaga cacaggatag gactccattt ctttcttcca ttccttcatg tctaggataa    3073
cttgctttct tctttccttt actcctggct caagccctga atttcttctt ttcctgcagg    3133
ggttgagagc tttctgcctt agcctaccat gtgaaactct accctgaaga aagggatgga    3193
taggaagtag acctctttt cttaccagtc tcctcccta ctctgccccc taagctggct       3253
gtacctgttc ctcccccata aaatgatcct gccaatct                             3291
```

<210> SEQ ID NO 4
<211> LENGTH: 851
<212> TYPE: PRT
<213> ORGANISM: Homo sapiens

<400> SEQUENCE: 4

```
Met Ala Gln Trp Glu Met Leu Gln Asn Leu Asp Ser Pro Phe Gln Asp
 1               5                  10                  15

Gln Leu His Gln Leu Tyr Ser His Ser Leu Leu Pro Val Asp Ile Arg
                20                  25                  30

Gln Tyr Leu Ala Val Trp Ile Glu Asp Gln Asn Trp Gln Glu Ala Ala
            35                  40                  45

Leu Gly Ser Asp Asp Ser Lys Ala Thr Met Leu Phe Phe His Phe Leu
        50                  55                  60

Asp Gln Leu Asn Tyr Glu Cys Gly Arg Cys Ser Gln Asp Pro Glu Ser
65                  70                  75                  80

Leu Leu Leu Gln His Asn Leu Arg Lys Phe Cys Arg Asp Ile Gln Pro
                85                  90                  95

Phe Ser Gln Asp Pro Thr Gln Leu Ala Glu Met Ile Phe Asn Leu Leu
            100                 105                 110

Leu Glu Glu Lys Arg Ile Leu Ile Gln Ala Gln Arg Ala Gln Leu Glu
        115                 120                 125

Gln Gly Glu Pro Val Leu Glu Thr Pro Val Glu Ser Gln Gln His Glu
    130                 135                 140

Ile Glu Ser Arg Ile Leu Asp Leu Arg Ala Met Met Glu Lys Leu Val
145                 150                 155                 160

Lys Ser Ile Ser Gln Leu Lys Asp Gln Gln Asp Val Phe Cys Phe Arg
                165                 170                 175

Tyr Lys Ile Gln Ala Lys Gly Lys Thr Pro Ser Leu Asp Pro His Gln
            180                 185                 190

Thr Lys Glu Gln Lys Ile Leu Gln Glu Thr Leu Asn Glu Leu Asp Lys
        195                 200                 205

Arg Arg Lys Glu Val Leu Asp Ala Ser Lys Ala Leu Leu Gly Arg Leu
    210                 215                 220

Thr Thr Leu Ile Glu Leu Leu Leu Pro Lys Leu Glu Glu Trp Lys Ala
225                 230                 235                 240

Gln Gln Gln Lys Ala Cys Ile Arg Ala Pro Ile Asp His Gly Leu Glu
                245                 250                 255

Gln Leu Glu Thr Trp Phe Thr Ala Gly Ala Lys Leu Leu Phe His Leu
            260                 265                 270

Arg Gln Leu Leu Lys Glu Leu Lys Gly Leu Ser Cys Leu Val Ser Tyr
        275                 280                 285
```

-continued

```
Gln Asp Asp Pro Leu Thr Lys Gly Val Asp Leu Arg Asn Ala Gln Val
    290                 295                 300
Thr Glu Leu Leu Gln Arg Leu Leu His Arg Ala Phe Val Val Glu Thr
305                 310                 315                 320
Gln Pro Cys Met Pro Gln Thr Pro His Arg Pro Leu Ile Leu Lys Thr
                325                 330                 335
Gly Ser Lys Phe Thr Val Arg Thr Arg Leu Leu Val Arg Leu Gln Glu
                340                 345                 350
Gly Asn Glu Ser Leu Thr Val Glu Val Ser Ile Asp Arg Asn Pro Pro
            355                 360                 365
Gln Leu Gln Gly Phe Arg Lys Phe Asn Ile Leu Thr Ser Asn Gln Lys
        370                 375                 380
Thr Leu Thr Pro Glu Lys Gly Gln Ser Gln Gly Leu Ile Trp Asp Phe
385                 390                 395                 400
Gly Tyr Leu Thr Leu Val Glu Gln Arg Ser Gly Ser Gly Lys Gly
                405                 410                 415
Ser Asn Lys Gly Pro Leu Gly Val Thr Glu Glu Leu His Ile Ile Ser
                420                 425                 430
Phe Thr Val Lys Tyr Thr Tyr Gln Gly Leu Lys Gln Glu Leu Lys Thr
                435                 440                 445
Asp Thr Leu Pro Val Val Ile Ile Ser Asn Met Asn Gln Leu Ser Ile
            450                 455                 460
Ala Trp Ala Ser Val Leu Trp Phe Asn Leu Leu Ser Pro Asn Leu Gln
465                 470                 475                 480
Asn Gln Gln Phe Phe Ser Asn Pro Pro Lys Ala Pro Trp Ser Leu Leu
                485                 490                 495
Gly Pro Ala Leu Ser Trp Gln Phe Ser Ser Tyr Val Gly Arg Gly Leu
                500                 505                 510
Asn Ser Asp Gln Leu Ser Met Leu Arg Asn Lys Leu Phe Gly Gln Asn
            515                 520                 525
Cys Arg Thr Glu Asp Pro Leu Leu Ser Trp Ala Asp Phe Thr Lys Arg
530                 535                 540
Glu Ser Pro Pro Gly Lys Leu Pro Phe Trp Thr Trp Leu Asp Lys Ile
545                 550                 555                 560
Leu Glu Leu Val His Asp His Leu Lys Asp Leu Trp Asn Asp Gly Arg
                565                 570                 575
Ile Met Gly Phe Val Ser Arg Ser Gln Glu Arg Arg Leu Leu Lys Lys
                580                 585                 590
Thr Met Ser Gly Thr Phe Leu Leu Arg Phe Ser Glu Ser Ser Glu Gly
            595                 600                 605
Gly Ile Thr Cys Ser Trp Val Glu His Gln Asp Asp Asp Lys Val Leu
        610                 615                 620
Ile Tyr Ser Val Gln Pro Tyr Thr Lys Glu Val Leu Gln Ser Leu Pro
625                 630                 635                 640
Leu Thr Glu Ile Ile Arg His Tyr Gln Leu Leu Thr Glu Glu Asn Ile
                645                 650                 655
Pro Glu Asn Pro Leu Arg Phe Leu Tyr Pro Arg Ile Pro Arg Asp Glu
                660                 665                 670
Ala Phe Gly Cys Tyr Tyr Gln Glu Lys Val Asn Leu Gln Glu Arg Arg
                675                 680                 685
Lys Tyr Leu Lys His Arg Leu Ile Val Val Ser Asn Arg Gln Val Asp
        690                 695                 700
```

```
Glu Leu Gln Gln Pro Leu Glu Leu Lys Pro Glu Pro Glu Leu Glu Ser
705                 710                 715                 720

Leu Glu Leu Glu Leu Gly Leu Val Pro Glu Pro Glu Leu Ser Leu Asp
            725                 730                 735

Leu Glu Pro Leu Leu Lys Ala Gly Leu Asp Leu Gly Pro Glu Leu Glu
        740                 745                 750

Ser Val Leu Glu Ser Thr Leu Glu Pro Val Ile Glu Pro Thr Leu Cys
    755                 760                 765

Met Val Ser Gln Thr Val Pro Glu Pro Asp Gln Gly Pro Val Ser Gln
770                 775                 780

Pro Val Pro Glu Pro Asp Leu Pro Cys Asp Leu Arg His Leu Asn Thr
785                 790                 795                 800

Glu Pro Met Glu Ile Phe Arg Asn Cys Val Lys Ile Glu Glu Ile Met
                805                 810                 815

Pro Asn Gly Asp Pro Leu Leu Ala Gly Gln Asn Thr Val Asp Glu Val
            820                 825                 830

Tyr Val Ser Arg Pro Ser His Phe Tyr Thr Asp Gly Pro Leu Met Pro
        835                 840                 845

Ser Asp Phe
    850

<210> SEQ ID NO 5
<211> LENGTH: 2787
<212> TYPE: DNA
<213> ORGANISM: Homo sapiens
<220> FEATURE:
<221> NAME/KEY: CDS
<222> LOCATION: (221)...(2533)

<400> SEQUENCE: 5
cagctggaat tcggggcggc ggcgcagact gggaggggga gccgggggtt ccgacgtcgc      60
agccgaggga acaagcccca accggatcct ggacaggcac cccggcttgg cgctgtctct     120 cccctcggc tcggagaggc ccttcggcct gagggagcct cgccgcccgt ccccggcaca      180
cgcgcagccc cggcctctcg gcctctgccg gagaaacagg atg gcc caa tgg aat      235
                                              Met Ala Gln Trp Asn
                                                1               5 cag cta cag cag ctt gac aca cgg tac ctg gag cag ctc cat cag ctc      283
Gln Leu Gln Gln Leu Asp Thr Arg Tyr Leu Glu Gln Leu His Gln Leu
             10                  15                  20 tac agt gac agc ttc cca atg gag ctg cgg cag ttt ctg gcc cct tgg      331
Tyr Ser Asp Ser Phe Pro Met Glu Leu Arg Gln Phe Leu Ala Pro Trp
         25                  30                  35 att gag agt caa gat tgg gca tat gcg gcc agc aaa gaa tca cat gcc      379
Ile Glu Ser Gln Asp Trp Ala Tyr Ala Ala Ser Lys Glu Ser His Ala
     40                  45                  50 act ttg gtg ttt cat aat ctc ctg gga gag att gac cag cag tat agc      427
Thr Leu Val Phe His Asn Leu Leu Gly Glu Ile Asp Gln Gln Tyr Ser
 55                  60                  65 cgc ttc ctg caa gag tcg aat gtt ctc tat cag cac aat cta cga aga      475
Arg Phe Leu Gln Glu Ser Asn Val Leu Tyr Gln His Asn Leu Arg Arg
 70                  75                  80                  85 atc aag cag ttt ctt cag agc agg tat ctt gag aag cca atg gag att      523
Ile Lys Gln Phe Leu Gln Ser Arg Tyr Leu Glu Lys Pro Met Glu Ile
                 90                  95                 100 gcc cgg att gtg gcc cgg tgc ctg tgg gaa gaa tca cgc ctt cta cag      571
Ala Arg Ile Val Ala Arg Cys Leu Trp Glu Glu Ser Arg Leu Leu Gln
            105                 110                 115
```

```
                                              -continued act gca gcc act gcg gcc cag caa ggg ggc cag gcc aac cac ccc aca       619
Thr Ala Ala Thr Ala Ala Gln Gln Gly Gly Gln Ala Asn His Pro Thr
            120                 125                 130 gca gcc gtg gtg acg gag aag cag cag atg ctg gag cag cac ctt cag       667
Ala Ala Val Val Thr Glu Lys Gln Gln Met Leu Glu Gln His Leu Gln
        135                 140                 145 gat gtc cgg aag aga gtg cag gat cta gaa cag aaa atg aaa gtg gta       715
Asp Val Arg Lys Arg Val Gln Asp Leu Glu Gln Lys Met Lys Val Val
150                 155                 160                 165 gag aat ctc cag gat gac ttt gat ttc aac tat aaa acc ctc aag agt       763
Glu Asn Leu Gln Asp Asp Phe Asp Phe Asn Tyr Lys Thr Leu Lys Ser
                170                 175                 180 caa gga gac atg caa gat ctg aat gga aac aac cag tca gtg acc agg       811
Gln Gly Asp Met Gln Asp Leu Asn Gly Asn Asn Gln Ser Val Thr Arg
            185                 190                 195 cag aag atg cag cag ctg gaa cag atg ctc act gcg ctg gac cag atg       859
Gln Lys Met Gln Gln Leu Glu Gln Met Leu Thr Ala Leu Asp Gln Met
        200                 205                 210 cgg aga agc atc gtg agt gag ctg gcg ggg ctt ttg tca gcg atg gag       907
Arg Arg Ser Ile Val Ser Glu Leu Ala Gly Leu Leu Ser Ala Met Glu
215                 220                 225 tac gtg cag aaa act ctc acg gac gag gag ctg gct gac tgg aag agg       955
Tyr Val Gln Lys Thr Leu Thr Asp Glu Glu Leu Ala Asp Trp Lys Arg
230                 235                 240                 245 cgg caa cag att gcc tgc att gga ggc ccg ccc aac atc tgc cta gat      1003
Arg Gln Gln Ile Ala Cys Ile Gly Gly Pro Pro Asn Ile Cys Leu Asp
                250                 255                 260 cgg cta gaa aac tgg ata acg tca tta gca gaa tct caa ctt cag acc      1051
Arg Leu Glu Asn Trp Ile Thr Ser Leu Ala Glu Ser Gln Leu Gln Thr
            265                 270                 275 cgt caa caa att aag aaa ctg gag gag ttg cac caa aaa gtt tcc tac      1099
Arg Gln Gln Ile Lys Lys Leu Glu Glu Leu His Gln Lys Val Ser Tyr
        280                 285                 290 aaa ggg gac ccc att gta cag cac cgg ccg atg ctg gag gag agg atc      1147
Lys Gly Asp Pro Ile Val Gln His Arg Pro Met Leu Glu Glu Arg Ile
295                 300                 305 gtg gag ctg ttc aga aac tta atg aaa agt gcc ttt gtg gtg gag cgg      1195
Val Glu Leu Phe Arg Asn Leu Met Lys Ser Ala Phe Val Val Glu Arg
310                 315                 320                 325 cag ccc tgc atg ccc atg cat cct gac cgg ccc ctc gtc atc aag acc      1243
Gln Pro Cys Met Pro Met His Pro Asp Arg Pro Leu Val Ile Lys Thr
                330                 335                 340 ggc gtc cag ttc act act aaa gtc agg ttg ctg gtc aag ttc cct gag      1291
Gly Val Gln Phe Thr Thr Lys Val Arg Leu Leu Val Lys Phe Pro Glu
            345                 350                 355 ttg aat tat cag ctt aaa att aaa gtg tgc att gac aaa gac tct ggg      1339
Leu Asn Tyr Gln Leu Lys Ile Lys Val Cys Ile Asp Lys Asp Ser Gly
        360                 365                 370 gac gtt gca gct ctc aga gga tcc cgg aaa ttt aac att ctg ggc aca      1387
Asp Val Ala Ala Leu Arg Gly Ser Arg Lys Phe Asn Ile Leu Gly Thr
375                 380                 385 aac aca aaa gtg atg aac atg gaa gaa tcc aac aac ggc agc ctc tct      1435
Asn Thr Lys Val Met Asn Met Glu Glu Ser Asn Asn Gly Ser Leu Ser
390                 395                 400                 405 gca gaa ttc aaa cac ttg acc ctg agg gag cag aga tgt ggg aat ggg      1483
Ala Glu Phe Lys His Leu Thr Leu Arg Glu Gln Arg Cys Gly Asn Gly
                410                 415                 420 ggc cga gcc aat tgt gat gct tcc ctg att gtg act gag gag ctg cac      1531
Gly Arg Ala Asn Cys Asp Ala Ser Leu Ile Val Thr Glu Glu Leu His
            425                 430                 435
```

```
ctg atc acc ttt gag acc gag gtg tat cac caa ggt ctc aag att gac    1579
Leu Ile Thr Phe Glu Thr Glu Val Tyr His Gln Gly Leu Lys Ile Asp
        440                 445                 450 cta gag acc cac tcc ttg tca gtt gtg gtg atc tcc aac atc tgt cag    1627
Leu Glu Thr His Ser Leu Ser Val Val Val Ile Ser Asn Ile Cys Gln
    455                 460                 465 atg cca aat gcc tgg gcg tcc atc ctg tgg tac aac atg ctg acc aac    1675
Met Pro Asn Ala Trp Ala Ser Ile Leu Trp Tyr Asn Met Leu Thr Asn
470                 475                 480                 485 aat ccc aag aat gtg aac ttc ttc act aag ccg cca att gga acc tgg    1723
Asn Pro Lys Asn Val Asn Phe Phe Thr Lys Pro Pro Ile Gly Thr Trp
                490                 495                 500 gac caa gtg gcc gag gtg ctc agc tgg cag ttc tcg tcc acc acc aag    1771
Asp Gln Val Ala Glu Val Leu Ser Trp Gln Phe Ser Ser Thr Thr Lys
            505                 510                 515 cgg ggg ctg agc atc gag cag ctg aca acg ctg gct gag aag ctc cta    1819
Arg Gly Leu Ser Ile Glu Gln Leu Thr Thr Leu Ala Glu Lys Leu Leu
        520                 525                 530 ggg cct ggt gtg aac tac tca ggg tgt cag atc aca tgg gct aac ttc    1867
Gly Pro Gly Val Asn Tyr Ser Gly Cys Gln Ile Thr Trp Ala Asn Phe
    535                 540                 545 tgc aaa gaa aac atg gct ggc aag ggc ttc tcc tac tgg gtc tgg cta    1915
Cys Lys Glu Asn Met Ala Gly Lys Gly Phe Ser Tyr Trp Val Trp Leu
550                 555                 560                 565 gac aat atc atc gac ctt gtg aaa aag tat atc ttg gcc ctt tgg aat    1963
Asp Asn Ile Ile Asp Leu Val Lys Lys Tyr Ile Leu Ala Leu Trp Asn
                570                 575                 580 gaa ggg tac atc atg ggt ttc atc agc aag gag cgg gag cgg gcc atc    2011
Glu Gly Tyr Ile Met Gly Phe Ile Ser Lys Glu Arg Glu Arg Ala Ile
            585                 590                 595 ttg agc act aag ccc cca ggc acc ttc ctg ctg cgc ttc agt gaa agc    2059
Leu Ser Thr Lys Pro Pro Gly Thr Phe Leu Leu Arg Phe Ser Glu Ser
        600                 605                 610 agc aaa gaa gga ggc gtc act ttc act tgg gtg gag aag gac atc agc    2107
Ser Lys Glu Gly Gly Val Thr Phe Thr Trp Val Glu Lys Asp Ile Ser
    615                 620                 625 ggt aag acc cag atc cag tcc gtg gaa cca tac aca aag cag cag ctg    2155
Gly Lys Thr Gln Ile Gln Ser Val Glu Pro Tyr Thr Lys Gln Gln Leu
630                 635                 640                 645 aac aac atg tca ttt gct gaa atc atc atg ggc tat aag atc atg gat    2203
Asn Asn Met Ser Phe Ala Glu Ile Ile Met Gly Tyr Lys Ile Met Asp
                650                 655                 660 gct acc aat atc ctg ttg tct cca ctt gtc tat ctc tat cct gac att    2251
Ala Thr Asn Ile Leu Leu Ser Pro Leu Val Tyr Leu Tyr Pro Asp Ile
            665                 670                 675 ccc aag gag gag gca ttc ggg aag tat tgt cgg cca gag agc cag gag    2299
Pro Lys Glu Glu Ala Phe Gly Lys Tyr Cys Arg Pro Glu Ser Gln Glu
        680                 685                 690 cat cct gaa gct gac cca ggt agc gct gcc cca tac ctg aag acc aag    2347
His Pro Glu Ala Asp Pro Gly Ser Ala Ala Pro Tyr Leu Lys Thr Lys
    695                 700                 705 ttt atc tgt gtg aca cca acg acc tgc agc aat acc att gac ctg ccg    2395
Phe Ile Cys Val Thr Pro Thr Thr Cys Ser Asn Thr Ile Asp Leu Pro
710                 715                 720                 725 atg tcc ccc cgc gct tta gat tca ttg atg cag ttt gga aat aat ggt    2443
Met Ser Pro Arg Ala Leu Asp Ser Leu Met Gln Phe Gly Asn Asn Gly
                730                 735                 740 gaa ggt gct gaa ccc tca gca gga ggg cag ttt gag tcc ctc acc ttt    2491
Glu Gly Ala Glu Pro Ser Ala Gly Gly Gln Phe Glu Ser Leu Thr Phe
```

```
                745                 750                 755
gac atg gag ttg acc tcg gag tgc gct acc tcc ccc atg tga              2533
Asp Met Glu Leu Thr Ser Glu Cys Ala Thr Ser Pro Met *
        760                 765                 770 ggagctgaga acggaagctg cagaaagata cgactgaggc gcctacctgc attctgccac    2593
ccctcacaca gccaaacccc agatcatctg aaactactaa ctttgtggtt ccagattttt    2653
tttaatctcc tacttctgct atctttgagc aatctgggca cttttaaaaa tagagaaatg    2713
agtgaatgtg ggtgatctgc ttttatctaa atgcaaataa ggatgtgttc tctgagaccc    2773
atgatcaggg gatg                                                      2787
```

<210> SEQ ID NO 6
<211> LENGTH: 770
<212> TYPE: PRT
<213> ORGANISM: Homo sapiens

<400> SEQUENCE: 6

```
Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu His
        275                 280                 285

Gln Lys Val Ser Tyr Lys Gly Asp Pro Ile Val Gln His Arg Pro Met
```

```
            290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
                340                 345                 350
Val Lys Phe Pro Glu Leu Asn Tyr Gln Leu Lys Ile Lys Val Cys Ile
                355                 360                 365
Asp Lys Asp Ser Gly Asp Val Ala Ala Leu Arg Gly Ser Arg Lys Phe
                370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                405                 410                 415
Arg Cys Gly Asn Gly Gly Arg Ala Asn Cys Asp Ala Ser Leu Ile Val
                420                 425                 430
Thr Glu Glu Leu His Leu Ile Thr Phe Glu Thr Glu Val Tyr His Gln
                435                 440                 445
Gly Leu Lys Ile Asp Leu Glu Thr His Ser Leu Ser Val Val Val Ile
450                 455                 460
Ser Asn Ile Cys Gln Met Pro Asn Ala Trp Ala Ser Ile Leu Trp Tyr
465                 470                 475                 480
Asn Met Leu Thr Asn Asn Pro Lys Asn Val Asn Phe Phe Thr Lys Pro
                485                 490                 495
Pro Ile Gly Thr Trp Asp Gln Val Ala Glu Val Leu Ser Trp Gln Phe
                500                 505                 510
Ser Ser Thr Thr Lys Arg Gly Leu Ser Ile Glu Gln Leu Thr Thr Leu
                515                 520                 525
Ala Glu Lys Leu Leu Gly Pro Gly Val Asn Tyr Ser Gly Cys Gln Ile
530                 535                 540
Thr Trp Ala Asn Phe Cys Lys Glu Asn Met Ala Gly Lys Gly Phe Ser
545                 550                 555                 560
Tyr Trp Val Trp Leu Asp Asn Ile Ile Asp Leu Val Lys Lys Tyr Ile
                565                 570                 575
Leu Ala Leu Trp Asn Glu Gly Tyr Ile Met Gly Phe Ile Ser Lys Glu
                580                 585                 590
Arg Glu Arg Ala Ile Leu Ser Thr Lys Pro Pro Gly Thr Phe Leu Leu
                595                 600                 605
Arg Phe Ser Glu Ser Ser Lys Glu Gly Gly Val Thr Phe Thr Trp Val
                610                 615                 620
Glu Lys Asp Ile Ser Gly Lys Thr Gln Ile Gln Ser Val Glu Pro Tyr
625                 630                 635                 640
Thr Lys Gln Gln Leu Asn Asn Met Ser Phe Ala Glu Ile Ile Met Gly
                645                 650                 655
Tyr Lys Ile Met Asp Ala Thr Asn Ile Leu Leu Ser Pro Leu Val Tyr
                660                 665                 670
Leu Tyr Pro Asp Ile Pro Lys Glu Glu Ala Phe Gly Lys Tyr Cys Arg
                675                 680                 685
Pro Glu Ser Gln Glu His Pro Glu Ala Asp Pro Gly Ser Ala Ala Pro
                690                 695                 700
Tyr Leu Lys Thr Lys Phe Ile Cys Val Thr Pro Thr Thr Cys Ser Asn
705                 710                 715                 720
```

```
Thr Ile Asp Leu Pro Met Ser Pro Arg Ala Leu Asp Ser Leu Met Gln
            725                 730                 735

Phe Gly Asn Asn Gly Glu Gly Ala Glu Pro Ser Ala Gly Gly Gln Phe
        740                 745                 750

Glu Ser Leu Thr Phe Asp Met Glu Leu Thr Ser Glu Cys Ala Thr Ser
    755                 760                 765

Pro Met
    770

<210> SEQ ID NO 7
<211> LENGTH: 2588
<212> TYPE: DNA
<213> ORGANISM: Homo sapiens
<220> FEATURE:
<221> NAME/KEY: CDS
<222> LOCATION: (82)...(2328)

<400> SEQUENCE: 7
gctttctcct agggactgtg aggggcgctt ctgactttgg acttgagcac tgcctgggac      60
ctgtgctgag agagcgctag c atg tct cag tgg aat caa gtc caa cag tta      111
                        Met Ser Gln Trp Asn Gln Val Gln Gln Leu
                          1               5                  10 gaa atc aag ttt ttg gag cag gtg gat caa ttc tat gat gac aac ttt      159
Glu Ile Lys Phe Leu Glu Gln Val Asp Gln Phe Tyr Asp Asp Asn Phe
             15                  20                  25 ccc atg gaa att cgg cat ctg ttg gcc caa tgg att gaa aat caa gac      207
Pro Met Glu Ile Arg His Leu Leu Ala Gln Trp Ile Glu Asn Gln Asp
         30                  35                  40 tgg gag gca gct tct aac aat gaa acc atg gca acg att ctt ctt caa      255
Trp Glu Ala Ala Ser Asn Asn Glu Thr Met Ala Thr Ile Leu Leu Gln
     45                  50                  55 aac ttg tta ata caa ctg gat gaa cag tta ggt cgt gtt tcc aaa gag      303
Asn Leu Leu Ile Gln Leu Asp Glu Gln Leu Gly Arg Val Ser Lys Glu
 60                  65                  70 aaa aac cta ctc ttg ata cac aat cta aaa aga att agg aag gtc ctt      351
Lys Asn Leu Leu Leu Ile His Asn Leu Lys Arg Ile Arg Lys Val Leu
 75                  80                  85                  90 cag gga aaa ttt cat gga aat cca atg cat gta gct gtg gtt att tca      399
Gln Gly Lys Phe His Gly Asn Pro Met His Val Ala Val Val Ile Ser
                 95                 100                 105 aac tgt tta agg gaa gag agg aga ata ttg gct gca gcc aac atg cct      447
Asn Cys Leu Arg Glu Glu Arg Arg Ile Leu Ala Ala Ala Asn Met Pro
             110                 115                 120 gtc cag ggg cct cta gag aaa tcc tta caa agt tct tca gtt tca gaa      495
Val Gln Gly Pro Leu Glu Lys Ser Leu Gln Ser Ser Ser Val Ser Glu
         125                 130                 135 aga cag agg aat gtg gag cac aaa gtg gct gcc att aaa aac agt gtg      543
Arg Gln Arg Asn Val Glu His Lys Val Ala Ala Ile Lys Asn Ser Val
     140                 145                 150 cag atg aca gaa caa gat acc aaa tac tta gaa gat ctg caa gac gaa      591
Gln Met Thr Glu Gln Asp Thr Lys Tyr Leu Glu Asp Leu Gln Asp Glu
155                 160                 165                 170 ttt gac tac agg tat aaa aca att cag aca atg gat cag agt gac aag      639
Phe Asp Tyr Arg Tyr Lys Thr Ile Gln Thr Met Asp Gln Ser Asp Lys
                 175                 180                 185 aat agt gcc atg gtg aat cag gaa gtt ttg aca ctg cag gaa atg ctt      687
Asn Ser Ala Met Val Asn Gln Glu Val Leu Thr Leu Gln Glu Met Leu
             190                 195                 200 aac agc ctc gat ttc aag aga aag gag gct ctc agt aaa atg acc caa      735
```

```
Asn Ser Leu Asp Phe Lys Arg Lys Glu Ala Leu Ser Lys Met Thr Gln
        205                 210                 215 atc atc cat gag aca gac ctg tta atg aac acc atg ctc ata gaa gag       783
Ile Ile His Glu Thr Asp Leu Leu Met Asn Thr Met Leu Ile Glu Glu
220                 225                 230 ctg caa gac tgg aag cgg cgg cag caa atc gcc tgc atc ggg ggt cca       831
Leu Gln Asp Trp Lys Arg Arg Gln Gln Ile Ala Cys Ile Gly Gly Pro
235                 240                 245                 250 ctc cac aat ggg ctc gac cag ctt cag aac tgc ttt aca cta ttg gca       879
Leu His Asn Gly Leu Asp Gln Leu Gln Asn Cys Phe Thr Leu Leu Ala
                255                 260                 265 gaa agt ctt ttc caa ctg aga agg caa ttg gag aaa cta gag gag caa       927
Glu Ser Leu Phe Gln Leu Arg Arg Gln Leu Glu Lys Leu Glu Glu Gln
                270                 275                 280 tct acc aaa atg aca tat gaa ggt gat cca att cca atg caa aga act       975
Ser Thr Lys Met Thr Tyr Glu Gly Asp Pro Ile Pro Met Gln Arg Thr
                285                 290                 295 cac atg cta gaa aga gtc acc ttc ttg atc tac aac ctt ttc aag aac      1023
His Met Leu Glu Arg Val Thr Phe Leu Ile Tyr Asn Leu Phe Lys Asn
        300                 305                 310 tca ttt gtg gtt gag cga cag cca tgt atg cca acc cac cct cag agg      1071
Ser Phe Val Val Glu Arg Gln Pro Cys Met Pro Thr His Pro Gln Arg
315                 320                 325                 330 ccg ttg gta ctt aaa acc cta att cag ttc act gta aaa cta agg cta      1119
Pro Leu Val Leu Lys Thr Leu Ile Gln Phe Thr Val Lys Leu Arg Leu
                335                 340                 345 cta ata aaa ttg cca gaa cta aac tat cag gta aag gtt aag gca tca      1167
Leu Ile Lys Leu Pro Glu Leu Asn Tyr Gln Val Lys Val Lys Ala Ser
                350                 355                 360 att gac aag aat gtt tca act cta agc aac cga aga ttt gta ctt tgt      1215
Ile Asp Lys Asn Val Ser Thr Leu Ser Asn Arg Arg Phe Val Leu Cys
                365                 370                 375 gga act aat gtc aaa gcc atg tct att gaa gaa tct tcc aat ggg agt      1263
Gly Thr Asn Val Lys Ala Met Ser Ile Glu Glu Ser Ser Asn Gly Ser
        380                 385                 390 ctc tca gta gaa ttt cga cat ttg caa cca aag gaa atg aag tcc agt      1311
Leu Ser Val Glu Phe Arg His Leu Gln Pro Lys Glu Met Lys Ser Ser
395                 400                 405                 410 gct gga ggt aaa gga aat gag ggc tgt cac atg gtg act gaa gaa ctt      1359
Ala Gly Gly Lys Gly Asn Glu Gly Cys His Met Val Thr Glu Glu Leu
                415                 420                 425 cat tcc ata acg ttt gaa aca cag atc tgc ctc tat ggc ctg acc ata      1407
His Ser Ile Thr Phe Glu Thr Gln Ile Cys Leu Tyr Gly Leu Thr Ile
                430                 435                 440 gat ttg gag acc agc tca ttg cct gtg gtg atg att tcc aat gtc agt      1455
Asp Leu Glu Thr Ser Ser Leu Pro Val Val Met Ile Ser Asn Val Ser
                445                 450                 455 cag tta cct aat gct tgg gca tcc atc att tgg tac aac gtg tca acc      1503
Gln Leu Pro Asn Ala Trp Ala Ser Ile Ile Trp Tyr Asn Val Ser Thr
        460                 465                 470 aac gat tcc cag aac ttg gtt ttc ttt aat aat cct cca cct gcc aca      1551
Asn Asp Ser Gln Asn Leu Val Phe Phe Asn Asn Pro Pro Pro Ala Thr
475                 480                 485                 490 ttg agt caa cta ctg gag gtg atg agc tgg cag ttt tca tcg tac gtt      1599
Leu Ser Gln Leu Leu Glu Val Met Ser Trp Gln Phe Ser Ser Tyr Val
                495                 500                 505 ggt cgt ggt ctt aac tca gat caa ctc cat atg ctg gca gag aag ctt      1647
Gly Arg Gly Leu Asn Ser Asp Gln Leu His Met Leu Ala Glu Lys Leu
        510                 515                 520
```

```
aca gtc caa tct agc tac agt gat ggt cac ctc acc tgg gcc aag ttc    1695
Thr Val Gln Ser Ser Tyr Ser Asp Gly His Leu Thr Trp Ala Lys Phe
        525                 530                 535 tgc aag gaa cat tta cct ggt aaa tca ttt acc ttt tgg aca tgg ctt    1743
Cys Lys Glu His Leu Pro Gly Lys Ser Phe Thr Phe Trp Thr Trp Leu
540                 545                 550 gaa gca ata ttg gat cta att aag aaa cac att ctt ccc ctt tgg att    1791
Glu Ala Ile Leu Asp Leu Ile Lys Lys His Ile Leu Pro Leu Trp Ile
555                 560                 565                 570 gat ggg tat gtc atg ggc ttt gtt agc aaa gag aag gaa cgg ctg ttg    1839
Asp Gly Tyr Val Met Gly Phe Val Ser Lys Glu Lys Glu Arg Leu Leu
                575                 580                 585 cta aag gat aaa atg cct ggc acc ttt tta tta aga ttc agt gaa agc    1887
Leu Lys Asp Lys Met Pro Gly Thr Phe Leu Leu Arg Phe Ser Glu Ser
            590                 595                 600 cat ctc gga gga ata act ttc acc tgg gtg gac cat tct gaa agt ggg    1935
His Leu Gly Gly Ile Thr Phe Thr Trp Val Asp His Ser Glu Ser Gly
        605                 610                 615 gaa gtg aga ttc cac tct gta gaa ccc tac aat aaa ggc cgg ttg tct    1983
Glu Val Arg Phe His Ser Val Glu Pro Tyr Asn Lys Gly Arg Leu Ser
620                 625                 630 gct ctg cca ttc gct gac atc ctg cga gac tac aaa gtt att atg gct    2031
Ala Leu Pro Phe Ala Asp Ile Leu Arg Asp Tyr Lys Val Ile Met Ala
635                 640                 645                 650 gaa aac att cct gaa aac cct ctg aag tac cta tat cct gac att ccc    2079
Glu Asn Ile Pro Glu Asn Pro Leu Lys Tyr Leu Tyr Pro Asp Ile Pro
                655                 660                 665 aaa gac aaa gcc ttc ggt aaa cac tac agc tct cag cct tgc gaa gtt    2127
Lys Asp Lys Ala Phe Gly Lys His Tyr Ser Ser Gln Pro Cys Glu Val
            670                 675                 680 tca aga cca aca gaa agg ggt gac aaa ggt tat gtt cct tct gtt ttt    2175
Ser Arg Pro Thr Glu Arg Gly Asp Lys Gly Tyr Val Pro Ser Val Phe
        685                 690                 695 atc ccc atc tca aca atc cga agt gat tca aca gag cca cat tct cca    2223
Ile Pro Ile Ser Thr Ile Arg Ser Asp Ser Thr Glu Pro His Ser Pro
700                 705                 710 tca gac ctt ctt ccc atg tct cca agt gtg tat gcg gtg ttg aga gaa    2271
Ser Asp Leu Leu Pro Met Ser Pro Ser Val Tyr Ala Val Leu Arg Glu
715                 720                 725                 730 aac ctg agt ccc aca aca att gaa act gca atg aag tct cct tat tct    2319
Asn Leu Ser Pro Thr Thr Ile Glu Thr Ala Met Lys Ser Pro Tyr Ser
                735                 740                 745 gct gaa tga caggataaac tctgacgcac caagaaagga agcaaatgaa            2368
Ala Glu * aaagtttaaa gactgttctt tgcccaataa ccacatttta tttcttcagc tttgtaaata  2428
ccaggttcta ggaaatgttt gacatctgaa gctctcttca cactcccgtg gcactcctca  2488
attgggagtg ttgtgactga aatgcttgaa accaaagctt cagataaact tgcaagataa  2548
gacaacttta agaaaccagt gttaataaca atattaacag                        2588

<210> SEQ ID NO 8
<211> LENGTH: 748
<212> TYPE: PRT
<213> ORGANISM: Homo sapiens

<400> SEQUENCE: 8

Met Ser Gln Trp Asn Gln Val Gln Gln Leu Glu Ile Lys Phe Leu Glu
 1               5                  10                  15
```

-continued

```
Gln Val Asp Gln Phe Tyr Asp Asp Asn Phe Pro Met Glu Ile Arg His
         20                  25                  30

Leu Leu Ala Gln Trp Ile Glu Asn Gln Asp Trp Glu Ala Ala Ser Asn
             35                  40                  45

Asn Glu Thr Met Ala Thr Ile Leu Leu Gln Asn Leu Leu Ile Gln Leu
 50                  55                  60

Asp Glu Gln Leu Gly Arg Val Ser Lys Glu Lys Asn Leu Leu Leu Ile
 65                  70                  75                  80

His Asn Leu Lys Arg Ile Arg Lys Val Leu Gln Gly Lys Phe His Gly
                 85                  90                  95

Asn Pro Met His Val Ala Val Val Ile Ser Asn Cys Leu Arg Glu Glu
                100                 105                 110

Arg Arg Ile Leu Ala Ala Ala Asn Met Pro Val Gln Gly Pro Leu Glu
            115                 120                 125

Lys Ser Leu Gln Ser Ser Val Ser Glu Arg Gln Arg Asn Val Glu
130                 135                 140

His Lys Val Ala Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Ser Asp Lys Asn Ser Ala Met Val Asn
            180                 185                 190

Gln Glu Val Leu Thr Leu Gln Glu Met Leu Asn Ser Leu Asp Phe Lys
            195                 200                 205

Arg Lys Glu Ala Leu Ser Lys Met Thr Gln Ile Ile His Glu Thr Asp
210                 215                 220

Leu Leu Met Asn Thr Met Leu Ile Glu Glu Leu Gln Asp Trp Lys Arg
225                 230                 235                 240

Arg Gln Gln Ile Ala Cys Ile Gly Gly Pro Leu His Asn Gly Leu Asp
                245                 250                 255

Gln Leu Gln Asn Cys Phe Thr Leu Leu Ala Glu Ser Leu Phe Gln Leu
            260                 265                 270

Arg Arg Gln Leu Glu Lys Leu Glu Glu Gln Ser Thr Lys Met Thr Tyr
        275                 280                 285

Glu Gly Asp Pro Ile Pro Met Gln Arg Thr His Met Leu Glu Arg Val
    290                 295                 300

Thr Phe Leu Ile Tyr Asn Leu Phe Lys Asn Ser Phe Val Val Glu Arg
305                 310                 315                 320

Gln Pro Cys Met Pro Thr His Pro Gln Arg Pro Leu Val Leu Lys Thr
                325                 330                 335

Leu Ile Gln Phe Thr Val Lys Leu Arg Leu Leu Ile Lys Leu Pro Glu
            340                 345                 350

Leu Asn Tyr Gln Val Lys Val Lys Ala Ser Ile Asp Lys Asn Val Ser
            355                 360                 365

Thr Leu Ser Asn Arg Arg Phe Val Leu Cys Gly Thr Asn Val Lys Ala
    370                 375                 380

Met Ser Ile Glu Glu Ser Ser Asn Gly Ser Leu Ser Val Glu Phe Arg
385                 390                 395                 400

His Leu Gln Pro Lys Glu Met Lys Ser Ser Ala Gly Gly Lys Gly Asn
                405                 410                 415

Glu Gly Cys His Met Val Thr Glu Glu Leu His Ser Ile Thr Phe Glu
            420                 425                 430

Thr Gln Ile Cys Leu Tyr Gly Leu Thr Ile Asp Leu Glu Thr Ser Ser
```

|   |   |   |   |   | 435 |   |   |   |   | 440 |   |   |   |   | 445 |   |
|---|---|---|---|---|---|---|---|---|---|---|---|---|---|---|---|---|

Leu Pro Val Val Met Ile Ser Asn Val Ser Gln Leu Pro Asn Ala Trp
     450                   455               460

Ala Ser Ile Ile Trp Tyr Asn Val Ser Thr Asn Asp Ser Gln Asn Leu
465                   470               475               480

Val Phe Asn Asn Pro Pro Ala Thr Leu Ser Gln Leu Leu Glu
             485               490               495

Val Met Ser Trp Gln Phe Ser Ser Tyr Val Gly Arg Gly Leu Asn Ser
     500                   505               510

Asp Gln Leu His Met Leu Ala Glu Lys Leu Thr Val Gln Ser Ser Tyr
        515               520               525

Ser Asp Gly His Leu Thr Trp Ala Lys Phe Cys Lys Glu His Leu Pro
530                   535               540

Gly Lys Ser Phe Thr Phe Trp Thr Trp Leu Glu Ala Ile Leu Asp Leu
545                   550               555               560

Ile Lys Lys His Ile Leu Pro Leu Trp Ile Asp Gly Tyr Val Met Gly
        565               570               575

Phe Val Ser Lys Glu Lys Glu Arg Leu Leu Leu Lys Asp Lys Met Pro
     580                   585               590

Gly Thr Phe Leu Leu Arg Phe Ser Glu Ser His Leu Gly Gly Ile Thr
        595               600               605

Phe Thr Trp Val Asp His Ser Glu Ser Gly Glu Val Arg Phe His Ser
     610                   615               620

Val Glu Pro Tyr Asn Lys Gly Arg Leu Ser Ala Leu Pro Phe Ala Asp
625                   630               635               640

Ile Leu Arg Asp Tyr Lys Val Ile Met Ala Glu Asn Ile Pro Glu Asn
            645             650               655

Pro Leu Lys Tyr Leu Tyr Pro Asp Ile Pro Lys Asp Lys Ala Phe Gly
        660               665               670

Lys His Tyr Ser Ser Gln Pro Cys Glu Val Ser Arg Pro Thr Glu Arg
        675               680               685

Gly Asp Lys Gly Tyr Val Pro Ser Val Phe Ile Pro Ile Ser Thr Ile
     690                   695               700

Arg Ser Asp Ser Thr Glu Pro His Ser Pro Ser Asp Leu Leu Pro Met
705                   710               715               720

Ser Pro Ser Val Tyr Ala Val Leu Arg Glu Asn Leu Ser Pro Thr Thr
            725             730               735

Ile Glu Thr Ala Met Lys Ser Pro Tyr Ser Ala Glu
        740               745

<210> SEQ ID NO 9
<211> LENGTH: 3046
<212> TYPE: DNA
<213> ORGANISM: Homo sapiens
<220> FEATURE:
<221> NAME/KEY: CDS
<222> LOCATION: (166)...(2709)

<400> SEQUENCE: 9

| | | |
|---|---|---|
| atcttatttt tcttttttggt ggtggtggtg gaagggggga ggtgctagca gggccagcct | 60 | |
| tgaactcgct ggacagagct acagacctat ggggcctgga agtgcccgct gagaaaggga | 120 | |
| gaagacagca gaggggttgc cgaggcaacc tccaagtccc agatc atg tct ctg tgg | 177 | |
|                                                                   Met Ser Leu Trp | | |
|                                                                                                 1 | | |
| ggt ctg gtc tcc aag atg ccc cca gaa aaa gtg cag cgg ctc tat gtc | 225 | |

```
Gly Leu Val Ser Lys Met Pro Pro Glu Lys Val Gln Arg Leu Tyr Val
 5              10                  15                  20 gac ttt ccc caa cac ctg cgg cat ctt ctg ggt gac tgg ctg gag agc         273
Asp Phe Pro Gln His Leu Arg His Leu Leu Gly Asp Trp Leu Glu Ser
             25                  30                  35 cag ccc tgg gag ttc ctg gtc ggc tcc gac gcc ttc tgc tgc aac ttg         321
Gln Pro Trp Glu Phe Leu Val Gly Ser Asp Ala Phe Cys Cys Asn Leu
             40                  45                  50 gct agt gcc cta ctt tca gac act gtc cag cac ctt cag gcc tcg gtg         369
Ala Ser Ala Leu Leu Ser Asp Thr Val Gln His Leu Gln Ala Ser Val
         55                  60                  65 gga gag cag ggg gag ggg agc acc atc ttg caa cac atc agc acc ctt         417
Gly Glu Gln Gly Glu Gly Ser Thr Ile Leu Gln His Ile Ser Thr Leu
 70                  75                  80 gag agc ata tat cag agg gac ccc ctg aag ctg gtg gcc act ttc aga         465
Glu Ser Ile Tyr Gln Arg Asp Pro Leu Lys Leu Val Ala Thr Phe Arg
 85                  90                  95                 100 caa ata ctt caa gga gag aaa aaa gct gtt atg gaa cag ttc cgc cac         513
Gln Ile Leu Gln Gly Glu Lys Lys Ala Val Met Glu Gln Phe Arg His
                105                 110                 115 ttg cca atg cct ttc cac tgg aag cag gaa gaa ctc aag ttt aag aca         561
Leu Pro Met Pro Phe His Trp Lys Gln Glu Glu Leu Lys Phe Lys Thr
            120                 125                 130 ggc ttg cgg agg ctg cag cac cga gta ggg gag atc cac ctt ctc cga         609
Gly Leu Arg Arg Leu Gln His Arg Val Gly Glu Ile His Leu Leu Arg
        135                 140                 145 gaa gcc ctg cag aag ggg gct gag gct ggc caa gtg tct ctg cac agc         657
Glu Ala Leu Gln Lys Gly Ala Glu Ala Gly Gln Val Ser Leu His Ser
150                 155                 160 ttg ata gaa act cct gct aat ggg act ggg cca agt gag gcc ctg gcc         705
Leu Ile Glu Thr Pro Ala Asn Gly Thr Gly Pro Ser Glu Ala Leu Ala
165                 170                 175                 180 atg cta ctg cag gag acc act gga gag cta gag gca gcc aaa gcc cta         753
Met Leu Leu Gln Glu Thr Thr Gly Glu Leu Glu Ala Ala Lys Ala Leu
            185                 190                 195 gtg ctg aag agg atc cag att tgg aaa cgg cag cag cag ctg gca ggg         801
Val Leu Lys Arg Ile Gln Ile Trp Lys Arg Gln Gln Gln Leu Ala Gly
        200                 205                 210 aat ggc gca ccg ttt gag gag agc ctg gcc cca ctc cag gag agg tgt         849
Asn Gly Ala Pro Phe Glu Glu Ser Leu Ala Pro Leu Gln Glu Arg Cys
    215                 220                 225 gaa agc ctg gtg gac att tat tcc cag cta cag cag gag gta ggg gcg         897
Glu Ser Leu Val Asp Ile Tyr Ser Gln Leu Gln Gln Glu Val Gly Ala
230                 235                 240 gct ggt ggg gag ctt gag ccc aag acc cgg gca tcg ctg act ggc cgg         945
Ala Gly Gly Glu Leu Glu Pro Lys Thr Arg Ala Ser Leu Thr Gly Arg
245                 250                 255                 260 ctg gat gaa gtc ctg aga acc ctc gtc acc agt tgc ttc ctg gtg gag         993
Leu Asp Glu Val Leu Arg Thr Leu Val Thr Ser Cys Phe Leu Val Glu
            265                 270                 275 aag cag ccc ccc cag gta ctg aag act cag acc aag ttc cag gct gga        1041
Lys Gln Pro Pro Gln Val Leu Lys Thr Gln Thr Lys Phe Gln Ala Gly
        280                 285                 290 gtt cga ttc ctg ttg ggc ttg agg ttc ctg ggg gcc cca gcc aag cct        1089
Val Arg Phe Leu Leu Gly Leu Arg Phe Leu Gly Ala Pro Ala Lys Pro
    295                 300                 305 ccg ctg gtc agg gcc gac atg gtg aca gag aag cag gcg cgg gag ctg        1137
Pro Leu Val Arg Ala Asp Met Val Thr Glu Lys Gln Ala Arg Glu Leu
310                 315                 320
```

```
                                                    -continued agt gtg cct cag ggt cct ggg gct gga gca gaa agc act gga gaa atc        1185
Ser Val Pro Gln Gly Pro Gly Ala Gly Ala Glu Ser Thr Gly Glu Ile
325             330                 335                 340 atc aac aac act gtg ccc ttg gag aac agc att cct ggg aac tgc tgc        1233
Ile Asn Asn Thr Val Pro Leu Glu Asn Ser Ile Pro Gly Asn Cys Cys
                345                 350                 355 tct gcc ctg ttc aag aac ctg ctt ctc aag aag atc aag cgg tgt gag        1281
Ser Ala Leu Phe Lys Asn Leu Leu Leu Lys Lys Ile Lys Arg Cys Glu
            360                 365                 370 cgg aag ggc act gag tct gtc aca gag gag aag tgc gct gtg ctc ttc        1329
Arg Lys Gly Thr Glu Ser Val Thr Glu Glu Lys Cys Ala Val Leu Phe
        375                 380                 385 tct gcc agc ttc aca ctt ggc ccc ggc aaa ctc ccc atc cag ctc cag        1377
Ser Ala Ser Phe Thr Leu Gly Pro Gly Lys Leu Pro Ile Gln Leu Gln
    390                 395                 400 gcc ctg tct ctg ccc ctg gtg gtc atc gtc cat ggc aac caa gac aac        1425
Ala Leu Ser Leu Pro Leu Val Val Ile Val His Gly Asn Gln Asp Asn
405                 410                 415                 420 aat gcc aaa gcc act atc ctg tgg gac aat gcc ttc tct gag atg gac        1473
Asn Ala Lys Ala Thr Ile Leu Trp Asp Asn Ala Phe Ser Glu Met Asp
                425                 430                 435 cgc gtg ccc ttt gtg gtg gct gag cgg gtg ccc tgg gag aag atg tgt        1521
Arg Val Pro Phe Val Val Ala Glu Arg Val Pro Trp Glu Lys Met Cys
                440                 445                 450 gaa act ctg aac ctg aag ttc atg gct gag gtg ggg acc aac cgg ggg        1569
Glu Thr Leu Asn Leu Lys Phe Met Ala Glu Val Gly Thr Asn Arg Gly
            455                 460                 465 ctg ctc cca gag cac ttc ctc ttc ctg gcc cag aag atc ttc aat gac        1617
Leu Leu Pro Glu His Phe Leu Phe Leu Ala Gln Lys Ile Phe Asn Asp
        470                 475                 480 aac agc ctc agt atg gag gcc ttc cag cac cgt tct gtg tcc tgg tcg        1665
Asn Ser Leu Ser Met Glu Ala Phe Gln His Arg Ser Val Ser Trp Ser
485                 490                 495                 500 cag ttc aac aag gag atc ctg ctg ggc cgt ggc ttc acc ttt tgg cag        1713
Gln Phe Asn Lys Glu Ile Leu Leu Gly Arg Gly Phe Thr Phe Trp Gln
                505                 510                 515 tgg ttt gat ggt gtc ctg gac ctc acc aaa cgc tgt ctc cgg agc tac        1761
Trp Phe Asp Gly Val Leu Asp Leu Thr Lys Arg Cys Leu Arg Ser Tyr
                520                 525                 530 tgg tct gac cgg ctg atc att ggc ttc atc agc aaa cag tac gtt act        1809
Trp Ser Asp Arg Leu Ile Ile Gly Phe Ile Ser Lys Gln Tyr Val Thr
            535                 540                 545 agc ctt ctt ctc aat gag ccc gac gga acc ttt ctc ctc cgc ttc agc        1857
Ser Leu Leu Leu Asn Glu Pro Asp Gly Thr Phe Leu Leu Arg Phe Ser
        550                 555                 560 gac tca gag att ggg ggc atc acc att gcc cat gtc atc cgg ggc cag        1905
Asp Ser Glu Ile Gly Gly Ile Thr Ile Ala His Val Ile Arg Gly Gln
565                 570                 575                 580 gat ggc tct cca cag ata gag aac atc cag cca ttc tct gcc aaa gac        1953
Asp Gly Ser Pro Gln Ile Glu Asn Ile Gln Pro Phe Ser Ala Lys Asp
                585                 590                 595 ctg tcc att cgc tca ctg ggg gac cga atc cgg gat ctt gct cag ctc        2001
Leu Ser Ile Arg Ser Leu Gly Asp Arg Ile Arg Asp Leu Ala Gln Leu
            600                 605                 610 aaa aat ctc tat ccc aag aag ccc aag gat gag gct ttc cgg agc cac        2049
Lys Asn Leu Tyr Pro Lys Lys Pro Lys Asp Glu Ala Phe Arg Ser His
        615                 620                 625 tac aag cct gaa cag atg ggt aag gat ggc agg ggt tat gtc cca gct        2097
Tyr Lys Pro Glu Gln Met Gly Lys Asp Gly Arg Gly Tyr Val Pro Ala
630                 635                 640
```

```
acc atc aag atg acc gtg gaa agg gac caa cca ctt cct acc cca gag     2145
Thr Ile Lys Met Thr Val Glu Arg Asp Gln Pro Leu Pro Thr Pro Glu
645                 650                 655                 660 ctc cag atg cct acc atg gtg cct tct tat gac ctt gga atg gcc cct     2193
Leu Gln Met Pro Thr Met Val Pro Ser Tyr Asp Leu Gly Met Ala Pro
                665                 670                 675 gat tcc tcc atg agc atg cag ctt ggc cca gat atg gtg ccc cag gtg     2241
Asp Ser Ser Met Ser Met Gln Leu Gly Pro Asp Met Val Pro Gln Val
            680                 685                 690 tac cca cca cac tct cac tcc atc ccc ccg tat caa ggc ctc tcc cca     2289
Tyr Pro Pro His Ser His Ser Ile Pro Pro Tyr Gln Gly Leu Ser Pro
        695                 700                 705 gaa gaa tca gtc aac gtg ttg tca gcc ttc cag gag cct cac ctg cag     2337
Glu Glu Ser Val Asn Val Leu Ser Ala Phe Gln Glu Pro His Leu Gln
    710                 715                 720 atg ccc ccc agc ctg ggc cag atg agc ctg ccc ttt gac cag cct cac     2385
Met Pro Pro Ser Leu Gly Gln Met Ser Leu Pro Phe Asp Gln Pro His
725                 730                 735                 740 ccc cag ggc ctg ctg ccg tgc cag cct cag gag cat gct gtg tcc agc     2433
Pro Gln Gly Leu Leu Pro Cys Gln Pro Gln Glu His Ala Val Ser Ser
                745                 750                 755 cct gac ccc ctg ctc tgc tca gat gtg acc atg gtg gaa gac agc tgc     2481
Pro Asp Pro Leu Leu Cys Ser Asp Val Thr Met Val Glu Asp Ser Cys
            760                 765                 770 ctg agc cag cca gtg aca gcg ttt cct cag ggc act tgg att ggt gaa     2529
Leu Ser Gln Pro Val Thr Ala Phe Pro Gln Gly Thr Trp Ile Gly Glu
        775                 780                 785 gac ata ttc cct cct ctg ctg cct ccc act gaa cag gac ctc act aag     2577
Asp Ile Phe Pro Pro Leu Leu Pro Pro Thr Glu Gln Asp Leu Thr Lys
    790                 795                 800 ctt ctc ctg gag ggg caa ggg gag tcg ggg gga ggg tcc ttg ggg gca     2625
Leu Leu Leu Glu Gly Gln Gly Glu Ser Gly Gly Gly Ser Leu Gly Ala
805                 810                 815                 820 cag ccc ctc ctg cag ccc tcc cac tat ggg caa tct ggg atc tca atg     2673
Gln Pro Leu Leu Gln Pro Ser His Tyr Gly Gln Ser Gly Ile Ser Met
                825                 830                 835 tcc cac atg gac cta agg gcc aac ccc agt tgg tga tcccagctgg          2719
Ser His Met Asp Leu Arg Ala Asn Pro Ser Trp *
            840                 845 agggagaacc caaagagaca gctcttctac taccccacac gacctgctct ggacacttgc   2779
tcatgccctg ccaagcagca gatggggagg gtgccctcct atccccacct actcctgggt   2839
caggaggaaa agactaacag gagaatgcac agtgggtgga gccaatccac tccttccttt   2899
ctatcattcc cctgcccacc tccttccagc actgactgga agggaagttc aggctctgag   2959
acacgcccca acatgcctgc acctgcagcg cgcacacgca cgcacacaca catacagagc   3019
tctctgaggg tgatggggct gagcagg                                       3046

<210> SEQ ID NO 10
<211> LENGTH: 847
<212> TYPE: PRT
<213> ORGANISM: Homo sapiens

<400> SEQUENCE: 10

Met Ser Leu Trp Gly Leu Val Ser Lys Met Pro Pro Glu Lys Val Gln
1               5                   10                  15

Arg Leu Tyr Val Asp Phe Pro Gln His Leu Arg His Leu Leu Gly Asp
            20                  25                  30
```

-continued

```
Trp Leu Glu Ser Gln Pro Trp Glu Phe Leu Val Gly Ser Asp Ala Phe
     35                  40                  45

Cys Cys Asn Leu Ala Ser Ala Leu Leu Ser Asp Thr Val Gln His Leu
 50                  55                  60

Gln Ala Ser Val Gly Glu Gln Gly Glu Gly Ser Thr Ile Leu Gln His
 65                  70                  75                  80

Ile Ser Thr Leu Glu Ser Ile Tyr Gln Arg Asp Pro Leu Lys Leu Val
                 85                  90                  95

Ala Thr Phe Arg Gln Ile Leu Gln Gly Glu Lys Lys Ala Val Met Glu
                100                 105                 110

Gln Phe Arg His Leu Pro Met Pro Phe His Trp Lys Gln Glu Glu Leu
            115                 120                 125

Lys Phe Lys Thr Gly Leu Arg Arg Leu Gln His Arg Val Gly Glu Ile
    130                 135                 140

His Leu Leu Arg Glu Ala Leu Gln Lys Gly Ala Glu Ala Gly Gln Val
145                 150                 155                 160

Ser Leu His Ser Leu Ile Glu Thr Pro Ala Asn Gly Thr Gly Pro Ser
                165                 170                 175

Glu Ala Leu Ala Met Leu Leu Gln Glu Thr Thr Gly Glu Leu Glu Ala
                180                 185                 190

Ala Lys Ala Leu Val Leu Lys Arg Ile Gln Ile Trp Lys Arg Gln Gln
            195                 200                 205

Gln Leu Ala Gly Asn Gly Ala Pro Phe Glu Glu Ser Leu Ala Pro Leu
    210                 215                 220

Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Ser
                245                 250                 255

Leu Thr Gly Arg Leu Asp Glu Val Leu Arg Thr Leu Val Thr Ser Cys
                260                 265                 270

Phe Leu Val Glu Lys Gln Pro Pro Gln Val Leu Lys Thr Gln Thr Lys
            275                 280                 285

Phe Gln Ala Gly Val Arg Phe Leu Leu Gly Leu Arg Phe Leu Gly Ala
    290                 295                 300

Pro Ala Lys Pro Pro Leu Val Arg Ala Asp Met Val Thr Glu Lys Gln
305                 310                 315                 320

Ala Arg Glu Leu Ser Val Pro Gln Gly Pro Gly Ala Gly Ala Glu Ser
                325                 330                 335

Thr Gly Glu Ile Ile Asn Asn Thr Val Pro Leu Glu Asn Ser Ile Pro
            340                 345                 350

Gly Asn Cys Cys Ser Ala Leu Phe Lys Asn Leu Leu Leu Lys Lys Ile
    355                 360                 365

Lys Arg Cys Glu Arg Lys Gly Thr Glu Ser Val Thr Glu Glu Lys Cys
    370                 375                 380

Ala Val Leu Phe Ser Ala Ser Phe Thr Leu Gly Pro Gly Lys Leu Pro
385                 390                 395                 400

Ile Gln Leu Gln Ala Leu Ser Leu Pro Leu Val Val Ile Val His Gly
                405                 410                 415

Asn Gln Asp Asn Asn Ala Lys Ala Thr Ile Leu Trp Asp Asn Ala Phe
            420                 425                 430

Ser Glu Met Asp Arg Val Pro Phe Val Val Ala Glu Arg Val Pro Trp
    435                 440                 445

Glu Lys Met Cys Glu Thr Leu Asn Leu Lys Phe Met Ala Glu Val Gly
```

```
             450                 455                 460
    Thr Asn Arg Gly Leu Leu Pro Glu His Phe Leu Phe Leu Ala Gln Lys
    465                 470                 475                 480
    Ile Phe Asn Asp Asn Ser Leu Ser Met Glu Ala Phe Gln His Arg Ser
                        485                 490                 495
    Val Ser Trp Ser Gln Phe Asn Lys Glu Ile Leu Leu Gly Arg Gly Phe
                    500                 505                 510
    Thr Phe Trp Gln Trp Phe Asp Gly Val Leu Asp Leu Thr Lys Arg Cys
                515                 520                 525
    Leu Arg Ser Tyr Trp Ser Asp Arg Leu Ile Ile Gly Phe Ile Ser Lys
    530                 535                 540
    Gln Tyr Val Thr Ser Leu Leu Asn Glu Pro Asp Gly Thr Phe Leu
    545                 550                 555                 560
    Leu Arg Phe Ser Asp Ser Glu Ile Gly Gly Ile Thr Ile Ala His Val
                        565                 570                 575
    Ile Arg Gly Gln Asp Gly Ser Pro Gln Ile Glu Asn Ile Gln Pro Phe
                    580                 585                 590
    Ser Ala Lys Asp Leu Ser Ile Arg Ser Leu Gly Asp Arg Ile Arg Asp
                595                 600                 605
    Leu Ala Gln Leu Lys Asn Leu Tyr Pro Lys Lys Pro Lys Asp Glu Ala
    610                 615                 620
    Phe Arg Ser His Tyr Lys Pro Glu Gln Met Gly Lys Asp Gly Arg Gly
    625                 630                 635                 640
    Tyr Val Pro Ala Thr Ile Lys Met Thr Val Glu Arg Asp Gln Pro Leu
                        645                 650                 655
    Pro Thr Pro Glu Leu Gln Met Pro Thr Met Val Pro Ser Tyr Asp Leu
                    660                 665                 670
    Gly Met Ala Pro Asp Ser Ser Met Ser Met Gln Leu Gly Pro Asp Met
                675                 680                 685
    Val Pro Gln Val Tyr Pro Pro His Ser His Ser Ile Pro Pro Tyr Gln
    690                 695                 700
    Gly Leu Ser Pro Glu Glu Ser Val Asn Val Leu Ser Ala Phe Gln Glu
    705                 710                 715                 720
    Pro His Leu Gln Met Pro Pro Ser Leu Gly Gln Met Ser Leu Pro Phe
                        725                 730                 735
    Asp Gln Pro His Pro Gln Gly Leu Leu Pro Cys Gln Pro Gln Glu His
                    740                 745                 750
    Ala Val Ser Ser Pro Asp Pro Leu Leu Cys Ser Asp Val Thr Met Val
                755                 760                 765
    Glu Asp Ser Cys Leu Ser Gln Pro Val Thr Ala Phe Pro Gln Gly Thr
    770                 775                 780
    Trp Ile Gly Glu Asp Ile Phe Pro Pro Leu Leu Pro Pro Thr Glu Gln
    785                 790                 795                 800
    Asp Leu Thr Lys Leu Leu Leu Glu Gly Gln Gly Glu Ser Gly Gly Gly
                        805                 810                 815
    Ser Leu Gly Ala Gln Pro Leu Leu Gln Pro Ser His Tyr Gly Gln Ser
                    820                 825                 830
    Gly Ile Ser Met Ser His Met Asp Leu Arg Ala Asn Pro Ser Trp
                835                 840                 845

<210> SEQ ID NO 11
    <211> LENGTH: 908
    <212> TYPE: DNA
    <213> ORGANISM: Homo sapiens
```

```
<220> FEATURE:
<221> NAME/KEY: CDS
<222> LOCATION: (14)...(649)

<400> SEQUENCE: 11
ccccttctgt agg atg gta gca cac aac cag gtg gca gcc gac aat gca        49
            Met Val Ala His Asn Gln Val Ala Ala Asp Asn Ala
            1               5                  10 gtc tcc aca gca gca gag ccc cga cgg cgg cca gaa cct tcc tcc tct        97
Val Ser Thr Ala Ala Glu Pro Arg Arg Arg Pro Glu Pro Ser Ser Ser
        15                  20                  25 tcc tcc tcc tcg ccc gcg gcc ccc gcg cgc ccg cgg ccg tgc ccc gcg       145
Ser Ser Ser Ser Pro Ala Ala Pro Ala Arg Pro Arg Pro Cys Pro Ala
        30                  35                  40 gtc ccg gcc ccg gcc ccc ggc gac acg cac ttc cgc aca ttc cgt tcg       193
Val Pro Ala Pro Ala Pro Gly Asp Thr His Phe Arg Thr Phe Arg Ser
45                  50                  55                  60 cac gcc gat tac cgg cgc atc acg cgc gcc agc gcg ctc ctg gac gcc       241
His Ala Asp Tyr Arg Arg Ile Thr Arg Ala Ser Ala Leu Leu Asp Ala
                65                  70                  75 tgc gga ttc tac tgg ggg ccc ctg agc gtg cac ggg gcg cac gag cgg       289
Cys Gly Phe Tyr Trp Gly Pro Leu Ser Val His Gly Ala His Glu Arg
            80                  85                  90 ctg cgc gcc gag ccc gtg ggc acc ttc ctg gtg cgc gac agc cgc cag       337
Leu Arg Ala Glu Pro Val Gly Thr Phe Leu Val Arg Asp Ser Arg Gln
        95                  100                 105 cgg aac tgc ttt ttc gcc ctt agc gtg aag atg gcc tcg gga ccc acg       385
Arg Asn Cys Phe Phe Ala Leu Ser Val Lys Met Ala Ser Gly Pro Thr
    110                 115                 120 agc atc cgc gtg cac ttt cag gcc ggc cgc ttt cac ctg gat ggc agc       433
Ser Ile Arg Val His Phe Gln Ala Gly Arg Phe His Leu Asp Gly Ser
125                 130                 135                 140 cgc gag agc ttc gac tgc ctc ttc gag ctg ctg gag cac tac gtg gcg       481
Arg Glu Ser Phe Asp Cys Leu Phe Glu Leu Leu Glu His Tyr Val Ala
                145                 150                 155 gcg ccg cgc cgc atg ctg ggg gcc ccg ctg cgc cag cgc cgc gtg cgg       529
Ala Pro Arg Arg Met Leu Gly Ala Pro Leu Arg Gln Arg Arg Val Arg
            160                 165                 170 ccg ctg cag gag ctg tgc cgc cag cgc atc gtg gcc acc gtg ggc cgc       577
Pro Leu Gln Glu Leu Cys Arg Gln Arg Ile Val Ala Thr Val Gly Arg
        175                 180                 185 gag aac ctg gct cgc atc ccc ctc aac ccc gtc ctc cgc gac tac ctg       625
Glu Asn Leu Ala Arg Ile Pro Leu Asn Pro Val Leu Arg Asp Tyr Leu
    190                 195                 200 agc tcc ttc ccc ttc cag att tga ccggcagcgc ccgccgtgca cgcagcatta     679
Ser Ser Phe Pro Phe Gln Ile *
205                 210 actgggatgc cgtgttattt tgttattact tgcctggaac catgtgggta ccctccccgg    739
cctgggttgg agggagcgga tgggtgtagg ggcgaggcgc ctcccgccct cggctggaga    799
cgaggccgca gacccttct cacctcttga gggggtcctc cccctcctgg tgctccctct     859
gggtccccct ggttgttgta gcagcttaac tgtatctgga gccaggacc                908

<210> SEQ ID NO 12
<211> LENGTH: 211
<212> TYPE: PRT
<213> ORGANISM: Homo sapiens

<400> SEQUENCE: 12

Met Val Ala His Asn Gln Val Ala Ala Asp Asn Ala Val Ser Thr Ala
```

```
  1               5                   10                  15
Ala Glu Pro Arg Arg Pro Glu Pro Ser Ser Ser Ser Ser Ser
                 20                  25                  30

Pro Ala Ala Pro Ala Arg Pro Arg Pro Cys Pro Ala Val Pro Ala Pro
             35                  40                  45

Ala Pro Gly Asp Thr His Phe Arg Thr Phe Arg Ser His Ala Asp Tyr
         50                  55                  60

Arg Arg Ile Thr Arg Ala Ser Ala Leu Leu Asp Ala Cys Gly Phe Tyr
 65                  70                  75                  80

Trp Gly Pro Leu Ser Val His Gly Ala His Glu Arg Leu Arg Ala Glu
                 85                  90                  95

Pro Val Gly Thr Phe Leu Val Arg Asp Ser Arg Gln Arg Asn Cys Phe
            100                 105                 110

Phe Ala Leu Ser Val Lys Met Ala Ser Gly Pro Thr Ser Ile Arg Val
            115                 120                 125

His Phe Gln Ala Gly Arg Phe His Leu Asp Gly Ser Arg Glu Ser Phe
            130                 135                 140

Asp Cys Leu Phe Glu Leu Leu Glu His Tyr Val Ala Ala Pro Arg Arg
145                 150                 155                 160

Met Leu Gly Ala Pro Leu Arg Gln Arg Val Arg Pro Leu Gln Glu
                165                 170                 175

Leu Cys Arg Gln Arg Ile Val Ala Thr Val Gly Arg Glu Asn Leu Ala
                180                 185                 190

Arg Ile Pro Leu Asn Pro Val Leu Arg Asp Tyr Leu Ser Ser Phe Pro
            195                 200                 205

Phe Gln Ile
        210

<210> SEQ ID NO 13
<211> LENGTH: 682
<212> TYPE: DNA
<213> ORGANISM: Homo sapiens
<220> FEATURE:
<221> NAME/KEY: CDS
<222> LOCATION: (1)...(678)

<400> SEQUENCE: 13 atg gtc acc cac agc aag ttt ccc gcc gcc ggg atg agc cgc ccc ctg      48
Met Val Thr His Ser Lys Phe Pro Ala Ala Gly Met Ser Arg Pro Leu
 1               5                  10                  15 gac acc agc ctg cgc ctc aag acc ttc agc tcc aag agc gag tac cag      96
Asp Thr Ser Leu Arg Leu Lys Thr Phe Ser Ser Lys Ser Glu Tyr Gln
             20                  25                  30 ctg gtg gtg aac gca gtg cgc aag ctg cag gag agc ggc ttc tac tgg     144
Leu Val Val Asn Ala Val Arg Lys Leu Gln Glu Ser Gly Phe Tyr Trp
         35                  40                  45 agc gca gtg acc ggc ggc gag gcg aac ctg ctg ctc agc gcc gag ccc     192
Ser Ala Val Thr Gly Gly Glu Ala Asn Leu Leu Leu Ser Ala Glu Pro
     50                  55                  60 gcc ggc acc ttt ctg atc cgc gac agc tcg gac cag cgc cac ttc ttc     240
Ala Gly Thr Phe Leu Ile Arg Asp Ser Ser Asp Gln Arg His Phe Phe
 65                  70                  75                  80 acg ctc agc gtc aag acc cag tct ggg acc aag aac ctg cgc atc cag     288
Thr Leu Ser Val Lys Thr Gln Ser Gly Thr Lys Asn Leu Arg Ile Gln
             85                  90                  95 tgt gag ggg ggc agc ttc tct ctg cag agc gat ccc cgg agc acg cag     336
Cys Glu Gly Gly Ser Phe Ser Leu Gln Ser Asp Pro Arg Ser Thr Gln
            100                 105                 110
```

-continued

```
ccc gtg ccc cgc ttc gac tgc gtg ctc aag ctg gtg cac cac tac atg    384
Pro Val Pro Arg Phe Asp Cys Val Leu Lys Leu Val His His Tyr Met
        115                 120                 125 ccg ccc cct gga gcc ccc tcc ttc ccc tcg cca cct act gaa ccc tcc    432
Pro Pro Pro Gly Ala Pro Ser Phe Pro Ser Pro Thr Glu Pro Ser
    130                 135                 140 tcc gag gtg ccc gag cag ccg tct gcc cag cca ctc cct ggg agt ccc    480
Ser Glu Val Pro Glu Gln Pro Ser Ala Gln Pro Leu Pro Gly Ser Pro
145                 150                 155                 160 ccc aga aga gcc tat tac atc tac tcc ggg ggc gag aag atc ccc ctg    528
Pro Arg Arg Ala Tyr Tyr Ile Tyr Ser Gly Gly Glu Lys Ile Pro Leu
                165                 170                 175 gtg ttg agc cgg ccc ctc tcc tcc aac gtg gcc act ctt cag cat ctc    576
Val Leu Ser Arg Pro Leu Ser Ser Asn Val Ala Thr Leu Gln His Leu
            180                 185                 190 tgt cgg aag acc gtc aac ggc cac ctg gac tcc tat gag aaa gtc acc    624
Cys Arg Lys Thr Val Asn Gly His Leu Asp Ser Tyr Glu Lys Val Thr
        195                 200                 205 cag ctg ccg ggg ccc att cgg gag ttc ctg gac cag tac gat gcc ccg    672
Gln Leu Pro Gly Pro Ile Arg Glu Phe Leu Asp Gln Tyr Asp Ala Pro
    210                 215                 220 ctt taa gggg                                                       682
Leu *
225

<210> SEQ ID NO 14
<211> LENGTH: 225
<212> TYPE: PRT
<213> ORGANISM: Homo sapiens

<400> SEQUENCE: 14

Met Val Thr His Ser Lys Phe Pro Ala Ala Gly Met Ser Arg Pro Leu
 1               5                  10                  15

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
        35                  40                  45

Ser Ala Val Thr Gly Gly Glu Ala Asn Leu Leu Leu Ser Ala Glu Pro
    50                  55                  60

Ala Gly Thr Phe Leu Ile Arg Asp Ser Ser Asp Gln Arg His Phe Phe
65                  70                  75                  80

Thr Leu Ser Val Lys Thr Gln Ser Gly Thr Lys Asn Leu Arg Ile Gln
                85                  90                  95

Cys Glu Gly Gly Ser Phe Ser Leu Gln Ser Asp Pro Arg Ser Thr Gln
            100                 105                 110

Pro Val Pro Arg Phe Asp Cys Val Leu Lys Leu Val His His Tyr Met
        115                 120                 125

Pro Pro Pro Gly Ala Pro Ser Phe Pro Ser Pro Thr Glu Pro Ser
    130                 135                 140

Ser Glu Val Pro Glu Gln Pro Ser Ala Gln Pro Leu Pro Gly Ser Pro
145                 150                 155                 160

Pro Arg Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
        195                 200                 205
```

```
Gln Leu Pro Gly Pro Ile Arg Glu Phe Leu Asp Gln Tyr Asp Ala Pro
    210                 215                 220

Leu
225

<210> SEQ ID NO 15
<211> LENGTH: 5117
<212> TYPE: DNA
<213> ORGANISM: Homo sapiens
<220> FEATURE:
<221> NAME/KEY: CDS
<222> LOCATION: (478)...(3876)

<400> SEQUENCE: 15
aattcggcac gagggggggc agcagcggac gccgctaacg gcctccctcg gcgctgacag      60
gctgggccgg cgcccggctc gcttgggtgt tcgcgtcgcc acttcggctt ctcggccggt     120
cgggcccctc ggcccgggct tgcggcgcgc gtcgggggctg agggctgctg cggcgcaggg    180
agaggcctgg tcctcgctgc cgagggatgt gagtgggagc tgagcccaca ctggagggcc     240
cccgagggcc cagcctggag gtcgttcaga gccgtgcccg ccccggggct tcgcagacct     300
tgacccgccg ggtaggagcc gcccctgcgg gctcgagggc gcgctctggt cgcccgatct     360
gtgtagccgg tttcagaagc aggcaacagg aacaagatgt gaactgtttc tcttctgcag     420 aaaagaggc tcttcctcct cctcccgcga cggcaaatgt tctgaaaaag actctgc atg     480
                                                             Met
                                                              1 gga atg gcc tgc ctt acg atg aca gaa atg gag gga aca tcc acc tct     528
Gly Met Ala Cys Leu Thr Met Thr Glu Met Glu Gly Thr Ser Thr Ser
          5                  10                  15 tct ata tat cag aat ggt gat att tct gga aat gcc aat tct atg aag     576
Ser Ile Tyr Gln Asn Gly Asp Ile Ser Gly Asn Ala Asn Ser Met Lys
         20                  25                  30 caa ata gat cca gtt ctt cag gtg tat ctt tac cat tcc ctt ggg aaa     624
Gln Ile Asp Pro Val Leu Gln Val Tyr Leu Tyr His Ser Leu Gly Lys
     35                  40                  45 tct gag gca gat tat ctg acc ttt cca tct ggg gag tat gtt gca gaa     672
Ser Glu Ala Asp Tyr Leu Thr Phe Pro Ser Gly Glu Tyr Val Ala Glu
 50                  55                  60                  65 gaa atc tgt att gct gct tct aaa gct tgt ggt atc aca cct gtg tat     720
Glu Ile Cys Ile Ala Ala Ser Lys Ala Cys Gly Ile Thr Pro Val Tyr
                  70                  75                  80 cat aat atg ttt gct tta atg agt gaa aca gaa agg atc tgg tat cca     768
His Asn Met Phe Ala Leu Met Ser Glu Thr Glu Arg Ile Trp Tyr Pro
              85                  90                  95 ccc aac cat gtc ttc cat ata gat gag tca acc agg cat aat gta ctc     816
Pro Asn His Val Phe His Ile Asp Glu Ser Thr Arg His Asn Val Leu
            100                 105                 110 tac aga ata aga ttt tac ttt cct cgt tgg tat tgc agt ggc agc aac     864
Tyr Arg Ile Arg Phe Tyr Phe Pro Arg Trp Tyr Cys Ser Gly Ser Asn
        115                 120                 125 aga gcc tat cgg cat gga ata tct cga ggt gct gaa gct cct ctt ctt     912
Arg Ala Tyr Arg His Gly Ile Ser Arg Gly Ala Glu Ala Pro Leu Leu
130                 135                 140                 145 gat gac ttt gtc atg tct tac ctc ttt gct cag tgg cgg cat gat ttt     960
Asp Asp Phe Val Met Ser Tyr Leu Phe Ala Gln Trp Arg His Asp Phe
                150                 155                 160 gtg cac gga tgg ata aaa gta cct gtg act cat gaa aca cag gaa gaa    1008
Val His Gly Trp Ile Lys Val Pro Val Thr His Glu Thr Gln Glu Glu
            165                 170                 175
```

```
tgt ctt ggg atg gca gtg tta gat atg atg aga ata gcc aaa gaa aac    1056
Cys Leu Gly Met Ala Val Leu Asp Met Met Arg Ile Ala Lys Glu Asn
        180                 185                 190 gat caa acc cca ctg gcc atc tat aac tct atc agc tac aag aca ttc    1104
Asp Gln Thr Pro Leu Ala Ile Tyr Asn Ser Ile Ser Tyr Lys Thr Phe
    195                 200                 205 tta cca aaa tgt att cga gca aag atc caa gac tat cat att ttg aca    1152
Leu Pro Lys Cys Ile Arg Ala Lys Ile Gln Asp Tyr His Ile Leu Thr
210                 215                 220                 225 agg aag cga ata agg tac aga ttt cgc aga ttt att cag caa ttc agc    1200
Arg Lys Arg Ile Arg Tyr Arg Phe Arg Arg Phe Ile Gln Gln Phe Ser
                230                 235                 240 caa tgc aaa gcc act gcc aga aac ttg aaa ctt aag tat ctt ata aat    1248
Gln Cys Lys Ala Thr Ala Arg Asn Leu Lys Leu Lys Tyr Leu Ile Asn
            245                 250                 255 ctg gaa act ctg cag tct gcc ttc tac aca gag aaa ttt gaa gta aaa    1296
Leu Glu Thr Leu Gln Ser Ala Phe Tyr Thr Glu Lys Phe Glu Val Lys
        260                 265                 270 gaa cct gga agt ggt cct tca ggt gag gag att ttt gca acc att ata    1344
Glu Pro Gly Ser Gly Pro Ser Gly Glu Glu Ile Phe Ala Thr Ile Ile
    275                 280                 285 ata act gga aac ggt gga att cag tgg tca aga ggg aaa cat aaa gaa    1392
Ile Thr Gly Asn Gly Gly Ile Gln Trp Ser Arg Gly Lys His Lys Glu
290                 295                 300                 305 agt gag aca ctg aca gaa cag gat tta cag tta tat tgc gat ttt tct    1440
Ser Glu Thr Leu Thr Glu Gln Asp Leu Gln Leu Tyr Cys Asp Phe Ser
                310                 315                 320 aat att att gat gtc agt att aag caa gca aac caa gag ggt tca aat    1488
Asn Ile Ile Asp Val Ser Ile Lys Gln Ala Asn Gln Glu Gly Ser Asn
            325                 330                 335 gaa agc cga gtt gta act atc cat aag caa gat ggt aaa aat ctg gaa    1536
Glu Ser Arg Val Val Thr Ile His Lys Gln Asp Gly Lys Asn Leu Glu
        340                 345                 350 att gaa ctt agc tca tta agg gaa gct ttg tct ttc gtg tca tta att    1584
Ile Glu Leu Ser Ser Leu Arg Glu Ala Leu Ser Phe Val Ser Leu Ile
    355                 360                 365 gat gga tat tat aga tta act gca gat gca cat cat tac ctc tgt aaa    1632
Asp Gly Tyr Tyr Arg Leu Thr Ala Asp Ala His His Tyr Leu Cys Lys
370                 375                 380                 385 gaa gta gca cct cca gcc gtg ctt gaa aat ata caa agc aac tgt cat    1680
Glu Val Ala Pro Pro Ala Val Leu Glu Asn Ile Gln Ser Asn Cys His
                390                 395                 400 ggc cca att tcg atg gat ttt gcc att agt aaa ctg aag aaa gca ggt    1728
Gly Pro Ile Ser Met Asp Phe Ala Ile Ser Lys Leu Lys Lys Ala Gly
            405                 410                 415 aat cag act gga ctg tat gta ctt cga tgc agt cct aag gac ttt aat    1776
Asn Gln Thr Gly Leu Tyr Val Leu Arg Cys Ser Pro Lys Asp Phe Asn
        420                 425                 430 aaa tat ttt ttg act ttt gct gtc gag cga gaa aat gtc att gaa tat    1824
Lys Tyr Phe Leu Thr Phe Ala Val Glu Arg Glu Asn Val Ile Glu Tyr
    435                 440                 445 aaa cac tgt ttg att aca aaa aat gag aat gaa gag tac aac ctc agt    1872
Lys His Cys Leu Ile Thr Lys Asn Glu Asn Glu Glu Tyr Asn Leu Ser
450                 455                 460                 465 ggg aca aag aag aac ttc agc agt ctt aaa gat ctt ttg aat tgt tac    1920
Gly Thr Lys Lys Asn Phe Ser Ser Leu Lys Asp Leu Leu Asn Cys Tyr
                470                 475                 480 cag atg gaa act gtt cgc tca gac aat ata att ttc cag ttt act aaa    1968
Gln Met Glu Thr Val Arg Ser Asp Asn Ile Ile Phe Gln Phe Thr Lys
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 485 |     |     |     | 490 |     |     |     | 495 |     |     |     |     |      |
| tgc | tgt | ccc | cca | aag | cca | aaa | gat | aaa | tca | aac | ctt | cta | gtc | ttc | aga | 2016 |
| Cys | Cys | Pro | Pro | Lys | Pro | Lys | Asp | Lys | Ser | Asn | Leu | Leu | Val | Phe | Arg |      |
|     |     | 500 |     |     |     | 505 |     |     |     |     | 510 |     |     |     |     |      |
| acg | aat | ggt | gtt | tct | gat | gta | cca | acc | tca | cca | aca | tta | cag | agg | cct | 2064 |
| Thr | Asn | Gly | Val | Ser | Asp | Val | Pro | Thr | Ser | Pro | Thr | Leu | Gln | Arg | Pro |      |
|     | 515 |     |     |     |     | 520 |     |     |     |     | 525 |     |     |     |     |      |
| act | cat | atg | aac | caa | atg | gtg | ttt | cac | aaa | atc | aga | aat | gaa | gat | ttg | 2112 |
| Thr | His | Met | Asn | Gln | Met | Val | Phe | His | Lys | Ile | Arg | Asn | Glu | Asp | Leu |      |
| 530 |     |     |     |     | 535 |     |     |     |     | 540 |     |     |     |     | 545 |      |
| ata | ttt | aat | gaa | agc | ctt | ggc | caa | ggc | act | ttt | aca | aag | att | ttt | aaa | 2160 |
| Ile | Phe | Asn | Glu | Ser | Leu | Gly | Gln | Gly | Thr | Phe | Thr | Lys | Ile | Phe | Lys |      |
|     |     |     |     | 550 |     |     |     |     | 555 |     |     |     |     | 560 |     |      |
| ggc | gta | cga | aga | gaa | gta | gga | gac | tac | ggt | caa | ctg | cat | gaa | aca | gaa | 2208 |
| Gly | Val | Arg | Arg | Glu | Val | Gly | Asp | Tyr | Gly | Gln | Leu | His | Glu | Thr | Glu |      |
|     |     |     | 565 |     |     |     | 570 |     |     |     |     | 575 |     |     |     |      |
| gtt | ctt | tta | aaa | gtt | ctg | gat | aaa | gca | cac | aga | aac | tat | tca | gag | tct | 2256 |
| Val | Leu | Leu | Lys | Val | Leu | Asp | Lys | Ala | His | Arg | Asn | Tyr | Ser | Glu | Ser |      |
|     |     | 580 |     |     |     |     | 585 |     |     |     |     | 590 |     |     |     |      |
| ttc | ttt | gaa | gca | gca | agt | atg | atg | agc | aag | ctt | tct | cac | aag | cat | ttg | 2304 |
| Phe | Phe | Glu | Ala | Ala | Ser | Met | Met | Ser | Lys | Leu | Ser | His | Lys | His | Leu |      |
|     | 595 |     |     |     |     | 600 |     |     |     |     | 605 |     |     |     |     |      |
| gtt | tta | aat | tat | gga | gta | tgt | gtc | tgt | gga | gac | gag | aat | att | ctg | gtt | 2352 |
| Val | Leu | Asn | Tyr | Gly | Val | Cys | Val | Cys | Gly | Asp | Glu | Asn | Ile | Leu | Val |      |
| 610 |     |     |     |     | 615 |     |     |     |     | 620 |     |     |     |     | 625 |      |
| cag | gag | ttt | gta | aaa | ttt | gga | tca | cta | gat | aca | tat | ctg | aaa | aag | aat | 2400 |
| Gln | Glu | Phe | Val | Lys | Phe | Gly | Ser | Leu | Asp | Thr | Tyr | Leu | Lys | Lys | Asn |      |
|     |     |     |     | 630 |     |     |     |     | 635 |     |     |     |     | 640 |     |      |
| aaa | aat | tgt | ata | aat | ata | tta | tgg | aaa | ctt | gaa | gtt | gct | aaa | cag | ttg | 2448 |
| Lys | Asn | Cys | Ile | Asn | Ile | Leu | Trp | Lys | Leu | Glu | Val | Ala | Lys | Gln | Leu |      |
|     |     |     | 645 |     |     |     | 650 |     |     |     |     | 655 |     |     |     |      |
| gca | tgg | gcc | atg | cat | ttt | cta | gaa | gaa | aac | acc | ctt | att | cat | ggg | aat | 2496 |
| Ala | Trp | Ala | Met | His | Phe | Leu | Glu | Glu | Asn | Thr | Leu | Ile | His | Gly | Asn |      |
|     |     |     | 660 |     |     |     |     | 665 |     |     |     |     | 670 |     |     |      |
| gta | tgt | gcc | aaa | aat | att | ctg | ctt | atc | aga | gaa | gaa | gac | agg | aag | aca | 2544 |
| Val | Cys | Ala | Lys | Asn | Ile | Leu | Leu | Ile | Arg | Glu | Glu | Asp | Arg | Lys | Thr |      |
|     | 675 |     |     |     |     | 680 |     |     |     |     | 685 |     |     |     |     |      |
| gga | aat | cct | cct | ttc | atc | aaa | ctt | agt | gat | cct | ggc | att | agt | att | aca | 2592 |
| Gly | Asn | Pro | Pro | Phe | Ile | Lys | Leu | Ser | Asp | Pro | Gly | Ile | Ser | Ile | Thr |      |
| 690 |     |     |     |     | 695 |     |     |     |     | 700 |     |     |     |     | 705 |      |
| gtt | ttg | cca | aag | gac | att | ctt | cag | gag | aga | ata | cca | tgg | gta | cca | cct | 2640 |
| Val | Leu | Pro | Lys | Asp | Ile | Leu | Gln | Glu | Arg | Ile | Pro | Trp | Val | Pro | Pro |      |
|     |     |     |     | 710 |     |     |     |     | 715 |     |     |     |     | 720 |     |      |
| gaa | tgc | att | gaa | aat | cct | aaa | aat | tta | aat | ttg | gca | aca | gac | aaa | tgg | 2688 |
| Glu | Cys | Ile | Glu | Asn | Pro | Lys | Asn | Leu | Asn | Leu | Ala | Thr | Asp | Lys | Trp |      |
|     |     |     | 725 |     |     |     |     | 730 |     |     |     |     | 735 |     |     |      |
| agt | ttt | ggt | acc | act | ttg | tgg | gaa | atc | tgc | agt | gga | gga | gat | aaa | cct | 2736 |
| Ser | Phe | Gly | Thr | Thr | Leu | Trp | Glu | Ile | Cys | Ser | Gly | Gly | Asp | Lys | Pro |      |
|     |     |     | 740 |     |     |     |     | 745 |     |     |     |     | 750 |     |     |      |
| cta | agt | gct | ctg | gat | tct | caa | aga | aag | cta | caa | ttt | tat | gaa | gat | agg | 2784 |
| Leu | Ser | Ala | Leu | Asp | Ser | Gln | Arg | Lys | Leu | Gln | Phe | Tyr | Glu | Asp | Arg |      |
|     | 755 |     |     |     |     | 760 |     |     |     |     | 765 |     |     |     |     |      |
| cat | cag | ctt | cct | gca | cca | aag | tgg | gca | gaa | tta | gca | aac | ctt | ata | aat | 2832 |
| His | Gln | Leu | Pro | Ala | Pro | Lys | Trp | Ala | Glu | Leu | Ala | Asn | Leu | Ile | Asn |      |
| 770 |     |     |     |     | 775 |     |     |     |     | 780 |     |     |     |     | 785 |      |
| aat | tgt | atg | gat | tat | gaa | cca | gat | ttc | agg | cct | tct | ttc | aga | gcc | atc | 2880 |
| Asn | Cys | Met | Asp | Tyr | Glu | Pro | Asp | Phe | Arg | Pro | Ser | Phe | Arg | Ala | Ile |      |
|     |     |     |     | 790 |     |     |     |     | 795 |     |     |     |     | 800 |     |      |
| ata | cga | gat | ctt | aac | agt | ttg | ttt | act | cca | gat | tat | gaa | cta | tta | aca | 2928 |

```
                                                               -continued

Ile Arg Asp Leu Asn Ser Leu Phe Thr Pro Asp Tyr Glu Leu Leu Thr
            805                 810                 815 gaa aat gac atg tta cca aat atg agg ata ggt gcc ctg ggg ttt tct    2976
Glu Asn Asp Met Leu Pro Asn Met Arg Ile Gly Ala Leu Gly Phe Ser
        820                 825                 830 ggt gcc ttt gaa gac cgg gat cct aca cag ttt gaa gag aga cat ttg    3024
Gly Ala Phe Glu Asp Arg Asp Pro Thr Gln Phe Glu Glu Arg His Leu
835                 840                 845 aaa ttt cta cag caa ctt ggc aag ggt aat ttt ggg agt gtg gag atg    3072
Lys Phe Leu Gln Gln Leu Gly Lys Gly Asn Phe Gly Ser Val Glu Met
850                 855                 860                 865 tgc cgg tat gac cct cta cag gac aac act ggg gag gtg gtc gct gta    3120
Cys Arg Tyr Asp Pro Leu Gln Asp Asn Thr Gly Glu Val Val Ala Val
                870                 875                 880 aaa aag ctt cag cat agt act gaa gag cac cta aga gac ttt gaa agg    3168
Lys Lys Leu Gln His Ser Thr Glu Glu His Leu Arg Asp Phe Glu Arg
            885                 890                 895 gaa att gaa atc ctg aaa tcc cta cag cat gac aac att gta aag tac    3216
Glu Ile Glu Ile Leu Lys Ser Leu Gln His Asp Asn Ile Val Lys Tyr
        900                 905                 910 aag gga gtg tgc tac agt gct ggt cgg cgt aat cta aaa tta att atg    3264
Lys Gly Val Cys Tyr Ser Ala Gly Arg Arg Asn Leu Lys Leu Ile Met
    915                 920                 925 gaa tat tta cca tat gga agt tta cga gac tat ctt caa aaa cat aaa    3312
Glu Tyr Leu Pro Tyr Gly Ser Leu Arg Asp Tyr Leu Gln Lys His Lys
930                 935                 940                 945 gaa cgg ata gat cac ata aaa ctt ctg cag tac aca tct cag ata tgc    3360
Glu Arg Ile Asp His Ile Lys Leu Leu Gln Tyr Thr Ser Gln Ile Cys
                950                 955                 960 aag ggt atg gag tat ctt ggt aca aaa agg tat atc cac agg gat ctg    3408
Lys Gly Met Glu Tyr Leu Gly Thr Lys Arg Tyr Ile His Arg Asp Leu
            965                 970                 975 gca acg aga aat ata ttg gtg gag aac gag aac aga gtt aaa att gga    3456
Ala Thr Arg Asn Ile Leu Val Glu Asn Glu Asn Arg Val Lys Ile Gly
        980                 985                 990 gat ttt ggg tta acc aaa gtc ttg cca caa gac aaa gaa tac tat aaa    3504
Asp Phe Gly Leu Thr Lys Val Leu Pro Gln Asp Lys Glu Tyr Tyr Lys
    995                 1000                1005 gta aaa gaa cct ggt gaa agt ccc ata ttc tgg tat gct cca gaa tca    3552
Val Lys Glu Pro Gly Glu Ser Pro Ile Phe Trp Tyr Ala Pro Glu Ser
1010                1015                1020                1025 ctg aca gag agc aag ttt tct gtg gcc tca gat gtt tgg agc ttt gga    3600
Leu Thr Glu Ser Lys Phe Ser Val Ala Ser Asp Val Trp Ser Phe Gly
                1030                1035                1040 gtg gtt ctg tat gaa ctt ttc aca tac att gag aag agt aaa agt cca    3648
Val Val Leu Tyr Glu Leu Phe Thr Tyr Ile Glu Lys Ser Lys Ser Pro
            1045                1050                1055 cca gcg gaa ttt atg cgt atg att ggc aat gac aaa caa gga cag atg    3696
Pro Ala Glu Phe Met Arg Met Ile Gly Asn Asp Lys Gln Gly Gln Met
        1060                1065                1070 atc gtg ttc cat ttg ata gaa ctt ttg aag aat aat gga aga tta cca    3744
Ile Val Phe His Leu Ile Glu Leu Leu Lys Asn Asn Gly Arg Leu Pro
    1075                1080                1085 aga cca gat gga tgc cca gat gag atc tat atg atc atg aca gaa tgc    3792
Arg Pro Asp Gly Cys Pro Asp Glu Ile Tyr Met Ile Met Thr Glu Cys
1090                1095                1100                1105 tgg aac aat aat gta aat caa cgc ccc tcc ttt agg gat cta gct ctt    3840
Trp Asn Asn Asn Val Asn Gln Arg Pro Ser Phe Arg Asp Leu Ala Leu
                1110                1115                1120
```

-continued

```
cga gtg gat caa ata agg gat aac atg gct gga tga aagaaatgac      3886
Arg Val Asp Gln Ile Arg Asp Asn Met Ala Gly *
            1125                1130 cttcattctg agaccaaagt agatttacag aacaaagttt tatatttcac attgctgtgg    3946
actattatta catatatcat tattatataa atcatgatgc tagccagcaa agatgtgaaa    4006
atatctgctc aaaactttca agtttagta agttttctt catgaggcca ccagtaaaag      4066
acattaatga gaattcctta gcaaggattt tgtaagaagt ttcttaaaca ttgtcagtta    4126
acatcactct tgtctggcaa aagaaaaaaa atagactttt tcaactcagc tttttgagac    4186
ctgaaaaaat tattatgtaa attttgcaat gttaaagatg cacagaatat gtatgtatag    4246
tttttaccac agtggatgta taataccttg gcatcttgtg tgatgtttta cacacatgag    4306
ggctggtgtt cattaatact gttttctaat ttttccatag ttaatctata attaattact    4366
tcactataca aacaaattaa gatgttcaga taattgaata agtacctttg tgtccttgtt    4426
catttatatc gctggccagc attataagca ggtgtatact tttagcttgt agttccatgt    4486
actgtaaata ttttcacat aaagggaaca aatgtctagt tttatttgta taggaaattt     4546 ccctgacccct aaataataca ttttgaaatg aaacaagctt acaaagatat aatctatttt   4606
attatggttt cccttgtatc tatttgtggt gaatgtgttt tttaaatgga actatctcca    4666
aatttttcta agactactat gaacagtttt cttttaaaat tttgagatta agaatgccag    4726
gaatattgtc atcctttgag ctgctgactg ccaataacat tcttcgatct ctgggattta    4786
tgctcatgaa ctaaatttaa gcttaagcca taaaatagat tagattgttt tttaaaaatg    4846
gatagctcat taagaagtgc agcaggttaa gaattttttc ctaaagactg tatatttgag    4906
gggtttcaga attttgcatt gcagtcatag aagagattta tttcctttt agaggggaaa     4966 tgaggtaaat aagtaaaaaa gtatgcttgt taattttatt caagaatgcc agtagaaaat    5026
tcataacgtg tatctttaag aaaaatgagc atacatctta aatctttca attaaggtcg     5086 acgcggccgc ggtcgacgcg gccgcgaatt c                                    5117
```

<210> SEQ ID NO 16
<211> LENGTH: 1132
<212> TYPE: PRT
<213> ORGANISM: Homo sapiens

<400> SEQUENCE: 16

```
Met Gly Met Ala Cys Leu Thr Met Thr Glu Met Glu Gly Thr Ser Thr
 1               5                  10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
```

```
            130                 135                 140
Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
        275                 280                 285

Ile Ile Thr Gly Asn Gly Gly Ile Gln Trp Ser Arg Gly Lys His Lys
290                 295                 300

Glu Ser Glu Thr Leu Thr Glu Gln Asp Leu Gln Leu Tyr Cys Asp Phe
305                 310                 315                 320

Ser Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
        355                 360                 365

Ile Asp Gly Tyr Tyr Arg Leu Thr Ala Asp Ala His His Tyr Leu Cys
370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
        435                 440                 445

Tyr Lys His Cys Leu Ile Thr Lys Asn Glu Asn Glu Glu Tyr Asn Leu
450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
                485                 490                 495

Lys Cys Cys Pro Pro Lys Pro Lys Asp Lys Ser Asn Leu Leu Val Phe
            500                 505                 510

Arg Thr Asn Gly Val Ser Asp Val Pro Thr Ser Pro Thr Leu Gln Arg
        515                 520                 525

Pro Thr His Met Asn Gln Met Val Phe His Lys Ile Arg Asn Glu Asp
530                 535                 540

Leu Ile Phe Asn Glu Ser Leu Gly Gln Gly Thr Phe Thr Lys Ile Phe
545                 550                 555                 560
```

-continued

```
Lys Gly Val Arg Arg Glu Val Gly Asp Tyr Gly Gln Leu His Glu Thr
            565                 570                 575
Glu Val Leu Leu Lys Val Leu Asp Lys Ala His Arg Asn Tyr Ser Glu
            580                 585                 590
Ser Phe Phe Glu Ala Ala Ser Met Met Ser Lys Leu Ser His Lys His
            595                 600                 605
Leu Val Leu Asn Tyr Gly Val Cys Val Cys Gly Asp Glu Asn Ile Leu
            610                 615                 620
Val Gln Glu Phe Val Lys Phe Gly Ser Leu Asp Thr Tyr Leu Lys Lys
625                 630                 635                 640
Asn Lys Asn Cys Ile Asn Ile Leu Trp Lys Leu Glu Val Ala Lys Gln
            645                 650                 655
Leu Ala Trp Ala Met His Phe Leu Glu Glu Asn Thr Leu Ile His Gly
            660                 665                 670
Asn Val Cys Ala Lys Asn Ile Leu Leu Ile Arg Glu Glu Asp Arg Lys
            675                 680                 685
Thr Gly Asn Pro Pro Phe Ile Lys Leu Ser Asp Pro Gly Ile Ser Ile
            690                 695                 700
Thr Val Leu Pro Lys Asp Ile Leu Gln Glu Arg Ile Pro Trp Val Pro
705                 710                 715                 720
Pro Glu Cys Ile Glu Asn Pro Lys Asn Leu Asn Leu Ala Thr Asp Lys
            725                 730                 735
Trp Ser Phe Gly Thr Thr Leu Trp Glu Ile Cys Ser Gly Gly Asp Lys
            740                 745                 750
Pro Leu Ser Ala Leu Asp Ser Gln Arg Lys Leu Gln Phe Tyr Glu Asp
            755                 760                 765
Arg His Gln Leu Pro Ala Pro Lys Trp Ala Glu Leu Ala Asn Leu Ile
            770                 775                 780
Asn Asn Cys Met Asp Tyr Glu Pro Asp Phe Arg Pro Ser Phe Arg Ala
785                 790                 795                 800
Ile Ile Arg Asp Leu Asn Ser Leu Phe Thr Pro Asp Tyr Glu Leu Leu
            805                 810                 815
Thr Glu Asn Asp Met Leu Pro Asn Met Arg Ile Gly Ala Leu Gly Phe
            820                 825                 830
Ser Gly Ala Phe Glu Asp Arg Asp Pro Thr Gln Phe Glu Glu Arg His
            835                 840                 845
Leu Lys Phe Leu Gln Gln Leu Gly Lys Gly Asn Phe Gly Ser Val Glu
            850                 855                 860
Met Cys Arg Tyr Asp Pro Leu Gln Asp Asn Thr Gly Glu Val Val Ala
865                 870                 875                 880
Val Lys Lys Leu Gln His Ser Thr Glu Glu His Leu Arg Asp Phe Glu
            885                 890                 895
Arg Glu Ile Glu Ile Leu Lys Ser Leu Gln His Asp Asn Ile Val Lys
            900                 905                 910
Tyr Lys Gly Val Cys Tyr Ser Ala Gly Arg Arg Asn Leu Lys Leu Ile
            915                 920                 925
Met Glu Tyr Leu Pro Tyr Gly Ser Leu Arg Asp Tyr Leu Gln Lys His
            930                 935                 940
Lys Glu Arg Ile Asp His Ile Lys Leu Leu Gln Tyr Thr Ser Gln Ile
945                 950                 955                 960
Cys Lys Gly Met Glu Tyr Leu Gly Thr Lys Arg Tyr Ile His Arg Asp
            965                 970                 975
```

```
Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
        995                 1000                1005

Lys Val Lys Glu Pro Gly Glu Ser Pro Ile Phe Trp Tyr Ala Pro Glu
    1010                1015                1020

Ser Leu Thr Glu Ser Lys Phe Ser Val Ala Ser Asp Val Trp Ser Phe
1025                1030                1035                1040

Gly Val Val Leu Tyr Glu Leu Phe Thr Tyr Ile Glu Lys Ser Lys Ser
                1045                1050                1055

Pro Pro Ala Glu Phe Met Arg Met Ile Gly Asn Asp Lys Gln Gly Gln
            1060                1065                1070

Met Ile Val Phe His Leu Ile Glu Leu Leu Lys Asn Asn Gly Arg Leu
        1075                1080                1085

Pro Arg Pro Asp Gly Cys Pro Asp Glu Ile Tyr Met Ile Met Thr Glu
    1090                1095                1100

Cys Trp Asn Asn Asn Val Asn Gln Arg Pro Ser Phe Arg Asp Leu Ala
1105                1110                1115                1120

Leu Arg Val Asp Gln Ile Arg Asp Asn Met Ala Gly
                1125                1130

<210> SEQ ID NO 17
<211> LENGTH: 4176
<212> TYPE: DNA
<213> ORGANISM: Homo sapiens
<220> FEATURE:
<221> NAME/KEY: CDS
<222> LOCATION: (307)...(3870)

<400> SEQUENCE: 17
gacgcgggcg cggaaggagc gcggccggag gtcctcagga agaagccgcg gggactggct    60
gcgcttgaca ggctgcactt ggatgggagc acctggtgcc tcgggactgc tccgatgccc   120
gggtctgtgc tgaatgtgta atatgcggaa ctatattgaa acattacaac catcttttga   180
tggcaacacc ctgaggacct cccttttcca gatggggaaa ctgaggccca gaattgctaa   240
gtggcttgct tgagttgaca cagggagctc aggactcac cctcagctga gccacctgcc    300 gggagc atg cct ctg cgc cac tgg ggg atg gcc agg ggc agt aag ccc       348
       Met Pro Leu Arg His Trp Gly Met Ala Arg Gly Ser Lys Pro
       1               5                   10 gtt ggg gat gga gcc cag ccc atg gct gcc atg gga ggc ctg aag gtg     396
Val Gly Asp Gly Ala Gln Pro Met Ala Ala Met Gly Gly Leu Lys Val
15              20                  25                  30 ctt ctg cac tgg gct ggt cca ggc ggc ggg gag ccc tgg gtc act ttc     444
Leu Leu His Trp Ala Gly Pro Gly Gly Gly Glu Pro Trp Val Thr Phe
            35                  40                  45 agt gag tca tcg ctg aca gct gag gaa gtc tgc atc cac att gca cat     492
Ser Glu Ser Ser Leu Thr Ala Glu Glu Val Cys Ile His Ile Ala His
        50                  55                  60 aaa gtt ggt atc act cct cct tgc ttc aat ctc ttt gcc ctc ttc gat     540
Lys Val Gly Ile Thr Pro Pro Cys Phe Asn Leu Phe Ala Leu Phe Asp
65                  70                  75 gct cag gcc caa gtc tgg ttg ccc cca aac cac atc cta gag atc ccc     588
Ala Gln Ala Gln Val Trp Leu Pro Pro Asn His Ile Leu Glu Ile Pro
    80                  85                  90 aga gat gca agc ctg atg cta tat ttc cgc ata agg ttt tat ttc cgg     636
Arg Asp Ala Ser Leu Met Leu Tyr Phe Arg Ile Arg Phe Tyr Phe Arg
95                  100                 105                 110
```

```
aac tgg cat ggc atg aat cct cgg gaa ccg gct gtg tac cgt tgt ggg        684
Asn Trp His Gly Met Asn Pro Arg Glu Pro Ala Val Tyr Arg Cys Gly
            115                 120                 125 ccc cca gga acc gag gca tcc tca gat cag aca gca cag ggg atg caa        732
Pro Pro Gly Thr Glu Ala Ser Ser Asp Gln Thr Ala Gln Gly Met Gln
        130                 135                 140 ctc ctg gac cca gcc tca ttt gag tac ctc ttt gag cag ggc aag cat        780
Leu Leu Asp Pro Ala Ser Phe Glu Tyr Leu Phe Glu Gln Gly Lys His
            145                 150                 155 gag ttt gtg aat gac gtg gca tca ctg tgg gag ctg tcg acc gag gag        828
Glu Phe Val Asn Asp Val Ala Ser Leu Trp Glu Leu Ser Thr Glu Glu
160                 165                 170 gag atc cac cac ttt aag aat gag agc ctg ggc atg gcc ttt ctg cac        876
Glu Ile His His Phe Lys Asn Glu Ser Leu Gly Met Ala Phe Leu His
175                 180                 185                 190 ctc tgt cac ctc gct ctc cgc cat ggc atc ccc ctg gag gag gtg gcc        924
Leu Cys His Leu Ala Leu Arg His Gly Ile Pro Leu Glu Glu Val Ala
                195                 200                 205 aag aag acc agc ttc aag gac tgc atc ccg cgc tcc ttc cgc cgg cat        972
Lys Lys Thr Ser Phe Lys Asp Cys Ile Pro Arg Ser Phe Arg Arg His
            210                 215                 220 atc cgg cag cac agc gcc ctg acc cgg ctg cgc ctt cgg aac gtc ttc       1020
Ile Arg Gln His Ser Ala Leu Thr Arg Leu Arg Leu Arg Asn Val Phe
            225                 230                 235 cgc agg ttc ctg cgg gac ttc cag ccg ggc cga ctc tcc cag cag atg       1068
Arg Arg Phe Leu Arg Asp Phe Gln Pro Gly Arg Leu Ser Gln Gln Met
240                 245                 250 gtc atg gtc aaa tac cta gcc aca ctc gag cgg ctg gca ccc cgc ttc       1116
Val Met Val Lys Tyr Leu Ala Thr Leu Glu Arg Leu Ala Pro Arg Phe
255                 260                 265                 270 ggc aca gag cgt gtg ccc gtg tgc cac ctg agg ctg ctg gcc cag gcc       1164
Gly Thr Glu Arg Val Pro Val Cys His Leu Arg Leu Leu Ala Gln Ala
                275                 280                 285 gag ggg gag ccc tgc tac atc cgg gac agt ggg gtg gcc cct aca gac       1212
Glu Gly Glu Pro Cys Tyr Ile Arg Asp Ser Gly Val Ala Pro Thr Asp
            290                 295                 300 cct ggc cct gag tct gct gct ggg ccc cca acc cac gag gtg ctg gtg       1260
Pro Gly Pro Glu Ser Ala Ala Gly Pro Pro Thr His Glu Val Leu Val
            305                 310                 315 aca ggc act ggt ggc atc cag tgg tgg cca gta gag gag gag gtg aac       1308
Thr Gly Thr Gly Gly Ile Gln Trp Trp Pro Val Glu Glu Glu Val Asn
320                 325                 330 aag gag gag ggt tct agt ggc agc agt ggc agg aac ccc caa gcc agc       1356
Lys Glu Glu Gly Ser Ser Gly Ser Ser Gly Arg Asn Pro Gln Ala Ser
335                 340                 345                 350 ctg ttt ggg aag aag gcc aag gct cac aag gca ttc ggc cag ccg gca       1404
Leu Phe Gly Lys Lys Ala Lys Ala His Lys Ala Phe Gly Gln Pro Ala
            355                 360                 365 gac agg ccg cgg gag cca ctg tgg gcc tac ttc tgt gac ttc cgg gac       1452
Asp Arg Pro Arg Glu Pro Leu Trp Ala Tyr Phe Cys Asp Phe Arg Asp
            370                 375                 380 atc acc cac gtg gtg ctg aaa gag cac tgt gtc agc atc cac cgg cag       1500
Ile Thr His Val Val Leu Lys Glu His Cys Val Ser Ile His Arg Gln
            385                 390                 395 gac aac aag tgc ctg gag ctg agc ttg cct tcc cgg gct gcg gcg ctg       1548
Asp Asn Lys Cys Leu Glu Leu Ser Leu Pro Ser Arg Ala Ala Ala Leu
        400                 405                 410 tcc ttc gtg tcg ctg gtg gac ggc tat ttc cgc ctg acg gcc gac tcc       1596
Ser Phe Val Ser Leu Val Asp Gly Tyr Phe Arg Leu Thr Ala Asp Ser
415                 420                 425                 430
```

```
agc cac tac ctg tgc cac gag gtg gct ccc cca cgg ctg gtg atg agc    1644
Ser His Tyr Leu Cys His Glu Val Ala Pro Pro Arg Leu Val Met Ser
            435                 440                 445 atc cgg gat ggg atc cac gga ccc ctg ctg gag cca ttt gtg cag gcc    1692
Ile Arg Asp Gly Ile His Gly Pro Leu Leu Glu Pro Phe Val Gln Ala
            450                 455                 460 aag ctg cgg ccc gag gac ggc ctg tac ctc att cac tgg agc acc agc    1740
Lys Leu Arg Pro Glu Asp Gly Leu Tyr Leu Ile His Trp Ser Thr Ser
            465                 470                 475 cac ccc tac cgc ctg atc ctc aca gtg gcc cag cgt agc cag gca cca    1788
His Pro Tyr Arg Leu Ile Leu Thr Val Ala Gln Arg Ser Gln Ala Pro
480                 485                 490 gac ggc atg cag agc ttg cgg ctc cga aag ttc ccc att gag cag cag    1836
Asp Gly Met Gln Ser Leu Arg Leu Arg Lys Phe Pro Ile Glu Gln Gln
495                 500                 505                 510 gac ggg gcc ttc gtg ctg gag ggc tgg ggc cgg tcc ttc ccc agc gtt    1884
Asp Gly Ala Phe Val Leu Glu Gly Trp Gly Arg Ser Phe Pro Ser Val
                515                 520                 525 cgg gaa ctt ggg gct gcc ttg cag ggc tgc ttg ctg agg gcc ggg gat    1932
Arg Glu Leu Gly Ala Ala Leu Gln Gly Cys Leu Leu Arg Ala Gly Asp
            530                 535                 540 gac tgc ttc tct ctg cgt cgc tgt tgc ctg ccc caa cca gga gaa acc    1980
Asp Cys Phe Ser Leu Arg Arg Cys Cys Leu Pro Gln Pro Gly Glu Thr
            545                 550                 555 tcc aat ctc atc atc atg cgg ggg gct cgg gcc agc ccc agg aca ctc    2028
Ser Asn Leu Ile Ile Met Arg Gly Ala Arg Ala Ser Pro Arg Thr Leu
            560                 565                 570 aac ctc agc cag ctc agc ttc cac cgg gtt gac cag aag gag atc acc    2076
Asn Leu Ser Gln Leu Ser Phe His Arg Val Asp Gln Lys Glu Ile Thr
575                 580                 585                 590 cag ctg tcc cac ttg ggc cag ggc aca agg acc aac gtg tat gag ggc    2124
Gln Leu Ser His Leu Gly Gln Gly Thr Arg Thr Asn Val Tyr Glu Gly
                595                 600                 605 cgc ctg cga gtg gag ggc agc ggg gac cct gag gag ggc aag atg gat    2172
Arg Leu Arg Val Glu Gly Ser Gly Asp Pro Glu Glu Gly Lys Met Asp
            610                 615                 620 gac gag gac ccc ctc gtg cct ggc agg gac cgt ggg cag gag cta cga    2220
Asp Glu Asp Pro Leu Val Pro Gly Arg Asp Arg Gly Gln Glu Leu Arg
            625                 630                 635 gtg gtg ctc aaa gtg ctg gac cct agt cac cat gac atc gcc ctg gcc    2268
Val Val Leu Lys Val Leu Asp Pro Ser His His Asp Ile Ala Leu Ala
640                 645                 650 ttc tac gag aca gcc agc ctc atg agc cag gtc tcc cac acg cac ctg    2316
Phe Tyr Glu Thr Ala Ser Leu Met Ser Gln Val Ser His Thr His Leu
655                 660                 665                 670 gcc ttc gtg cat ggc gtc tgt gtg cgc ggc cct gaa aat agc atg gtg    2364
Ala Phe Val His Gly Val Cys Val Arg Gly Pro Glu Asn Ser Met Val
                675                 680                 685 aca gag tac gtg gag cac gga ccc ctg gat gtg tgg ctg cgg agg gag    2412
Thr Glu Tyr Val Glu His Gly Pro Leu Asp Val Trp Leu Arg Arg Glu
            690                 695                 700 cgg ggc cat gtg ccc atg gct tgg aag atg gtg gtg gcc cag cag ctg    2460
Arg Gly His Val Pro Met Ala Trp Lys Met Val Val Ala Gln Gln Leu
            705                 710                 715 gcc agc gcc ctc agc tac ctg gag aac aag aac ctg gtt cat ggt aat    2508
Ala Ser Ala Leu Ser Tyr Leu Glu Asn Lys Asn Leu Val His Gly Asn
720                 725                 730 gtg tgt ggc cgg aac atc ctg ctg gcc cgg ctg ggg ttg gca gag ggc    2556
Val Cys Gly Arg Asn Ile Leu Leu Ala Arg Leu Gly Leu Ala Glu Gly
```

```
                    -continued
735             740             745             750
acc agc ccc ttc atc aag ctg agt gat cct ggc gtg ggc ctg ggc gcc    2604
Thr Ser Pro Phe Ile Lys Leu Ser Asp Pro Gly Val Gly Leu Gly Ala
                755             760             765 ctc tcc agg gag gag cgg gtg gag agg atc ccc tgg ctg gcc ccc gaa    2652
Leu Ser Arg Glu Glu Arg Val Glu Arg Ile Pro Trp Leu Ala Pro Glu
        770             775             780 tgc cta cca ggt ggg gcc aac agc cta agc acc gcc atg gac aag tgg    2700
Cys Leu Pro Gly Gly Ala Asn Ser Leu Ser Thr Ala Met Asp Lys Trp
            785             790             795 ggg ttt ggc gcc acc ctc ctg gag atc tgc ttt gac gga gag gcc cct    2748
Gly Phe Gly Ala Thr Leu Leu Glu Ile Cys Phe Asp Gly Glu Ala Pro
        800             805             810 ctg cag agc cgc agt ccc tcc gag aag gag cat ttc tac cag agg cag    2796
Leu Gln Ser Arg Ser Pro Ser Glu Lys Glu His Phe Tyr Gln Arg Gln
815             820             825             830 cac cgg ctg ccc gag ccc tcc tgc cca cag ctg gcc aca ctc acc agc    2844
His Arg Leu Pro Glu Pro Ser Cys Pro Gln Leu Ala Thr Leu Thr Ser
                835             840             845 cag tgt ctg acc tat gag cca acc cag agg cca tca ttc cgc acc atc    2892
Gln Cys Leu Thr Tyr Glu Pro Thr Gln Arg Pro Ser Phe Arg Thr Ile
            850             855             860 ctg cgt gac ctc acc cgc gtg cag ccc cac aat ctt gct gac gtc ttg    2940
Leu Arg Asp Leu Thr Arg Val Gln Pro His Asn Leu Ala Asp Val Leu
        865             870             875 act gtg aac cgg gac tca ccg gcc gtc gga cct act act ttc cac aag    2988
Thr Val Asn Arg Asp Ser Pro Ala Val Gly Pro Thr Thr Phe His Lys
    880             885             890 cgc tat ttg aaa aag atc cga gat ctg ggc gag ggt cac ttc ggc aag    3036
Arg Tyr Leu Lys Lys Ile Arg Asp Leu Gly Glu Gly His Phe Gly Lys
895             900             905             910 gtc agc ttg tac tgc tac gat ccg acc aac gac ggc act ggc gag atg    3084
Val Ser Leu Tyr Cys Tyr Asp Pro Thr Asn Asp Gly Thr Gly Glu Met
                915             920             925 gtg gcg gtg aaa gcc ctc aag gca gac tgc ggc ccc cag cac cgc tcg    3132
Val Ala Val Lys Ala Leu Lys Ala Asp Cys Gly Pro Gln His Arg Ser
            930             935             940 ggc tgg aag cag gag att gac att ctg cgc acg ctc tac cac gag cac    3180
Gly Trp Lys Gln Glu Ile Asp Ile Leu Arg Thr Leu Tyr His Glu His
        945             950             955 atc atc aag tac aag ggc tgc tgc gag gac caa ggc gag aag tcg ctg    3228
Ile Ile Lys Tyr Lys Gly Cys Cys Glu Asp Gln Gly Glu Lys Ser Leu
    960             965             970 cag ctg gtc atg gag tac gtg ccc ctg ggc agc ctc cga gac tac ctg    3276
Gln Leu Val Met Glu Tyr Val Pro Leu Gly Ser Leu Arg Asp Tyr Leu
975             980             985             990 ccc cgg cac agc atc ggg ctg gcc cag ctg ctg ctc ttc gcc cag cag    3324
Pro Arg His Ser Ile Gly Leu Ala Gln Leu Leu Leu Phe Ala Gln Gln
                995             1000            1005 atc tgc gag ggc atg gcc tat ctg cac gcg cac gac tac atc cac cga    3372
Ile Cys Glu Gly Met Ala Tyr Leu His Ala His Asp Tyr Ile His Arg
            1010            1015            1020 gac cta gcc gcg cgc aac gtg ctg ctg gac aac gac agg ctg gtc aag    3420
Asp Leu Ala Ala Arg Asn Val Leu Leu Asp Asn Asp Arg Leu Val Lys
        1025            1030            1035 atc ggg gac ttt ggc cta gcc aag gcc gtg ccc gaa ggc cac gag tac    3468
Ile Gly Asp Phe Gly Leu Ala Lys Ala Val Pro Glu Gly His Glu Tyr
    1040            1045            1050 tac cgc gtg cgc gag gat ggg gac agc ccc gtg ttc tgg tat gcc cca    3516
```

```
Tyr Arg Val Arg Glu Asp Gly Asp Ser Pro Val Phe Trp Tyr Ala Pro
1055                1060                1065                1070 gag tgc ctg aag gag tat aag ttc tac tat gcg tca gat gtc tgg tcc    3564
Glu Cys Leu Lys Glu Tyr Lys Phe Tyr Tyr Ala Ser Asp Val Trp Ser
                    1075                1080                1085 ttc ggg gtg acc ctg tat gag ctg ctg acg cac tgt gac tcc agc cag    3612
Phe Gly Val Thr Leu Tyr Glu Leu Leu Thr His Cys Asp Ser Ser Gln
                1090                1095                1100 agc ccc ccc acg aaa ttc ctt gag ctc ata ggc att gct cag ggt cag    3660
Ser Pro Pro Thr Lys Phe Leu Glu Leu Ile Gly Ile Ala Gln Gly Gln
            1105                1110                1115 atg aca gtt ctg aga ctc act gag ttg ctg gaa cga ggg gag agg ctg    3708
Met Thr Val Leu Arg Leu Thr Glu Leu Leu Glu Arg Gly Glu Arg Leu
        1120                1125                1130 cca cgg ccc gac aaa tgt ccc tgt gag gtc tat cat ctc atg aag aac    3756
Pro Arg Pro Asp Lys Cys Pro Cys Glu Val Tyr His Leu Met Lys Asn
1135                1140                1145                1150 tgc tgg gag aca gag gcg tcc ttt cgc cca acc ttc gag aac ctc ata    3804
Cys Trp Glu Thr Glu Ala Ser Phe Arg Pro Thr Phe Glu Asn Leu Ile
                    1155                1160                1165 ccc att ctg aag aca gtc cat gag aag tac caa ggc cag gcc cct tca    3852
Pro Ile Leu Lys Thr Val His Glu Lys Tyr Gln Gly Gln Ala Pro Ser
                1170                1175                1180 gtg ttc agc gtg tgc tga ggcacaatgg cagccctgcc tgggaggact           3900
Val Phe Ser Val Cys  *
            1185 ggaccaggca gtggctgcag agggagcctc ctgctccctg ctccaggatg aaaccaagag  3960 ggggatgtca gcctcaccca caccgtgtgc cttactcctg tctagagacc ccacctctgt  4020 gaacttattt ttctttcttg gccgtgagcc taaccatgat cttgagggac ccaacatttg  4080 tagggcact aatccagccc ttaaatcccc cagcttccaa acttgaggcc caccatctcc   4140 accatctggt aataaactca tgttttctct gctggg                           4176

<210> SEQ ID NO 18
<211> LENGTH: 1187
<212> TYPE: PRT
<213> ORGANISM: Homo sapiens

<400> SEQUENCE: 18

Met Pro Leu Arg His Trp Gly Met Ala Arg Gly Ser Lys Pro Val Gly
1               5                   10                  15

Asp Gly Ala Gln Pro Met Ala Ala Met Gly Gly Leu Lys Val Leu Leu
            20                  25                  30

His Trp Ala Gly Pro Gly Gly Glu Pro Trp Val Thr Phe Ser Glu
        35                  40                  45

Ser Ser Leu Thr Ala Glu Glu Val Cys Ile His Ile Ala His Lys Val
    50                  55                  60

Gly Ile Thr Pro Pro Cys Phe Asn Leu Phe Ala Leu Phe Asp Ala Gln
65                  70                  75                  80

Ala Gln Val Trp Leu Pro Pro Asn His Ile Leu Glu Ile Pro Arg Asp
                85                  90                  95

Ala Ser Leu Met Leu Tyr Phe Arg Ile Arg Phe Tyr Phe Arg Asn Trp
            100                 105                 110

His Gly Met Asn Pro Arg Glu Pro Ala Val Tyr Arg Cys Gly Pro Pro
        115                 120                 125

Gly Thr Glu Ala Ser Ser Asp Gln Thr Ala Gln Gly Met Gln Leu Leu
    130                 135                 140
```

-continued

```
Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
                165                 170                 175

His His Phe Lys Asn Glu Ser Leu Gly Met Ala Phe Leu His Leu Cys
            180                 185                 190

His Leu Ala Leu Arg His Gly Ile Pro Leu Glu Glu Val Ala Lys Lys
        195                 200                 205

Thr Ser Phe Lys Asp Cys Ile Pro Arg Ser Phe Arg Arg His Ile Arg
    210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
            260                 265                 270

Glu Arg Val Pro Val Cys His Leu Arg Leu Leu Ala Gln Ala Glu Gly
        275                 280                 285

Glu Pro Cys Tyr Ile Arg Asp Ser Gly Val Ala Pro Thr Asp Pro Gly
    290                 295                 300

Pro Glu Ser Ala Ala Gly Pro Pro Thr His Glu Val Leu Val Thr Gly
305                 310                 315                 320

Thr Gly Gly Ile Gln Trp Trp Pro Val Glu Glu Val Asn Lys Glu
                325                 330                 335

Glu Gly Ser Ser Gly Ser Ser Gly Arg Asn Pro Gln Ala Ser Leu Phe
            340                 345                 350

Gly Lys Lys Ala Lys Ala His Lys Ala Phe Gly Gln Pro Ala Asp Arg
        355                 360                 365

Pro Arg Glu Pro Leu Trp Ala Tyr Phe Cys Asp Phe Arg Asp Ile Thr
    370                 375                 380

His Val Val Leu Lys Glu His Cys Val Ser Ile His Arg Gln Asp Asn
385                 390                 395                 400

Lys Cys Leu Glu Leu Ser Leu Pro Ser Arg Ala Ala Leu Ser Phe
                405                 410                 415

Val Ser Leu Val Asp Gly Tyr Phe Arg Leu Thr Ala Asp Ser Ser His
            420                 425                 430

Tyr Leu Cys His Glu Val Ala Pro Pro Arg Leu Val Met Ser Ile Arg
        435                 440                 445

Asp Gly Ile His Gly Pro Leu Leu Glu Pro Phe Val Gln Ala Lys Leu
    450                 455                 460

Arg Pro Glu Asp Gly Leu Tyr Leu Ile His Trp Ser Thr Ser His Pro
465                 470                 475                 480

Tyr Arg Leu Ile Leu Thr Val Ala Gln Arg Ser Gln Ala Pro Asp Gly
                485                 490                 495

Met Gln Ser Leu Arg Leu Arg Lys Phe Pro Ile Glu Gln Gln Asp Gly
            500                 505                 510

Ala Phe Val Leu Glu Gly Trp Gly Arg Ser Phe Pro Ser Val Arg Glu
        515                 520                 525

Leu Gly Ala Ala Leu Gln Gly Cys Leu Leu Arg Ala Gly Asp Asp Cys
    530                 535                 540

Phe Ser Leu Arg Arg Cys Cys Leu Pro Gln Pro Gly Glu Thr Ser Asn
545                 550                 555                 560
```

-continued

```
Leu Ile Ile Met Arg Gly Ala Arg Ala Ser Pro Arg Thr Leu Asn Leu
                565                 570                 575

Ser Gln Leu Ser Phe His Arg Val Asp Gln Lys Glu Ile Thr Gln Leu
            580                 585                 590

Ser His Leu Gly Gln Gly Thr Arg Thr Asn Val Tyr Glu Gly Arg Leu
        595                 600                 605

Arg Val Glu Gly Ser Gly Asp Pro Glu Glu Gly Lys Met Asp Asp Glu
    610                 615                 620

Asp Pro Leu Val Pro Gly Arg Asp Arg Gly Gln Glu Leu Arg Val Val
625                 630                 635                 640

Leu Lys Val Leu Asp Pro Ser His His Asp Ile Ala Leu Ala Phe Tyr
                645                 650                 655

Glu Thr Ala Ser Leu Met Ser Gln Val Ser His Thr His Leu Ala Phe
            660                 665                 670

Val His Gly Val Cys Val Arg Gly Pro Glu Asn Ser Met Val Thr Glu
        675                 680                 685

Tyr Val Glu His Gly Pro Leu Asp Val Trp Leu Arg Arg Glu Arg Gly
    690                 695                 700

His Val Pro Met Ala Trp Lys Met Val Val Ala Gln Gln Leu Ala Ser
705                 710                 715                 720

Ala Leu Ser Tyr Leu Glu Asn Lys Asn Leu Val His Gly Asn Val Cys
                725                 730                 735

Gly Arg Asn Ile Leu Leu Ala Arg Leu Gly Leu Ala Glu Gly Thr Ser
            740                 745                 750

Pro Phe Ile Lys Leu Ser Asp Pro Gly Val Gly Leu Gly Ala Leu Ser
        755                 760                 765

Arg Glu Glu Arg Val Glu Arg Ile Pro Trp Leu Ala Pro Glu Cys Leu
    770                 775                 780

Pro Gly Gly Ala Asn Ser Leu Ser Thr Ala Met Asp Lys Trp Gly Phe
785                 790                 795                 800

Gly Ala Thr Leu Leu Glu Ile Cys Phe Asp Gly Glu Ala Pro Leu Gln
                805                 810                 815

Ser Arg Ser Pro Ser Glu Lys Glu His Phe Tyr Gln Arg Gln His Arg
            820                 825                 830

Leu Pro Glu Pro Ser Cys Pro Gln Leu Ala Thr Leu Thr Ser Gln Cys
        835                 840                 845

Leu Thr Tyr Glu Pro Thr Gln Arg Pro Ser Phe Arg Thr Ile Leu Arg
    850                 855                 860

Asp Leu Thr Arg Val Gln Pro His Asn Leu Ala Asp Val Leu Thr Val
865                 870                 875                 880

Asn Arg Asp Ser Pro Ala Val Gly Pro Thr Thr Phe His Lys Arg Tyr
                885                 890                 895

Leu Lys Lys Ile Arg Asp Leu Gly Glu Gly His Phe Gly Lys Val Ser
            900                 905                 910

Leu Tyr Cys Tyr Asp Pro Thr Asn Asp Gly Thr Gly Glu Met Val Ala
        915                 920                 925

Val Lys Ala Leu Lys Ala Asp Cys Gly Pro Gln His Arg Ser Gly Trp
    930                 935                 940

Lys Gln Glu Ile Asp Ile Leu Arg Thr Leu Tyr His Glu His Ile Ile
945                 950                 955                 960

Lys Tyr Lys Gly Cys Cys Glu Asp Gln Gly Glu Lys Ser Leu Gln Leu
                965                 970                 975

Val Met Glu Tyr Val Pro Leu Gly Ser Leu Arg Asp Tyr Leu Pro Arg
```

```
                980             985             990
His Ser Ile Gly Leu Ala Gln Leu Leu Leu Phe Ala Gln Gln Ile Cys
            995             1000            1005

Glu Gly Met Ala Tyr Leu His Ala His Asp Tyr Ile His Arg Asp Leu
    1010            1015            1020

Ala Ala Arg Asn Val Leu Leu Asp Asn Asp Arg Leu Val Lys Ile Gly
1025            1030            1035            1040

Asp Phe Gly Leu Ala Lys Ala Val Pro Glu Gly His Glu Tyr Tyr Arg
                1045            1050            1055

Val Arg Glu Asp Gly Asp Ser Pro Val Phe Trp Tyr Ala Pro Glu Cys
            1060            1065            1070

Leu Lys Glu Tyr Lys Phe Tyr Tyr Ala Ser Asp Val Trp Ser Phe Gly
            1075            1080            1085

Val Thr Leu Tyr Glu Leu Leu Thr His Cys Asp Ser Ser Gln Ser Pro
    1090            1095            1100

Pro Thr Lys Phe Leu Glu Leu Ile Gly Ile Ala Gln Gly Gln Met Thr
1105            1110            1115            1120

Val Leu Arg Leu Thr Glu Leu Leu Glu Arg Gly Glu Arg Leu Pro Arg
            1125            1130            1135

Pro Asp Lys Cys Pro Cys Glu Val Tyr His Leu Met Lys Asn Cys Trp
            1140            1145            1150

Glu Thr Glu Ala Ser Phe Arg Pro Thr Phe Glu Asn Leu Ile Pro Ile
            1155            1160            1165

Leu Lys Thr Val His Glu Lys Tyr Gln Gly Gln Ala Pro Ser Val Phe
    1170            1175            1180

Ser Val Cys
1185

<210> SEQ ID NO 19
<211> LENGTH: 27
<212> TYPE: DNA
<213> ORGANISM: Artificial Sequence
<220> FEATURE:
<223> OTHER INFORMATION: antisense molecule

<400> SEQUENCE: 19
gctgaagctc gaaccactgt gacatcc                                       27

<210> SEQ ID NO 20
<211> LENGTH: 27
<212> TYPE: DNA
<213> ORGANISM: Artificial Sequence
<220> FEATURE:
<223> OTHER INFORMATION: antisense molecule

<400> SEQUENCE: 20
aagttcgtac cactgagaca tcctgcc                                       27

<210> SEQ ID NO 21
<211> LENGTH: 30
<212> TYPE: DNA
<213> ORGANISM: Artificial Sequence
<220> FEATURE:
<223> OTHER INFORMATION: antisense molecule

<400> SEQUENCE: 21
catctcccac tgcgccattt ggactcttca                                    30

<210> SEQ ID NO 22
```

```
<211> LENGTH: 27
<212> TYPE: DNA
<213> ORGANISM: Artificial Sequence
<220> FEATURE:
<223> OTHER INFORMATION: antisense molecule

<400> SEQUENCE: 22
cagcatttcc cactgcgcca tttgggc                                          27

<210> SEQ ID NO 23
<211> LENGTH: 31
<212> TYPE: DNA
<213> ORGANISM: Artificial Sequence
<220> FEATURE:
<223> OTHER INFORMATION: antisense molecule

<400> SEQUENCE: 23
ctggttccac tgagccatcc tgctgcatca g                                     31

<210> SEQ ID NO 24
<211> LENGTH: 27
<212> TYPE: DNA
<213> ORGANISM: Artificial Sequence
<220> FEATURE:
<223> OTHER INFORMATION: antisense molecule

<400> SEQUENCE: 24
ctgtagctga ttccattggg ccatcct                                          27

<210> SEQ ID NO 25
<211> LENGTH: 31
<212> TYPE: DNA
<213> ORGANISM: Artificial Sequence
<220> FEATURE:
<223> OTHER INFORMATION: antisense molecule

<400> SEQUENCE: 25
gattccactg agacatgctg ctctctctct c                                     31

<210> SEQ ID NO 26
<211> LENGTH: 27
<212> TYPE: DNA
<213> ORGANISM: Artificial Sequence
<220> FEATURE:
<223> OTHER INFORMATION: antisense molecule

<400> SEQUENCE: 26
gacttgattc cactgagaca tgctagc                                          27

<210> SEQ ID NO 27
<211> LENGTH: 30
<212> TYPE: DNA
<213> ORGANISM: Artificial Sequence
<220> FEATURE:
<223> OTHER INFORMATION: antisense molecule

<400> SEQUENCE: 27
gccaggccat tcccatctag agcttttttc                                       30

<210> SEQ ID NO 28
<211> LENGTH: 27
<212> TYPE: DNA
<213> ORGANISM: Artificial Sequence
<220> FEATURE:
<223> OTHER INFORMATION: antisense molecule

<400> SEQUENCE: 28
```
cgtaaggcag gccattccca tgcagag                                          27

<210> SEQ ID NO 29
<211> LENGTH: 30
<212> TYPE: DNA
<213> ORGANISM: Artificial Sequence
<220> FEATURE:
<223> OTHER INFORMATION: antisense molecule

<400> SEQUENCE: 29
cccacacaga ggcatggtcc ccaccattca                                       30

<210> SEQ ID NO 30
<211> LENGTH: 33
<212> TYPE: DNA
<213> ORGANISM: Artificial Sequence
<220> FEATURE:
<223> OTHER INFORMATION: antisense molecule

<400> SEQUENCE: 30
ggccatcccc cagtggcgca gaggcatgct ccc                                   33

<210> SEQ ID NO 31
<211> LENGTH: 33
<212> TYPE: DNA
<213> ORGANISM: Artificial Sequence
<220> FEATURE:
<223> OTHER INFORMATION: antisense molecule

<400> SEQUENCE: 31
cctggttgcg tgctaccatc ctactcgagg ggc                                   33

<210> SEQ ID NO 32
<211> LENGTH: 27
<212> TYPE: DNA
<213> ORGANISM: Artificial Sequence
<220> FEATURE:
<223> OTHER INFORMATION: antisense molecule

<400> SEQUENCE: 32
cacctggttg tgtgctacca tcctact                                          27

<210> SEQ ID NO 33
<211> LENGTH: 32
<212> TYPE: DNA
<213> ORGANISM: Artificial Sequence
<220> FEATURE:
<223> OTHER INFORMATION: antisense molecule

<400> SEQUENCE: 33
gctgtgggtg accatggcgc acggagccag cg                                    32

<210> SEQ ID NO 34
<211> LENGTH: 27
<212> TYPE: DNA
<213> ORGANISM: Artificial Sequence
<220> FEATURE:
<223> OTHER INFORMATION: antisense molecule

<400> SEQUENCE: 34
ggcgggaaac ttgctgtggg tgaccat                                          27

<210> SEQ ID NO 35
<211> LENGTH: 22
<212> TYPE: DNA

<213> ORGANISM: Artificial Sequence
<220> FEATURE:
<223> OTHER INFORMATION: primer

<400> SEQUENCE: 35
gaactttcag ctgttacttt cc                                              22

<210> SEQ ID NO 36
<211> LENGTH: 19
<212> TYPE: DNA
<213> ORGANISM: Artificial Sequence
<220> FEATURE:
<223> OTHER INFORMATION: primer

<400> SEQUENCE: 36
ctgtgctcat catactgtc                                                  19

<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
gtgttacagt cactcccact g                                               21

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
cctcaggcaa atctgactct g                                               21

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
gaaagtactg taggcccgag                                                 20

<210> SEQ ID NO 40
<211> LENGTH: 21
<212> TYPE: DNA
<213> ORGANISM: Artificial Sequence
<220> FEATURE:
<223> OTHER INFORMATION: primer

<400> SEQUENCE: 40
ctggaaccac aaagttagga g                                               21

<210> SEQ ID NO 41
<211> LENGTH: 22
<212> TYPE: DNA
<213> ORGANISM: Artificial Sequence
<220> FEATURE:
<223> OTHER INFORMATION: primer

<400> SEQUENCE: 41
gaagtgagat tccactctgt ag                                              22

```
<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
cactctccag tttcatctgc                                              20

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
cgaaagcagt tgacggatac g                                            21

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
ctccaactta gttgcctaaa cc                                           22

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
caagccgtta gaagcaggag                                              20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
ccatggttca caacctacag                                              20

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
gatgaggctt tccggagtca c                                            21

<210> SEQ ID NO 48
<211> LENGTH: 20
<212> TYPE: DNA
<213> ORGANISM: Artificial Sequence
<220> FEATURE:
```

```
<223> OTHER INFORMATION: primer

<400> SEQUENCE: 48
cagttgtatc acattcgagc                                                 20

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
ctgtgccgca gcattaagtg                                                 20

<210> SEQ ID NO 50
<211> LENGTH: 21
<212> TYPE: DNA
<213> ORGANISM: Artificial Sequence
<220> FEATURE:
<223> OTHER INFORMATION: primer

<400> SEQUENCE: 50
gtttattacc taaactggct g                                               21

<210> SEQ ID NO 51
<211> LENGTH: 21
<212> TYPE: DNA
<213> ORGANISM: Artificial Sequence
<220> FEATURE:
<223> OTHER INFORMATION: primer

<400> SEQUENCE: 51
ccaggtataa gtatttctct c                                               21

<210> SEQ ID NO 52
<211> LENGTH: 21
<212> TYPE: DNA
<213> ORGANISM: Artificial Sequence
<220> FEATURE:
<223> OTHER INFORMATION: primer

<400> SEQUENCE: 52
ggccatttga tcttgagcag c                                               21

<210> SEQ ID NO 53
<211> LENGTH: 21
<212> TYPE: DNA
<213> ORGANISM: Artificial Sequence
<220> FEATURE:
<223> OTHER INFORMATION: primer

<400> SEQUENCE: 53
gcagattggc ttcttcctca g                                               21

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54
ggcatttaag gcgagtctcc                                                 20
```

```
<210> SEQ ID NO 55
<211> LENGTH: 22
<212> TYPE: DNA
<213> ORGANISM: Artificial Sequence
<220> FEATURE:
<223> OTHER INFORMATION: primer

<400> SEQUENCE: 55
ggagcttact cgcagtaggc tc                                              22

<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56
gtaggagtct ctccgtgcaa gc                                              22

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
ccaactctga ctgagccagg                                                 20

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
catccatacg caggtggatg                                                 20

<210> SEQ ID NO 59
<211> LENGTH: 334
<212> TYPE: DNA
<213> ORGANISM: Artificial Sequence
<220> FEATURE:
<223> OTHER INFORMATION: probe

<400> SEQUENCE: 59
gaactttcag ctgttacttt cccagatatt attcgcaact acaaagtcat ggctgccgag     60
aacataccag agaatcccct gaagtatctg taccccaata ttgacaaaga ccacgccttt    120
gggaagtatt attccagacc aaaggaagca ccagaaccga tggagcttga cgaccctaag    180
cgaactggat acatcaagac tgagttgatt tctgtgtctg aagtccaccc ttctagactt    240
cagaccacag acaacctgct tcccatgtct ccagaggagt ttgatgagat gtcccggata    300 gtgggcccg aatttgacag tatgatgagc acag                                 334

<210> SEQ ID NO 60
<211> LENGTH: 694
<212> TYPE: DNA
<213> ORGANISM: Artificial Sequence
<220> FEATURE:
<223> OTHER INFORMATION: probe

<400> SEQUENCE: 60
```

-continued

| | |
|---|---|
| gtgttacagt cactcccact gacagagatc atccgccact accaggttct tgccgaagag | 60 |
| aacatccccg agaacccact ccgcttcctc tatccccgaa tccctcggga cgaagctttt | 120 |
| gggtgttact accaggaaaa agttaatttg gaagaacagg aggaatattt gaaacataaa | 180 |
| ctcattgtga tctctaacag acaggtggac gagctgcagc agcctctgga gctcaaacag | 240 |
| gattcagagt ccttagaagt gaatgcagag ctcttgttag cacacgacca ggagttgcca | 300 |
| ttgatgatgc agactgggct ggttctgggc acagagctga agtggacccc catactgagt | 360 |
| acagccccac aagtcctgct ggagccagcc ccacaagtcc tgctggagcc agccccacaa | 420 |
| gtcctgctgg agccagcccc acaagtcctg ctggagccag ccccacaagt cctgctggag | 480 |
| ccagccccac aagtcctgct ggagccagcc cacaagtcc tgctggagcc agccccacaa | 540 |
| gtccagctgg agccagcccc acaagtcctg ctggagctag ccccacaagt cctgctggag | 600 |
| ccagccccac aagtcctgct ggagctagcc ccacaagtcc agctggagcc agcacacttg | 660 |
| ctgcagcagc catcagagtc agatttgcct gagg | 694 |

<210> SEQ ID NO 61
<211> LENGTH: 373
<212> TYPE: DNA
<213> ORGANISM: Artificial Sequence
<220> FEATURE:
<223> OTHER INFORMATION: probe

<400> SEQUENCE: 61

| | |
|---|---|
| gaaagtactg taggcccgag agccaggagc accccgaagc cgacccaggt agtgctgccc | 60 |
| cgtacctgaa gaccaagttc atctgtgtga caccaacgac ctgcagcaat accattgacc | 120 |
| tgccgatgtc cccccgcact ttagattcat tgatgcagtt tggaaataac ggtgaaggtg | 180 |
| ctgagccctc agcaggaggg cagtttgagt cgctcacgtt tgacatggat ctgacctcgg | 240 |
| agtgtgctac ctcccccatg tgaggagctg aaaccagaag ctgcagagac gtgacttgag | 300 |
| acacctgccc cgtgctccac ccctaagcag ccgaacccca tatcgtctga aactcctaac | 360 |
| tttgtggttc cag | 373 |

<210> SEQ ID NO 62
<211> LENGTH: 442
<212> TYPE: DNA
<213> ORGANISM: Artificial Sequence
<220> FEATURE:
<223> OTHER INFORMATION: probe

<400> SEQUENCE: 62

| | |
|---|---|
| gaagtgagat tccactctgt agaaccctac aacaagggga gactgtcggc tctggccttc | 60 |
| gctgacatcc tgcgagacta caaggttatc atggctgaaa acatccctga aaaccctctg | 120 |
| aagtacctct accctgacat tcccaaagac aaagcctttg gcaaacacta cagctcccag | 180 |
| ccgtgcgaag tctcaagacc aaccgaacgg ggagacaagg gttacgtccc ctctgttttt | 240 |
| atccccattt caacaatccg aagcgattcc acggagccac aatctccttc agaccttctc | 300 |
| cccatgtctc caagtgcata tgctgtgctg agagaaaacc tgagcccaac gacaattgaa | 360 |
| actgcaatga attccccata ttctgctgaa tgacggtgca acggacact ttaaagaagg | 420 |
| aagcagatga aactggagag tg | 442 |

<210> SEQ ID NO 63
<211> LENGTH: 634
<212> TYPE: DNA
<213> ORGANISM: Artificial Sequence
<220> FEATURE:
<223> OTHER INFORMATION: probe

<400> SEQUENCE: 63

| | | | | | |
|---|---|---|---|---|---|
| cgaaagcagt | tgacggatac | gtgaagccac | agatcaagca | agtggtccct | gagttcgtca | 60 |
| atgcatccac | agatgccgga | gccagcgcca | cctacatgga | ccaggctcct | tccccagtcg | 120 |
| tgtgccctca | acctcactac | aacatgtacc | cacccaaccc | tgaccctgtc | cttgaccaag | 180 |
| atggcgagtt | tgacctggat | gagagcatgg | atgttgccag | gcacgtggaa | gaacttttac | 240 |
| gccggcccat | ggacagtctc | gacgcccgcc | tctcccacc | tgctggtctc | ttcacctccg | 300 |
| ctagaagctc | cctgtcctga | acgctggact | ccatgcttct | cttggaaacc | accttcagtg | 360 |
| taaggagccc | acgtcagttg | tagtatctct | gttcatacca | acaatggctt | tgcacgtttc | 420 |
| acagggctac | cttgcccaca | cagttctggg | tttgtggcta | aagcggtggt | gaccttttg | 480 |
| ttcagacctc | aagggccccc | agggcctctc | gtgtaagagc | tgaacctatc | attgctgaca | 540 |
| aacctatttc | tccggtgtcc | tttttctgtc | caatggccat | ttcagtgaaa | ttctagaaaa | 600 |
| ggcagggagg | caggtttagg | caactaagtt | ggag | | | 634 |

<210> SEQ ID NO 64
<211> LENGTH: 463
<212> TYPE: DNA
<213> ORGANISM: Artificial Sequence
<220> FEATURE:
<223> OTHER INFORMATION: probe

<400> SEQUENCE: 64

| | | | | | |
|---|---|---|---|---|---|
| caagccaagc | cgttagaagc | aggagcccct | ggccagtgcc | tggtcacgga | gctgagctgt | 60 |
| gtttagatgt | gttggctgct | cgtggtgaa | ggaagacccg | tctccagaaa | agcaatttag | 120 |
| gcaaaaggga | ttccgtttga | tggcagagtc | ccagtgctag | aaaggtagcg | aaggtggaca | 180 |
| gcttacagtc | tcaactcatt | tcgtcgtaaa | tgtcctcgta | acgacattga | ttcttctacc | 240 |
| tggataacct | tttgtttgtt | tgtttgtttg | tttttgtttt | gtttttcccc | tgtaaccatt | 300 |
| ttttttctg | acaagaaaac | attttaattt | tctaagcaag | aagcattttt | caaataccat | 360 |
| gtctgtgacc | caaagtaaaa | atggatgata | attcatgtaa | atgtgtgcaa | catagcaacc | 420 |
| tgaacctgca | cgcgattcgg | gctctgtagg | ttgtgaacca | tgg | | 463 |

<210> SEQ ID NO 65
<211> LENGTH: 894
<212> TYPE: DNA
<213> ORGANISM: Artificial Sequence
<220> FEATURE:
<223> OTHER INFORMATION: probe

<400> SEQUENCE: 65

| | | | | | |
|---|---|---|---|---|---|
| gatgaggctt | tccggagtca | ctataagccc | gaacagatgg | ggaaggacgg | gaggggttat | 60 |
| gtctctacta | ctatcaagat | gactgtggaa | agggaccagc | ccttcctac | tccagagccc | 120 |
| cagatgcctg | ccatggtgcc | acctatgat | cttggaatgg | cccctgatgc | ttccatgcaa | 180 |
| ctcagctcag | atatggggta | tcctccacag | tccatccact | catttcagag | cctagaagag | 240 |
| tccatgagtg | tactgccatc | ttttcaggag | cctcacctgc | aaatgccccc | caacatgagc | 300 |
| cagataacca | tgcccttttga | ccagcctcac | ccccagggtc | tgctgcagtg | ccagtcccag | 360 |
| gaacatgctg | tgtccagccc | tgaacccatg | ctttggtcag | atgtgactat | ggtagaggac | 420 |
| agttgcctaa | ctcagcctgt | gggaggtttc | ccccaaggca | cctgggtcag | tgaagacatg | 480 |

-continued

| | |
|---|---|
| tacccteccc tgctgcctcc cactgaacag gacctcacca agcttctcct ggagaaccaa | 540 |
| ggggagggag gagggtcctt aggaagccag cccctcctga aaccatctcc ttatgggcaa | 600 |
| tcagggatct cactgtccca cctggaccta aggaccaacc ccagctggtg atcccagctg | 660 |
| gagaagccca gaaacaaagc ctcttctgtc tctatggacc agctctggac acctgctcat | 720 |
| gcaggtgcct tccgtctcaa ctgttccttg gttaagagaa aagaactggc tgggagacca | 780 |
| tgtggtgtat ggaactgctg tgctctgtcc tacctgccat atcagggccc ccttttcca | 840 |
| gcactgggtg caaagggatg agtggggtgt aatgctcga atgtgataca actg | 894 |

<210> SEQ ID NO 66
<211> LENGTH: 381
<212> TYPE: DNA
<213> ORGANISM: Artificial Sequence
<220> FEATURE:
<223> OTHER INFORMATION: probe

<400> SEQUENCE: 66

| | |
|---|---|
| ctgtgccgca gcattaagtg ggggcgcctt attatttctt attattaatt attattattt | 60 |
| ttctggaacc acgtgggagc cctccccgcc tgggtcggag ggagtggttg tggagggtga | 120 |
| gatgcctccc acttctggct ggagacctca tcccacctct cagggtgggg ggtgctcccc | 180 |
| tcctggtgct ccctccgggt ccccctggt tgtagcagct tgtgtctggg gccaggacct | 240 |
| gaattccact cctacctctc catgtttaca tattcccagt atctttgcac aaaccagggg | 300 |
| tcggggaggg tctctggctt cattttctg ctgtgcagaa tatcctattt tatattttta | 360 |
| cagccagttt aggtaataaa c | 381 |

<210> SEQ ID NO 67
<211> LENGTH: 266
<212> TYPE: DNA
<213> ORGANISM: Artificial Sequence
<220> FEATURE:
<223> OTHER INFORMATION: probe

<400> SEQUENCE: 67

| | |
|---|---|
| ccaggtataa gtatttctct ctcttttcg tttttttta aaaaaaaaa aacacatgcc | 60 |
| tcatatagac tatctccgaa tgcagctatg tgaaagagaa cccagaggcc ctcctctgga | 120 |
| taactgcgca gaattctctc ttaaggacag ttgggctcag tctaacttaa aggtgtgaag | 180 |
| atgtagctag gtattttaaa gttcccctta ggtagtttta gctgaatgat gctttctttc | 240 |
| ctatggctgc tcaagatcaa atggcc | 266 |

<210> SEQ ID NO 68
<211> LENGTH: 728
<212> TYPE: DNA
<213> ORGANISM: Artificial Sequence
<220> FEATURE:
<223> OTHER INFORMATION: probe

<400> SEQUENCE: 68

| | |
|---|---|
| gcagattggc ttcttcctca ggccctccac tcccgcagag tagagctggc aggacctgga | 60 |
| attcgtctga ggggaggggg agctgccacc tgctttcccc cctcccccag ctccagcttc | 120 |
| tttcaagtgg agccagccgg cctggcctgg tgggacaata cctttgacaa gcggactctc | 180 |
| ccctcccctt cctccacacc ccctctgctt cccaagggag gtgggacac ctccaagtgt | 240 |
| tgaacttaga actgcaaggg gaatcttcaa actttcccgc tggaacttgt ttgcgctttg | 300 |
| atttggtttg atcaagagca ggcacctggg ggaaggatgg aagagaaaag ggtgtgtgaa | 360 |

-continued

```
gggtttttat gctggccaaa gaaataacca ctcccactgc ccaacctagg tgaggagtgg      420
tggctcctgg ctctggggag agtggcaagg ggtgacctga agagagctat actggtgcca      480
ggctcctctc catgggcag ctaatgaaac ctcgcagatc ccttgcaccc cagaaccctc       540
cccgttgtga agaggcagta gcatttagaa gggagacaga tgaggctggt gagctggccg      600 cctttccaa caccgaaggg aggcagatca acagatgagc catcttggag cccaggtttc       660
ccctggagca gatggagggt tctgctttgt ctctcctatg tggggctagg agactcgcct      720
taaatgcc                                                              728
```

<210> SEQ ID NO 69
<211> LENGTH: 379
<212> TYPE: DNA
<213> ORGANISM: Artificial Sequence
<220> FEATURE:
<223> OTHER INFORMATION: probe

<400> SEQUENCE: 69

```
ggagcttact cgcagtaggc tctcgctctt ctaatcaatg gataaagtgg ggaaaatgtg       60
gaacaactta aaatacagat gccagaatct cttcagccac gagggaggaa gccgtaatga     120
gaacgtggag atgaacccca acagatgtcc gtctgtcaaa gagaaagca tcagtctggg      180 agaggcagct ccccagcaag agagcagtcc cttaagagaa aatgttgcct tacagctggg     240
actgagccct tccaagacct tttccaggcg gaaccaaaac tgtgccgcag agatccctca     300
agtggttgaa atcagcatcg agaaagacag tgactcgggt gccaccccag gaacgaggct     360
tgcacggaga gactcctac                                                   379
```

<210> SEQ ID NO 70
<211> LENGTH: 688
<212> TYPE: DNA
<213> ORGANISM: Artificial Sequence
<220> FEATURE:
<223> OTHER INFORMATION: probe

<400> SEQUENCE: 70

```
ccaactctga ctgagccagg caccctgctc tgcctcacac agtcacatcc tggagggaac      60
acagtcccca gctggacttg gggttctgct gtcctttctt cagtcatcct ggtgcctgca     120
tgcatgtgac agctggacca gagaatgcca gcaagaacaa ggcaggtgga ggagggattg     180
tcacacaact ctgaggtcaa cgcctctagg tacaatatgg ctctttgtgg tgagccatgt     240
atcagagcga gacaggcagg acctcgtctc tccacagagg ctggacctag gtctccactc     300
acttgcctgc ccttgccacc tgaactgtgt ctattctccc agccctggtt tctcagtctg     360
ctgagtaggg caggcccct acccatgtat agaatagcga gcctgtttct gggagaatat     420
cagccagagg ttgatcatgc caaggcccct tatggggacg cagactgggc tagggggacta    480 cacagttata cagtatttat ttatttattc tccttgcagg ggttggggt ggaatgatgg      540 cgtgagccat cccacttctc tgccctgtgc tctggtggt ccagagaccc ccaggtctgg      600
ttcttccctg tggagacccc catcccaaaa cattgttggg cccaaagtag tctcgaatgt     660
cctgggccca tccacctgcg tatggatg                                        688
```